(12) United States Patent
Parham et al.

(10) Patent No.: US 11,643,414 B2
(45) Date of Patent: May 9, 2023

(54) MATERIALS FOR ORGANIC ELECTROLUMINESCENT DEVICES

(71) Applicant: Merck Patent GmbH, Darmstadt (DE)

(72) Inventors: Amir Parham, Frankfurt am Main (DE); Tobias Grossmann, Darmstadt (DE); Jonas Kroeber, Frankfurt Am Main (DE)

(73) Assignee: MERCK PATENT GMBH, Darmstadt (DE)

( * ) Notice: Subject to any disclaimer, the term of this patent is extended or adjusted under 35 U.S.C. 154(b) by 781 days.

(21) Appl. No.: 16/095,991

(22) PCT Filed: Apr. 26, 2017

(86) PCT No.: PCT/EP2017/059865
§ 371 (c)(1),
(2) Date: Oct. 24, 2018

(87) PCT Pub. No.: WO2017/186760
PCT Pub. Date: Nov. 2, 2017

(65) Prior Publication Data
US 2019/0135814 A1 May 9, 2019

(30) Foreign Application Priority Data
Apr. 29, 2016 (EP) .................................... 16167825

(51) Int. Cl.
| | | |
|---|---|---|
| *C07D 487/04* | (2006.01) | |
| *H01L 51/00* | (2006.01) | |
| *C07F 15/00* | (2006.01) | |
| *C07D 487/16* | (2006.01) | |
| *C07D 495/04* | (2006.01) | |
| *C07D 493/16* | (2006.01) | |
| *C09K 11/06* | (2006.01) | |
| *C07D 495/16* | (2006.01) | |
| *C07D 493/04* | (2006.01) | |
| *H01L 51/50* | (2006.01) | |
| *C07D 209/86* | (2006.01) | |
| *C07D 519/00* | (2006.01) | |

(52) U.S. Cl.
CPC ......... *C07D 487/04* (2013.01); *C07D 209/86* (2013.01); *C07D 487/16* (2013.01); *C07D 493/04* (2013.01); *C07D 493/16* (2013.01); *C07D 495/04* (2013.01); *C07D 495/16* (2013.01); *C07D 519/00* (2013.01); *C07F 15/0033* (2013.01); *C09K 11/06* (2013.01); *H01L 51/006* (2013.01); *H01L 51/0061* (2013.01); *H01L 51/0065* (2013.01); *H01L 51/0067* (2013.01); *H01L 51/0072* (2013.01); *H01L 51/0073* (2013.01); *H01L 51/0074* (2013.01); *H01L 51/5016* (2013.01); *H01L 51/5024* (2013.01); *H01L 51/5096* (2013.01); *H01L 51/5012* (2013.01); *H01L 51/5072* (2013.01); *H01L 2251/5384* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 4,539,507 A | 9/1985 | VanSlyke et al. | |
| 2012/0085997 A1 | 4/2012 | Sugita et al. | |
| 2012/0326141 A1* | 12/2012 | Pflumm | C09B 57/00 257/E51.026 |
| 2014/0142301 A1 | 5/2014 | Itoi | |
| 2015/0333271 A1 | 11/2015 | Chung et al. | |
| 2016/0118595 A1 | 4/2016 | Itoi | |
| 2016/0351826 A1* | 12/2016 | Kim | C07D 409/14 |

FOREIGN PATENT DOCUMENTS

| | | |
|---|---|---|
| EP | 2475020 A1 | 7/2012 |
| EP | 2977378 A1 | 1/2016 |
| JP | 2006-080271 A | 3/2006 |
| JP | 2014-103243 A | 6/2014 |
| KR | 10-2014-0034710 A | 3/2014 |
| KR | 10-2015-0002072 A | 1/2015 |
| KR | 10-2015-0080966 A | 7/2015 |
| WO | 2014/104545 A1 | 7/2014 |
| WO | 2015/105314 A1 | 7/2015 |
| WO | 2015/105315 A1 | 7/2015 |
| WO | 2015/105316 A1 | 7/2015 |

OTHER PUBLICATIONS

Jang et al., RSC Advances, (2014), 4, pp. 57679-57682. (Year: 2014).*
Ackermann, L., et al., "Palladium-Catalyzed Direct Arylation-Based Domino Synthesis of Annulated N-Heterocycles Using Alkenyl or (Hetero)Aryl 1,2-Dihalides", Synthesis 2009, No. 20, (2009), pp. 3493-3503.
Adib, M., et al., "A Novel and Simple Synthesis of 9H-Pyrimido[4,5-b]indoles under Microwave Irradiation and Solvent-Free Conditions", Synlett 2008, No. 2, (2008), pp. 0177-0180.
"Antimony(V) Chloride", e-EROS Encyclopedia of Reagents for Organic Synthesis [Online] 2001, pp. 1-3.
Borovik, V.P., et al., "H and C NMR Spectra of 9H-Pyrimido[4,5-b]indoles", Chemistry of Heterocyclic Compounds, vol. 39, No. 10, (2003), pp. 1348-1354.
Das, R., et al., "Silver-Nitrate-Catalyzed N-Arylation of Amines and O-Arylations of Phenols and Alcohols", Asian Journal of Organic Chemistry, vol. 2, No. 7, (2013), pp. 579-585.
Hernandez-Perez, A., et al., "Photochemical Synthesis of Complex Carbazoles: Evaluation of Electronic Effects in Both UV- and Visible-Light Methods in Continuous Flow", Chemistry—A European Journal, vol. 21, No. 46, (2015), pp. 16673-16678.

(Continued)

*Primary Examiner* — Dawn L Garrett
(74) *Attorney, Agent, or Firm* — Faegre Drinker Biddle & Reath LLP

(57) ABSTRACT

The present invention relates to compounds of formula (1). The compounds are suitable for use in electronic devices, in particular organic electroluminescent devices, comprising these compounds. In some embodiments, the compounds are used as matrix materials for phosphorescent or fluorescent emitters as well as a hole-blocking or electron-transport.

17 Claims, No Drawings

(56) References Cited

OTHER PUBLICATIONS

International Search Report for PCT/EP2017/059865 dated Jul. 21, 2017.
Jang, H.-G., et al., "Synthesis and blue phosphorescent device performances of a new bipolar host material containing pyrazino[2,3-b]indole moiety", RSC Advances, vol. 4, No. 101, (2014), pp. 57679-57682.
Koller, D., et al., "Organic plasmon-emitting diode", Nature Photonics, vol. 2, No. 11, (2008), pp. 1-4.
Li, B., et al., "Selective Access to 3-Cyano-1H-indoles, 9H-Pyrimido[4,5-b]indoles, or 9H-Pyrido[2,3-b]indoles through Copper-Catalyzed One-Pot Multicomponent Cascade Reactions", Journal of Organic Chemistry, vol. 80, No. 11, (2015), pp. 5444-5456.
Murthy, S., et al., "A New, Efficient and Recyclable Lanthanum(III) Oxide-Catalyzed C-N Cross Coupling", Advanced Synthesis and Catalysis, No. 352, No. 18, (2010), pp. 3241-3245.
Siddiqui, A., et al., "Synthesis and Antibacterial Activity of 1,4-Quinoxaline Derivatives", Asian Journal of Chemistry, vol. 14, No. 2, (2002), pp. 1109-1110.
Written Opinion of the International Searching Authority for PCT/EP2017/059865 dated Jul. 21, 2017.
International Preliminary Report on Patentability received for PCT Patent Application No. PCT/EP2017/059865, dated Nov. 8, 2018, 8 pages.

\* cited by examiner

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2017/059865, filed Apr. 26, 2017, which claims benefit of European Application No. 16167825.5, filed Apr. 29, 2016, both of which are incorporated herein by reference in their entirety.

The present invention relates to materials for use in electronic devices, in particular in organic electroluminescent devices, and to electronic devices, in particular organic electroluminescent devices, comprising these materials.

The structure of organic electroluminescent devices (OLEDs) in which organic semiconductors are employed as functional materials is described, for example in U.S. Pat. No. 4,539,507. The emitting materials employed here are increasingly organometallic complexes which exhibit phosphorescence instead of fluorescence. For quantum-mechanical reasons, an up to four-fold increase in the energy and power efficiency is possible using organometallic compounds as phosphorescence emitters. In general, however, there is still a need for improvement in the case of OLEDs, in particular also in the case of OLEDs which exhibit triplet emission (phosphorescence), for example with respect to efficiency, operating voltage and lifetime.

The properties of phosphorescent OLEDs are not only determined by the triplet emitters employed but also by the other materials used together with triplet emitters in OLEDs, such as matrix materials. Improvements in these materials and their charge-transport properties can thus also result in significant improvements in the OLED properties.

The use of indolocarbazole derivatives, indenocarbazole derivatives, or fluorene or spirobifluorene derivatives, inter alia, as matrix materials for phosphorescent emitters in organic electroluminescent devices is known. Furthermore, US 2014/0142301 discloses azacarbazole-carbazole derivatives, in which the carbazole group is bonded to the azacarbazole via its N atom.

Further improvements are desirable here, in particular with respect to the efficiency, the lifetime and the film formation of the materials.

The object of the present invention is the provision of compounds which are suitable for use in an OLED, in particular as matrix material for phosphorescent emitters. A further object of the present invention is to provide further organic semiconductors for organic electroluminescent devices so as to provide the person skilled in the art with a greater possible choice of materials for the production of OLEDs.

Surprisingly, it has been found that certain compounds described in greater detail below achieve this object, are highly suitable for use in OLEDs and result in improvements in the organic electroluminescent device. The improvements here relate, in particular, to the lifetime and/or the efficiency.

In addition, these compounds have improved film-formation properties in the case of processing from solution, since they simultaneously have a high glass transition temperature and high solubilities, which enables processing from solution and subsequent drying by heating. The present invention therefore relates to these compounds and to electronic devices, in particular organic electroluminescent devices, which comprise compounds of this type.

The present invention relates to a compound of the formula (1):

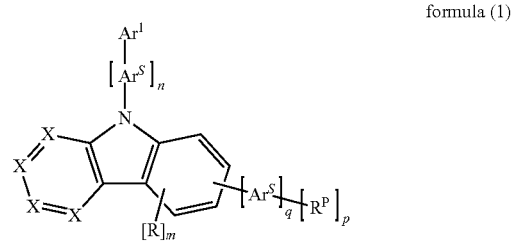

formula (1)

where:
X is N or CR$^X$, with the proviso that exactly two non-adjacent groups X are equal to N;
Ar$^S$ is on each occurrence, identically or differently, an aromatic or heteroaromatic ring system having 5 to 30 aromatic ring atoms, which may be substituted by one or more radicals R, with the proviso that when Ar$^S$ is a heteroaromatic ring system, then it is bonded via a C atom to the phenyl group or to the nitrogen atom of the azacarbazole moiety depicted in formula (1);
Ar$^1$ is an aromatic or heteroaromatic ring system having 5 to 60 aromatic ring atoms, which may be substituted by one or more radicals R;
R$^P$ is N(Ar)$_2$, C(=O)Ar, P(=O)(Ar)$_2$, or an aromatic or heteroaromatic ring system having 5 to 60 aromatic ring atoms, which may in each case be substituted by one or more radicals R, with the proviso that when R$^P$ is an heteroaromatic ring system and when q=0, then R$^P$ is bonded via a C atom to the phenyl group of the azacarbazole moiety of formula (1);
R$^X$ is on each occurrence, identically or differently, H, D, F, Cl, Br, I, CHO, N(Ar)$_2$, C(=O)Ar, P(=O)(Ar)$_2$, S(=O)Ar, S(=O)$_2$Ar, (R)C=C(R)Ar, CN, NO$_2$, Si(R)$_3$, B(OR)$_2$, B(R)$_2$, B(N(R)$_2$)$_2$, OSO$_2$R, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals R, where one or more, preferably non-adjacent CH$_2$ groups may be replaced by (R)C=C(R), C≡C, Si(R)$_2$, Ge(R)$_2$, Sn(R)$_2$, C=O, C=S, C=Se, P(=O)(R), SO, SO$_2$, N(R), O, S or CON(R) and where one or more H atoms may be replaced by D, F, Cl, Br, I, CN or NO$_2$, or an aromatic or heteroaromatic ring system having 5 to 60 aromatic ring atoms, which may in each case be substituted by one or more radicals R, or an aryloxy or heteroaryloxy group having 5 to 60 aromatic ring atoms, which may be substituted by one or more radicals R;
R is on each occurrence, identically or differently, H, D, F, Cl, Br, I, CHO, N(Ar)$_2$, C(=O)Ar, P(=O)(Ar)$_2$, S(=O)Ar, S(=O)$_2$Ar, (R)C=C(R)Ar, CN, NO$_2$, Si(R$^1$)$_3$, B(OR$^1$)$_2$, B(R$^1$)$_2$, B(N(R$^1$)$_2$)$_2$, OSO$_2$R$^1$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals R$^1$, where one or more, preferably non-adjacent CH$_2$ groups may be replaced by (R$^1$)C=C(R$^1$), C≡C, Si(R$^1$)$_2$, Ge(R$^1$)$_2$, Sn(R$^1$)$_2$, C=O, C=S, C=Se, P(=O)(R$^1$), SO, SO$_2$, N(R$^1$), O, S or CON(R$^1$) and where one or more H atoms may be replaced by D, F, Cl, Br, I, CN or NO$_2$, or an aromatic or heteroaromatic ring system having 5 to 60 aromatic ring atoms, which may in each case be substituted by one or more radicals R$^1$, or an aryloxy or heteroaryloxy group having 5 to 60 aromatic ring atoms, which may be substituted by one or more radicals $R^1$, where optionally two or more adjacent substituents R can form a mono- or polycyclic, aliphatic, aromatic or heteroaromatic ring system with one another;

Ar is an aromatic or heteroaromatic ring system having 5 to 60 aromatic ring atoms, which may be substituted by one or more radicals $R^1$;

$R^1$ is on each occurrence, identically or differently, H, D, F, Cl, Br, I, CHO, $N(R^2)_2$, $C(=O)R^2$, $P(=O)(R^2)_2$, $S(=O)R^2$, $S(=O)_2R^2$, $(R^2)C=C(R^2)_2$, CN, $NO_2$, $Si(R^2)_3$, $B(OR^2)_2$, $B(R^2)_2$, $B(N(R^2)_2)_2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^2$, where one or more, preferably non-adjacent $CH_2$ groups may be replaced by $(R^2)C=C(R^2)$, C≡C, $Si(R^2)_2$, $Ge(R^2)_2$, $Sn(R^2)_2$, C=O, C=S, C=Se, $P(=O)(R^2)$, SO, $SO_2$, $N(R^2)$, O, S or CON ($R^2$) and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, where optionally two or more adjacent substituents $R^1$ can form a mono- or polycyclic, aliphatic, aromatic or heteroaromatic ring system with one another;

$R^2$ is on each occurrence, identically or differently, H, D, F, Cl, Br, I, CHO, CN, $NO_2$, a straight-chain alkyl, alkoxy or thioalkoxy group having 1 to 20 C atoms or a straight-chain alkenyl or alkynyl group having 2 to 20 C atoms or a branched or cyclic alkyl, alkenyl, alkynyl, alkoxy or thioalkoxy group having 3 to 20 C atoms, or an aromatic or heteroaromatic ring system having 5 to 30 aromatic ring atoms or an aryloxy or heteroaryloxy group having 5 to 30 aromatic ring atoms; where optionally two or more adjacent substituents $R^2$ can form a mono- or polycyclic, aliphatic, aromatic or heteroaromatic ring system with one another;

n, m, q are, identically or differently, 0, 1, 2 or 3;

p is 0 or 1; and where the following compounds are excluded from the invention:

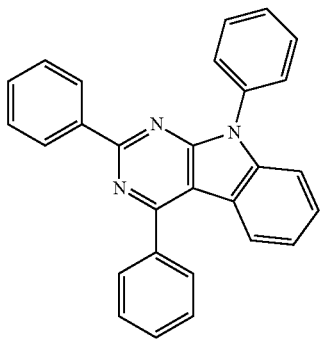

-continued

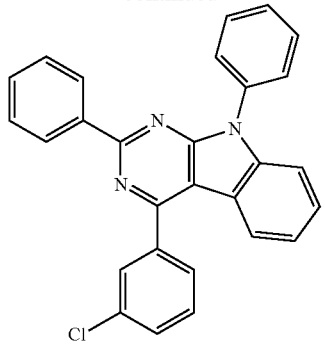

Adjacent substituents in the sense of the present invention are substituents which are bonded to carbon atoms which are linked directly to one another or which are bonded to the same carbon atom.

When n is 0, then the corresponding group $Ar^S$ connected to the nitrogen of the azacarbazole moiety in formula (1) is absent and the group $Ar^1$ is directly bonded to the nitrogen.

When q is 0, then the corresponding group $Ar^S$ connected to the phenyl ring of the azacarbazole moiety in formula (1) is absent so that the substituent $R^P$, if present, is directly bonded to this phenyl ring.

Furthermore, the following definitions of chemical groups apply for the purposes of the present application:

An aryl group in the sense of this invention contains 6 to 60 aromatic ring atoms; a heteroaryl group in the sense of this invention contains 5 to 60 aromatic ring atoms, at least one of which is a heteroatom. The hetero atoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an sp$^3$-hybridised C, Si, N or O atom, an sp$^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or CH$_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two radicals may form a ring with one another is, for the purposes of the present application, intended to be taken to mean, inter alia, that the two radicals are linked to one another by a chemical bond. This is illustrated by the following schemes:

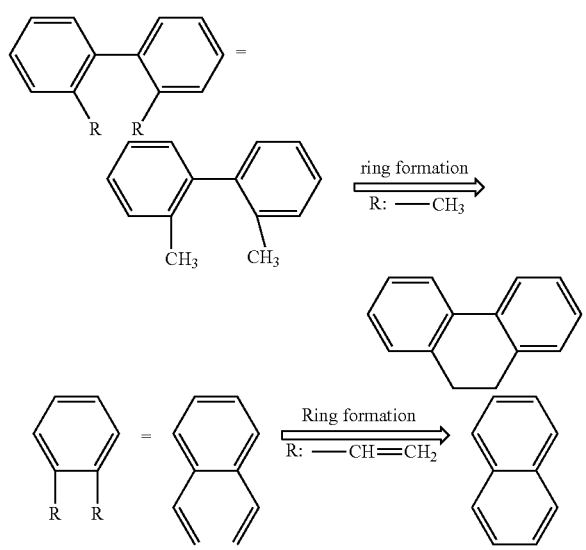

Furthermore, the above-mentioned formulation is also intended to be taken to mean that, in the case where one of the two radicals represents hydrogen, the second radical is bonded at the position to which the hydrogen atom was bonded, with formation of a ring. This is illustrated by the following scheme:

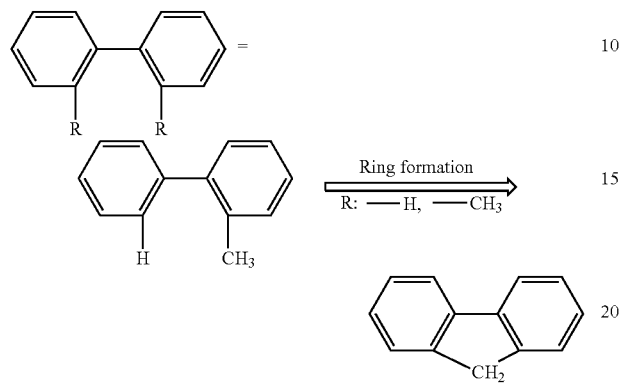

In accordance with a preferred embodiment of the invention, the compounds of formula (1) are selected from the compounds of the following formulae (2) to (4),

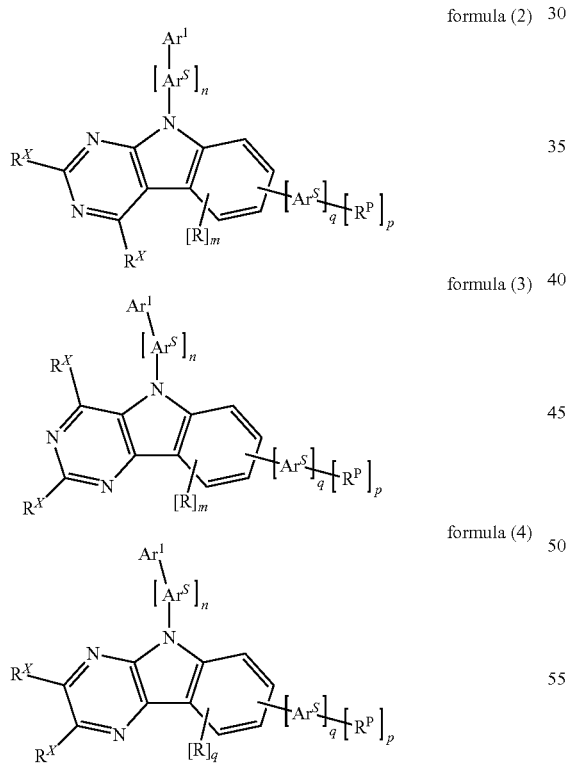

where the symbols and indices used have the same meanings as above. Among formulae (2), (3) and (4), formula (2) is preferred.

In accordance with a very preferred embodiment of the invention, the compounds of formulae (1), and (2) to (4) are selected from the compounds of the following formulae (2-1) to (4-6),

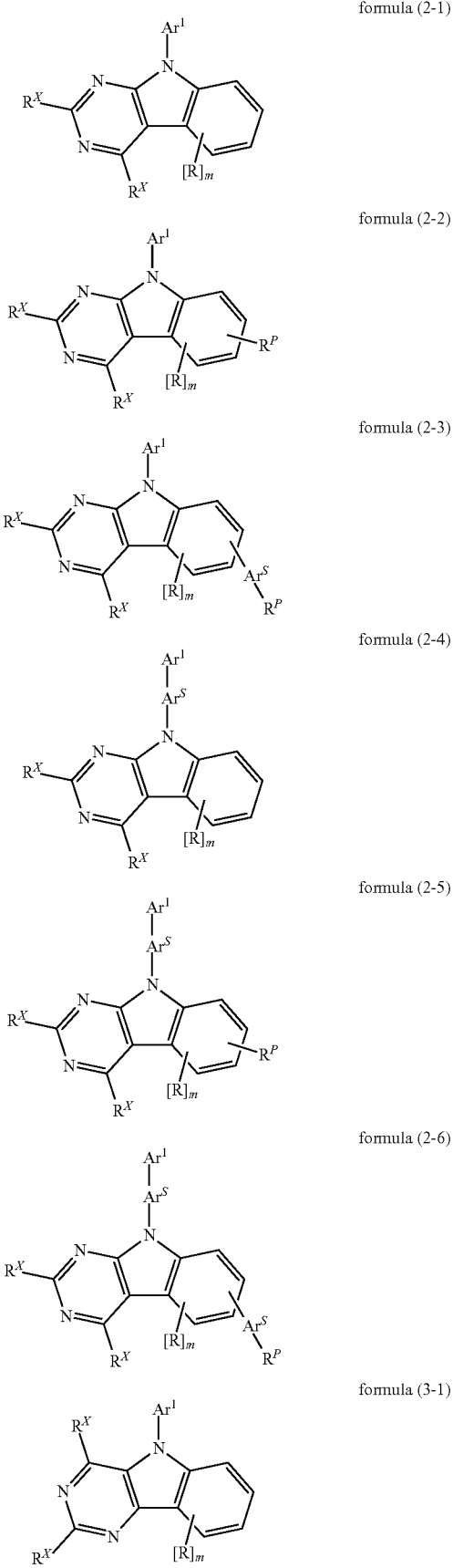

-continued formula (3-2)
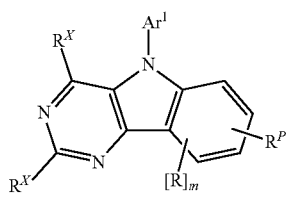

formula (3-3)
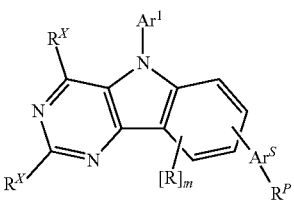

formula (3-4)
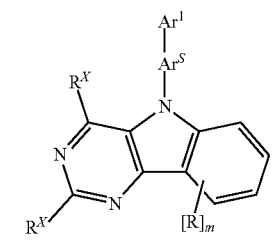

formula (3-5)
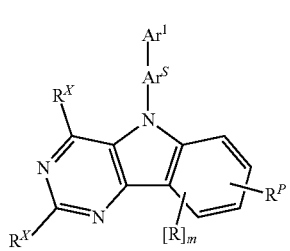

formula (3-6)
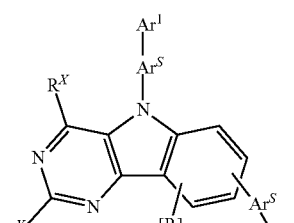

formula (4-1)
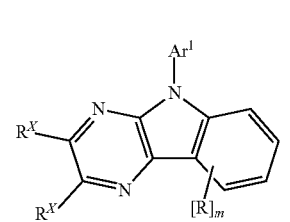

formula (4-2)
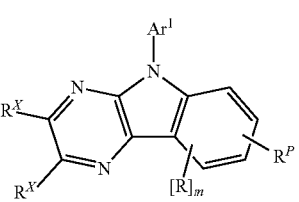

-continued formula (4-3)
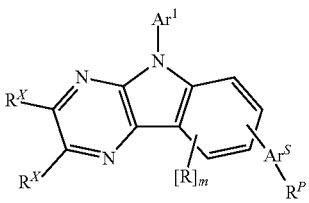

formula (4-4)
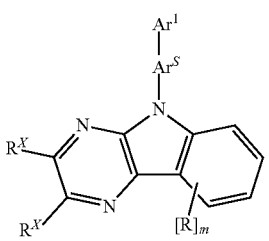

formula (4-5)
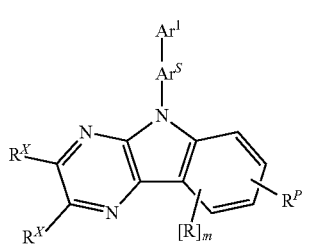

formula (4-6)
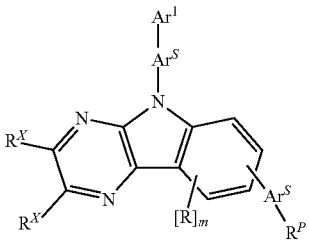

where the symbols and indices have the same meanings as above.

Among formulae (2-1) to (4-4), formulae (2-1) to (2-6) are preferred.

In accordance with a very particularly preferred embodiment of the invention, the compounds of formulae (1), (2) to (4) and (2-1) to (4-6) are selected from the compounds of the following formulae (2-1a) to (4-6a), formula (2-1a)
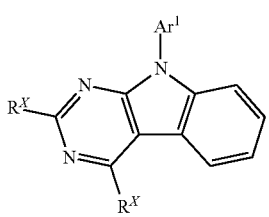

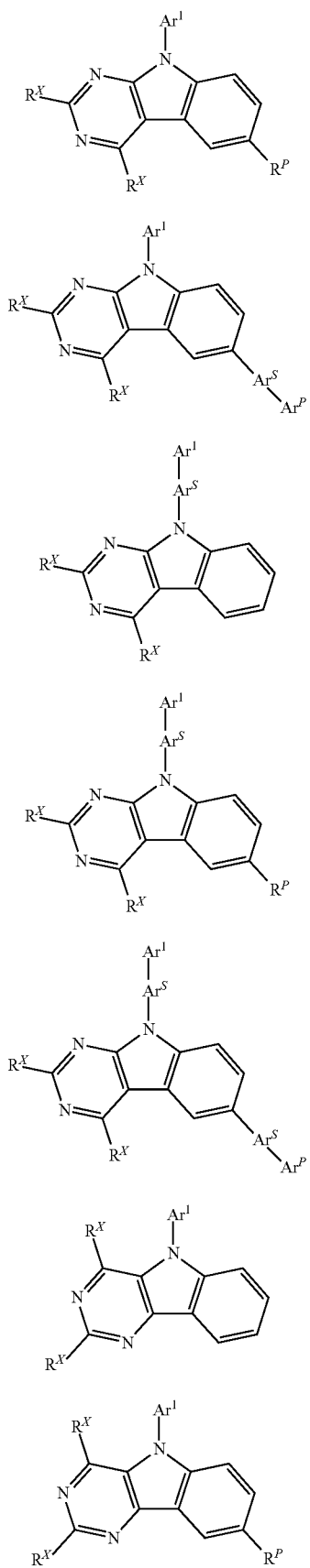

-continued

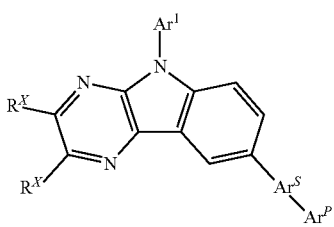

formula (4-3a)

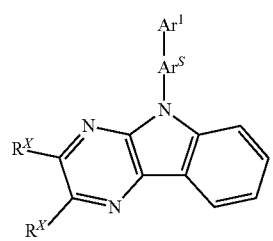

formula (4-4a)

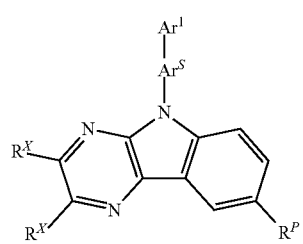

formula (4-5a)

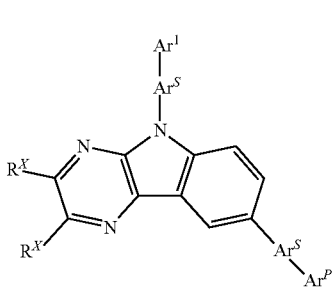

formula (4-6a)

where the symbols and indices used have the same meanings as above.

Among formulae (2-1a) to (4-4a), formulae (2-1a) to (2-6a) are preferred.

In accordance with a preferred embodiment of the invention, $Ar^1$ is an aromatic or heteroaromatic ring system having 5 to 40, more preferably 5 to 24 aromatic ring atoms, which may be substituted by one or more radicals R.

It is particularly preferred that $Ar^1$ stands for benzene, naphthalene, anthracene, biphenyl, terphenyl, fluorene, furan, benzofuran, dibenzofuran, thiophene, benzothiophene, dibenzothiophene, carbazole, indolocarbazole, indenocarbazole, pyridine, quinoline, isoquinoline, pyridazine, benzopyridazine, pyrimidine, benzopyrimidine, quinoxaline, pyrazine, azacarbazole, benzocarboline, phenanthroline, 1,3,5-triazine, 1,2,4-triazine, 1,2,3-triazine, each of which may be substituted by one or more radicals R.

It is very particularly preferred that $Ar^1$ stands for benzene, naphthalene, biphenyl, terphenyl, fluorene, furan, benzofuran, dibenzofuran, thiophene, benzothiophene, dibenzothiophene, carbazole, pyridine, pyridazine, pyrimidine, pyrazine, 1,3,5-triazine, 1,2,4-triazine, 1,2,3-triazine, each of which may be substituted by one or more radicals R.

In accordance with a preferred embodiment of the invention, $R^X$ is on each occurrence, identically or differently, an aromatic or heteroaromatic ring system having 5 to 40, more preferably 5 to 24 aromatic ring atoms, which may be substituted by one or more radicals R.

It is particularly preferred that $R^X$ stands on each occurrence, identically or differently, for benzene, naphthalene, anthracene, biphenyl, terphenyl, fluorene, spirobifluorene, cis- or trans-indenofluorene, furan, benzofuran, dibenzofuran, thiophene, benzothiophene, dibenzothiophene, carbazole, indolocarbazole, indenocarbazole, pyridine, quinoline, isoquinoline, pyridazine, benzopyridazine, pyrimidine, benzopyrimidine, quinoxaline, pyrazine, azacarbazole, benzocarboline, phenanthroline, 1,3,5-triazine, 1,2,4-triazine, 1,2,3-triazine, each of which may be substituted by one or more radicals R.

It is very particularly preferred that $R^X$ stands on each occurrence, identically or differently, for benzene, naphthalene, biphenyl or carbazole, each of which may be substituted by one or more radicals R.

Examples of suitable groups $R^X$ are the groups of formulae ($R^X$-1) to ($R^X$66),

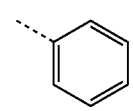

($R^X$-1)

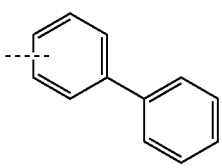

($R^X$-2)

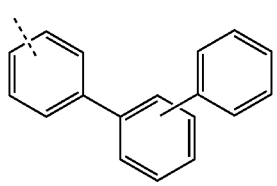

($R^X$-3)

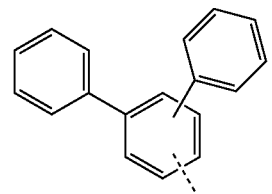

($R^X$-4)

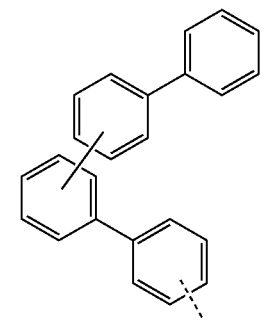

($R^X$-5)

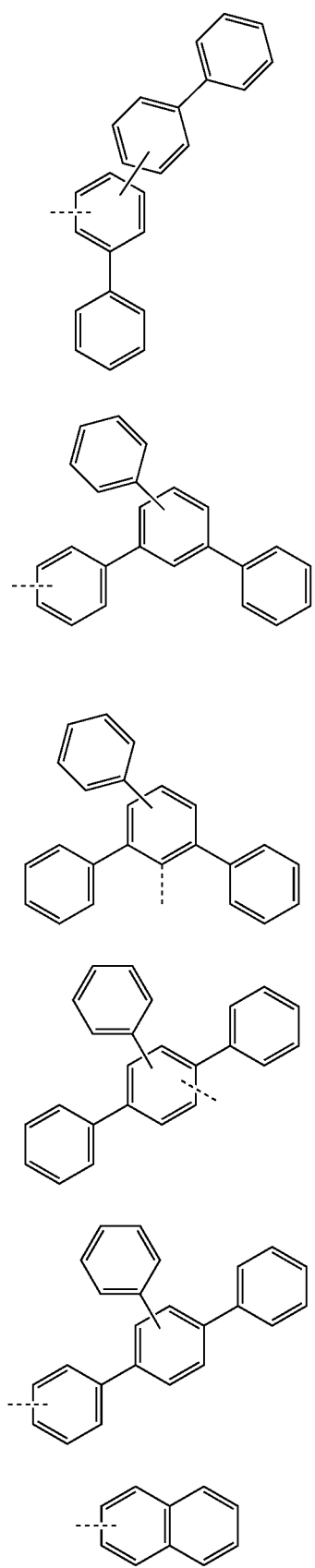
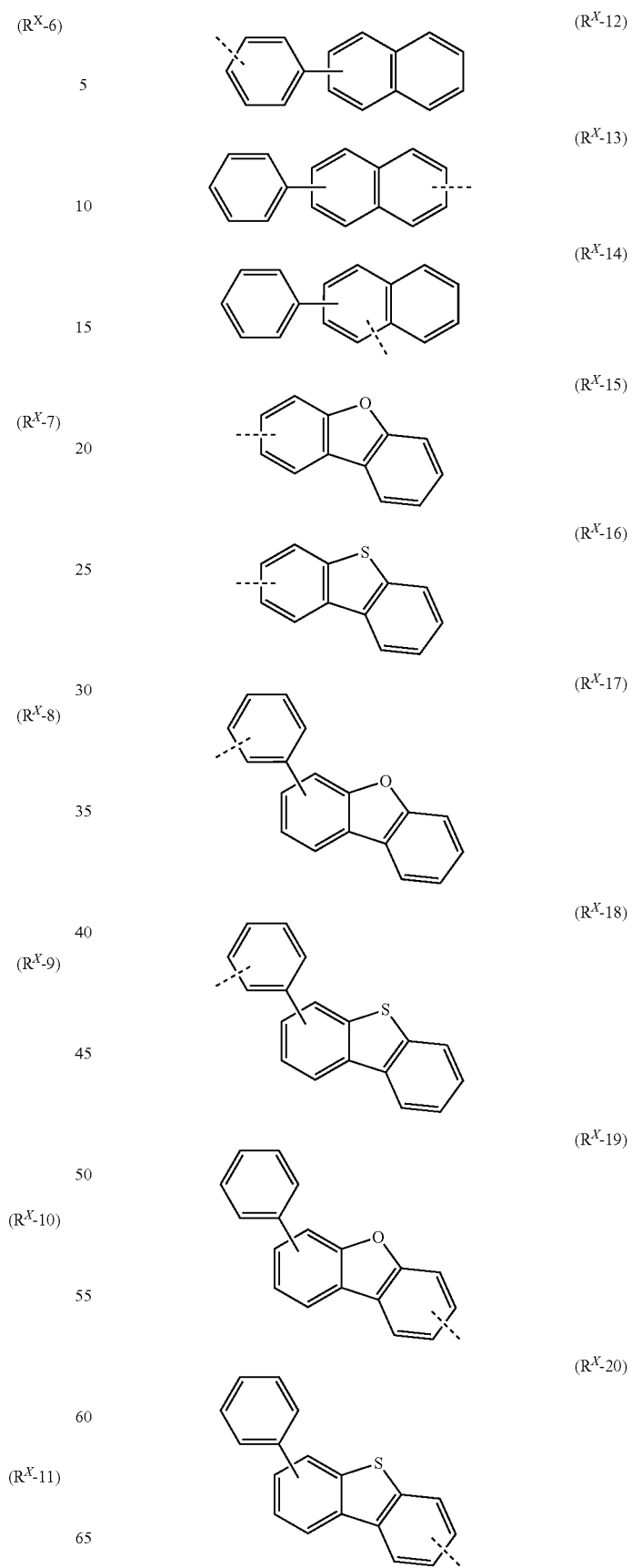

($R^X$-21)
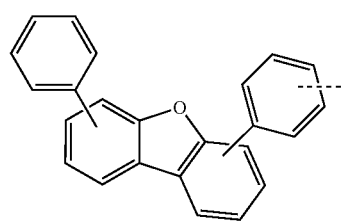
($R^X$-22)
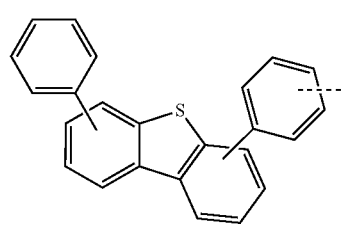
($R^X$-23)
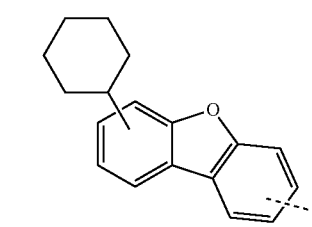
($R^X$-24)
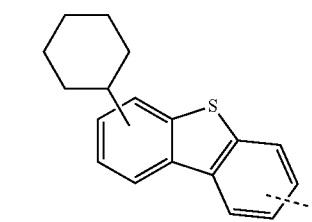
($R^X$-25)
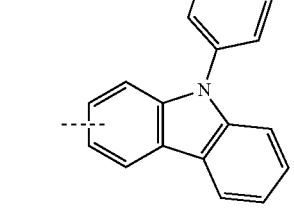
($R^X$-26)
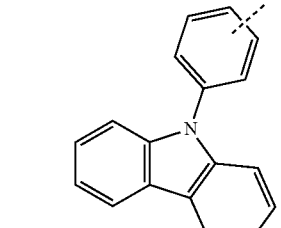
($R^X$-27)
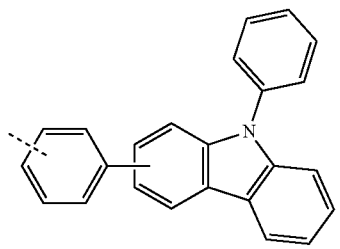
($R^X$-28)
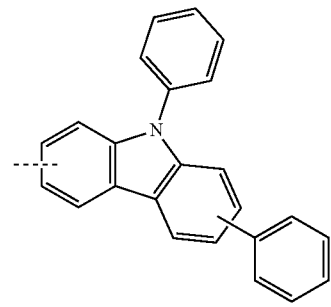
($R^X$-29)
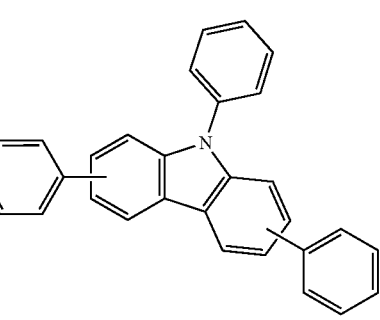
($R^X$-30)
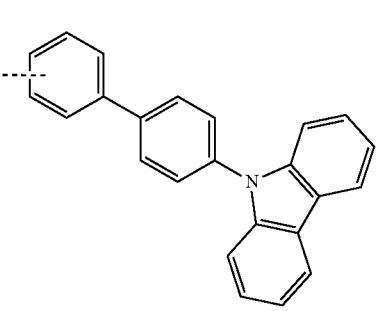
($R^X$-31)
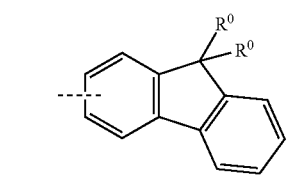
($R^X$-32)
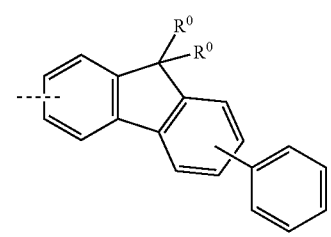

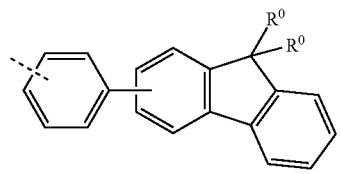
(R^X-33)
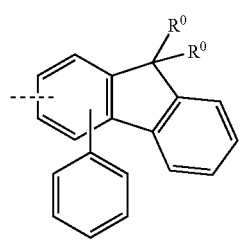
(R^X-34)
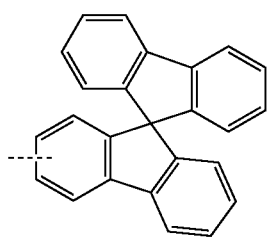
(R^X-35)
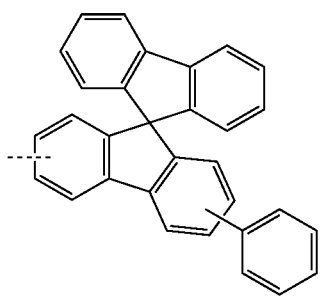
(R^X-36)
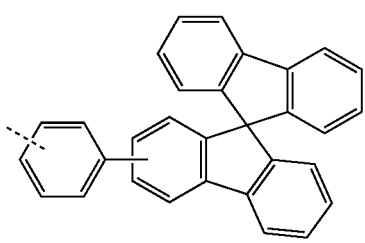
(R^X-37)
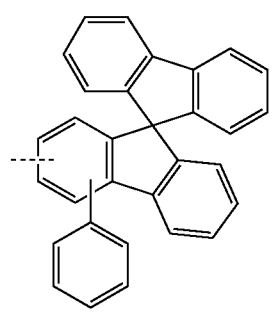
(R^X-38)
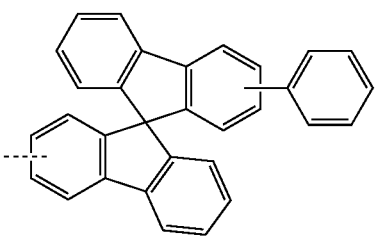
(R^X-39)
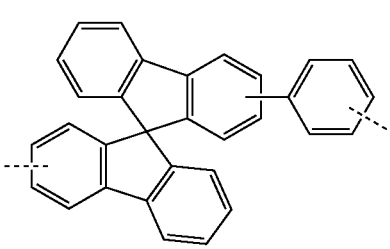
(R^X-40)
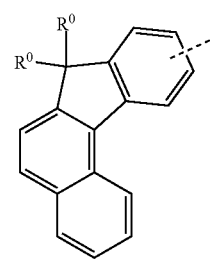
(R^X-41)
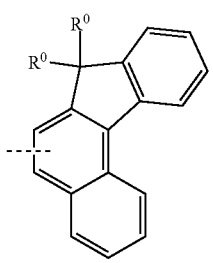
(R^X-42)
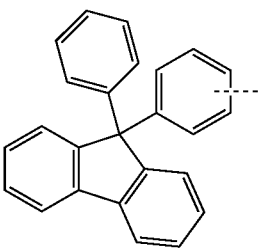
(R^X-43)
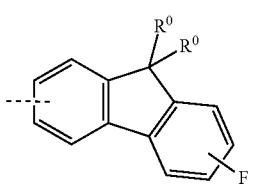
(R^X-44)

-continued
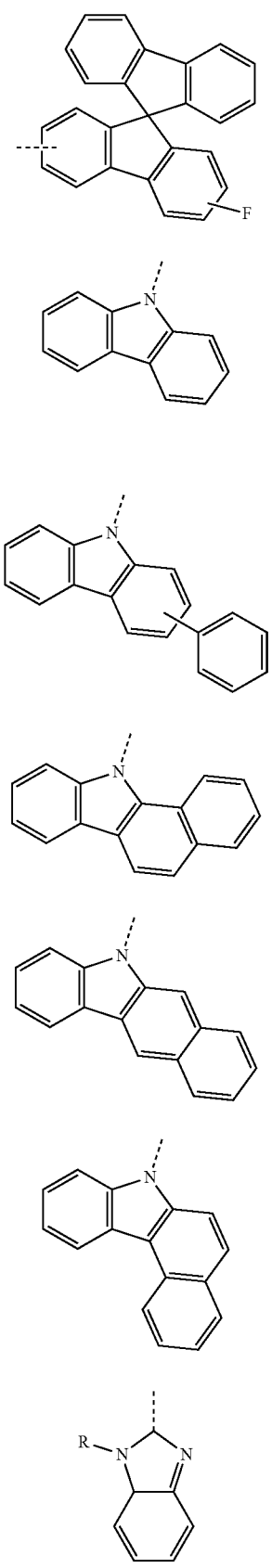
(R^X-45)
(R^X-46)
(R^X-47)
(R^X-48)
(R^X-49)
(R^X-50)
(R^X-51)
-continued
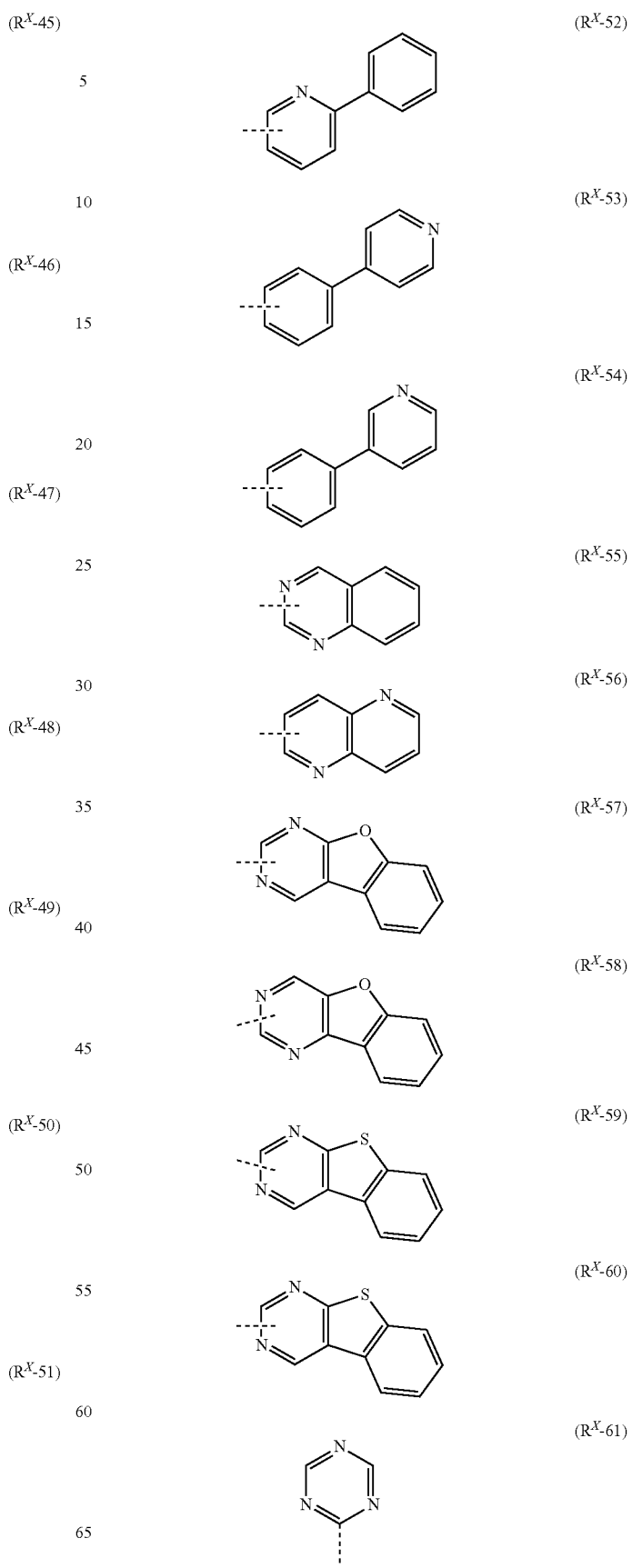
(R^X-52)
(R^X-53)
(R^X-54)
(R^X-55)
(R^X-56)
(R^X-57)
(R^X-58)
(R^X-59)
(R^X-60)
(R^X-61)

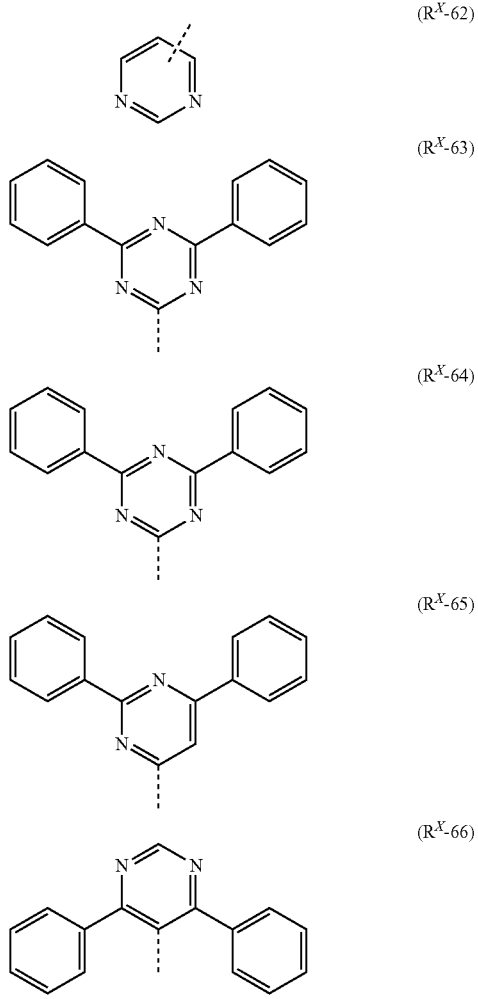

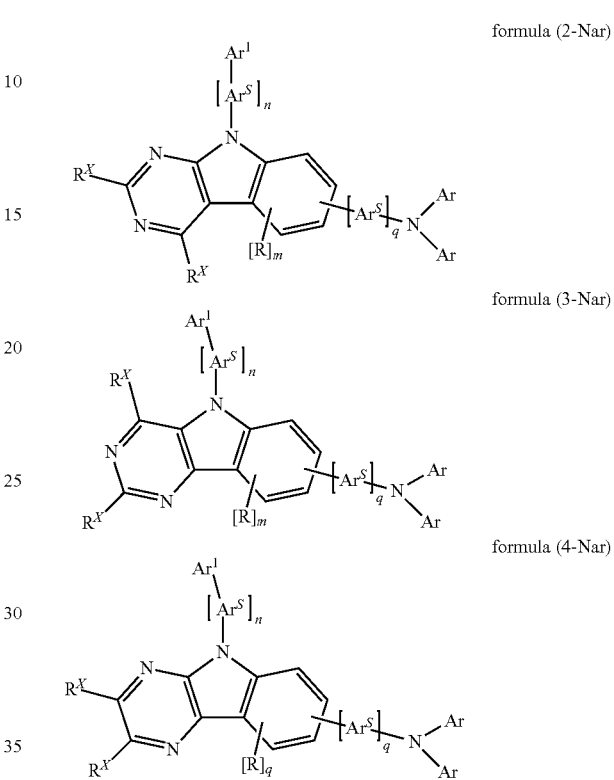

where the dashed bonds indicate the bonds to the azacarbazole as depicted in formula (1), and where
R, in formula ($R^X$-51), has the same meaning as above;
$R^0$, in formulae ($R^X$-31) to ($R^X$-34), ($R^X$-41), ($R^X$-42) and ($R^X$-44), is selected on each occurrence, identically or differently, from the group consisting of H, D, F, CN, Si($R^1$)$_3$, a straight-chain alkyl group having 1 to 10 C atoms or a branched or cyclic alkyl group having 3 to 10 C atoms, each of which may be substituted by one or more radicals $R^1$, an aryl or heteroaryl group having 5 to 18 aromatic ring atoms, which may in each case be substituted by one or more radicals $R^1$, where two or more adjacent substituents $R^0$ may optionally form a mono- or polycyclic, aliphatic ring system or aromatic ring system, which may be substituted by one or more radicals $R^1$, where $R^1$ is as defined above; and the groups of formulae ($R^X$-1) to ($R^X$-66) may further be substituted at each free position by a group R as defined above.

Among the groups of formulae ($R^X$-1) to ($R^X$-66), following groups are preferred: ($R^X$-1), ($R^X$-2), ($R^X$-11), ($R^X$-15) to ($R^X$-34), ($R^X$-46) to ($R^X$-48) and ($R^X$-61) to ($R^X$-66).

In accordance with a preferred embodiment, $R^P$ is selected from N(Ar)$_2$ or an aromatic or heteroaromatic ring system having 5 to 40 aromatic ring atoms, which may in each case be substituted by one or more radicals R, with the proviso that when $R^P$ is an heteroaromatic ring system and when n=0, then $R^P$ is bonded via a C atom to the phenyl group of the azacarbazole moiety of formula (1).

When $R^P$ stands for N(Ar)$_2$, it is preferred that the index q is 1, 2 or 3, more preferably q is 1 or 2.

Thus, in accordance with a preferred embodiment, the compounds of formulae (2) to (4) are selected from the compounds of the following formulae (2-NAr) to (4-NAr), where q is 1, 2 or 3 and where the other symbols and indices used have the same meanings as above.

The preferred embodiments mentioned for formulae (2), (3) and (4) also apply to formulae (2-Nar), (3-Nar) and (4-Nar).

When $R^P$ stands for an aromatic or heteroaromatic ring system, it is preferred that $R^P$ is an aromatic or heteroaromatic ring system having 5 to 24 aromatic ring atoms, which may in each case be substituted by one or more radicals R, with the proviso that when $R^P$ is an heteroaromatic ring system and when n=0, then $R^P$ is bonded via a C atom to the phenyl group of the azacarbazole moiety of formula (1).

It is particularly preferred that $R^P$, stands for benzene, naphthalene, anthracene, biphenyl, terphenyl, fluorene, spirobifluorene, cis- or trans-indenofluorene, furan, benzofuran, dibenzofuran, thiophene, benzothiophene, dibenzothiophene, pyrrole, indole, carbazole, pyridine, quinoline, isoquinoline, pyridazine, benzopyridazine, pyrimidine, benzopyrimidine, quinoxaline, pyrazine, 1,3,5-triazine, 1,2,4-triazine, 1,2,3-triazine, each of which may be substituted by one or more radicals R. It is very particularly preferred that $R^P$ stands on each occurrence, identically or differently, for benzene, naphthalene, biphenyl, fluorene, dibenzofuran, dibenzothiophene, carbazole, pyridine, pyrazine, 1,3,5-triazine, 1,2,4-triazine, 1,2,3-triazine, each of which may be substituted by one or more radicals R, with the proviso that when $R^P$ is an heteroaromatic ring system and when n=0, then $R^P$ is bonded via a C atom to the phenyl group of the azacarbazole moiety of formula (1).

Examples of suitable groups $R^P$, when $R^P$ stands for an aromatic or heteroaromatic ring system, are the groups of formulae ($R^P$-1) to ($R^P$-54),
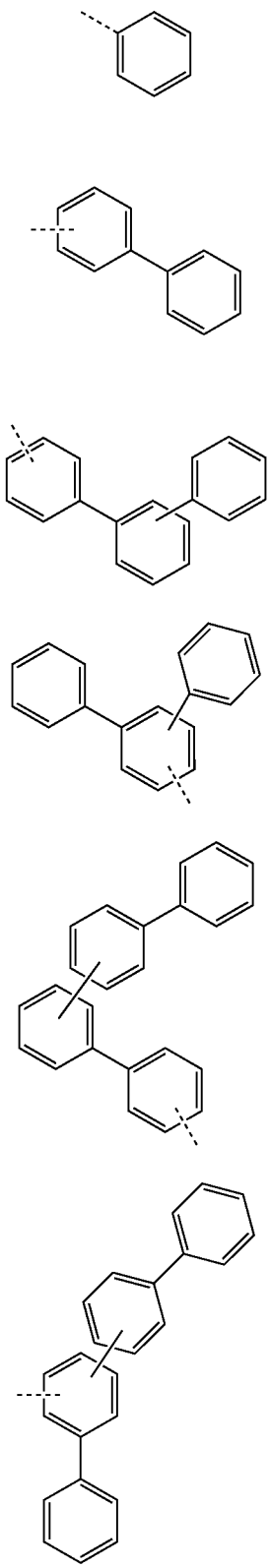
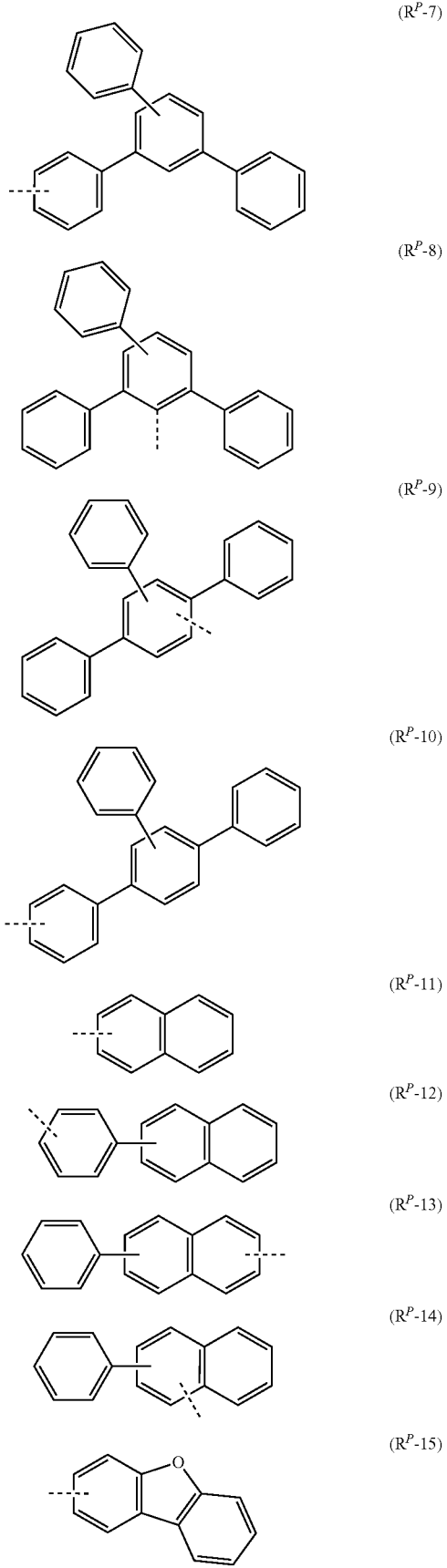

-continued
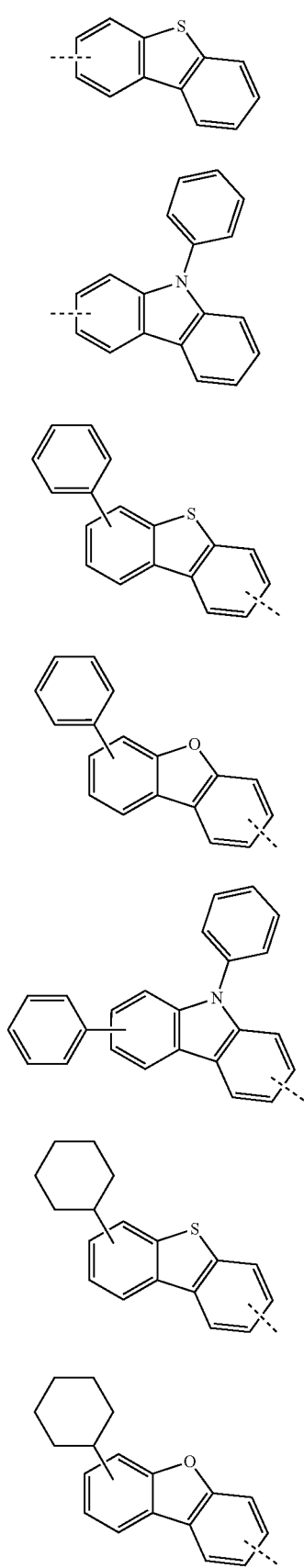
(R^P-16)
(R^P-17)
(R^P-18)
(R^P-19)
(R^P-20)
(R^P-21)
(R^P-22)
-continued
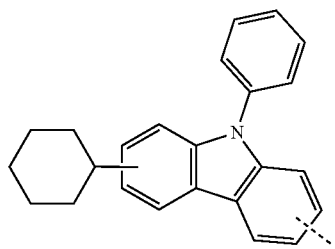
(R^P-23)
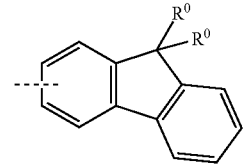
(R^P-24)
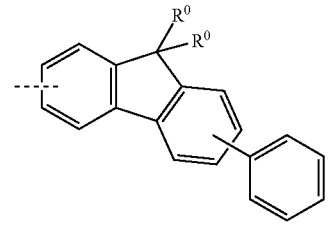
(R^P-25)
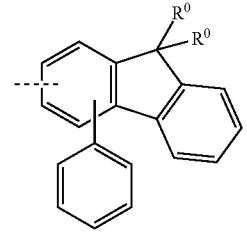
(R^P-26)
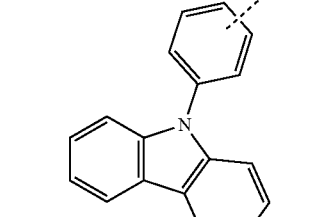
(R^P-27)
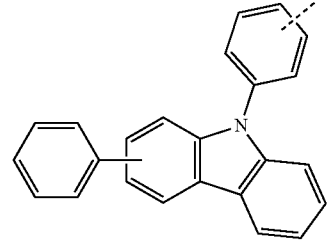
(R^P-28)

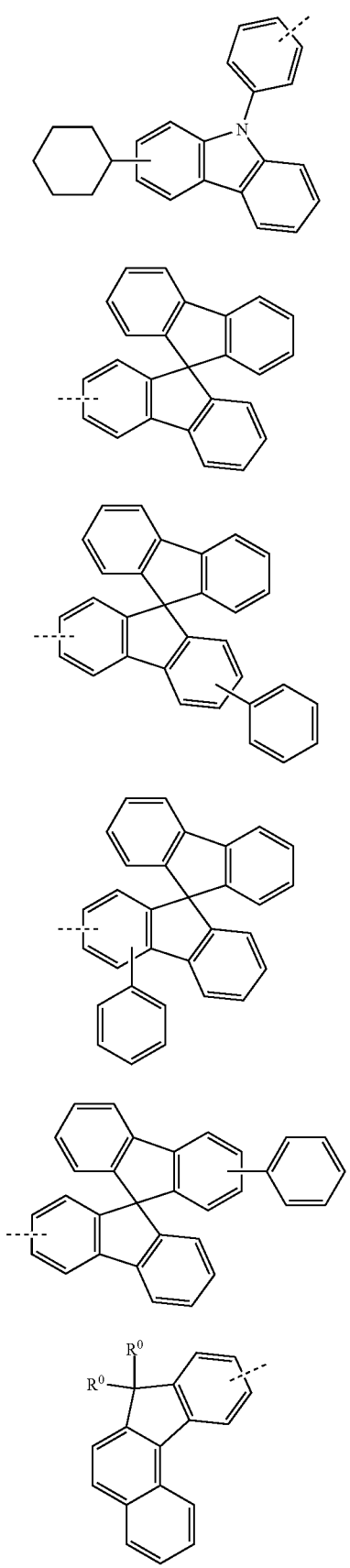
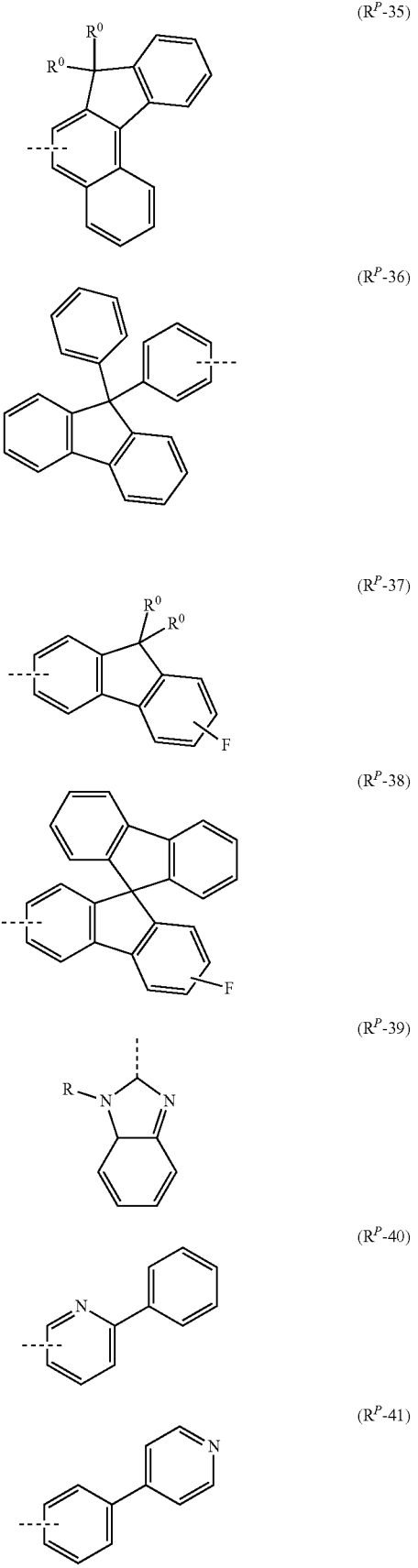

(R^P-42) 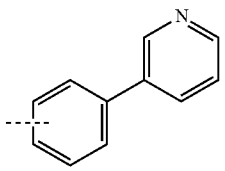

(R^P-43) 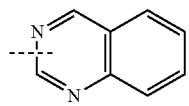

(R^P-44) 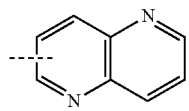

(R^P-45) 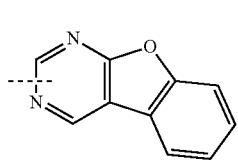

(R^P-46) 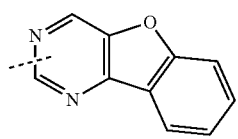

(R^P-47) 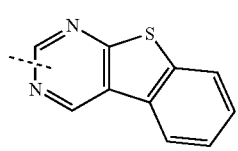

(R^P-48) 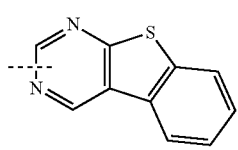

(R^P-49) 

(R^P-50) 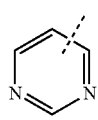

(R^P-51) 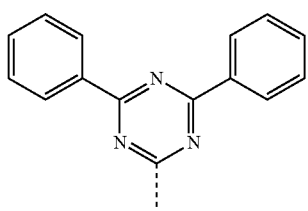

(R^P-52) 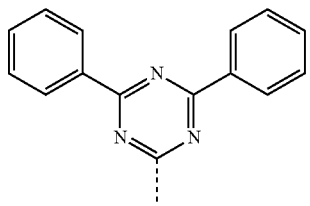

(R^P-53) 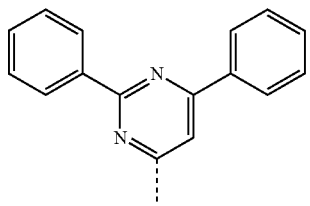

(R^P-54) 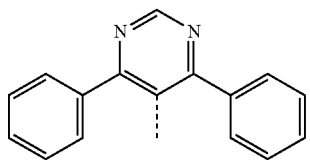

where the dashed bonds indicate, when n=0, the bonds to the azacarbazole as depicted in formula (1), and when n is 1, 2 or 3, the bonds to $Ar^S$, and where R, in formula ($R^P$-33), has the same meaning as above; $R^0$, in formulae ($R^P$-24) to ($R^P$-25), ($R^P$-26), ($R^P$-34), ($R^P$-35) and ($R^P$-37), is selected on each occurrence, identically or differently, from the group consisting of H, D, F, CN, $Si(R^1)_3$, a straight-chain alkyl group having 1 to 10 C atoms or a branched or cyclic alkyl group having 3 to 10 C atoms, each of which may be substituted by one or more radicals $R^1$, an aryl or heteroaryl group having 5 to 18 aromatic ring atoms, which may in each case be substituted by one or more radicals $R^1$, where two or more adjacent substituents $R^0$ may optionally form a mono- or polycyclic, aliphatic ring system or aromatic ring system, which may be substituted by one or more radicals $R^1$, where $R^1$ is as defined above; and the groups of formulae ($R^P$-1) to ($R^P$-54) may further be substituted at each free position by a group R as defined above.

Among groups $R^P$ of formulae ($R^P$-1) to ($R^P$-54), the groups of formulae ($R^P$1), ($R^P$-2), ($R^P$-11), ($R^P$-15) to ($R^P$-30), ($R^P$-39), ($R^P$-49) to ($R^P$-54) are preferred.

In accordance with a preferred embodiment of the invention, the compounds of the invention comprise at least one group $Ar^1$, $R^P$ or $R^X$ selected from triazine, pyrimidine, pyrazine, pyridazine, pyridine, imidazole, pyrazole, oxazole, oxadiazole, triazole, thiazole, thiadiazole, benzimidazole, quinolone, isoquinoline and quinoxaline, which may in each case be substituted by one or more radicals R.

In accordance with a preferred embodiment of the invention, the compounds of the invention comprise at least one group $Ar^1$, $R^P$ or $R^X$ selected from pyrrole, furan, thiophene, benzothiophene, benzofuran, indole, carbazole, dibenzothiophene, dibenzofuran and azacarbazole, which may in each case be substituted by one or more radicals R.

In accordance with a preferred embodiment of the invention, the compounds of the invention comprise at least one group $Ar^1$, $R^P$ or $R^X$, which is selected from triazine, pyrimidine, pyrazine, pyridazine, pyridine, imidazole, pyrazole, oxazole, oxadiazole, triazole, thiazole, thiadiazole, benzimidazole, quinolone, isoquinoline and quinoxaline, which may in each case be substituted by one or more radicals R and at least one group $Ar^1$, $R^P$ or $R^X$, which is selected from pyrrole, furan, thiophene, benzothiophene, benzofuran, indole, carbazole, dibenzothiophene, dibenzofuran and azacarbazole, which may in each case be substituted by one or more radicals R.

The group $Ar^S$ is, identically or differently on each occurrence, selected from aromatic or heteroaromatic ring systems having 5 to 30, preferably 5 to 18 aromatic ring atoms, which may in each case also be substituted by one or more radicals R, with the proviso that when $Ar^S$ is an heteroaromatic ring system, then it is bonded via a C atom to the phenyl group or to the nitrogen atom of the azacarbazole moiety depicted in formula (1). More preferably, $Ar^S$ is selected from benzene, biphenyl, fluorene, dibenzofurane, dibenzothiophene, carbazole, which may in each case be substituted by one or more radicals R. Very more preferably, $Ar^S$ is selected from benzene, biphenyl and fluorene, which may be substituted by one or more radicals R but is preferably not substituted.

Suitable groups $Ar^S$ are for example the groups of formulae $(Ar^S-1)$ to $(Ar^S35)$ below:

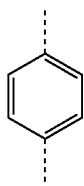

(Ar$^S$-1)

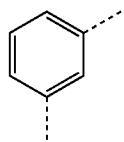

(Ar$^S$-2)

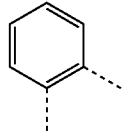

(Ar$^S$-3)

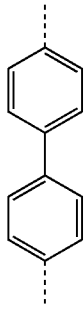

(Ar$^S$-4)

-continued

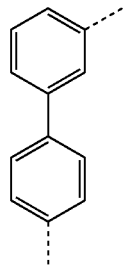

(Ar$^S$-5)

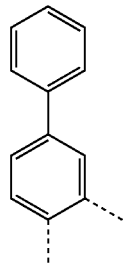

(Ar$^S$-6)

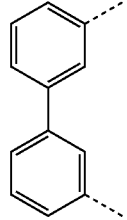

(Ar$^S$-7)

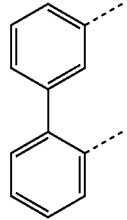

(Ar$^S$-8)

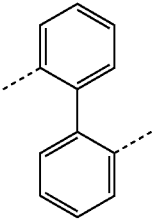

(Ar$^S$-9)

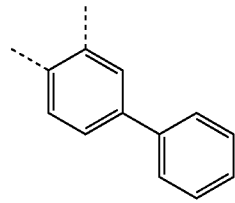

(Ar$^S$-10)

-continued
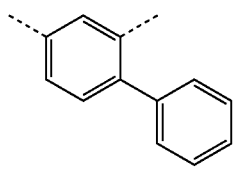
(Ar^S-11)
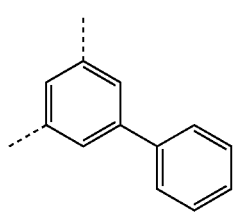
(Ar^S-12)
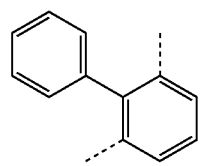
(Ar^S-13)
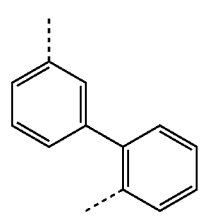
(Ar^S-14)
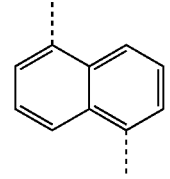
(Ar^S-15)
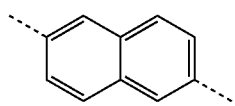
(Ar^S-16)
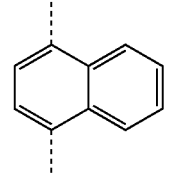
(Ar^S-17)
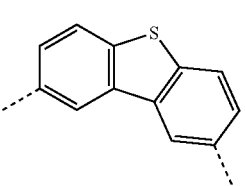
(Ar^S-18)
-continued
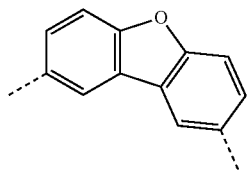
(Ar^S-19)
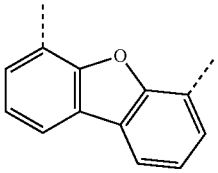
(ArS-20)
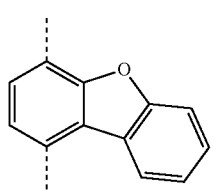
(ArS-21)
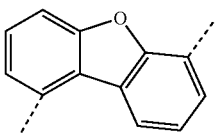
(ArS-22)
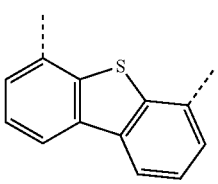
(ArS-23)
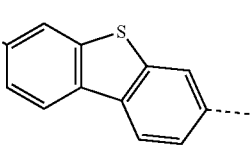
(ArS-24)
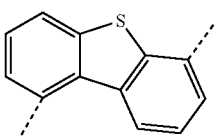
(ArS-25)
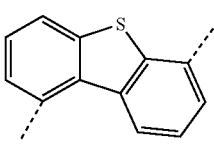
(ArS-26)
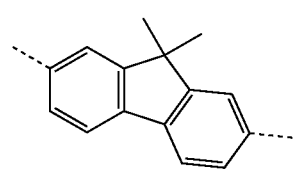
(ArS-27)

(Ar^S-28) 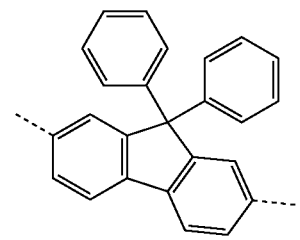

(Ar^S-29) 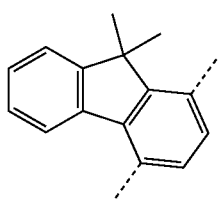

(Ar^S-30) 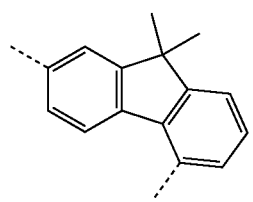

(Ar^S-31) 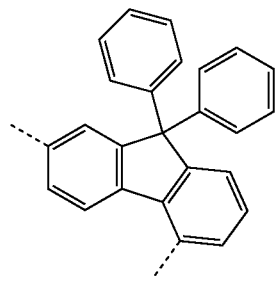

(Ar^S-32) 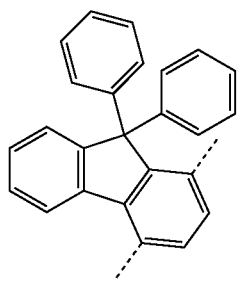

(Ar^S-33) 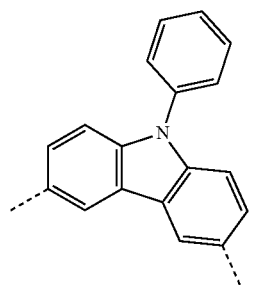

(Ar^S-34) 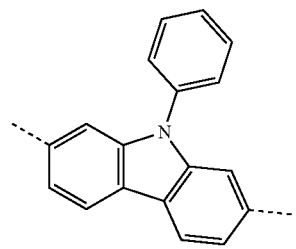

(Ar^S-35) 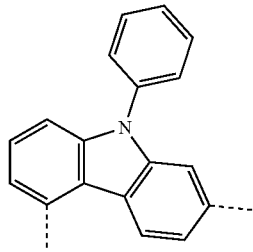

where the dashed bonds indicate the bonds to the nitrogen atom of the azacarbazole moiety of formula (1) and Ar$^1$ for n≥1 and the bonds to the phenyl ring of the azacarbazole moiety of formula (1) and R$^P$ for q≥1, and where the groups (Ar$^S$-1) to (Ar$^S$-35) may be substituted at each free position by a group R but are preferably unsubstituted.

Among the groups of formulae (Ar$^S$-1) to (Ar$^S$-35), the groups (Ar$^S$-1), (Ar$^S$-2) and (Ar$^S$-3) are preferred.

In accordance with a preferred embodiment, R is on each occurrence, identically or differently, H, D, F, CN, a straight-chain alkyl, alkoxy or thioalkoxy group having 1 to 10 C atoms or a straight-chain alkenyl or alkynyl group having 2 to 10 C atoms or a branched or cyclic alkyl, alkenyl, alkynyl, alkoxy or thioalkoxy group having 3 to 10 C atoms, each of which may be substituted by one or more radicals R$^1$, where one or more, preferably non-adjacent CH$_2$ groups may be replaced by O or S and where one or more H atoms may be replaced by D or F, or an aryl or heteroaryl group having 5 to 20 aromatic ring atoms, which may in each case be substituted by one or more radicals R$^1$;

In accordance with a preferred embodiment, the index m is equal to 0.

In accordance with a preferred embodiment, R$^1$ is on each occurrence, identically or differently, H, D, F, CN, a straight-chain alkyl, alkoxy or thioalkoxy group having 1 to 10 C atoms or a straight-chain alkenyl or alkynyl group having 2 to 10 C atoms or a branched or cyclic alkyl, alkenyl, alkynyl, alkoxy or thioalkoxy group having 3 to 10 C atoms, each of which may be substituted by one or more radicals R$^2$, where one or more, preferably non-adjacent CH$_2$ groups may be replaced by O or S and where one or more H atoms may be replaced by D or F, or an aryl or heteroaryl group having 5 to 20 aromatic ring atoms, which may in each case be substituted by one or more radicals R$^2$.

Furthermore, R$^2$ is preferably on each occurrence, identically or differently, H, D, F, a straight-chain alkyl having 1 to 10 C atoms or a branched or cyclic alkyl having 3 to 10 C atoms or an aryl or heteroaryl group having 5 to 18 C atoms.

In accordance with a preferred embodiment, the group Ar is an aromatic or heteroaromatic ring system having 5 to 40, even more preferably 5 to 24 aromatic ring atoms, which may be substituted by one or more radicals R$^1$.

Particularly preferred groups Ar are benzene, naphthalene, biphenyl, terphenyl, fluorene, spirobifluorene, cis- or trans-indenofluorene, furan, benzofuran, isobenzofuran, dibenzofuran, thiophene, benzothiophene, isobenzothiophene, dibenzothiophene, carbazole, indolocarbazole and indenocarbazole, which may be substituted by one or more radicals R¹.

Examples of suitable compounds according to the invention are the structures shown below.

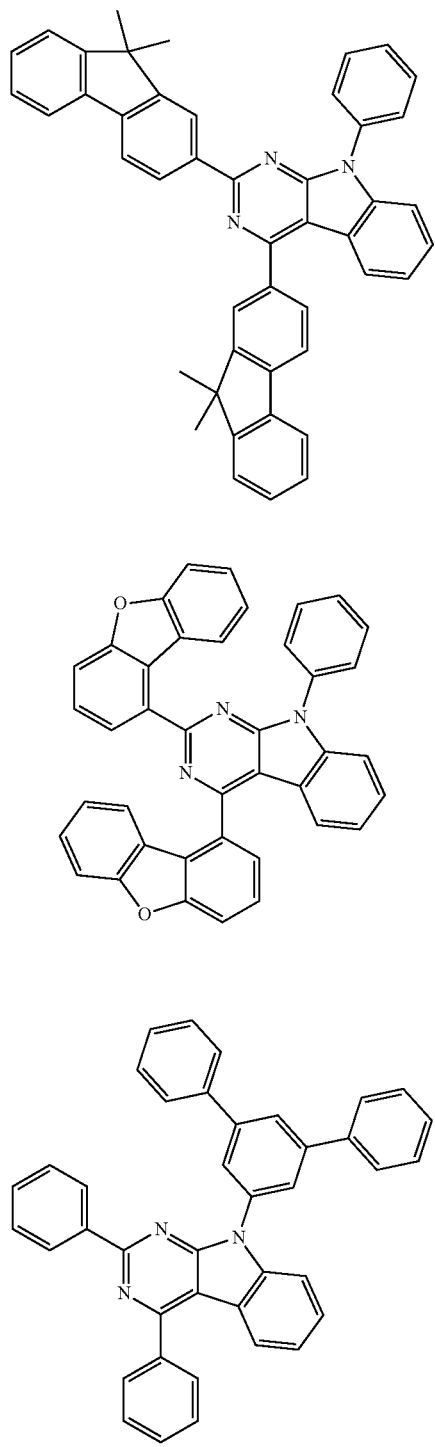

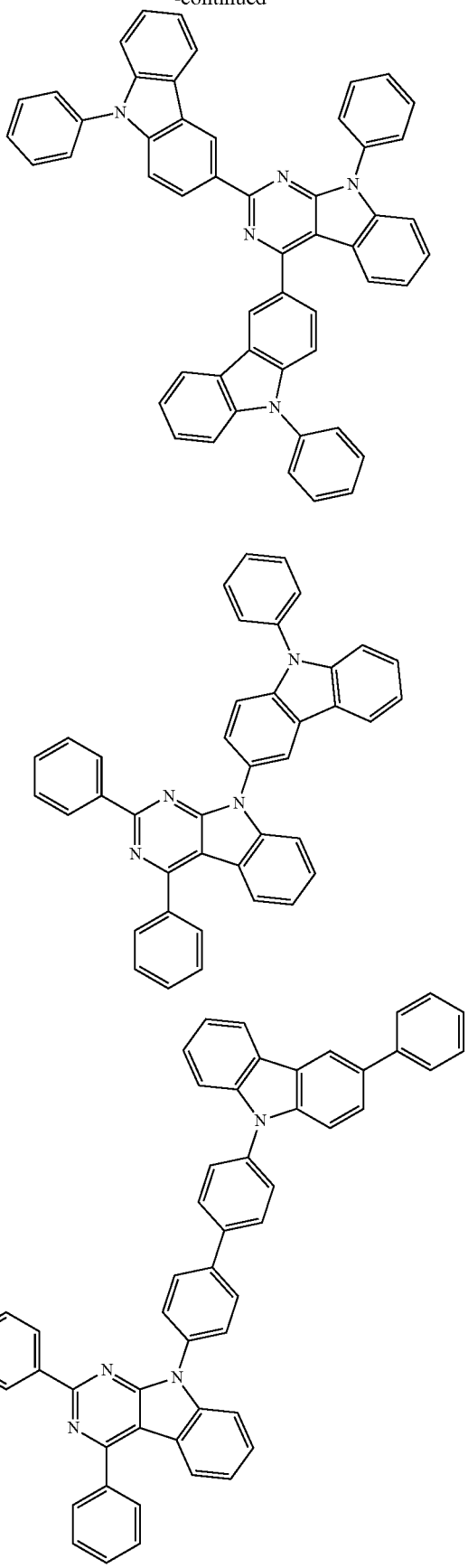

-continued

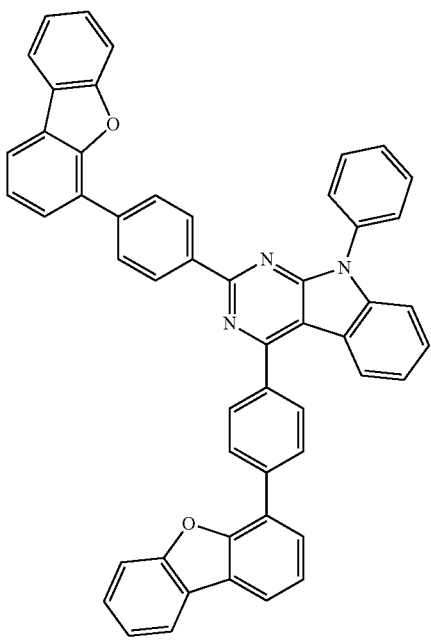
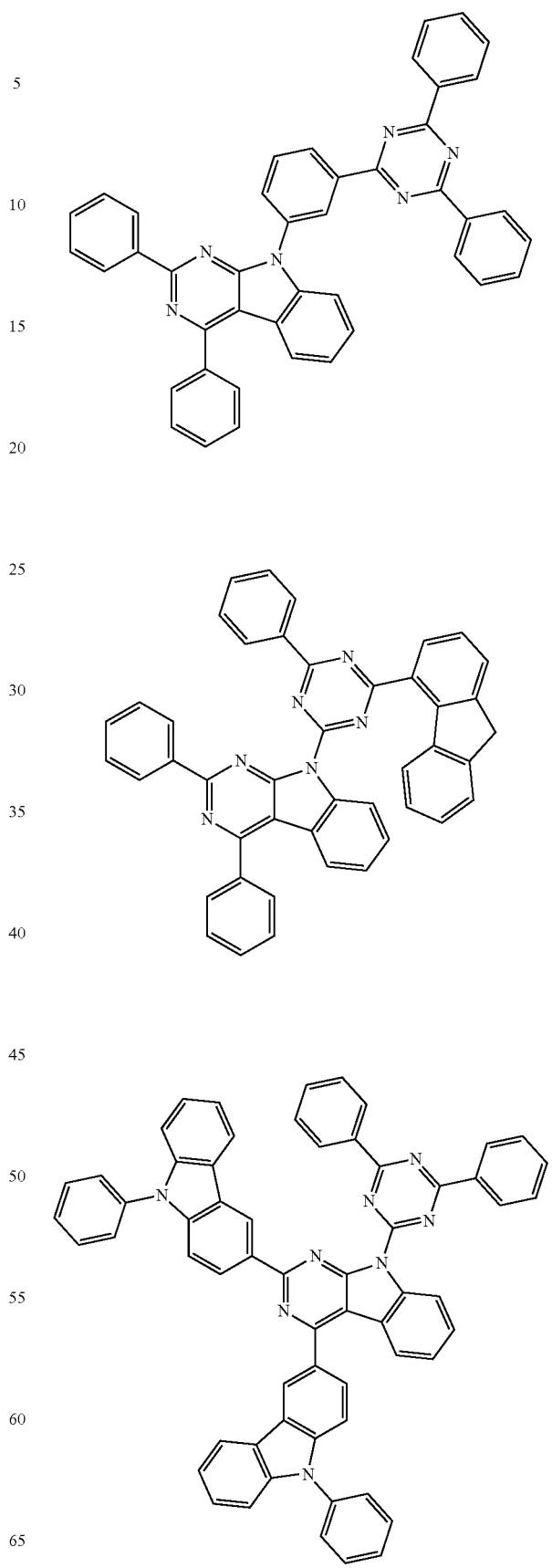

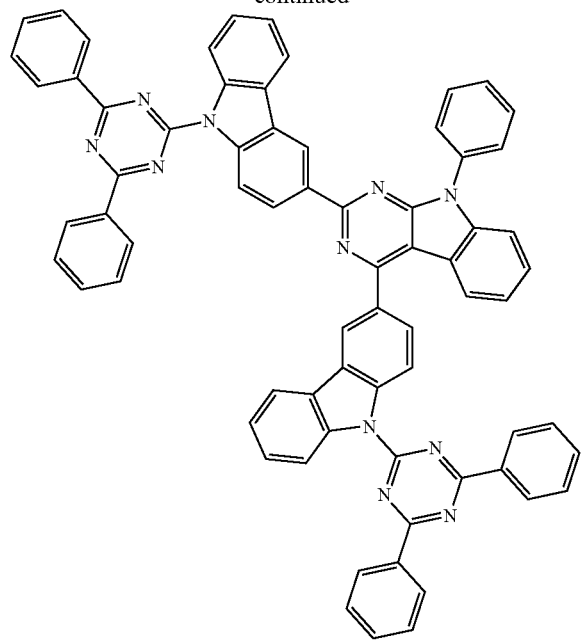
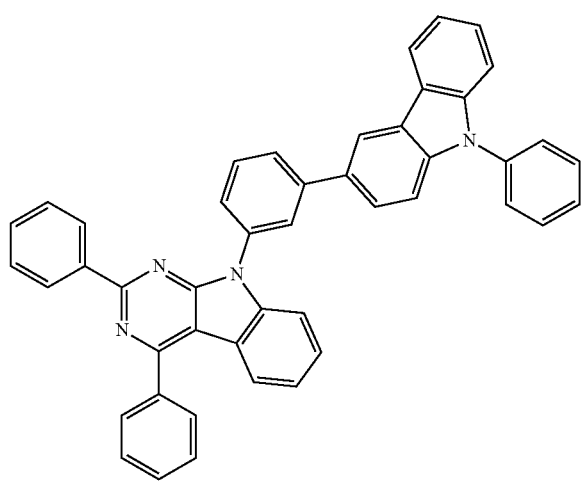
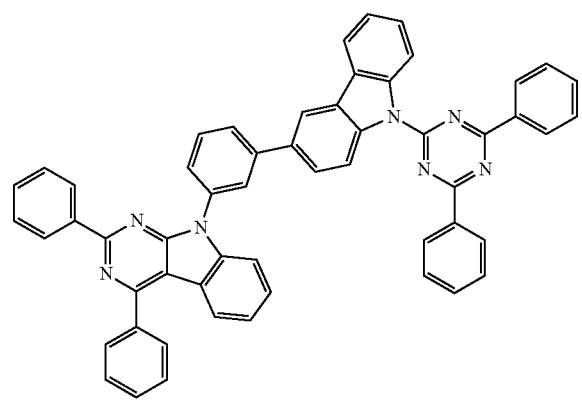
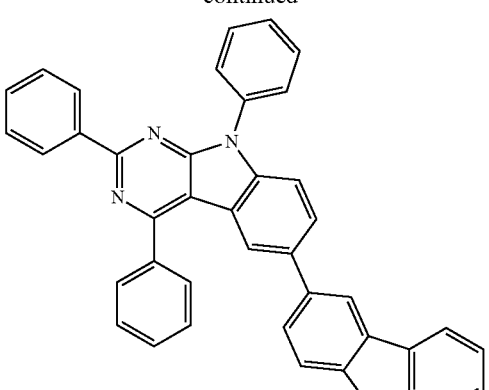
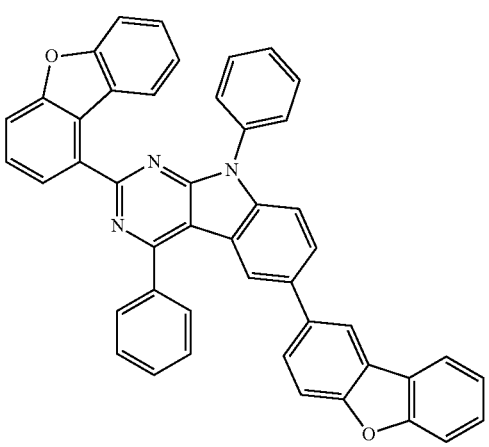
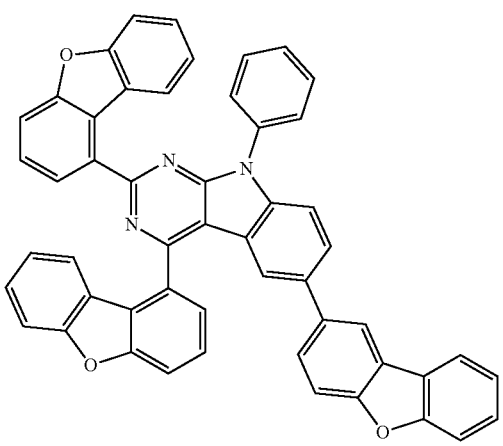
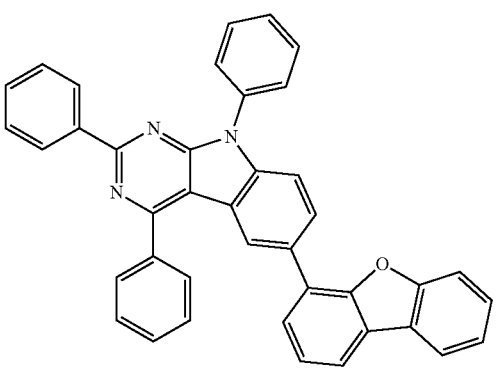

45
-continued
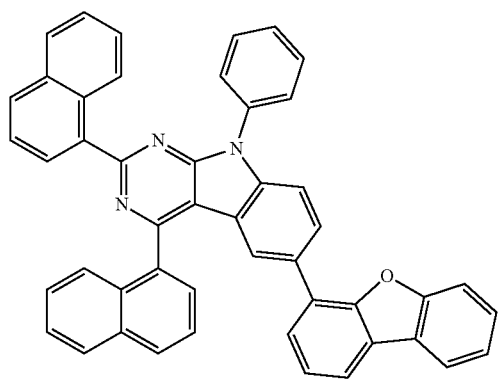
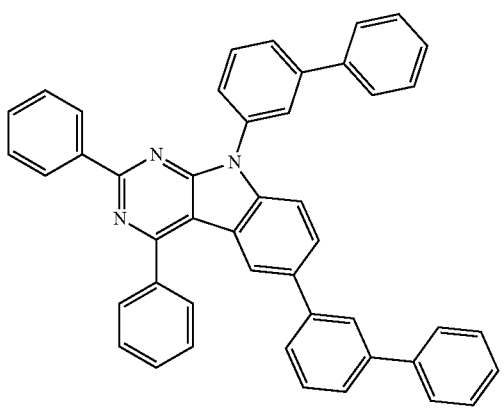
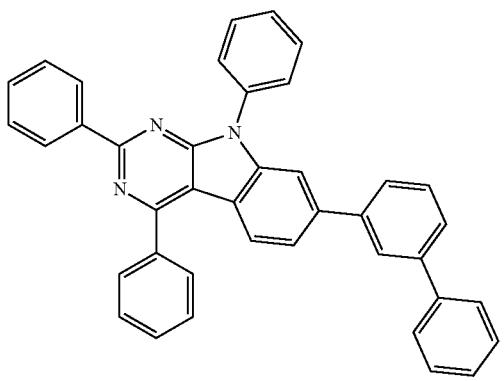
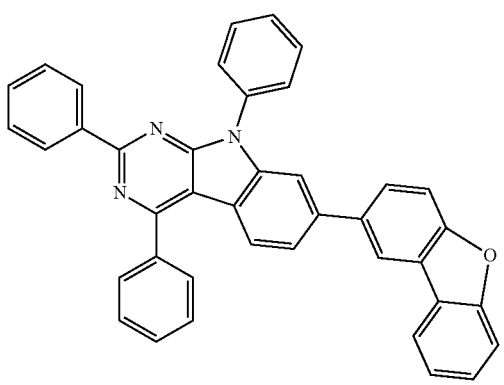
46
-continued
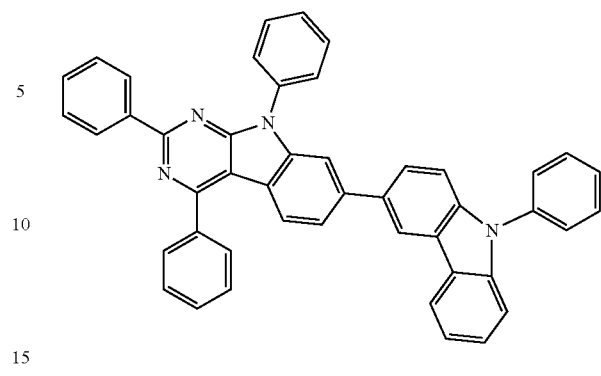
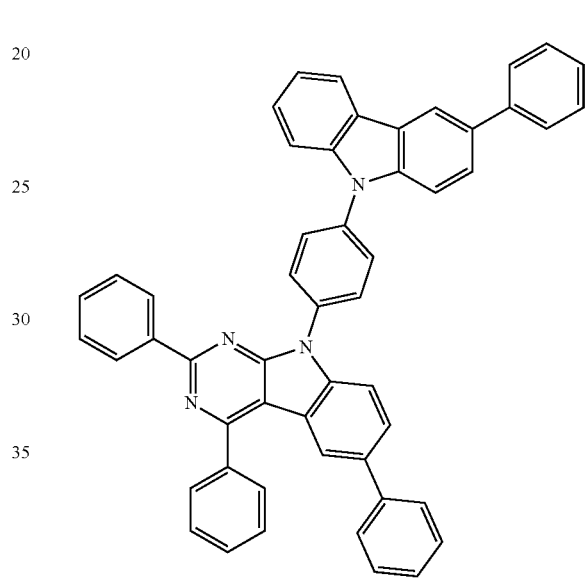
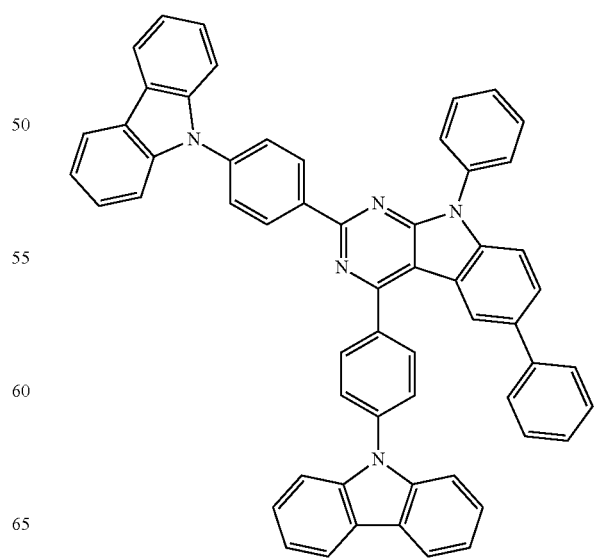

47
-continued
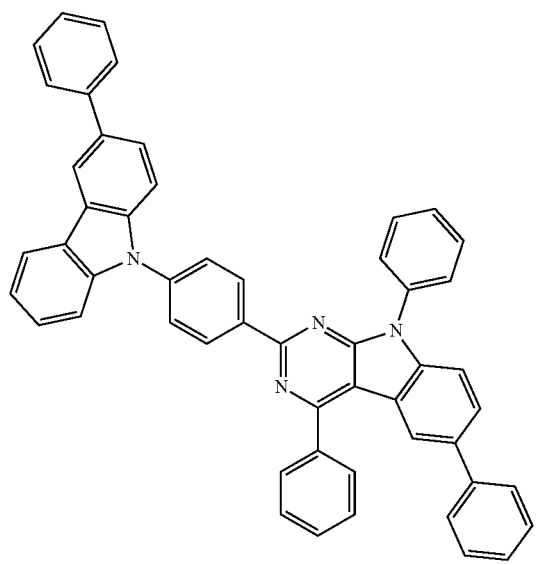
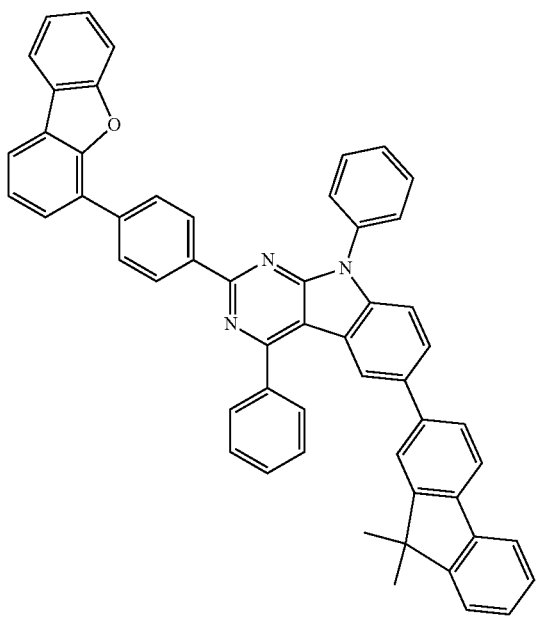
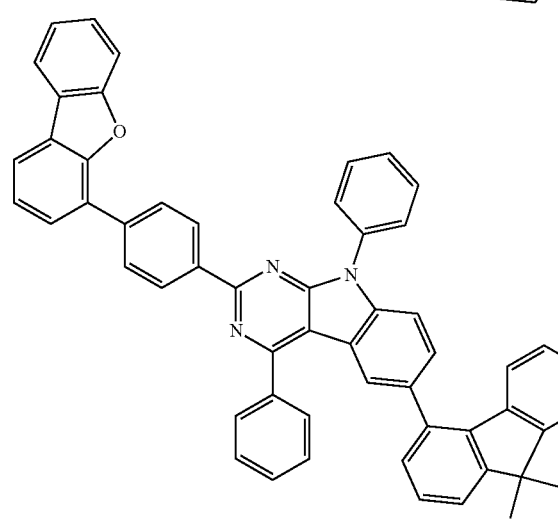
48
-continued
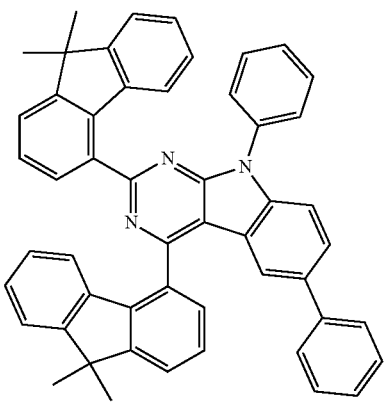
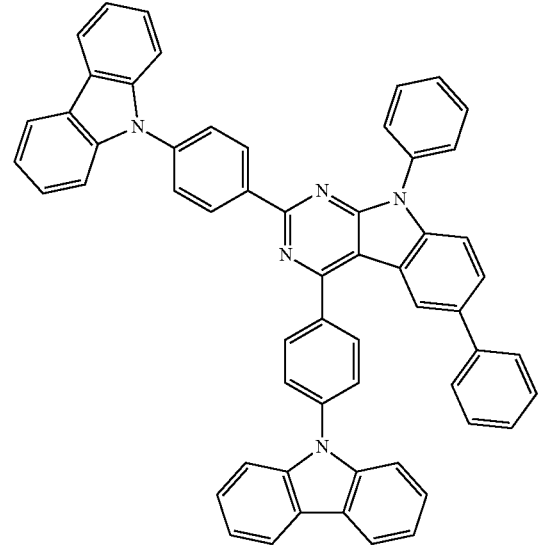
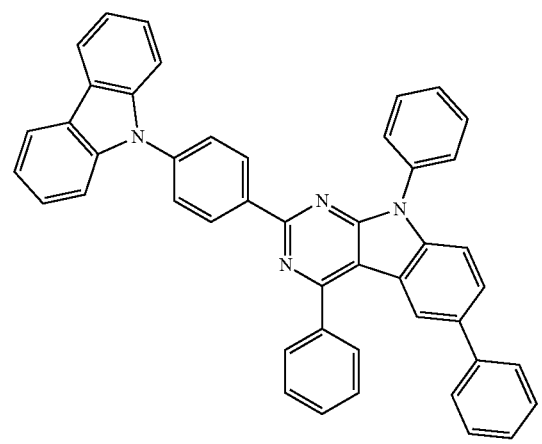

49
-continued
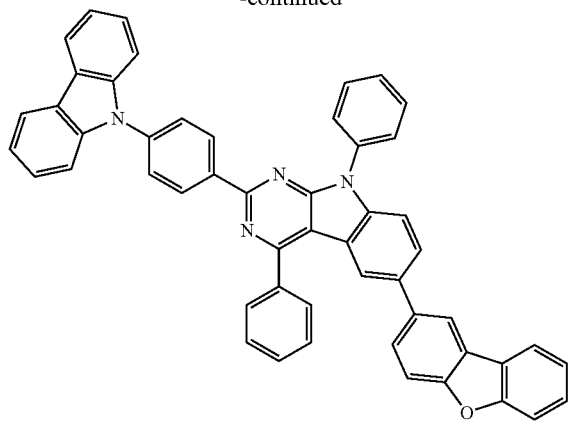
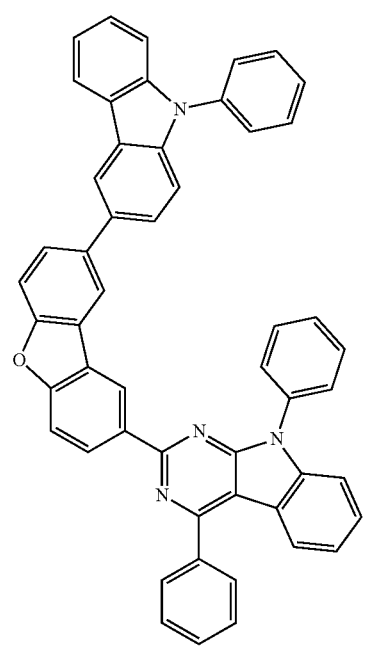
50
-continued
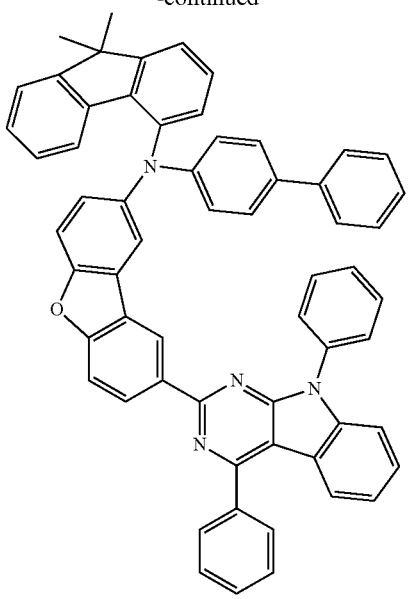
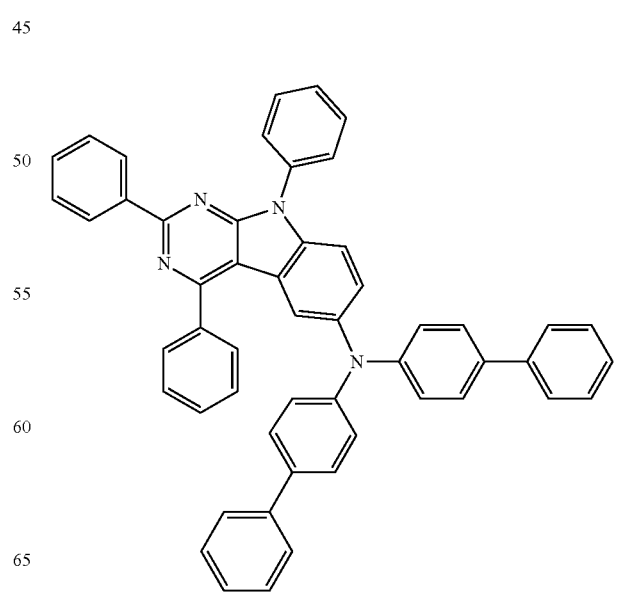

51
-continued
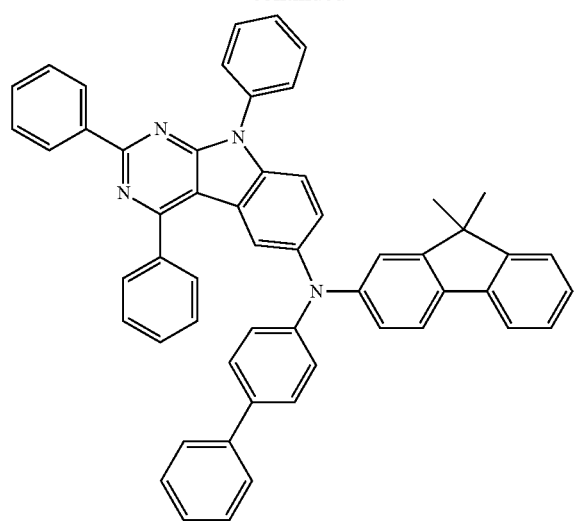
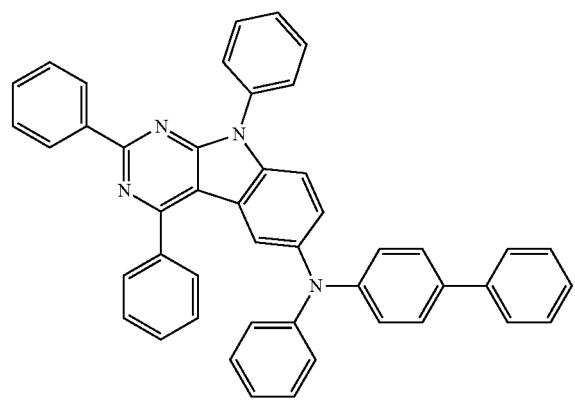
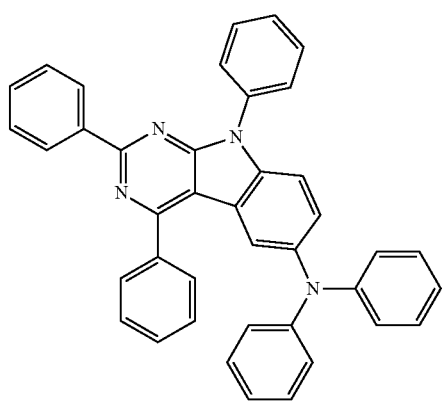
52
-continued
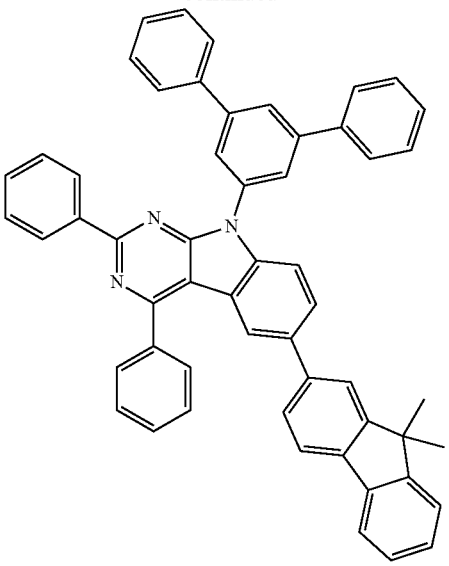
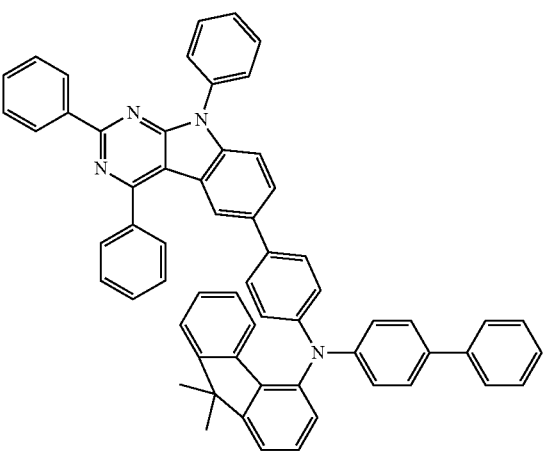
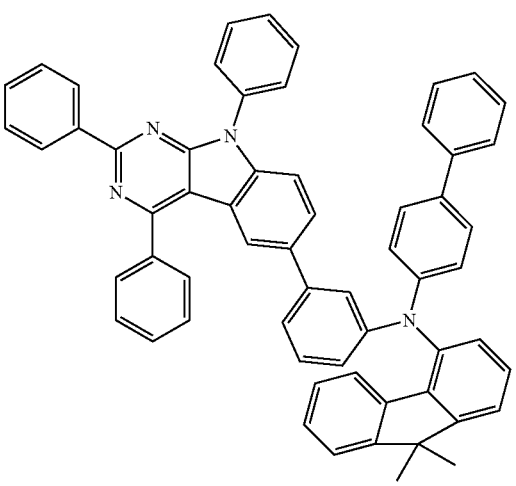

53
-continued
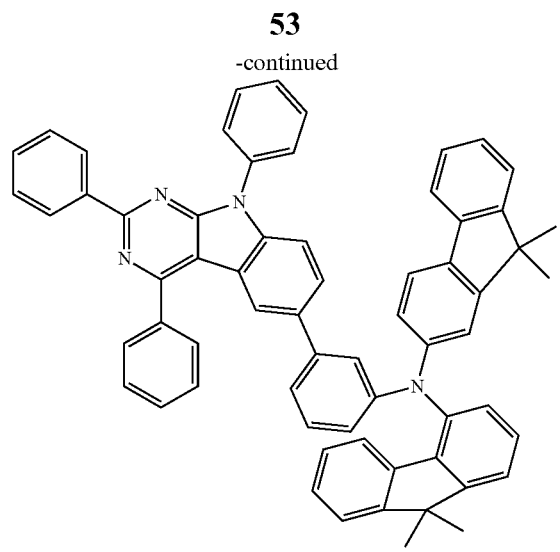
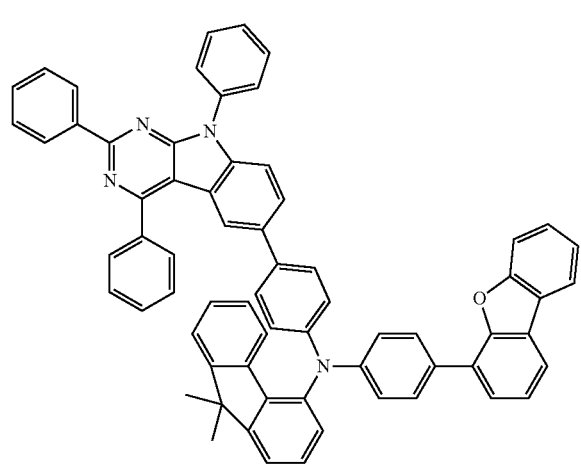
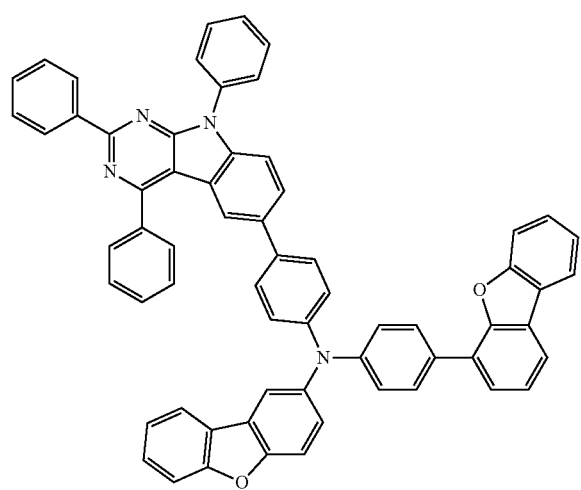
54
-continued
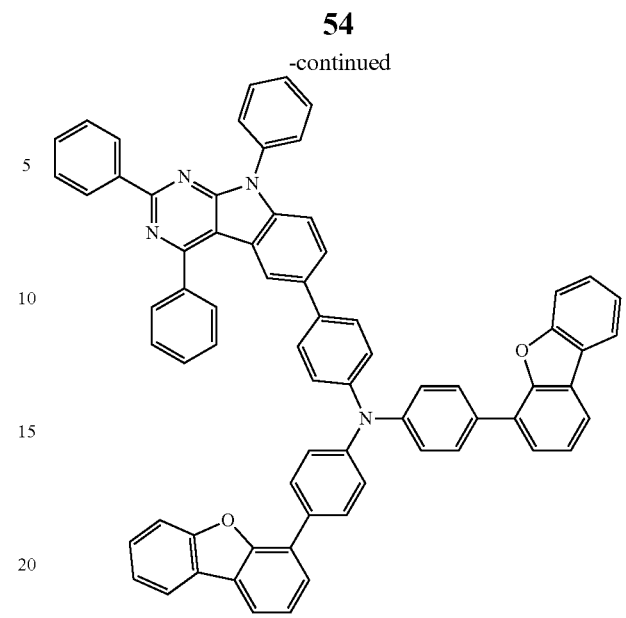
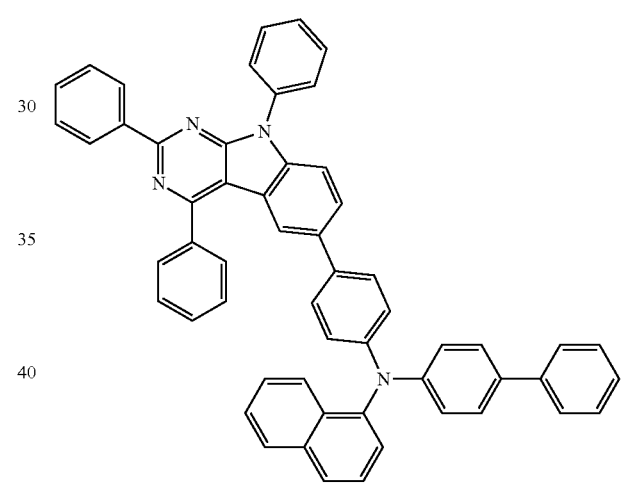
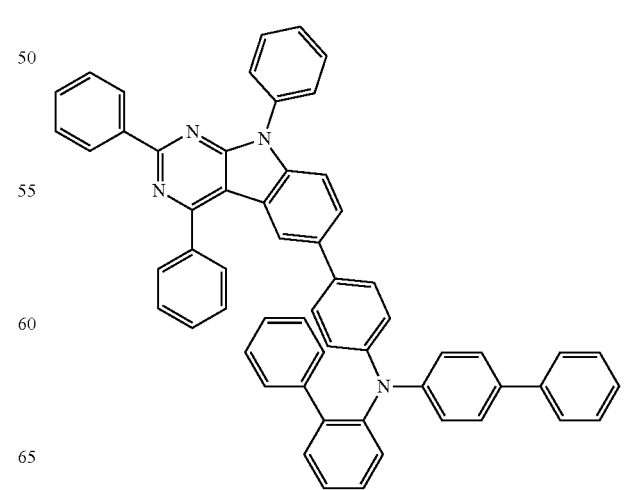

55
-continued
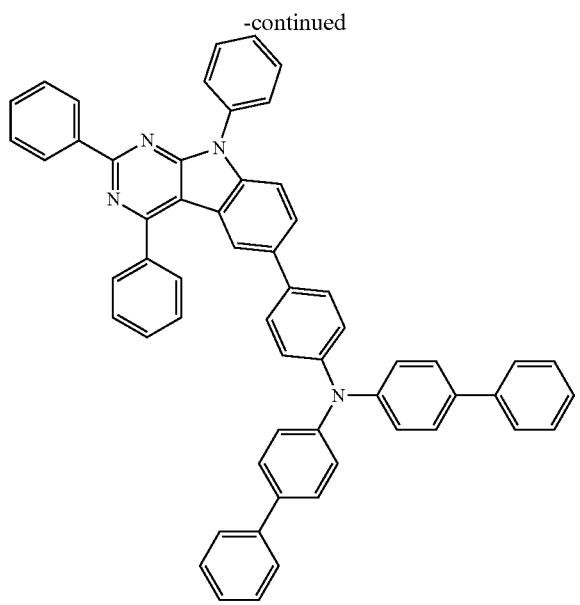
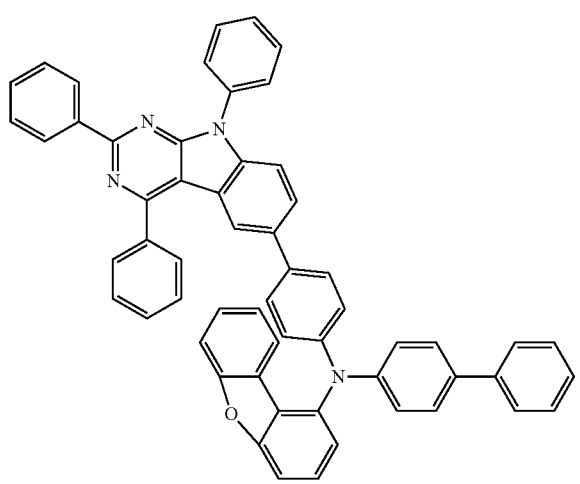
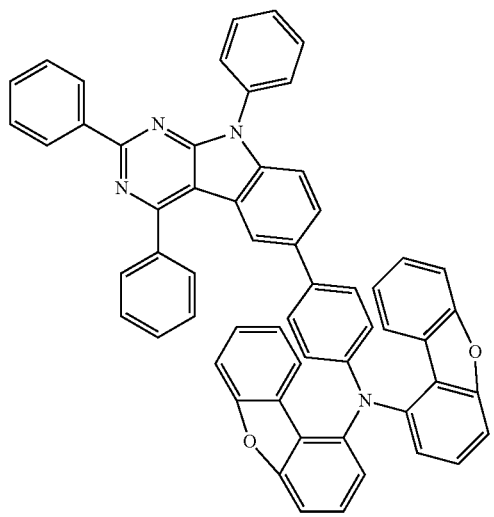
56
-continued
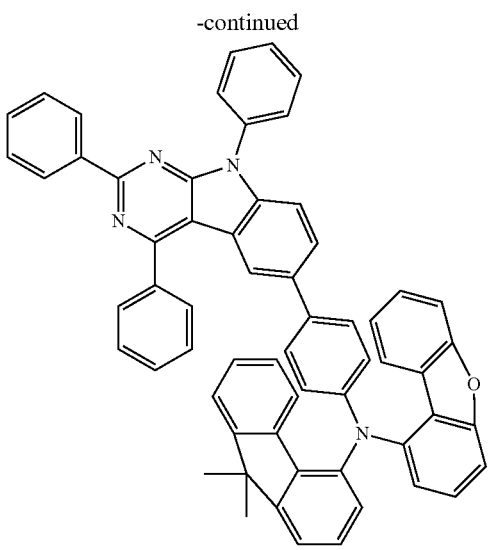
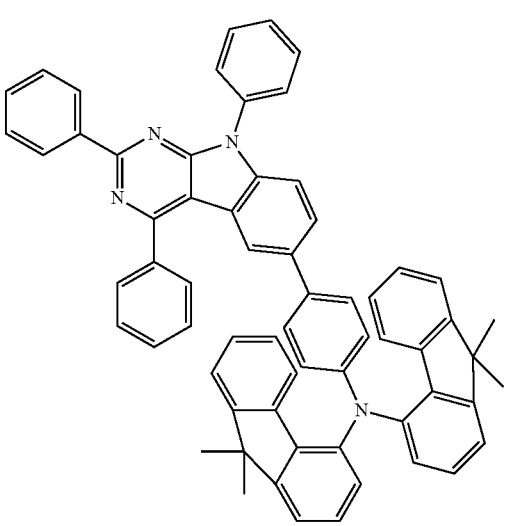
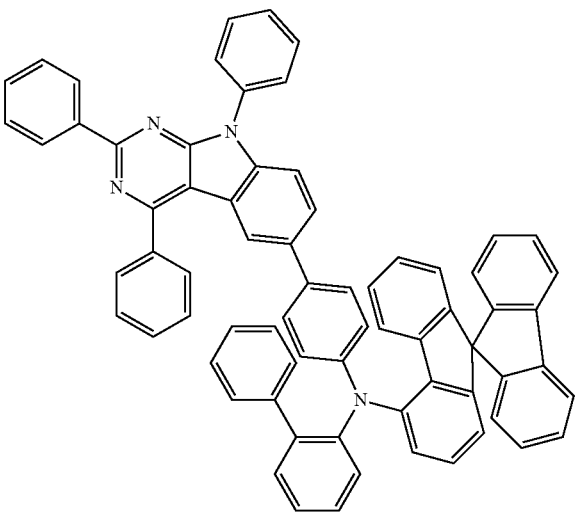

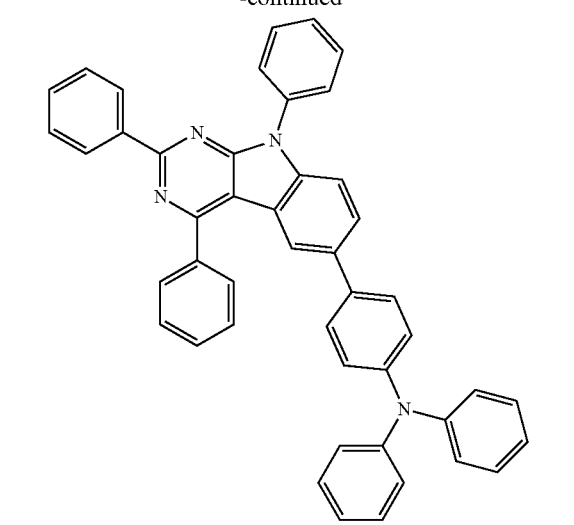
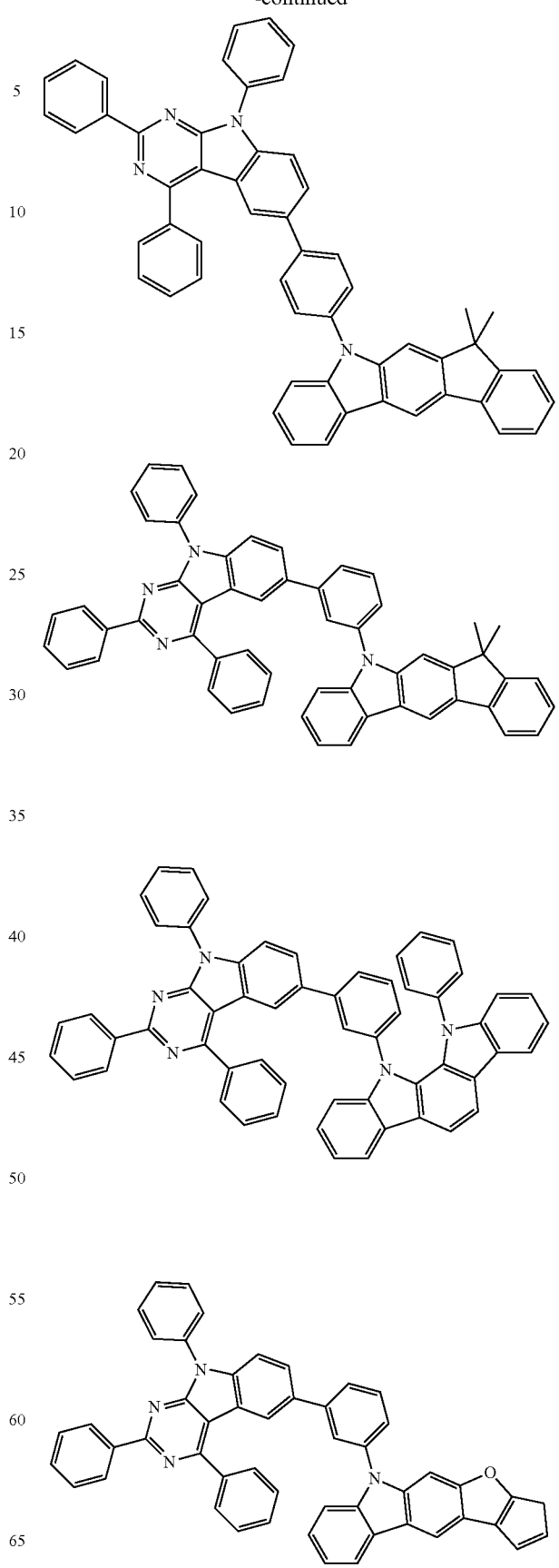

-continued
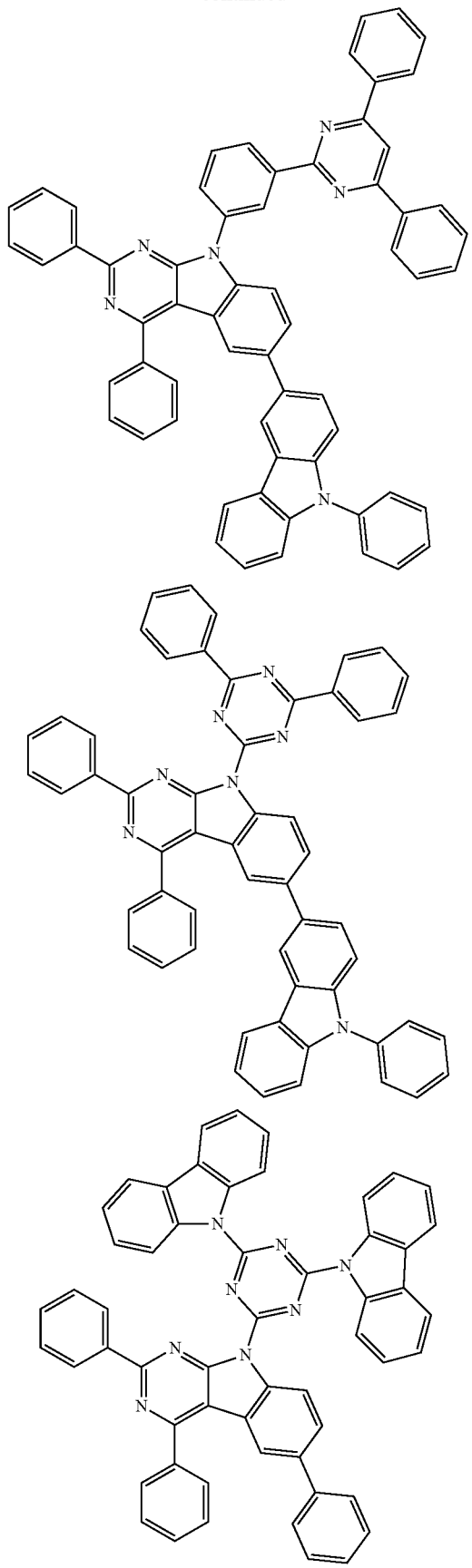
-continued
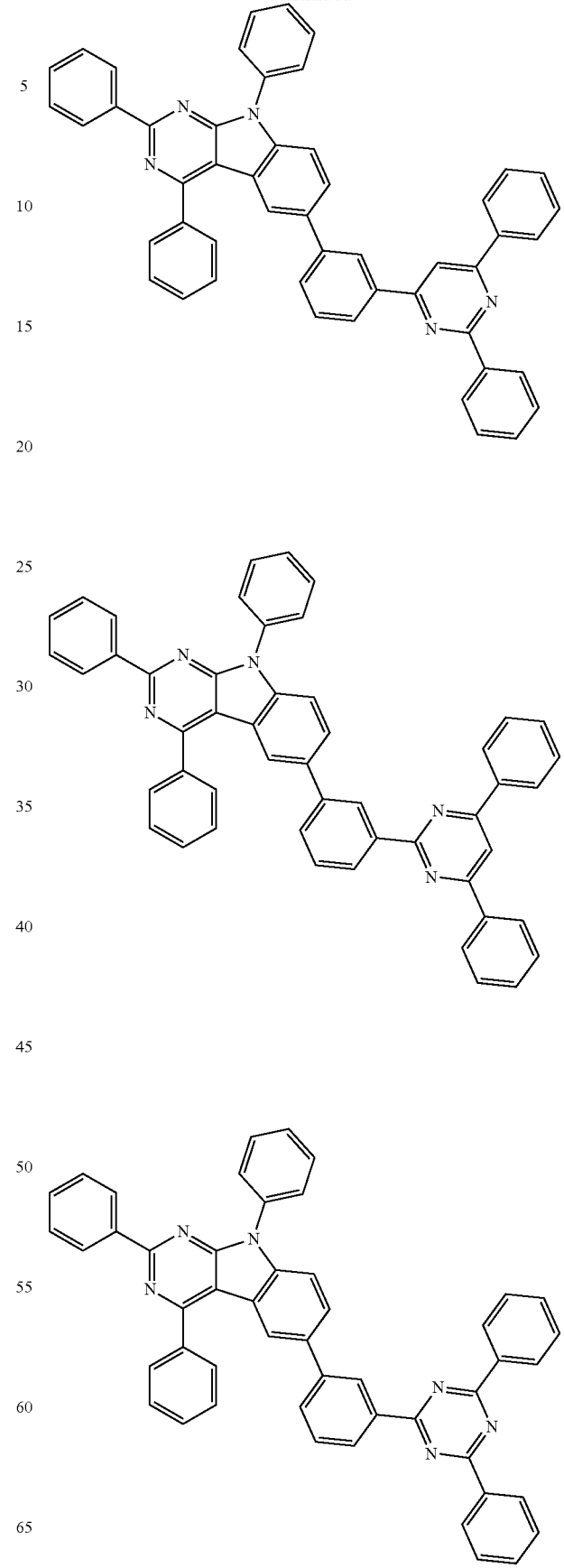

-continued

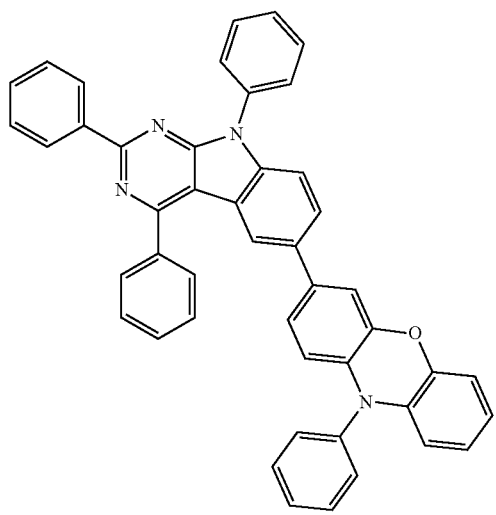
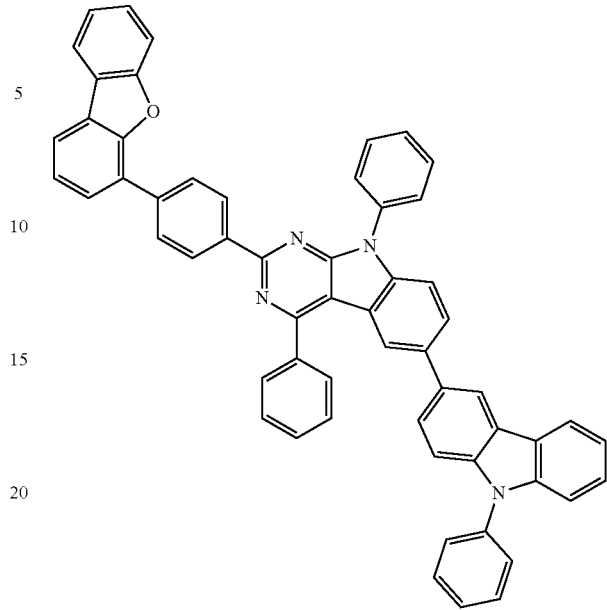
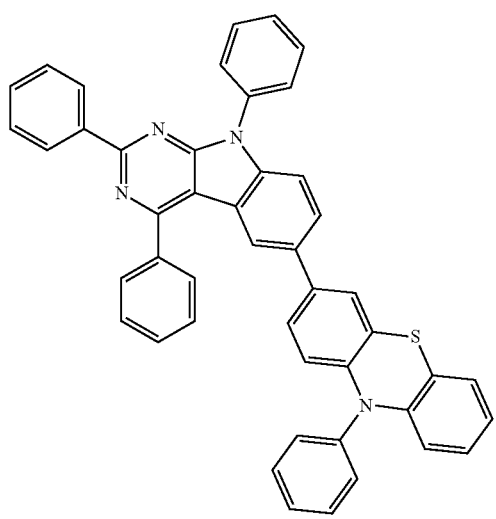
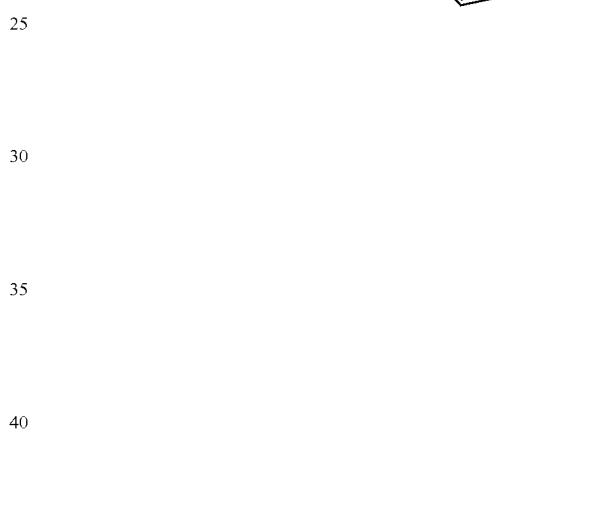
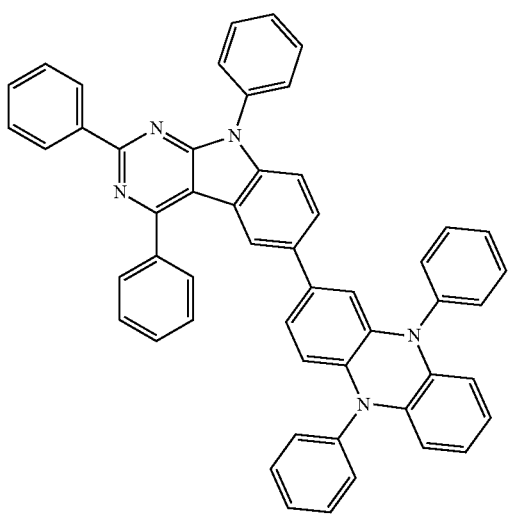
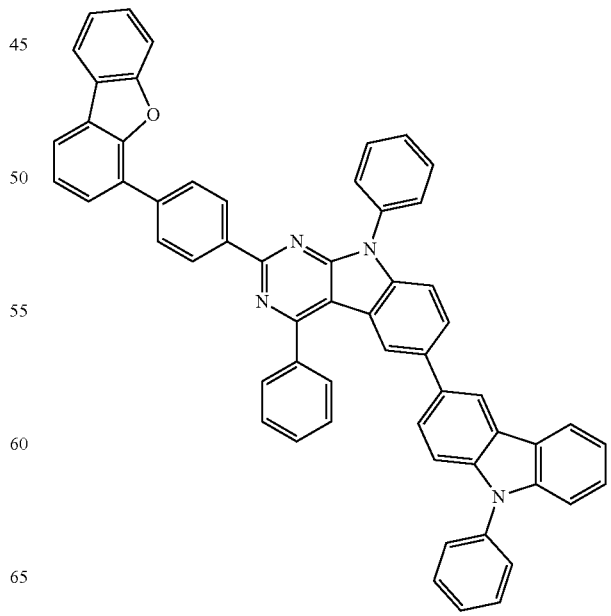

65
-continued
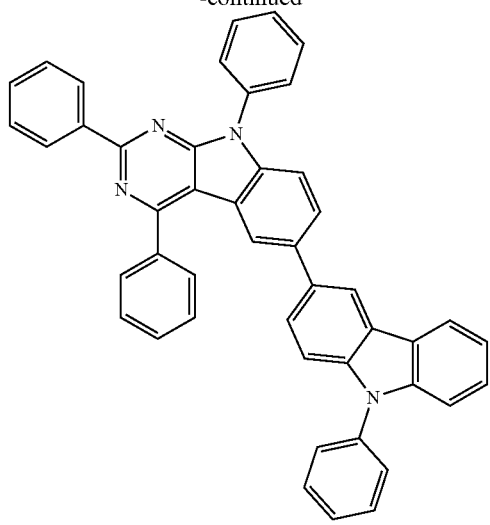
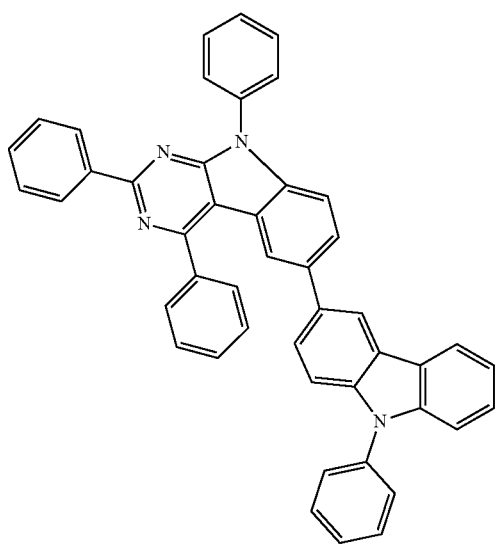
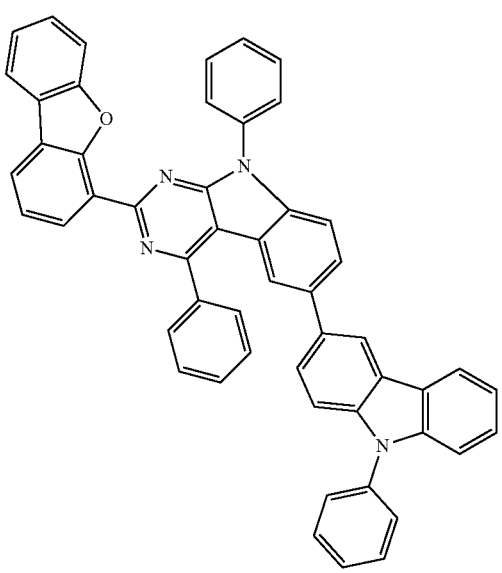
66
-continued
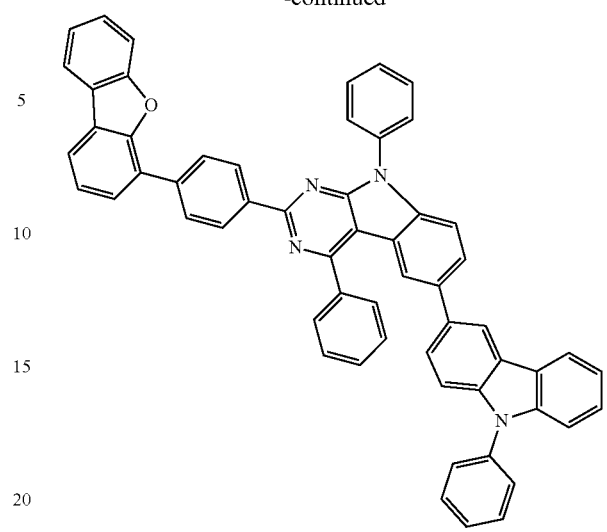
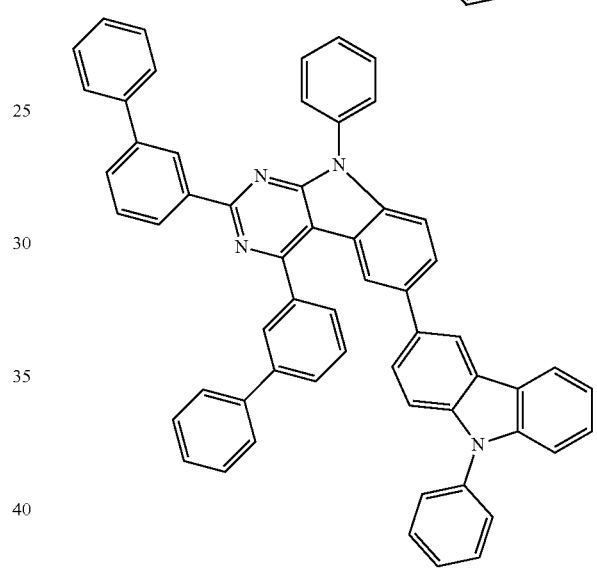

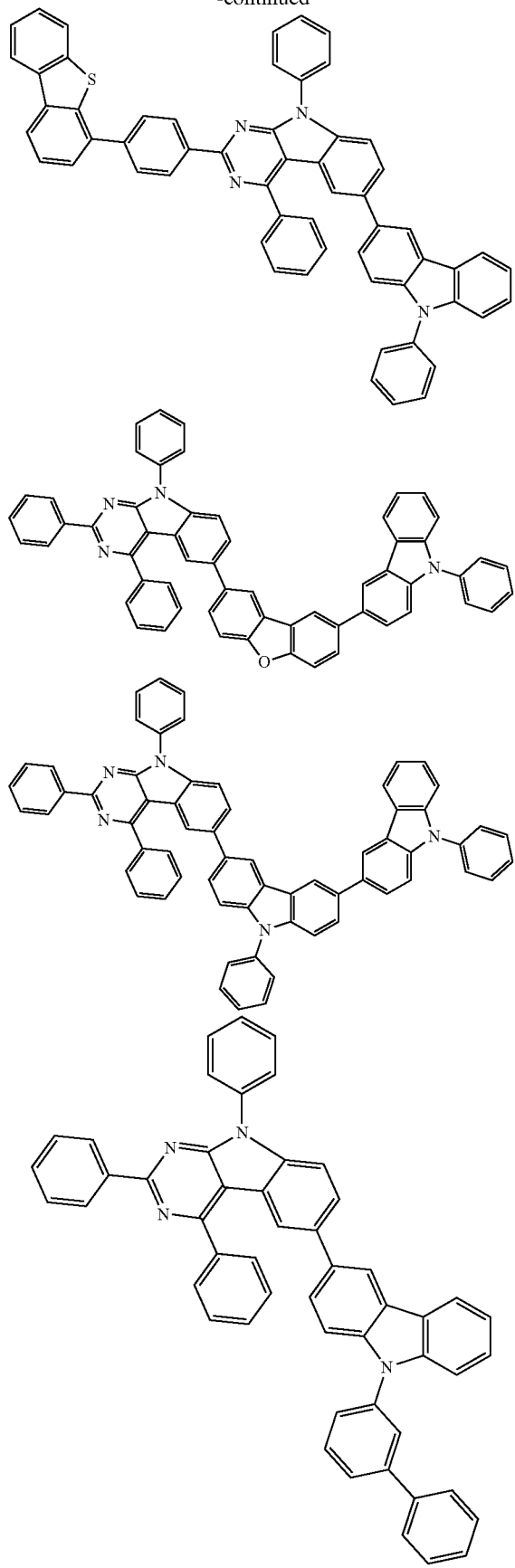
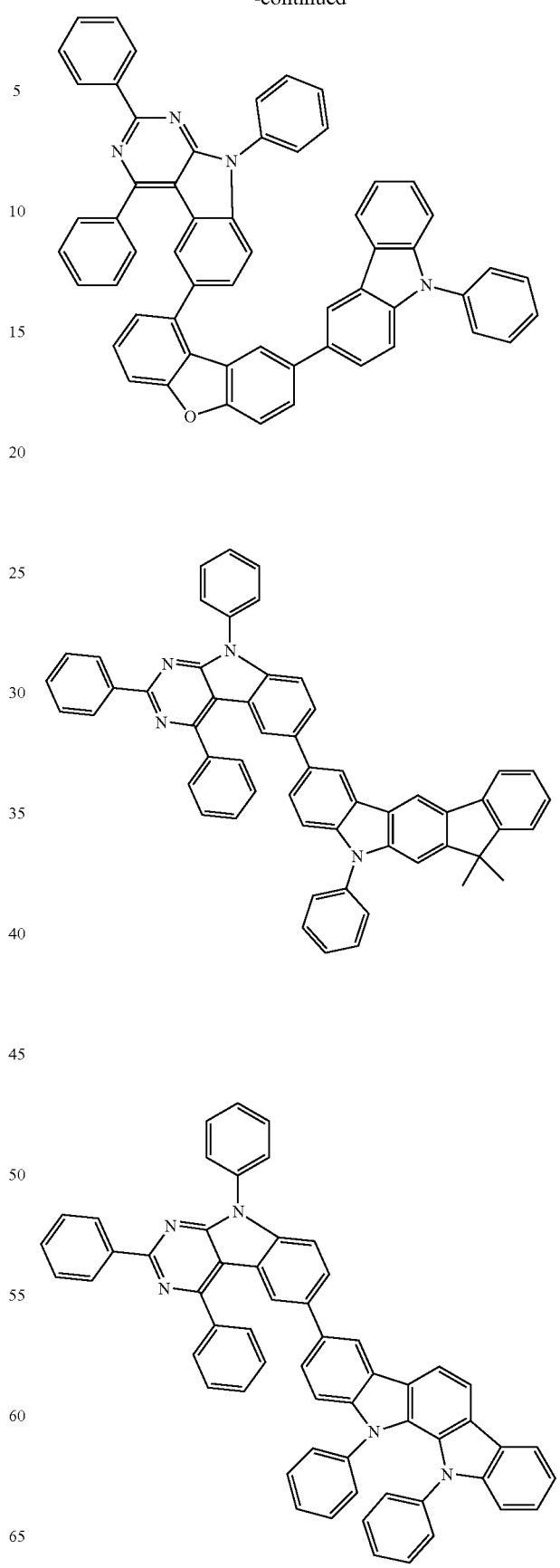

69
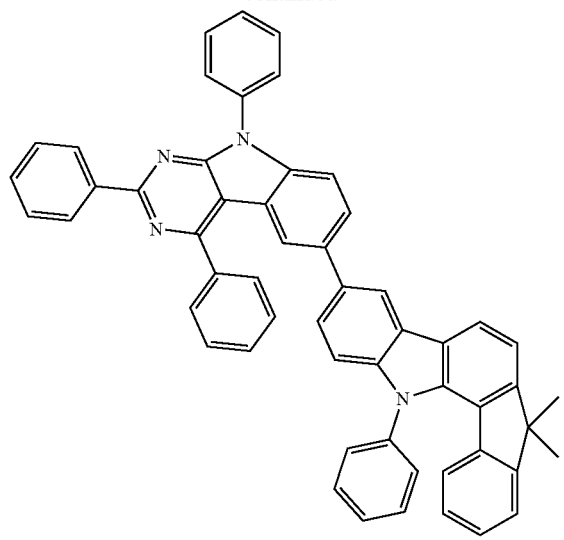
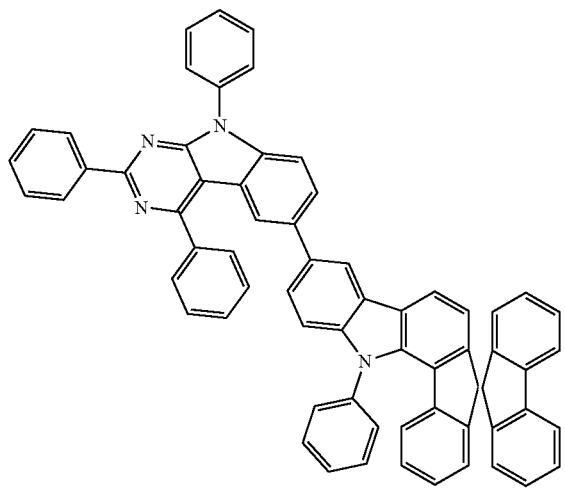
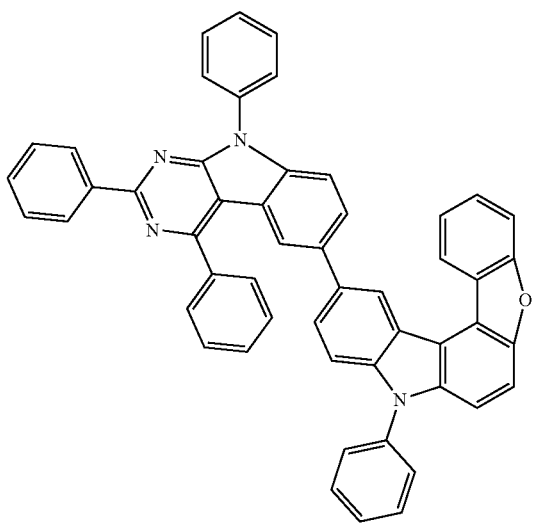
70
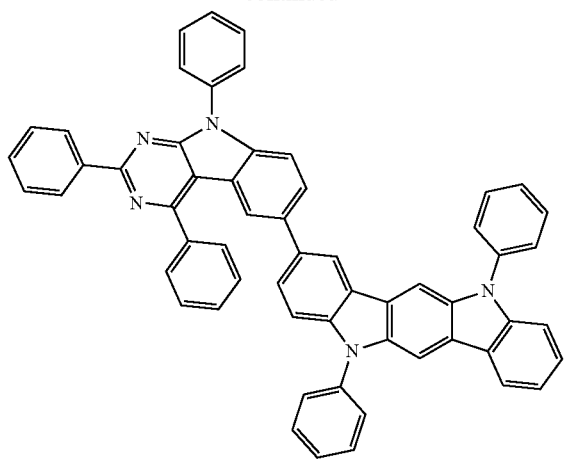
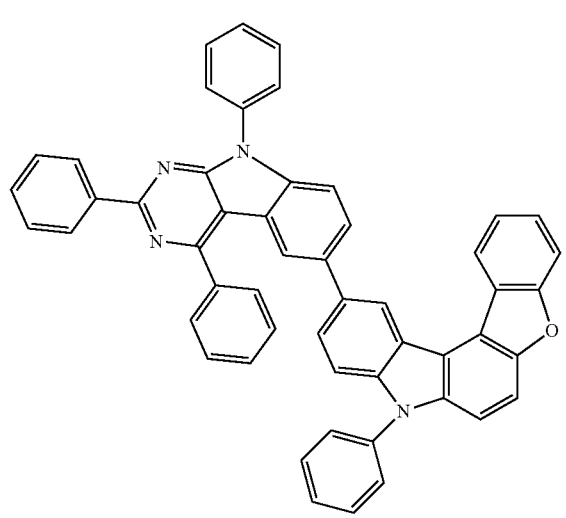
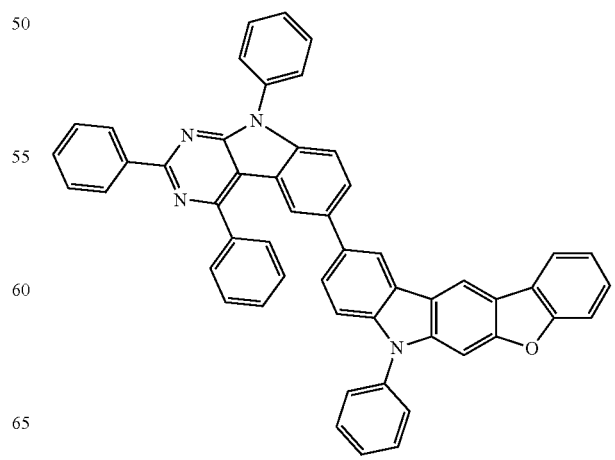

71
-continued
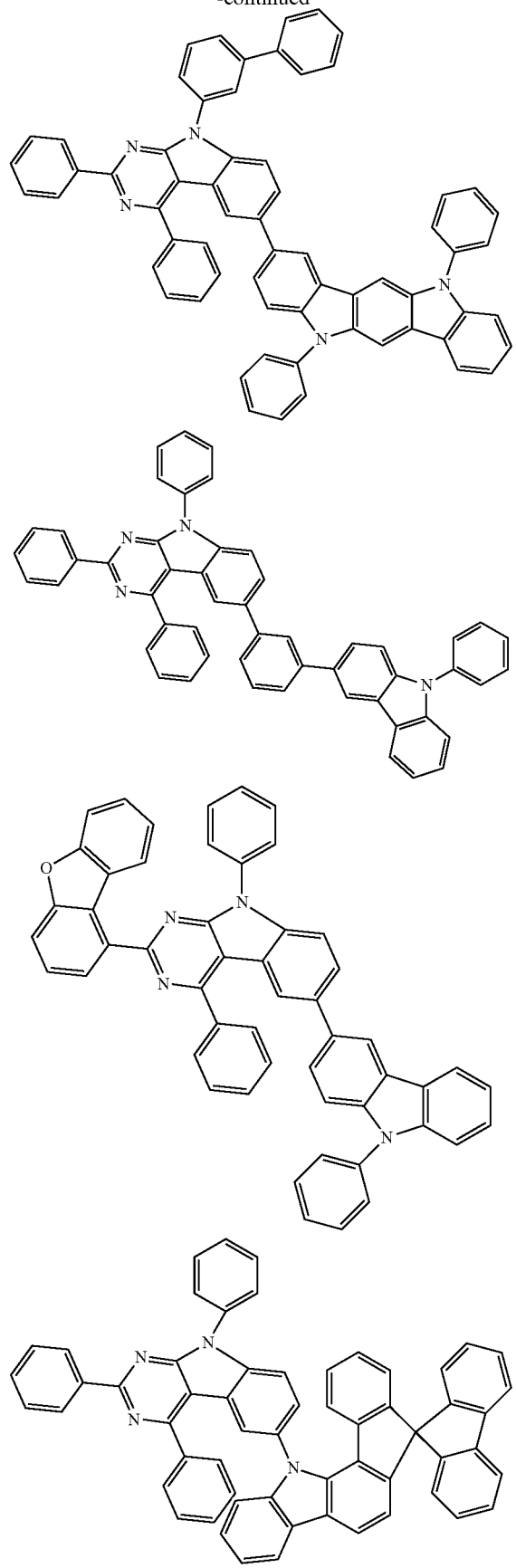
72
-continued
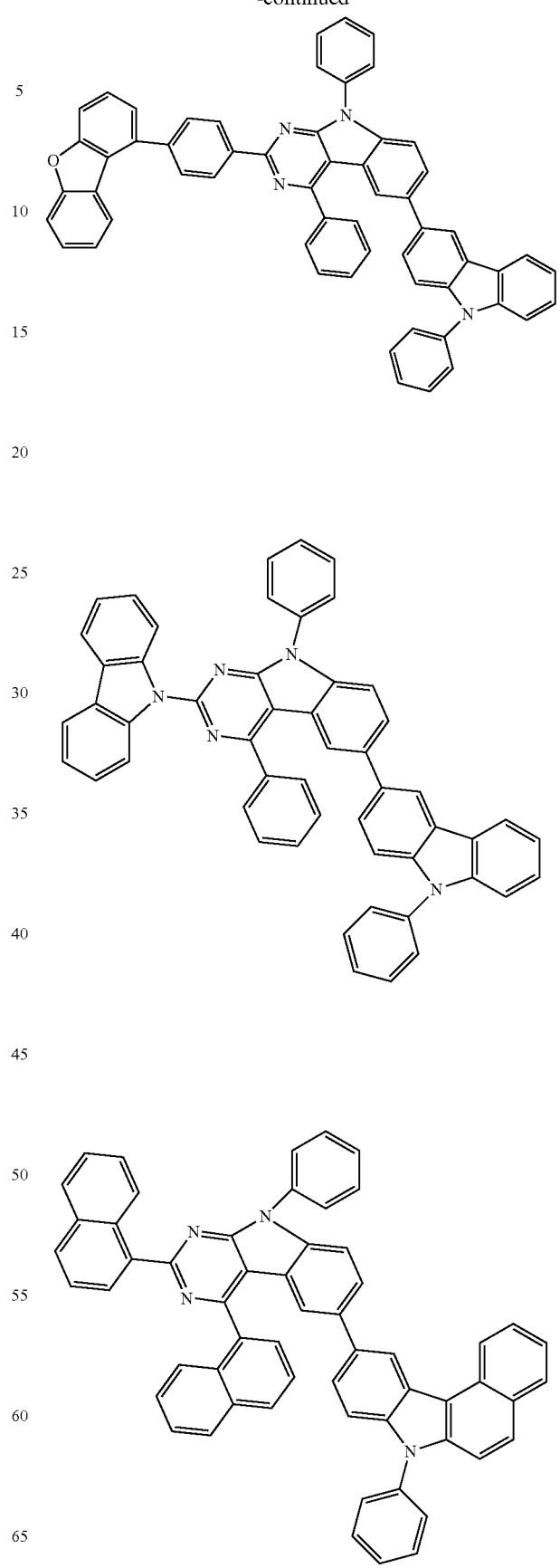

73
-continued
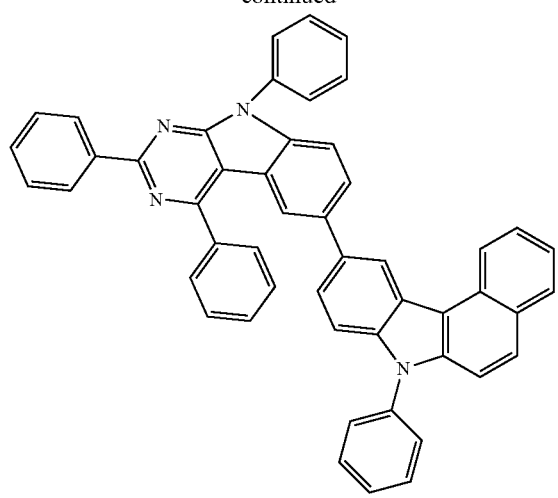
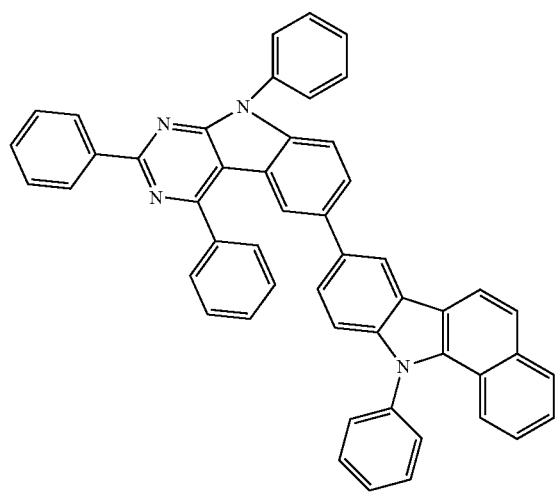
74
-continued
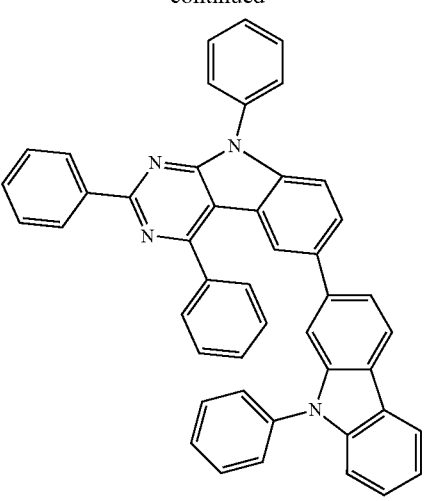
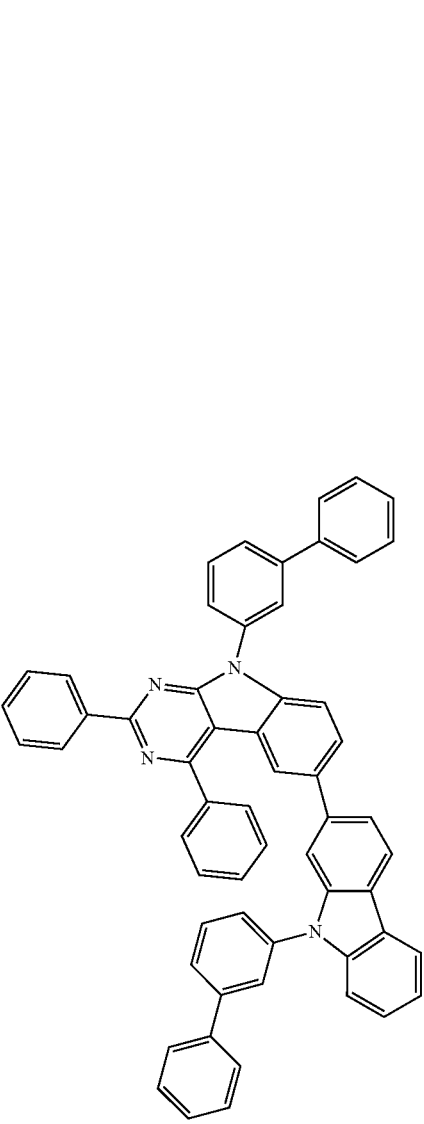

75
-continued
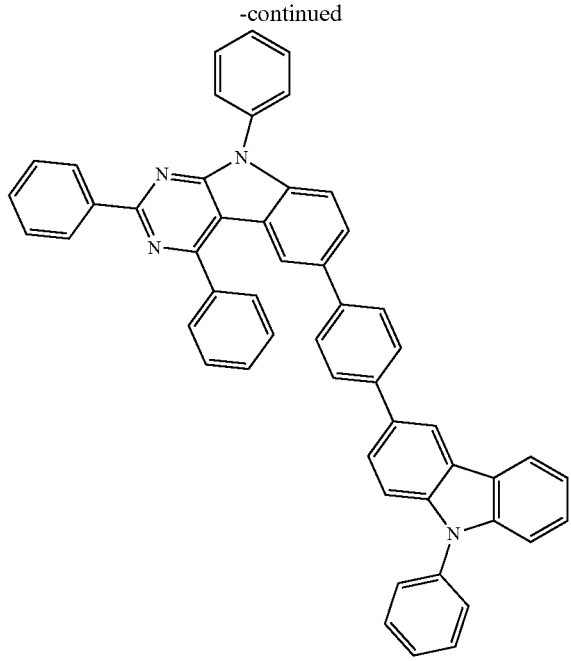
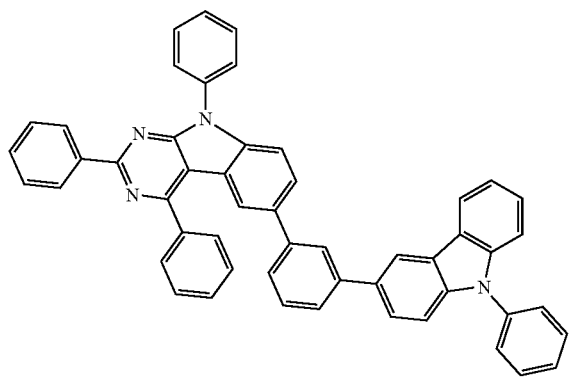
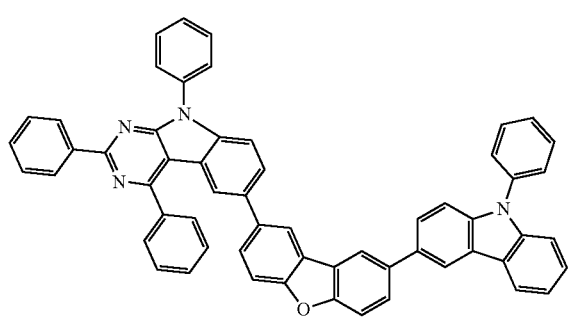
76
-continued
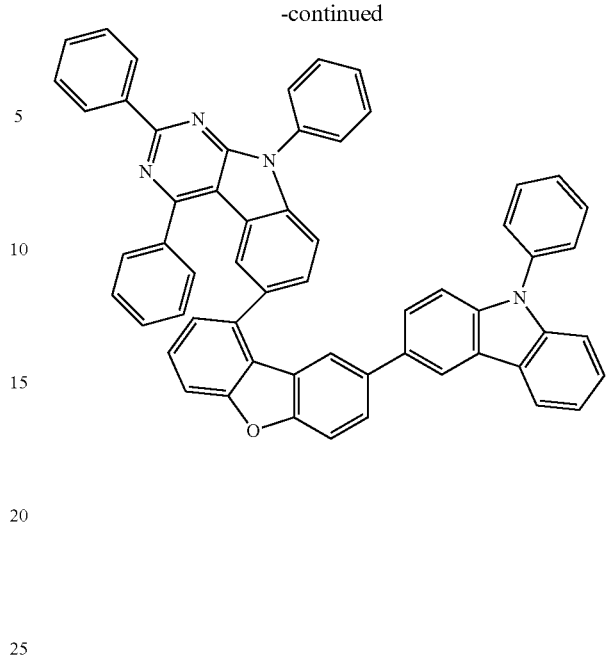
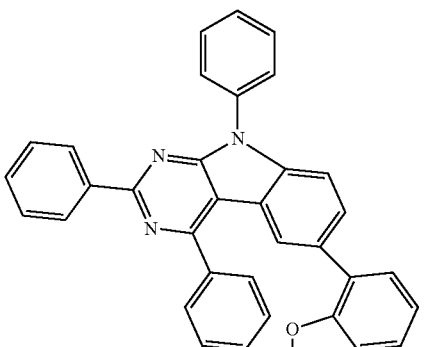
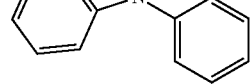

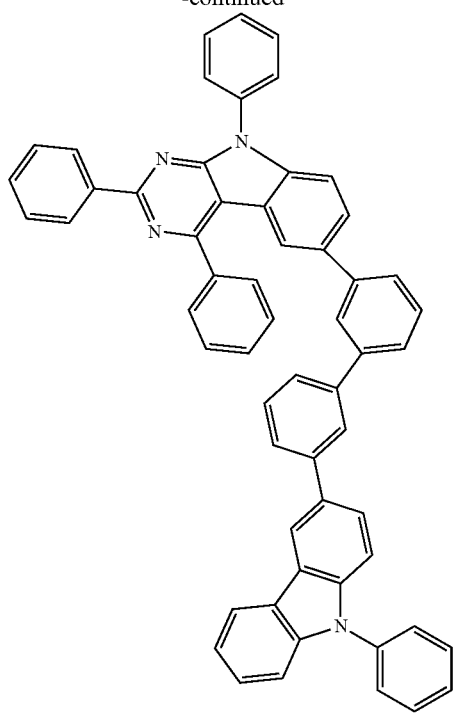
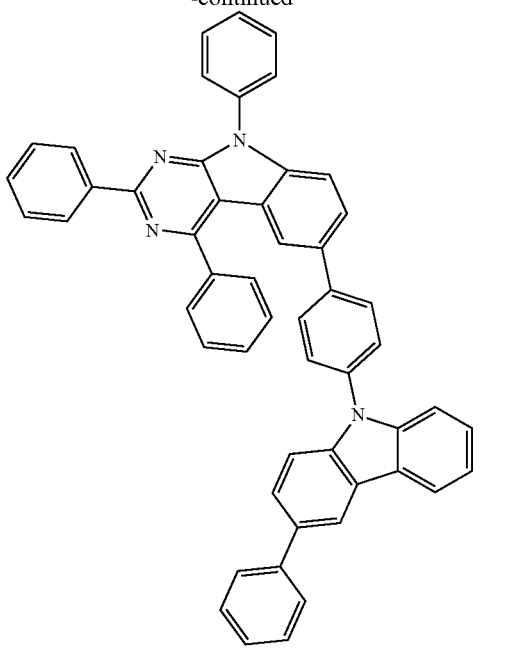
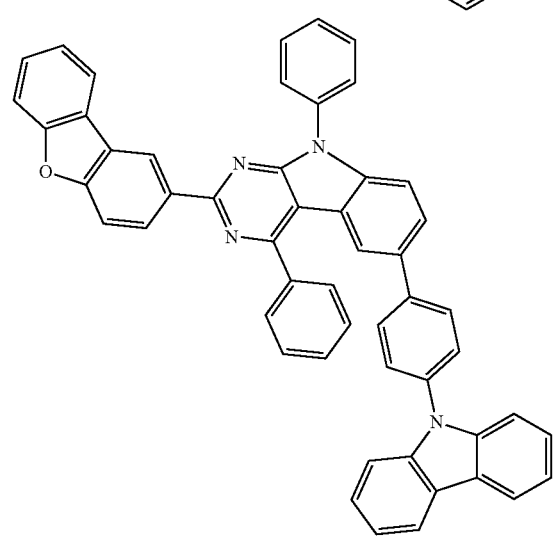
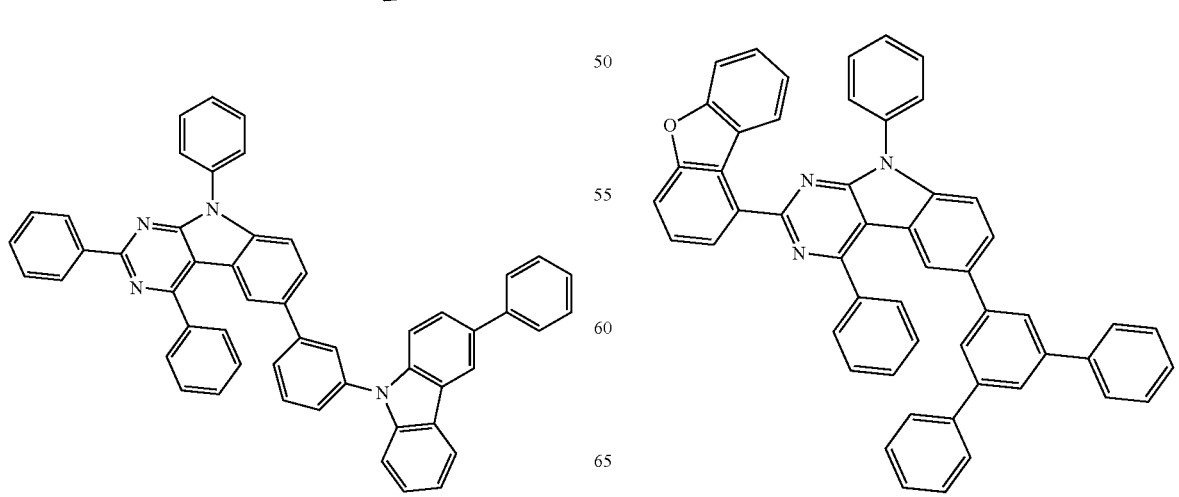

79
-continued
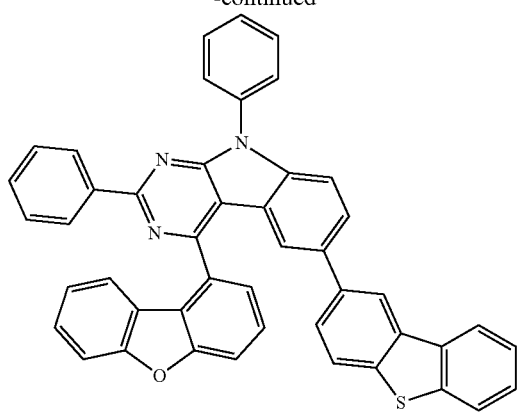
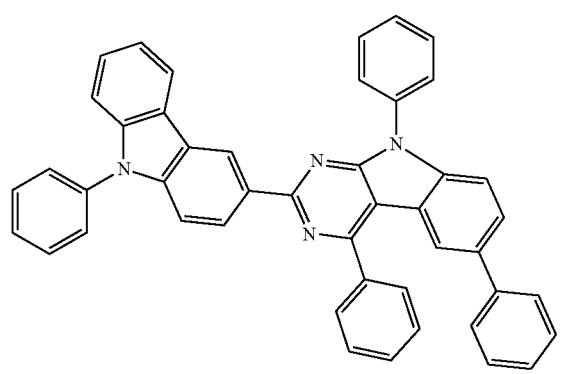
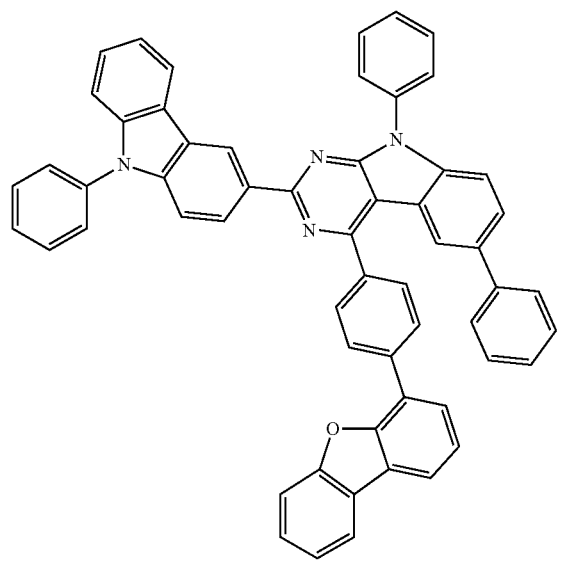
80
-continued
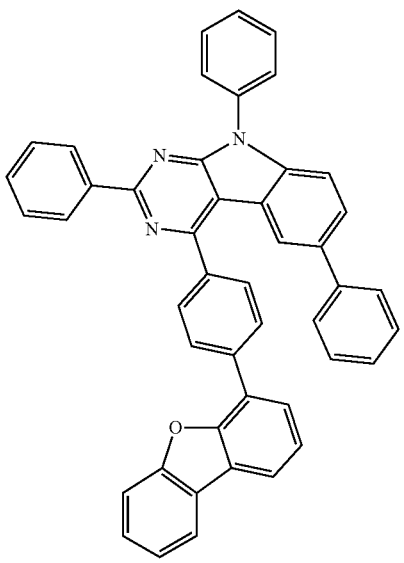
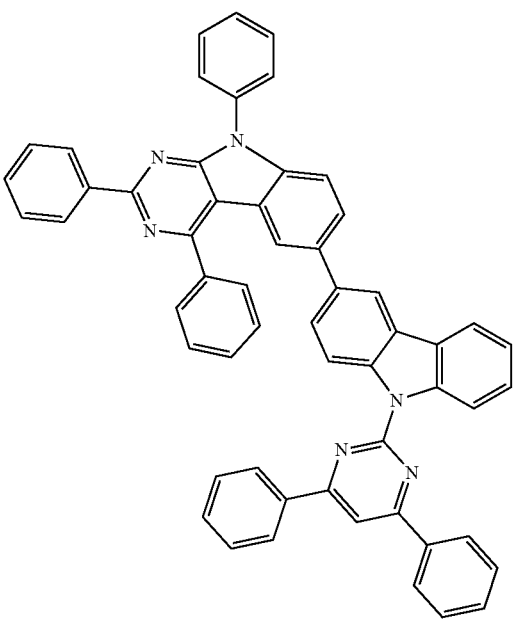

81
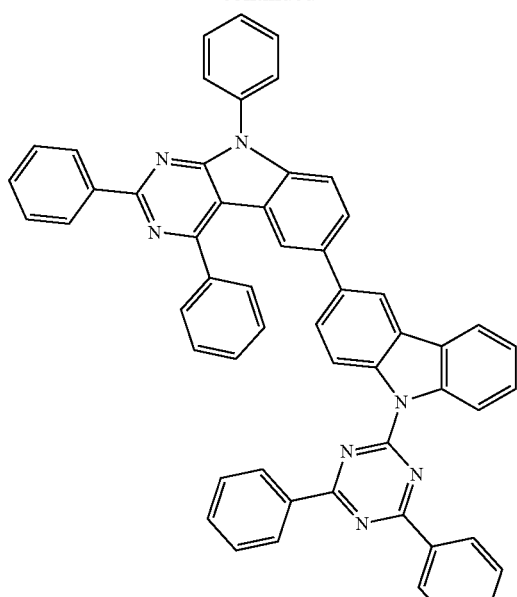
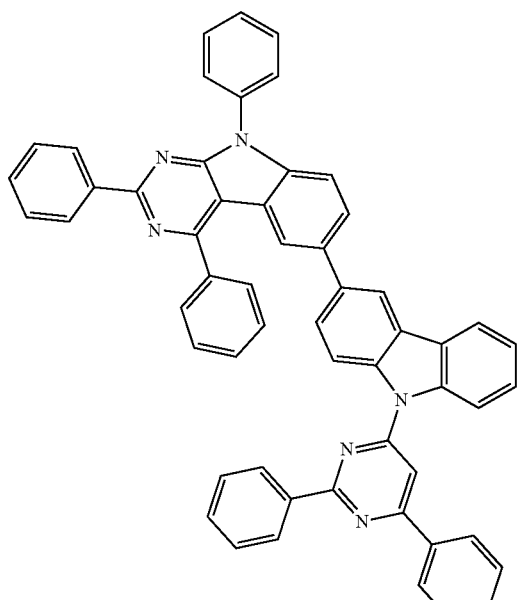
82
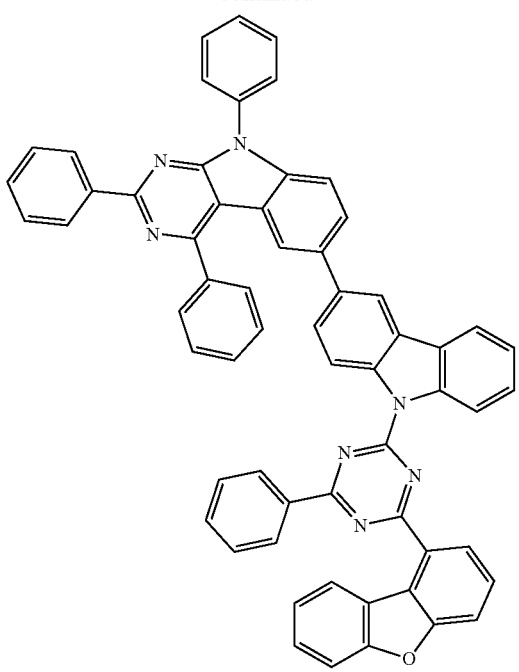
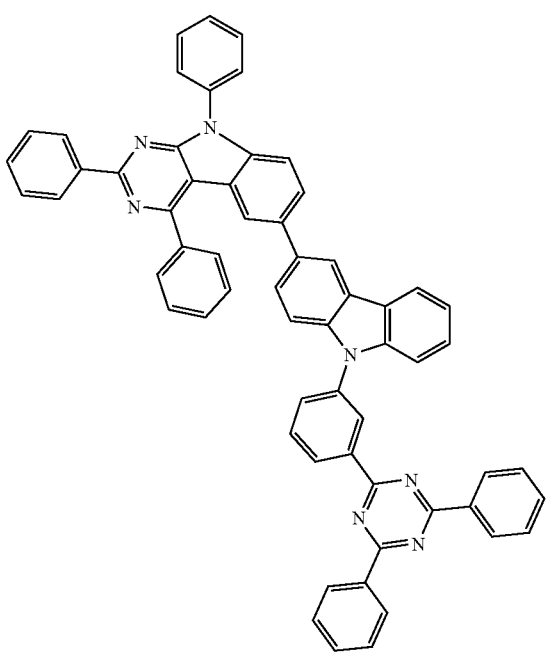

83
-continued
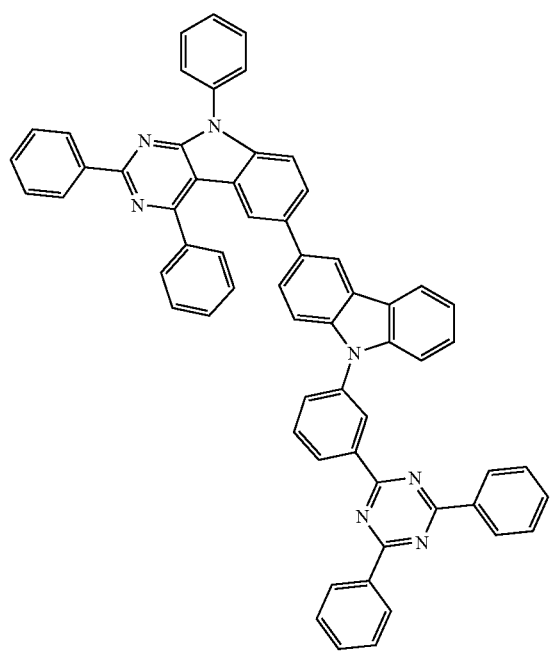
84
-continued
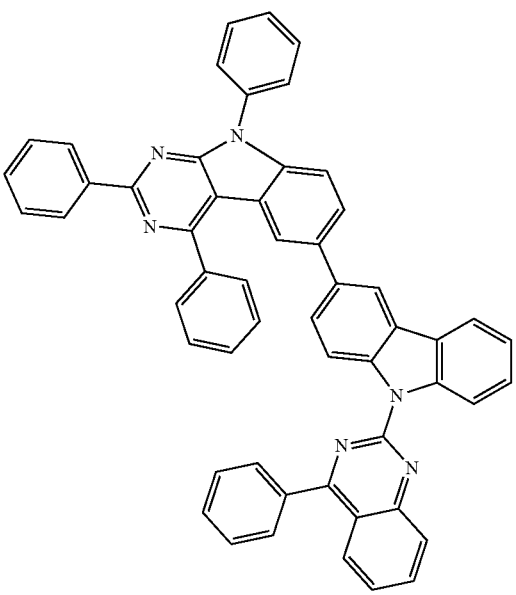
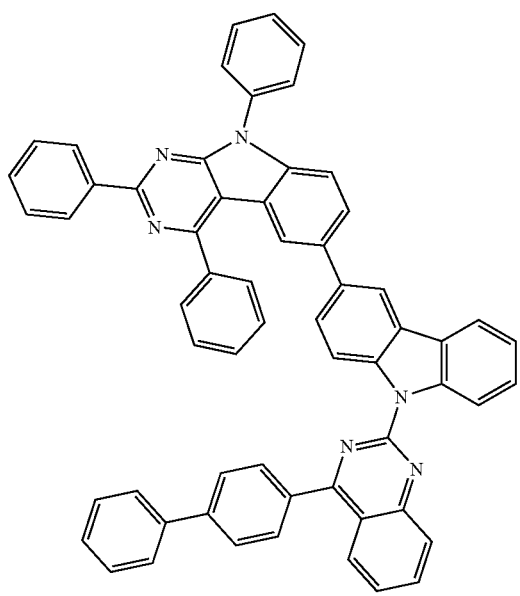
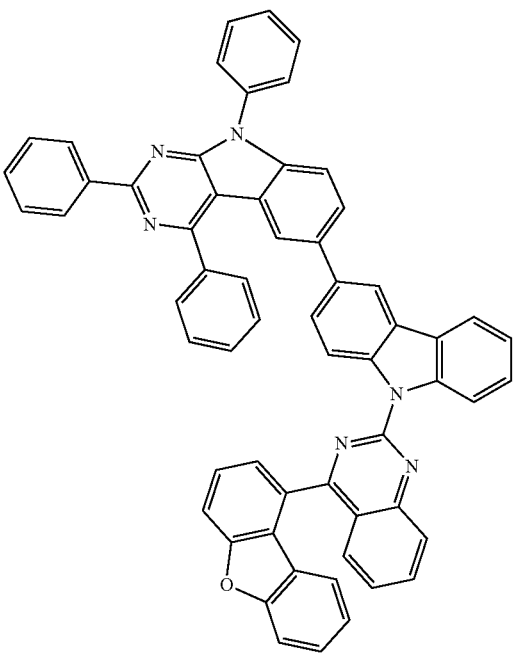

85
-continued
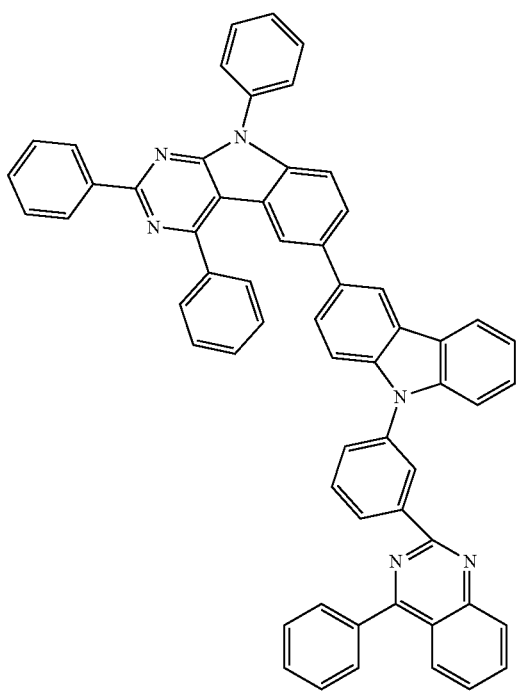
86
-continued
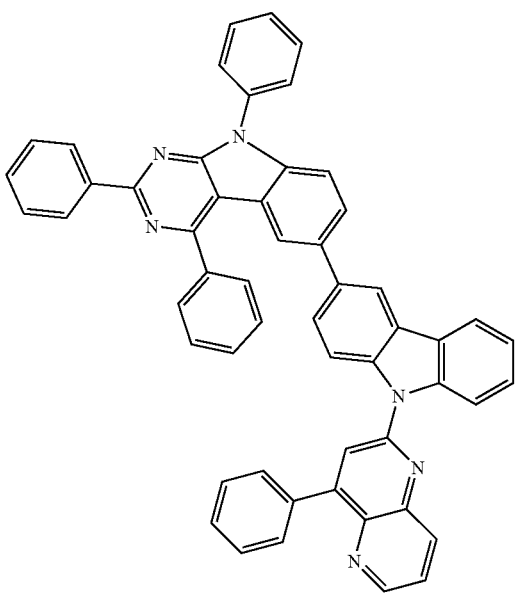
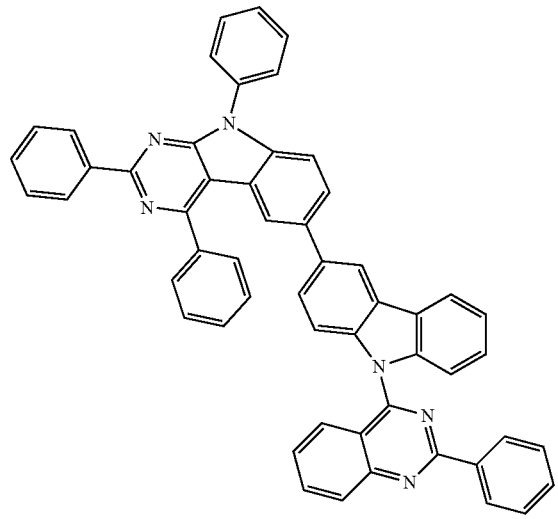
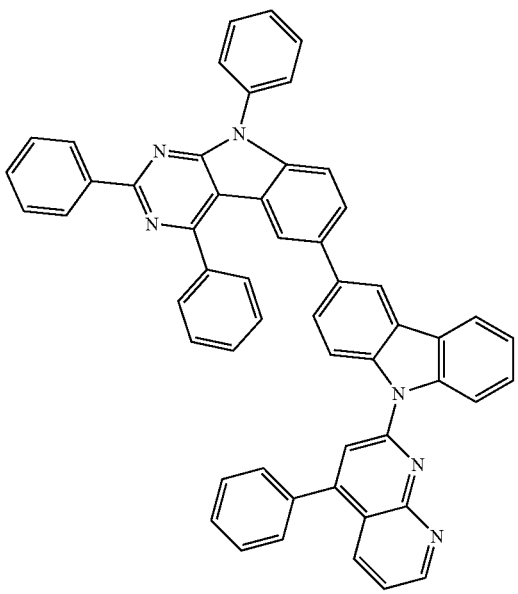

87
-continued
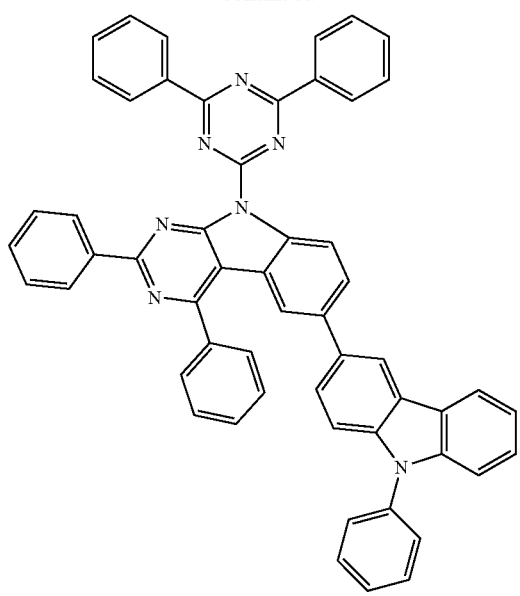
88
-continued
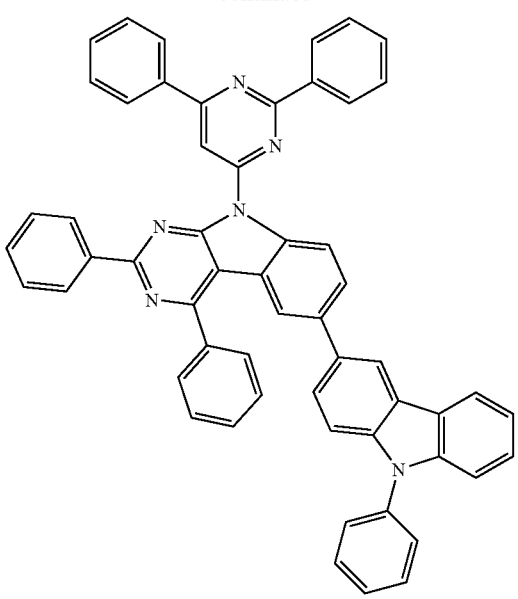
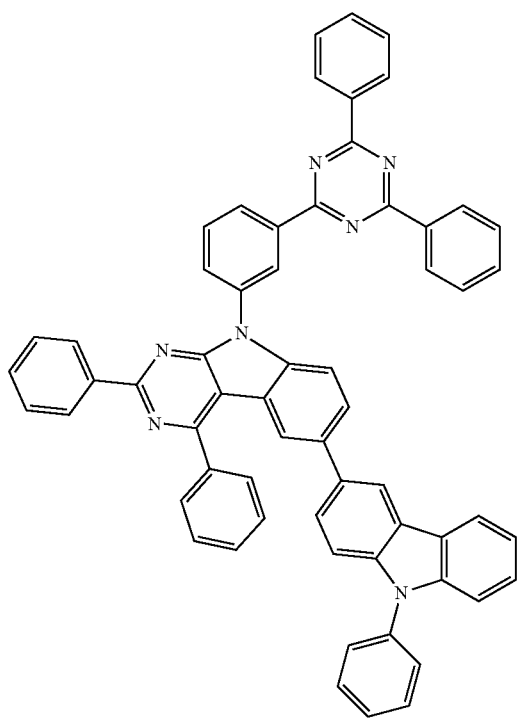
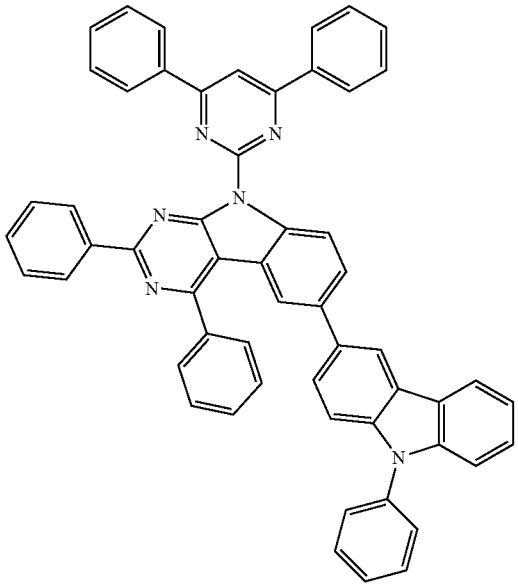

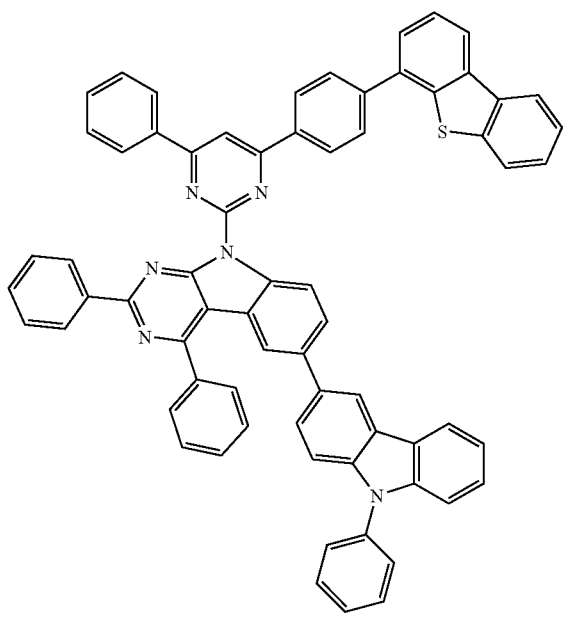
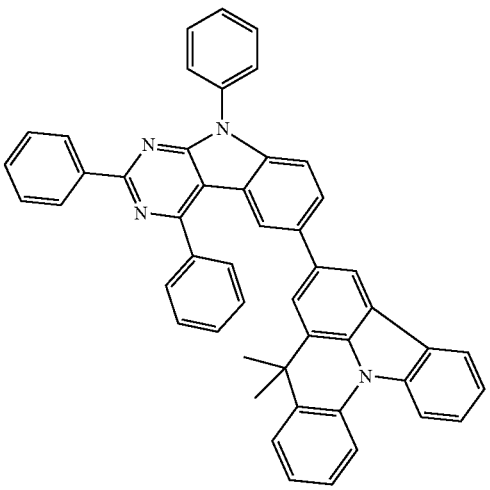

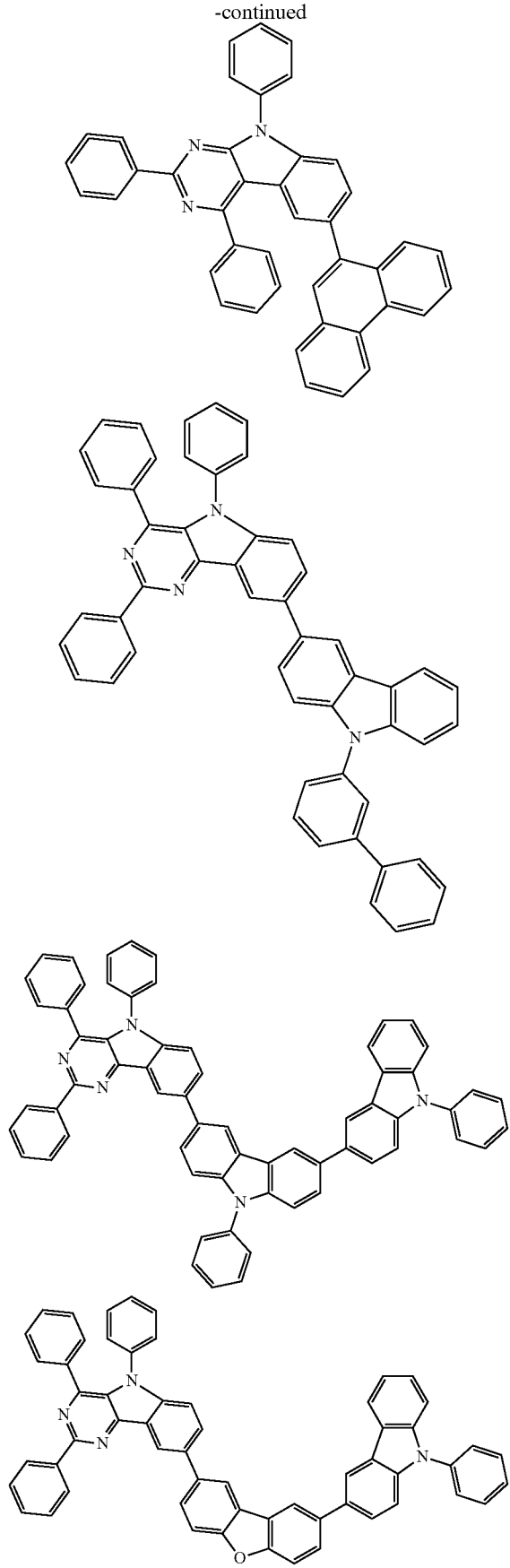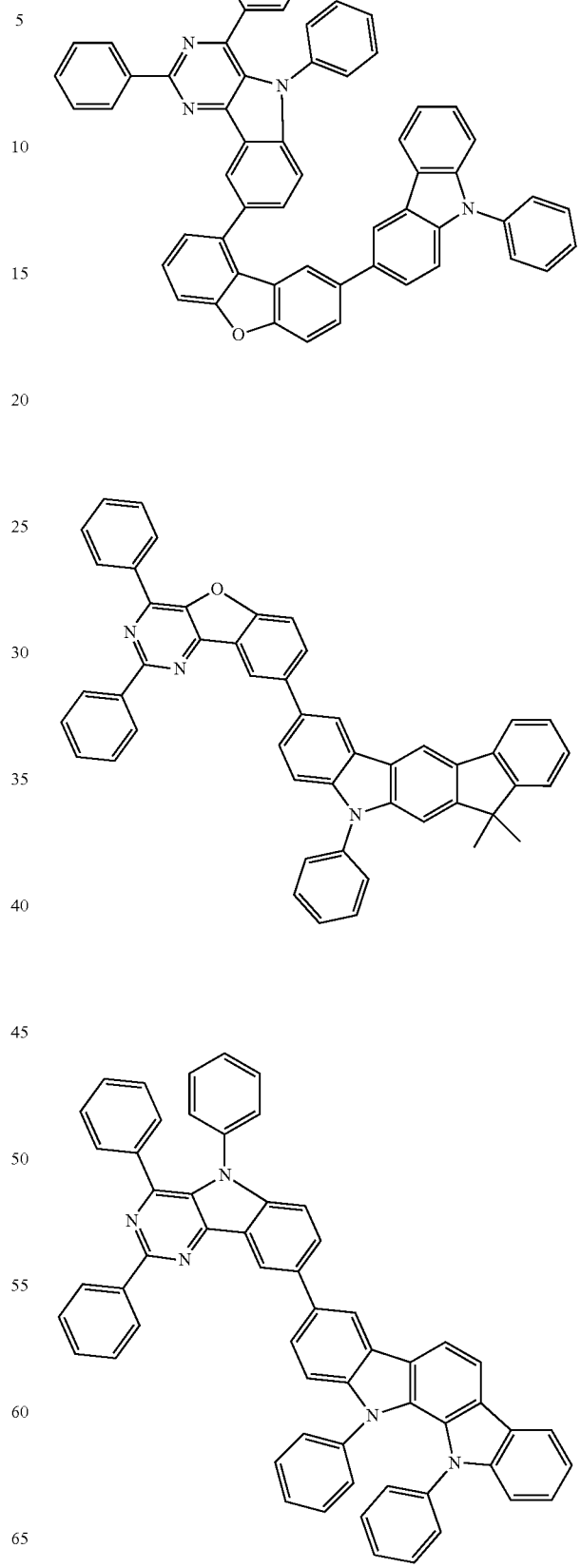

93
-continued
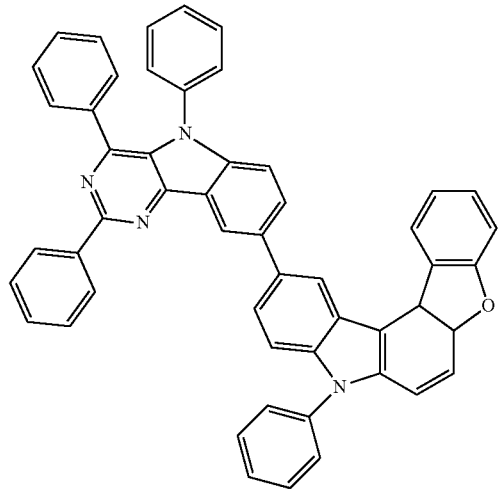
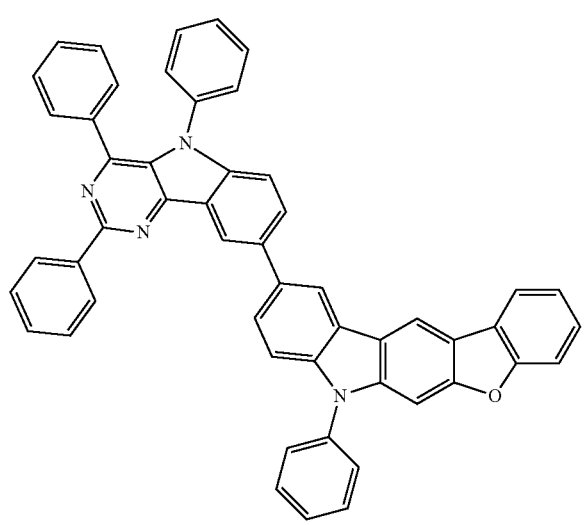
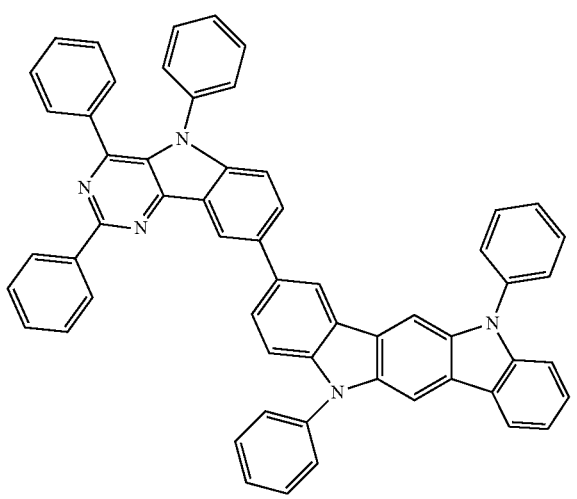
94
-continued
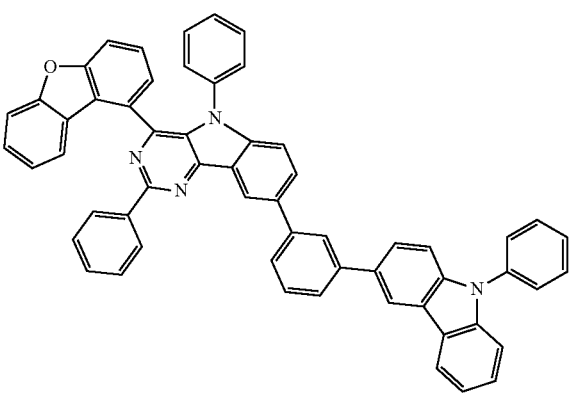
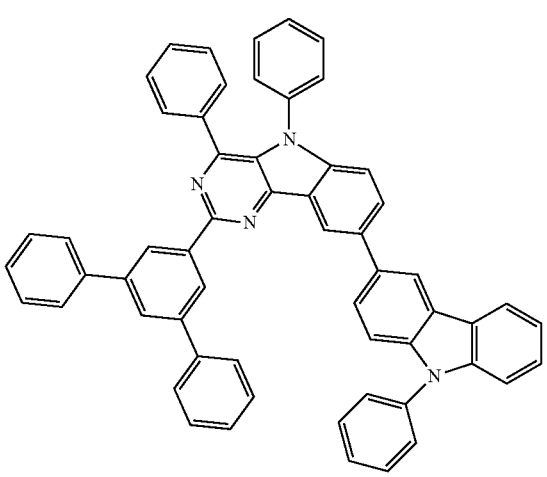
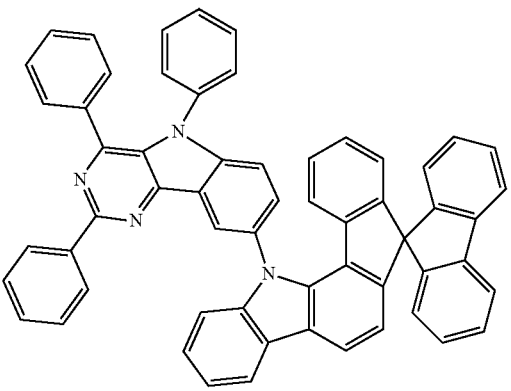

95
-continued
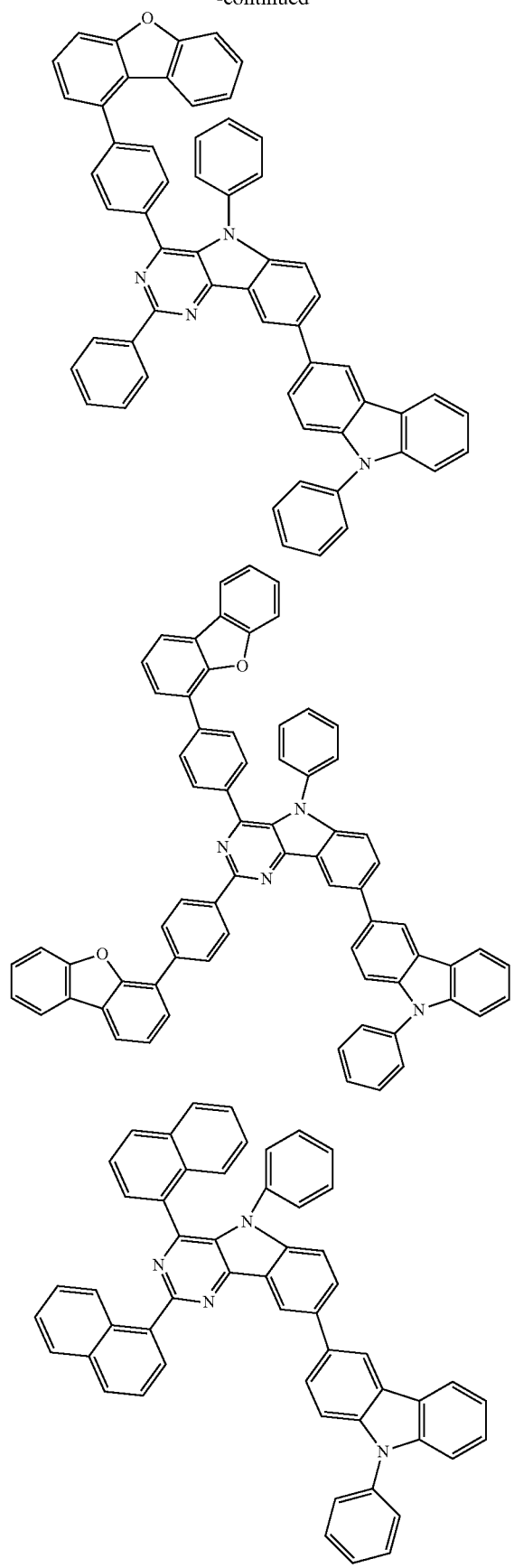
96
-continued
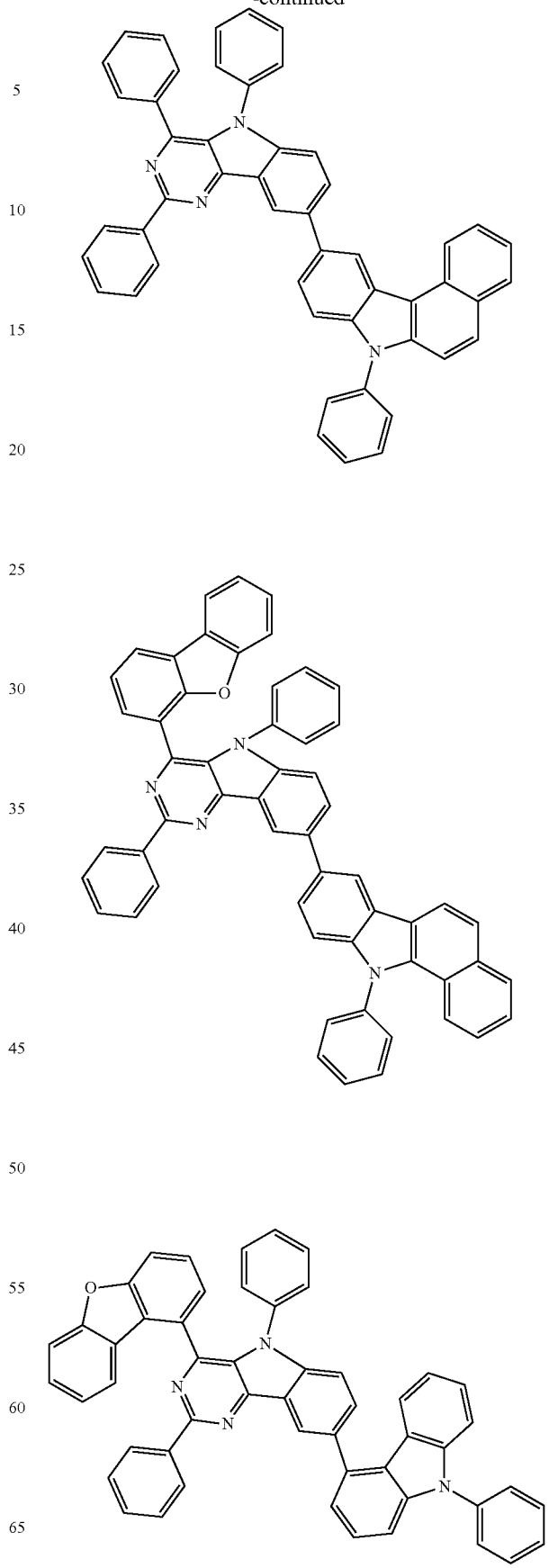

97
-continued
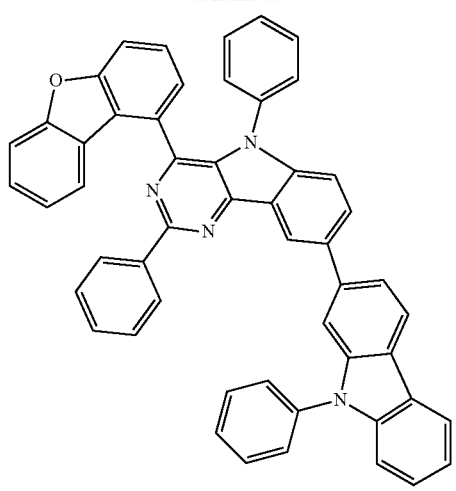
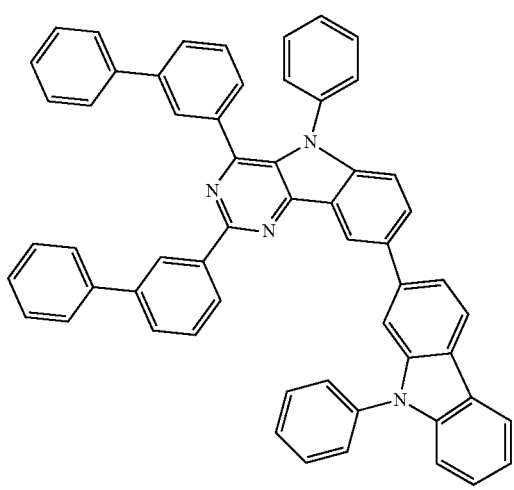
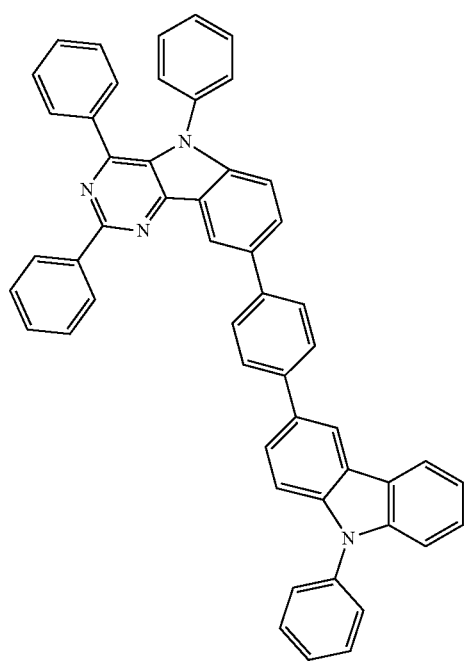
98
-continued
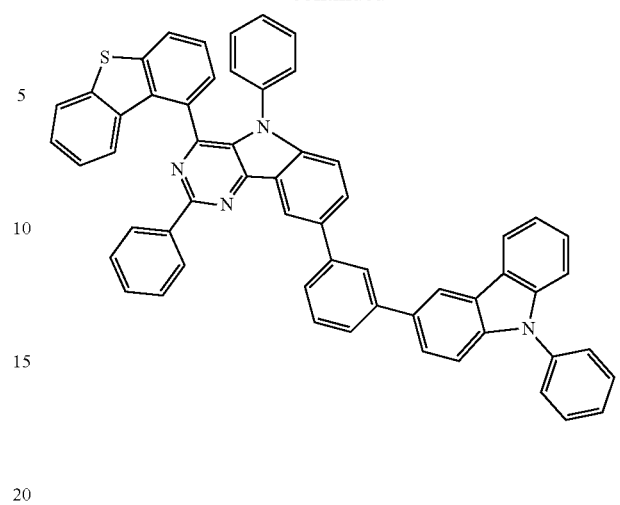
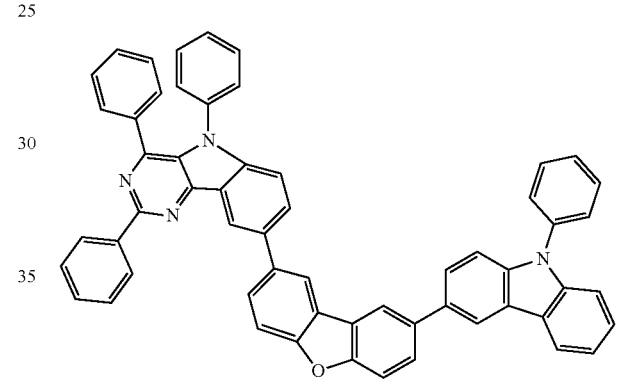
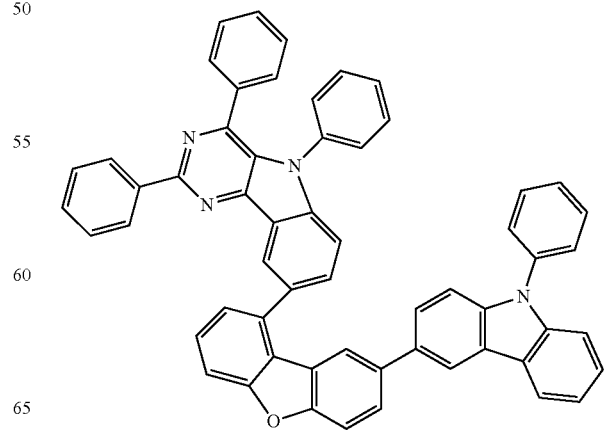

99
-continued
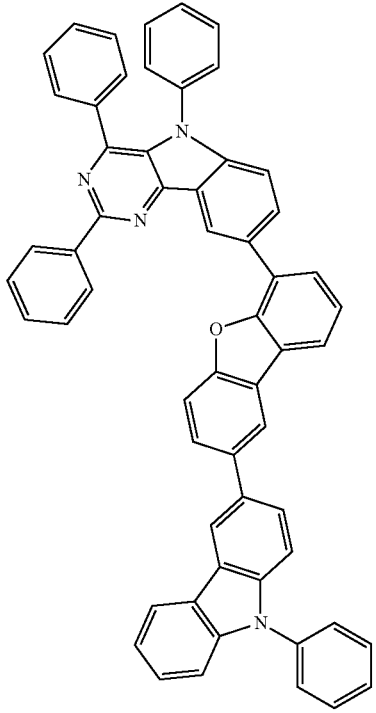
100
-continued
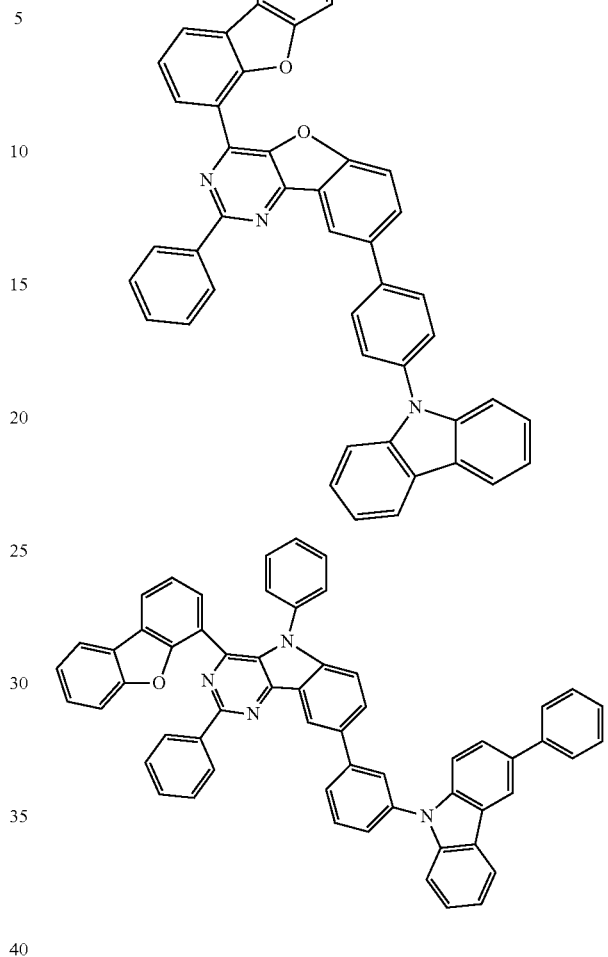
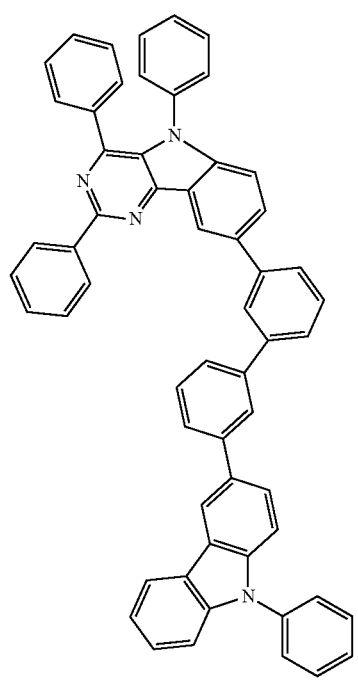
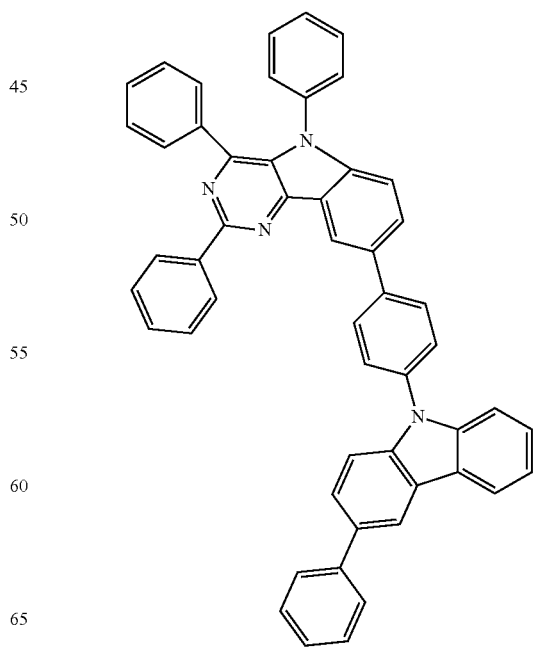

101
-continued
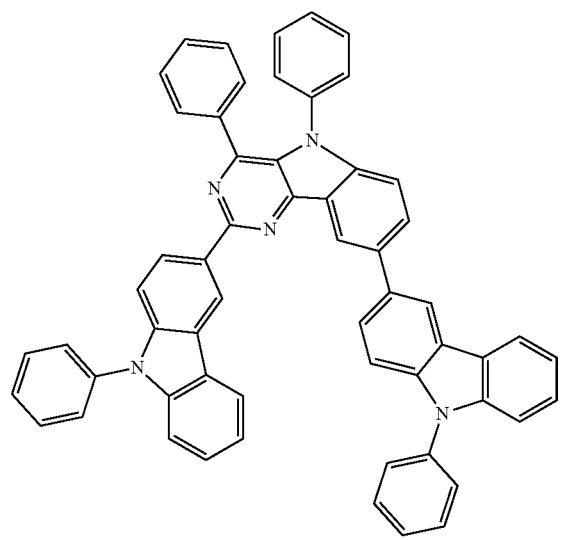
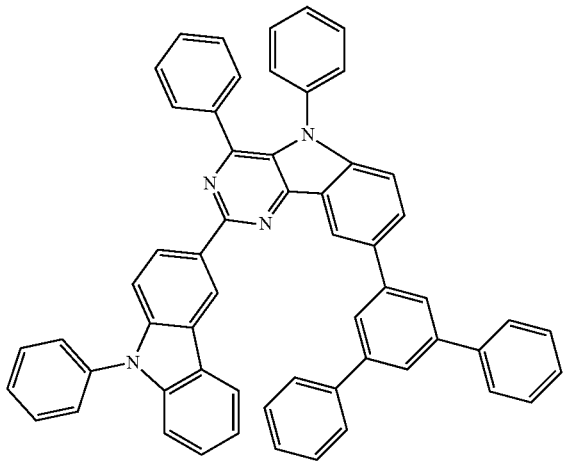
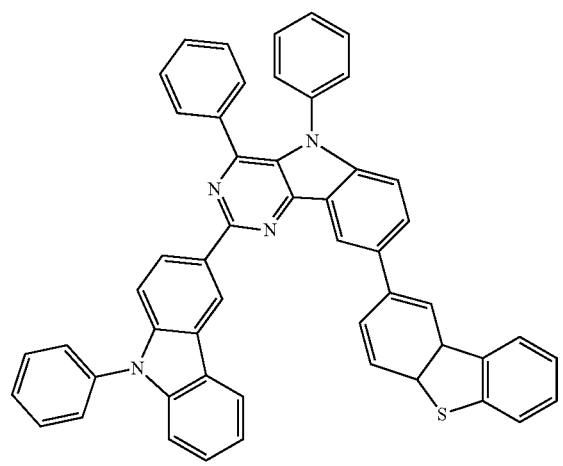
102
-continued
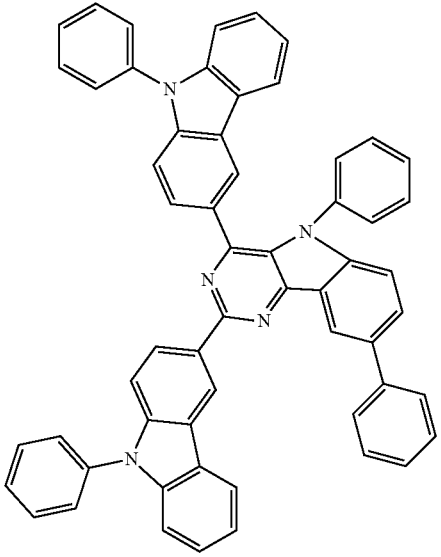
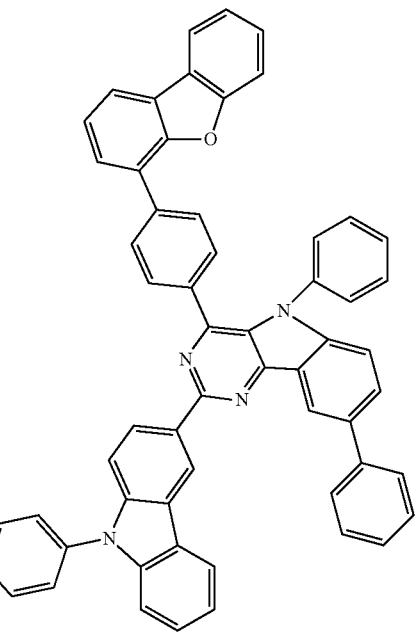
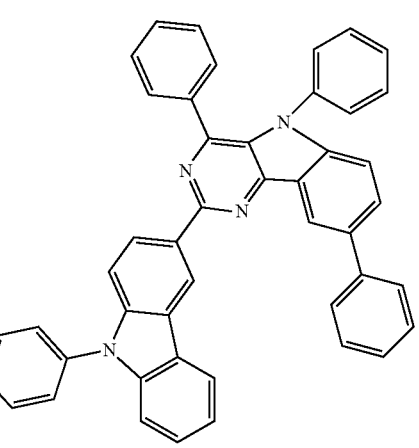

103
-continued
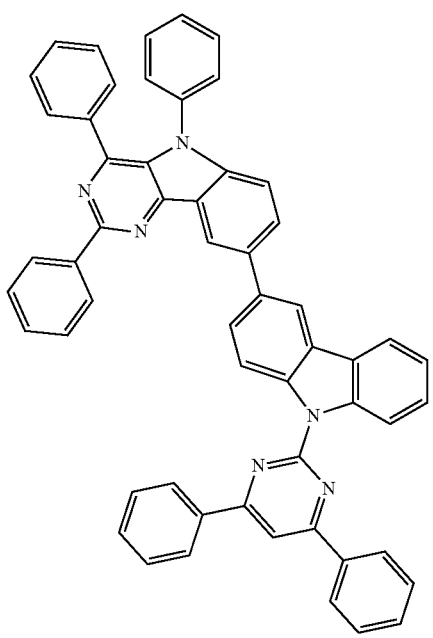
104
-continued
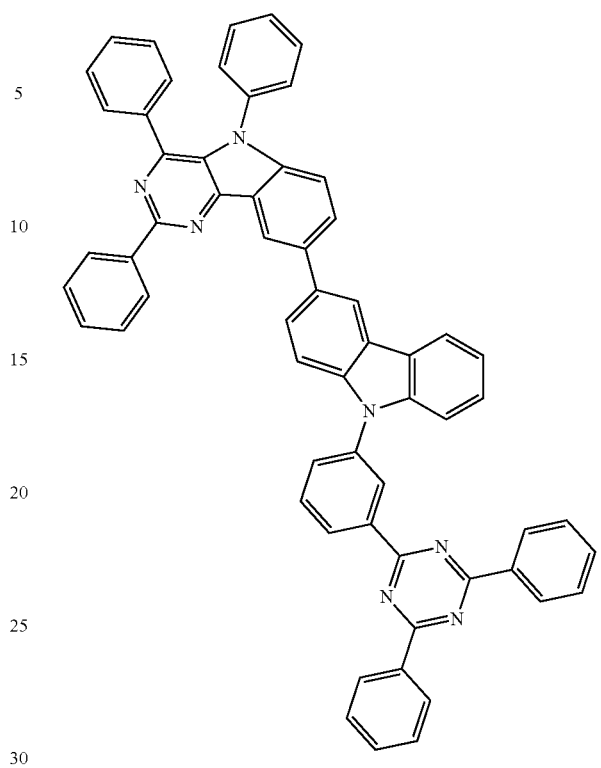
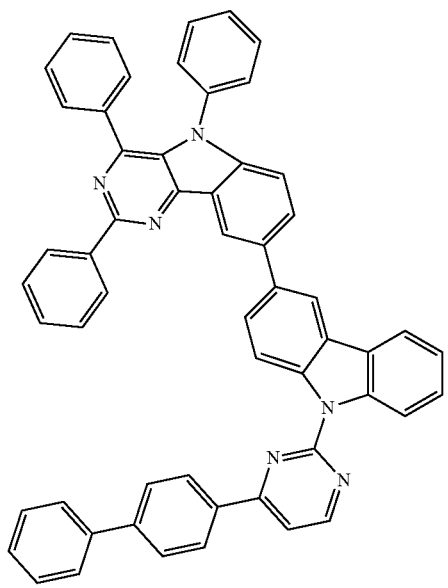
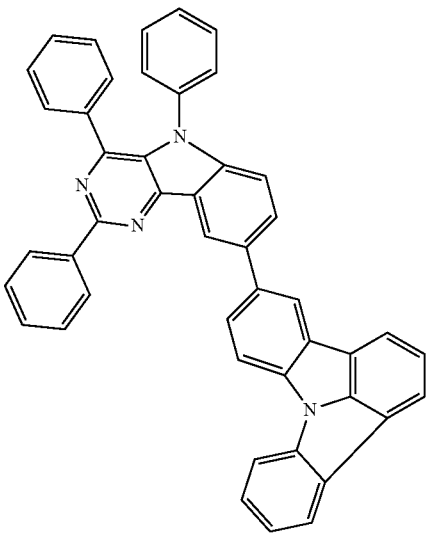

105
-continued
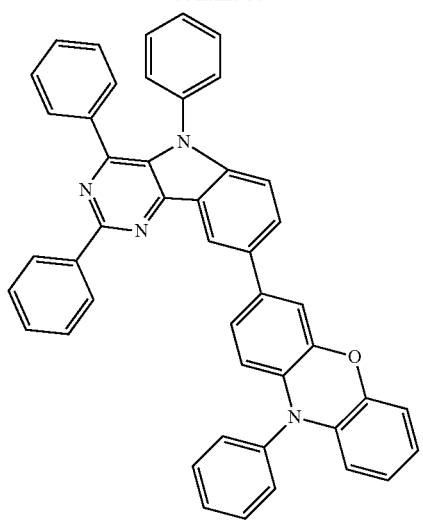
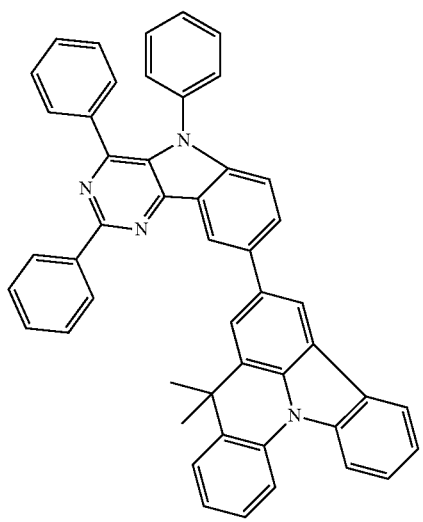
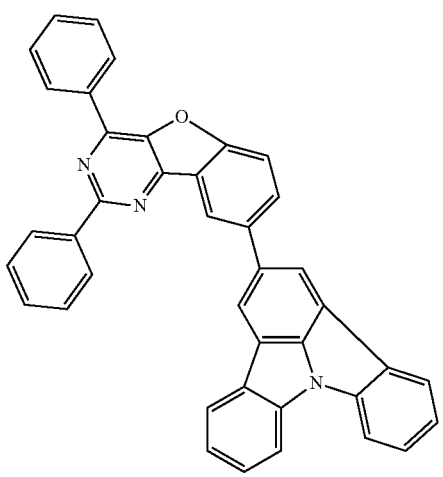
106
-continued
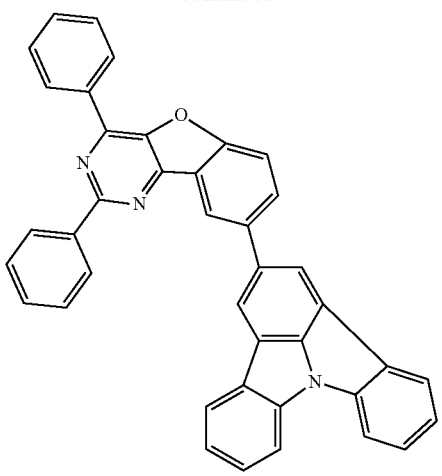
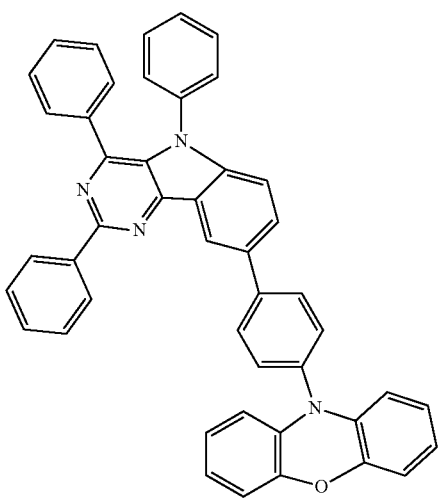
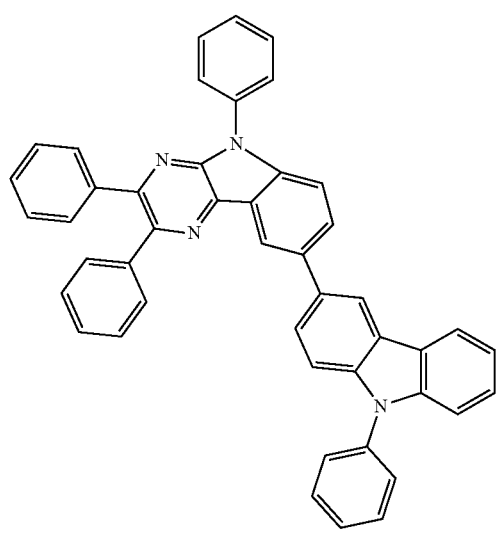

107
-continued
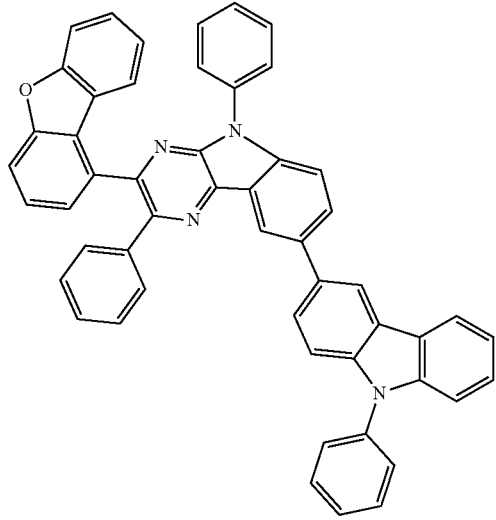
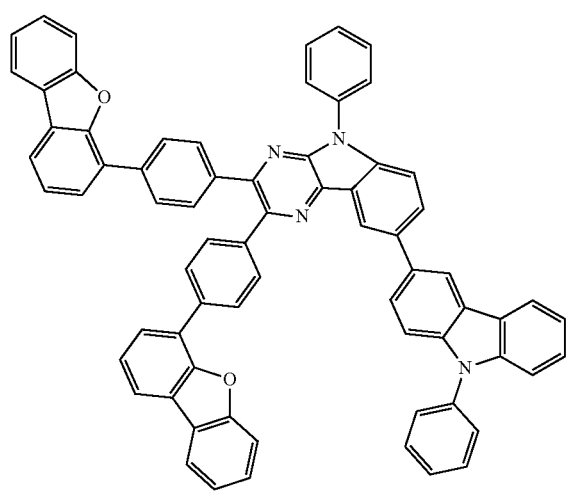
108
-continued
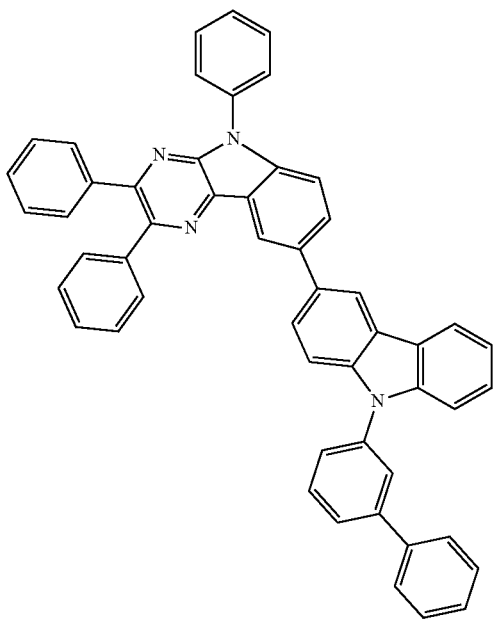
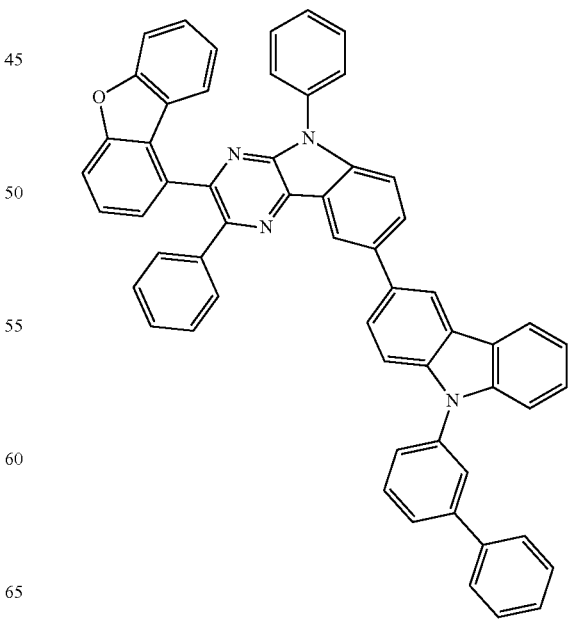

109
-continued
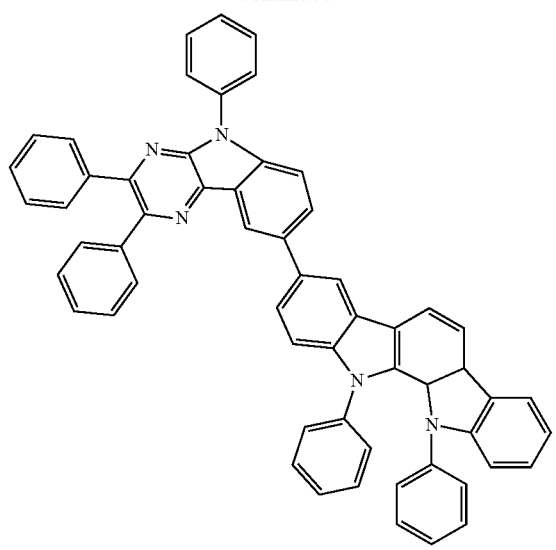
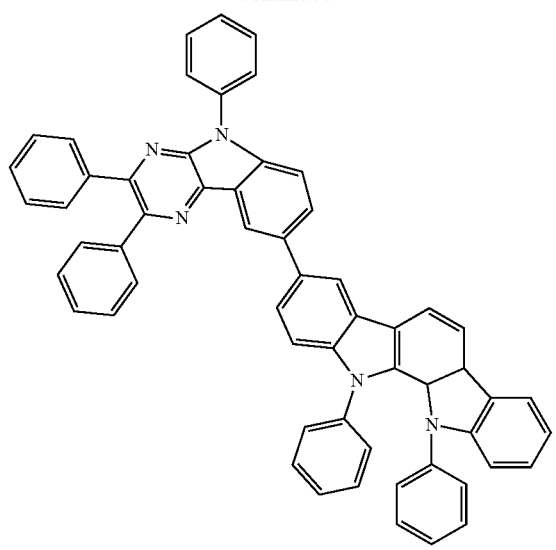
110
-continued
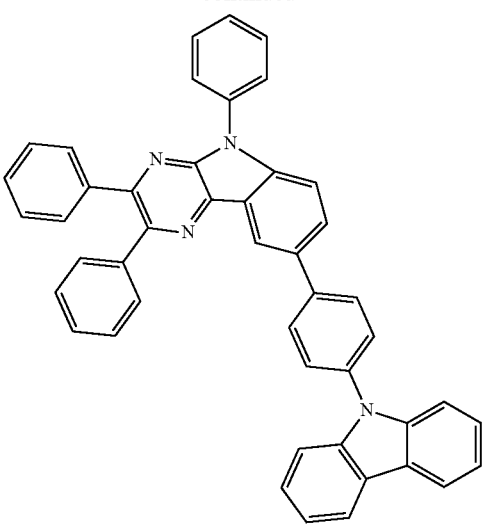
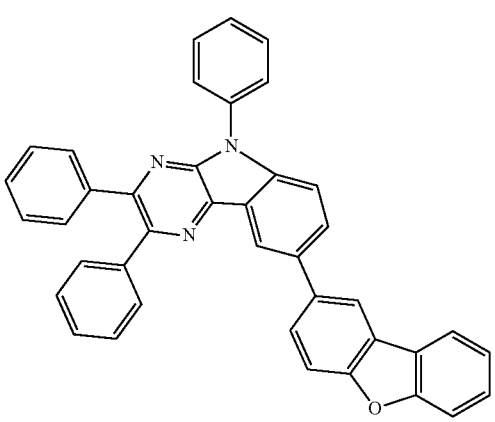
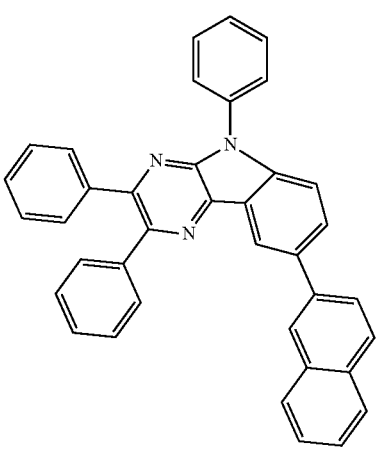

111
-continued
112
-continued
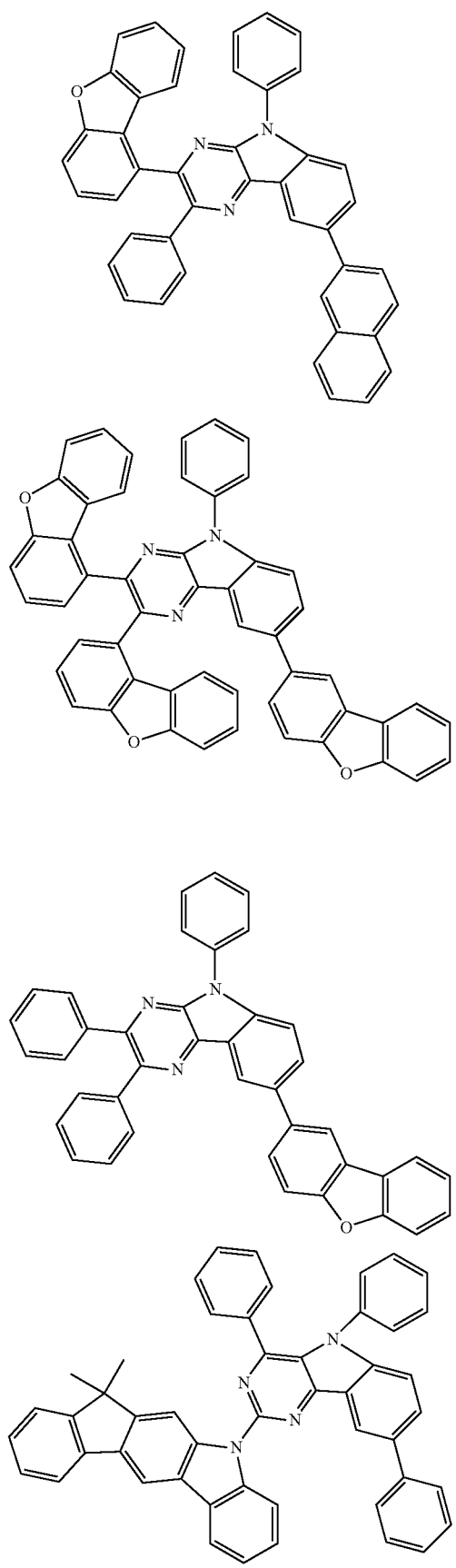
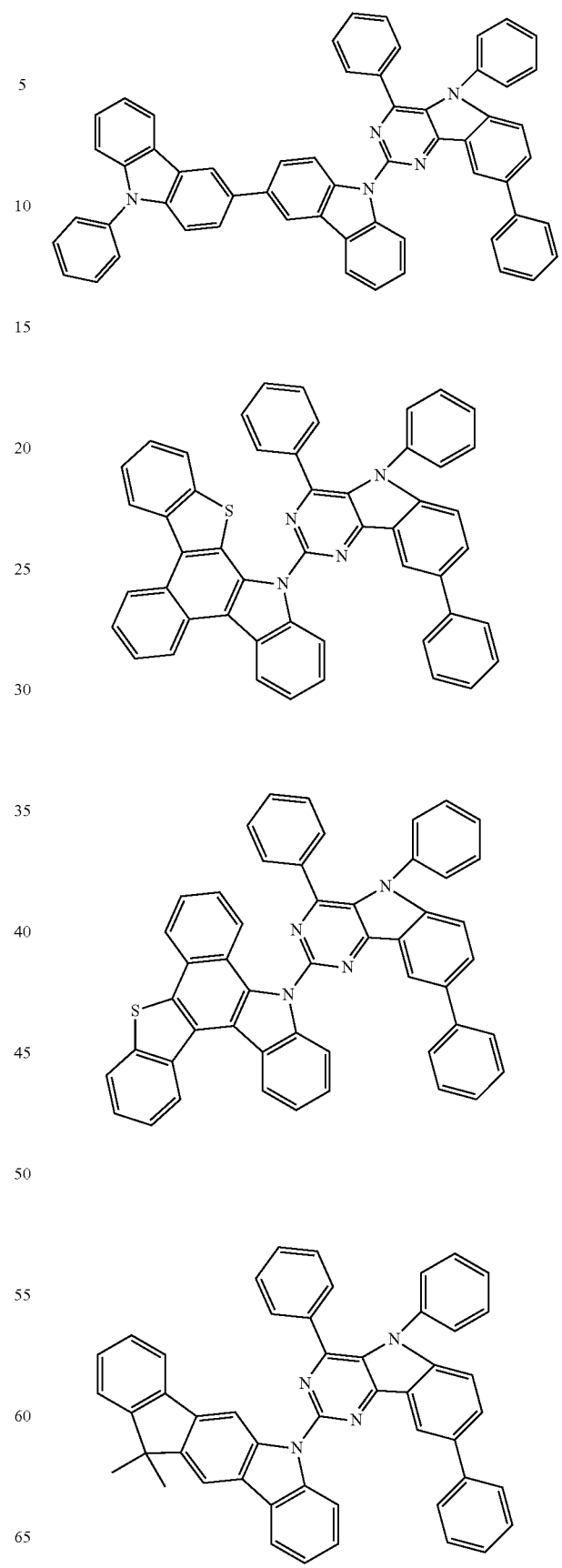

113
-continued
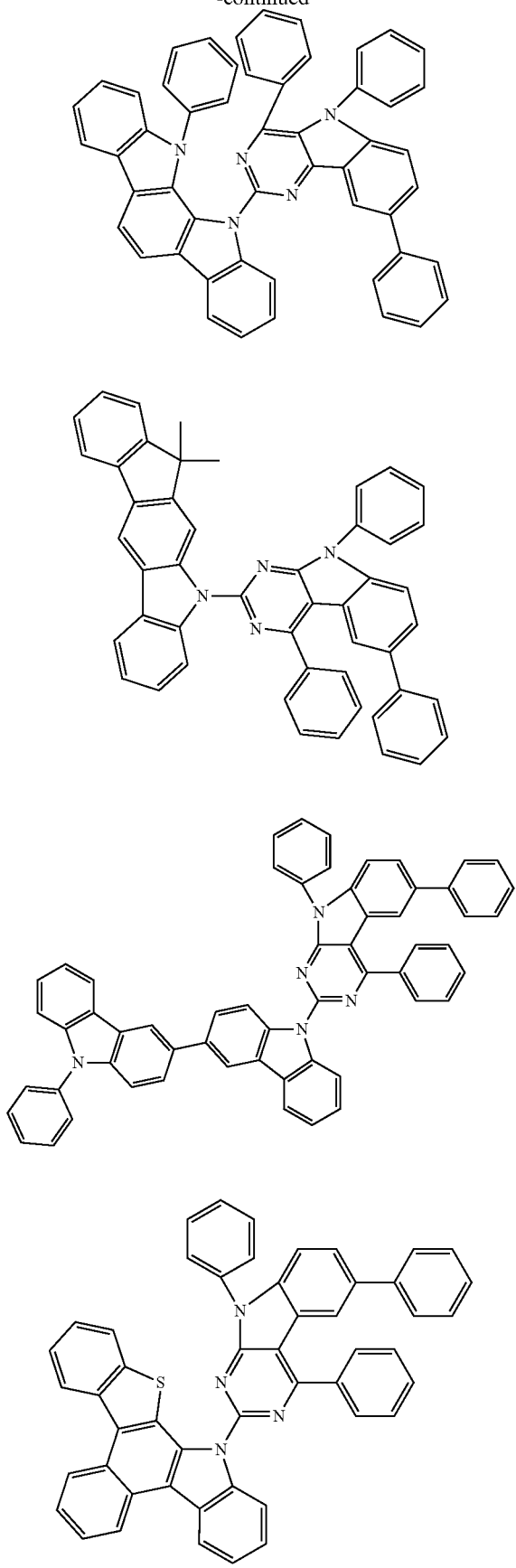
114
-continued

115
-continued
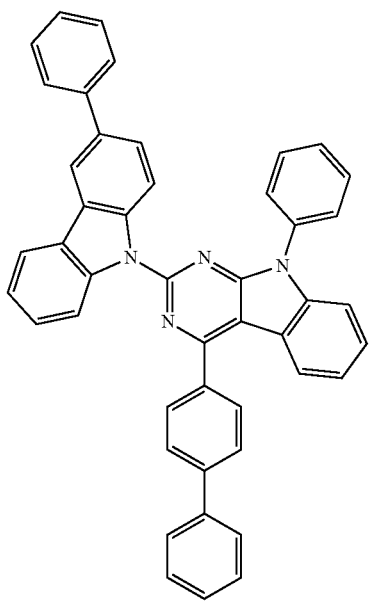
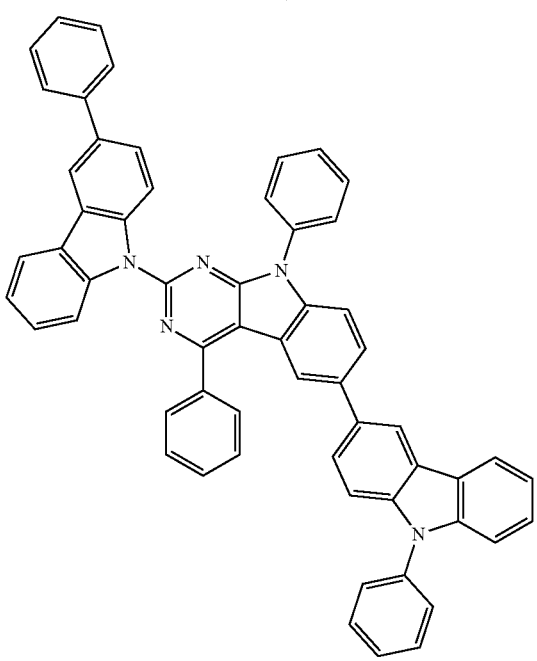
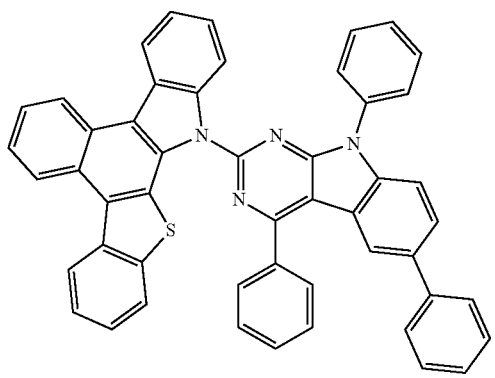
116
-continued
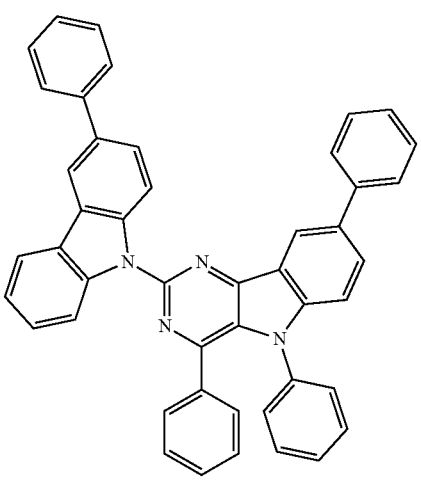
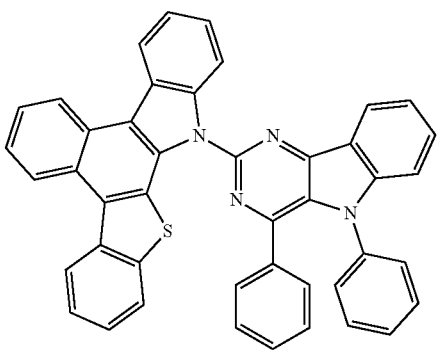

117
-continued
118
-continued
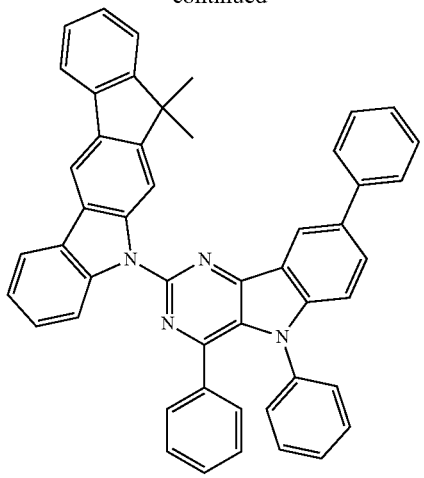
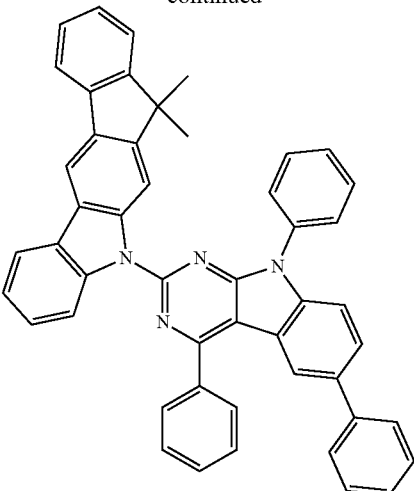
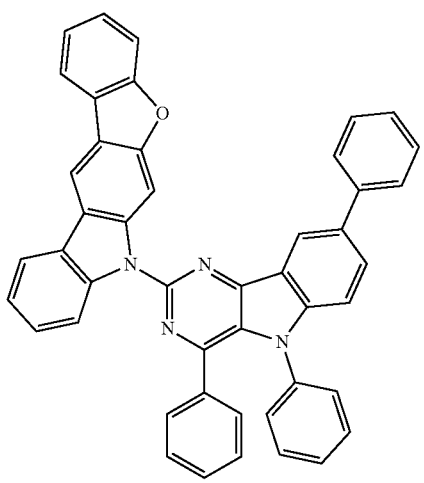
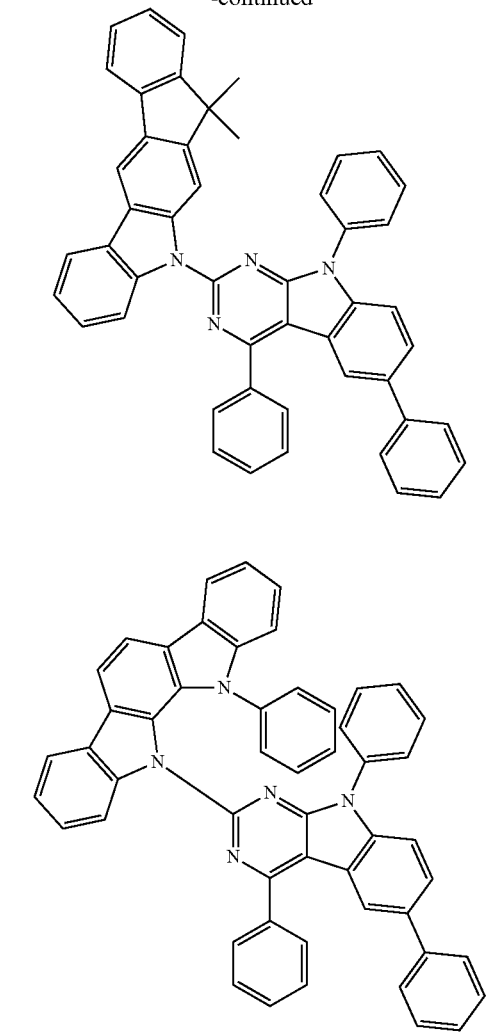
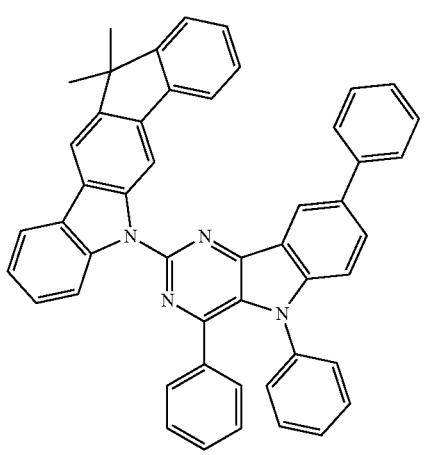
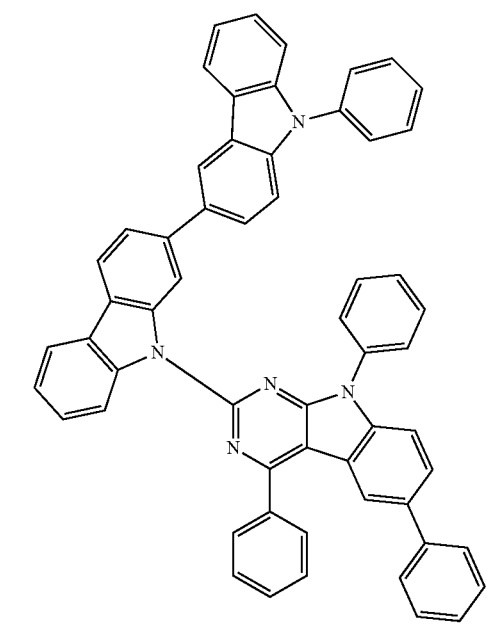

119
-continued
120
-continued
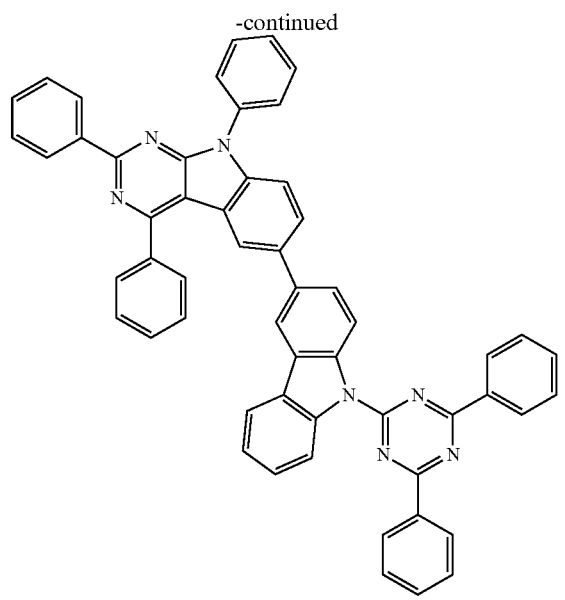
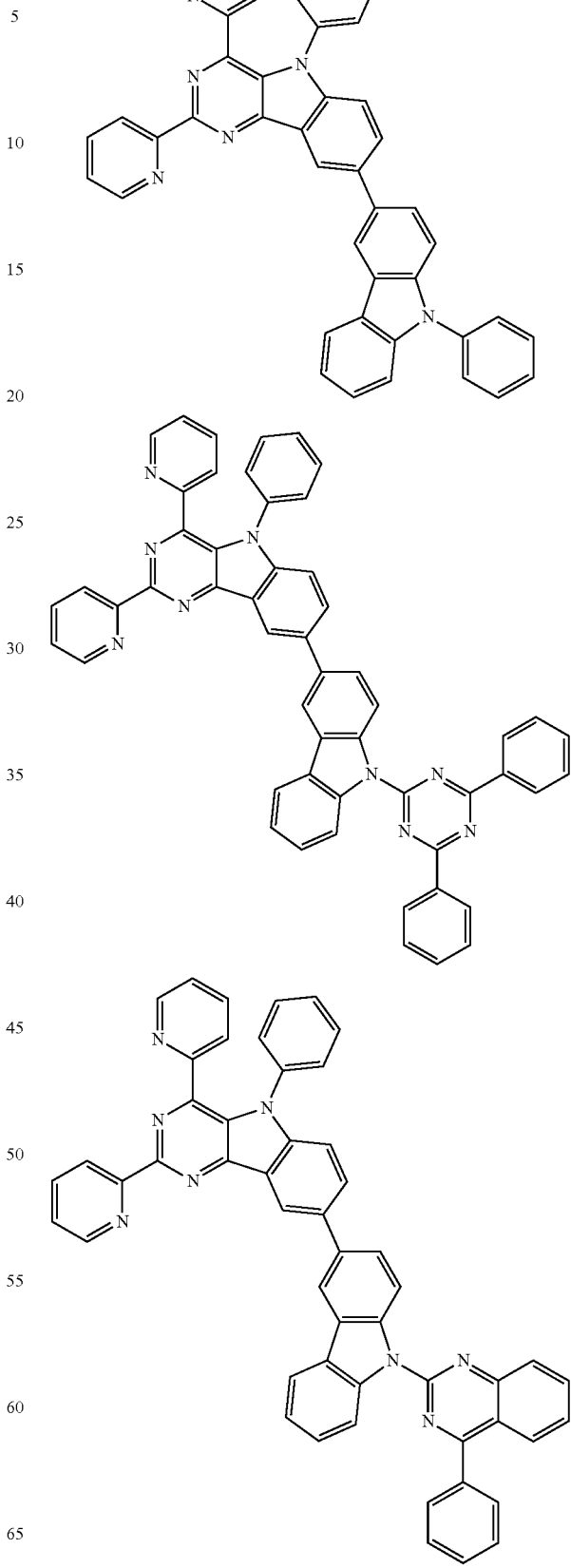

121
-continued
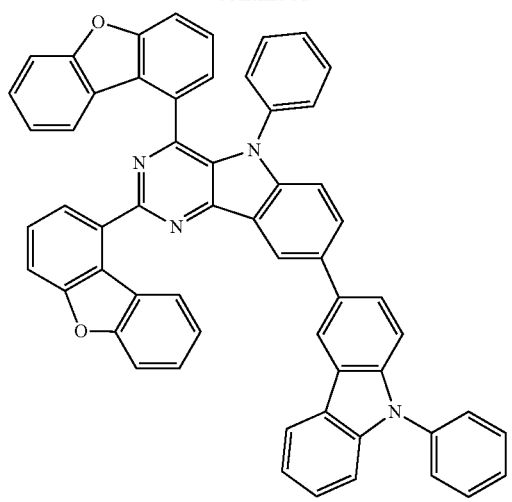
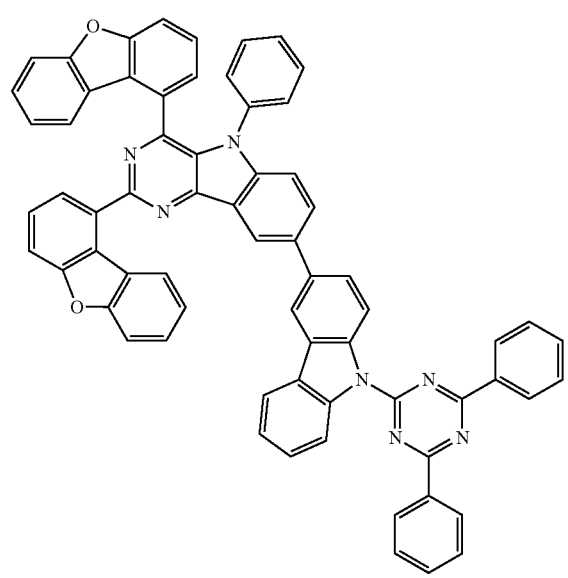
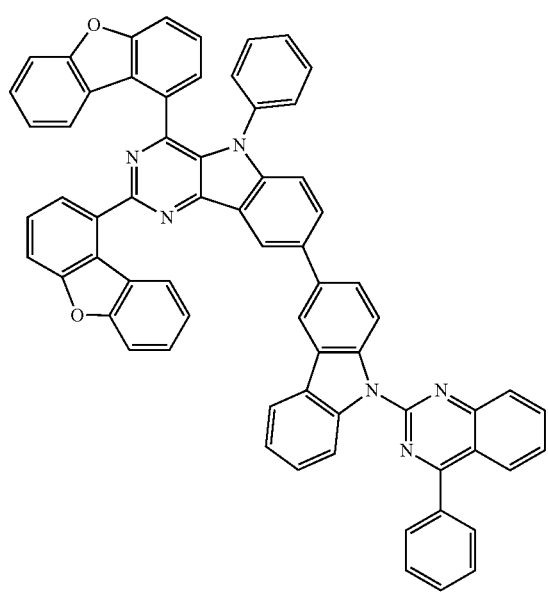
122
-continued
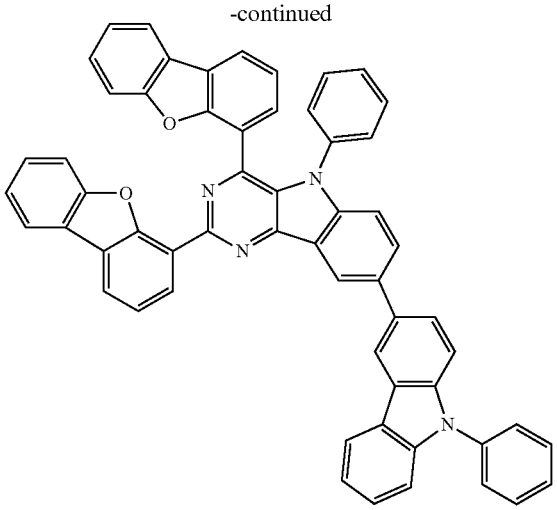
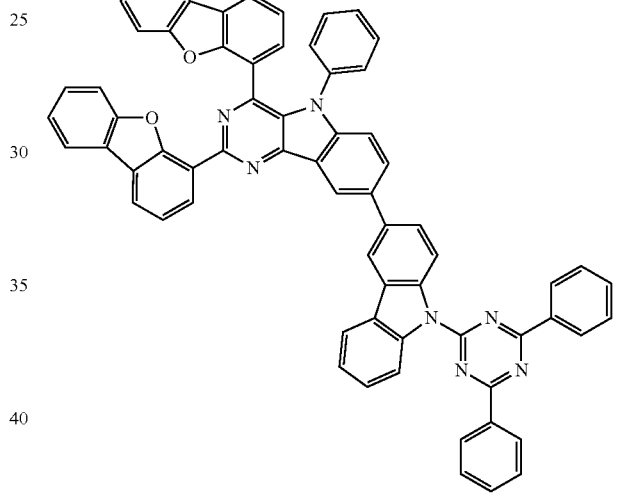
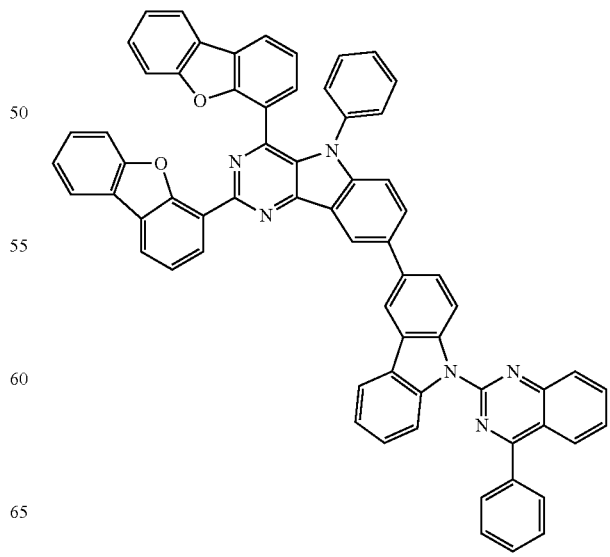

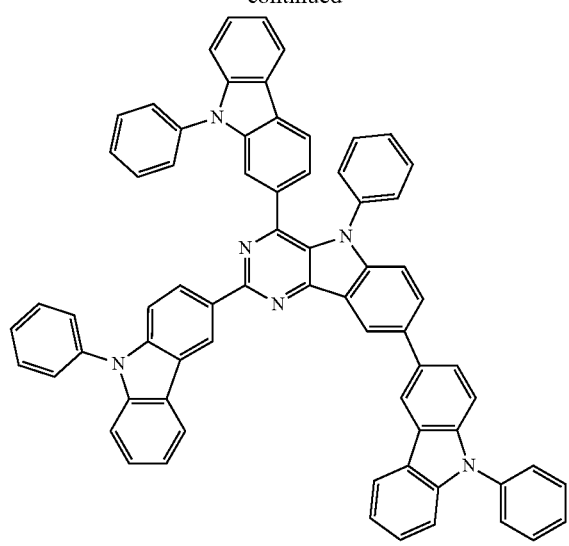
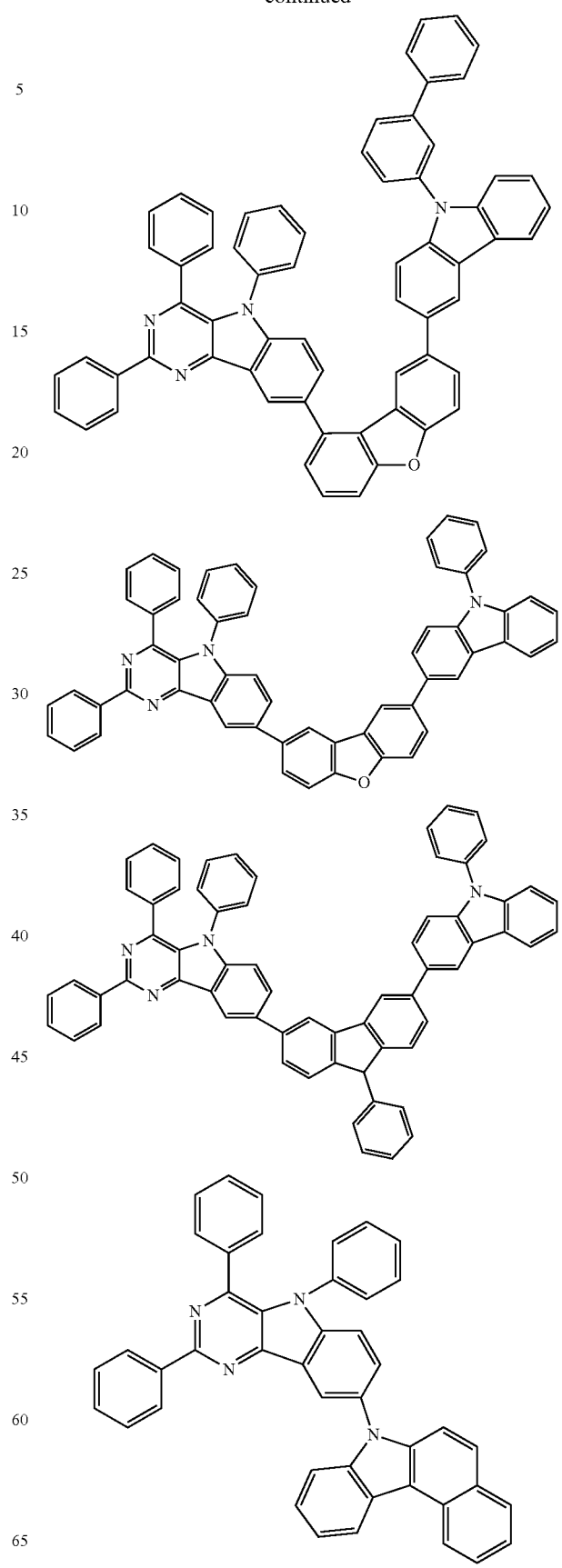

125
-continued
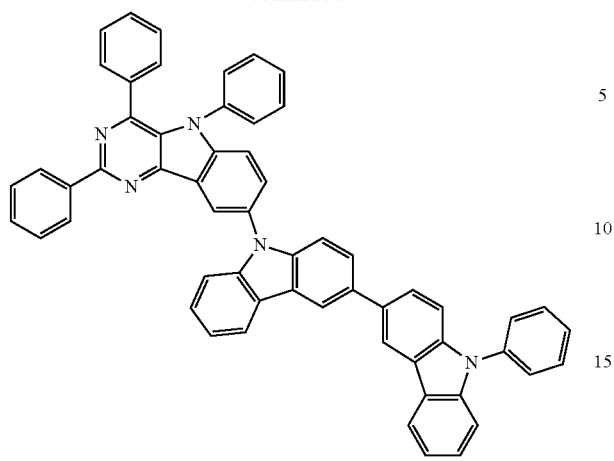
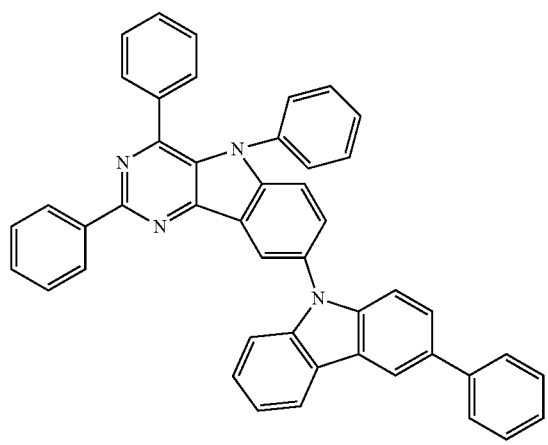
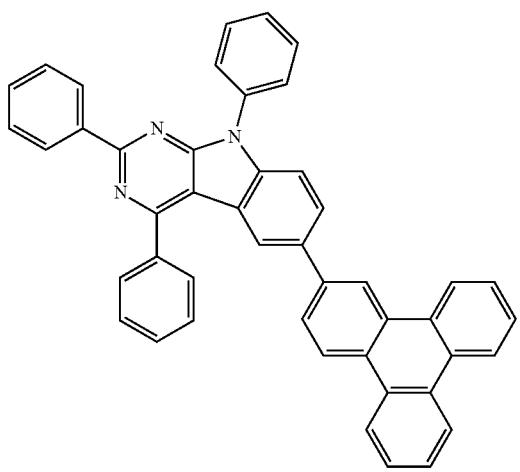
126
-continued
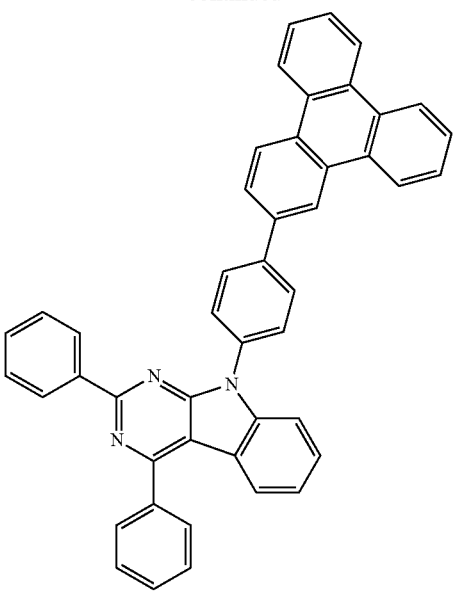
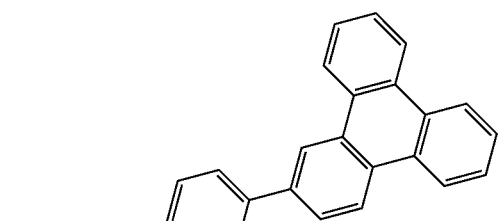
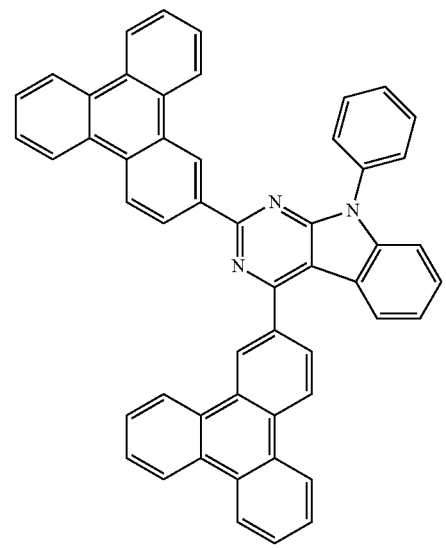

127
-continued
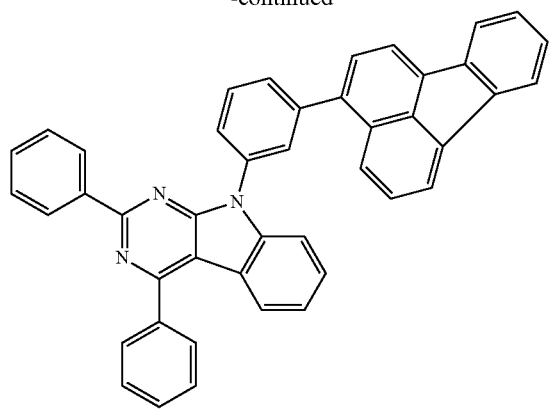
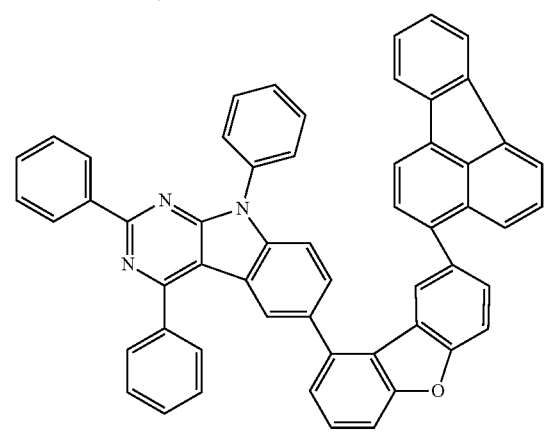
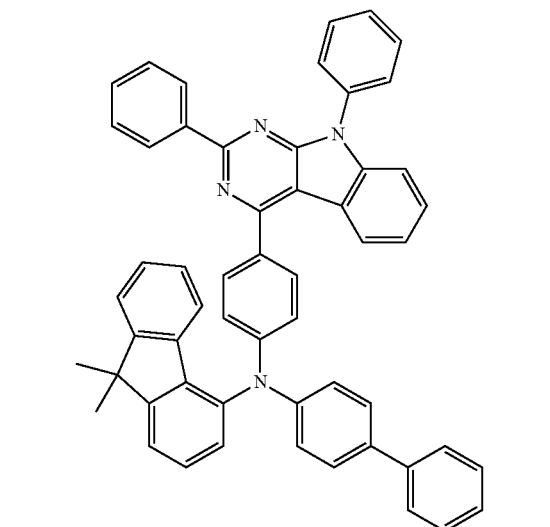
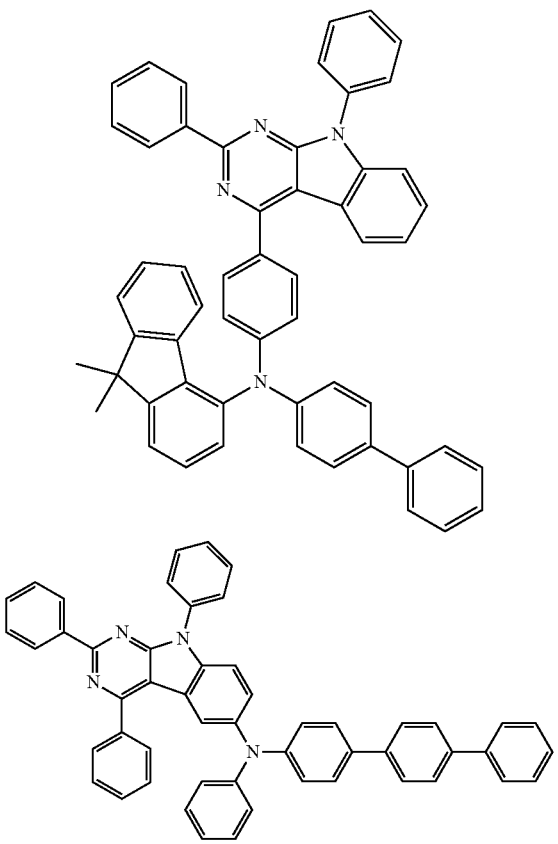
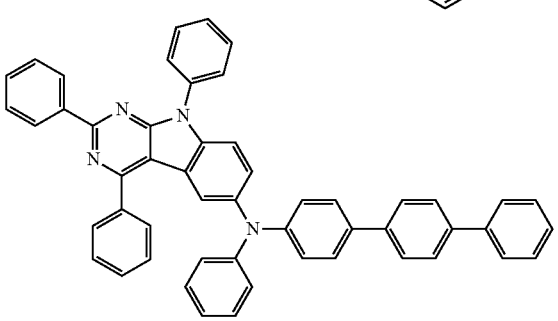
128
-continued
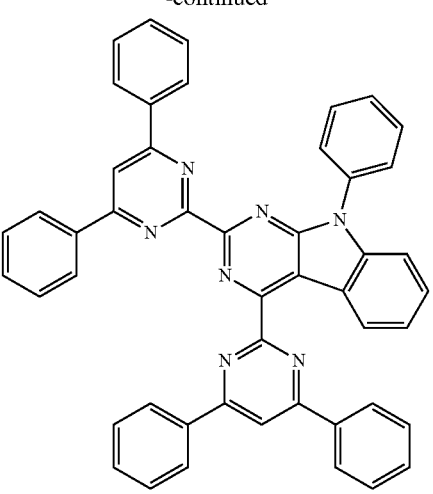
The compounds according to the invention can be prepared by synthesis steps known to the person skilled in the art, such as, for example, bromination, Suzuki coupling, Ullmann coupling, Hartwig-Buchwald coupling, etc. Suitable synthesis processes are depicted in general terms in Schemes 1-5 below.
Scheme 1
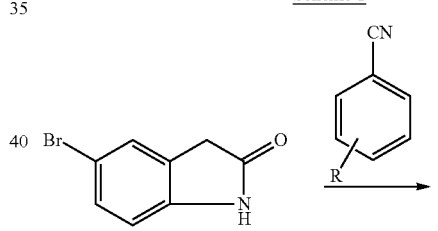
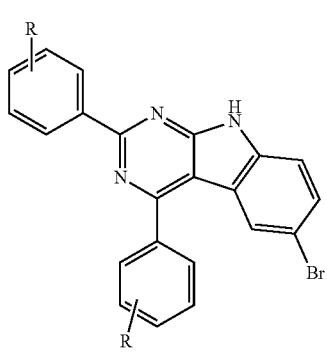
Synlett, (2), 177-180; 2008
Ar'—B(OH)2 / Ullmann \ Ar—I -continued

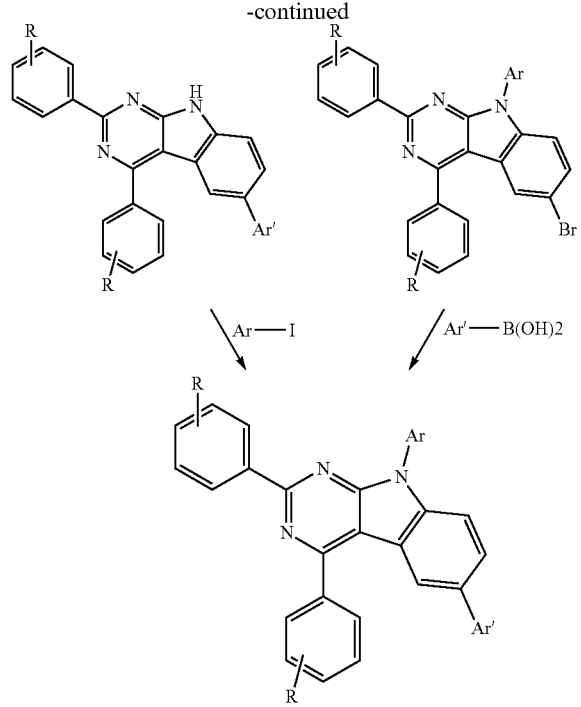

The compounds of the formula (1) may be synthesised starting from the literature-known compounds corresponding to halogenated diarylpyrimidoindole derivative (Synlett (2), 177-180, 2008). An aromatic/heteroaromatic group (Ar) may be then connected to the nitrogen atom by a C—N coupling reaction, like the Ullmann reaction, followed by the introduction of another aromatic/heteroaromatic group (Ar') introduced by a C—C coupling reaction, like a Suzuki coupling reaction. Alternatively, the group Ar' may be introduced before the group Ar.

These general processes described above for the synthesis of the compounds according to the invention are illustrative. The person skilled in the art will be able to develop alternative synthetic routes in the bounds of his general expert knowledge.

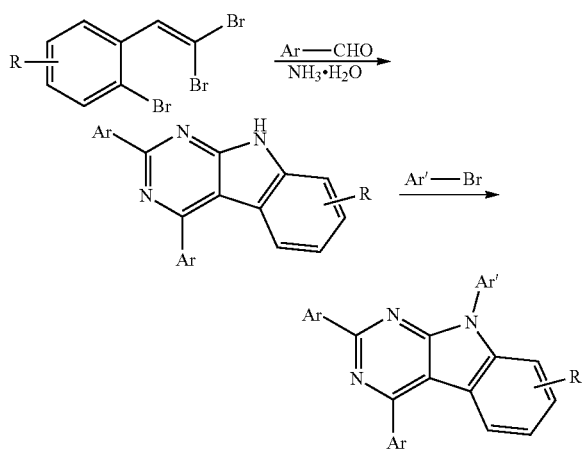

J. Org. Chem. 2015, 80, 5444-5456

An aromatic/heteroaromatic group is connected to the nitrogen atom of a literature-known compound (J. Org. Chem. 2015, 80, 5444-5456) by a C—N coupling reaction.

Scheme 3

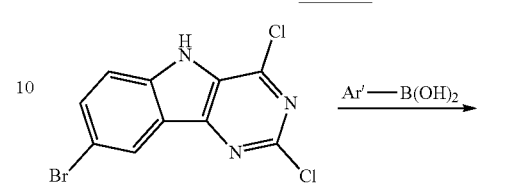

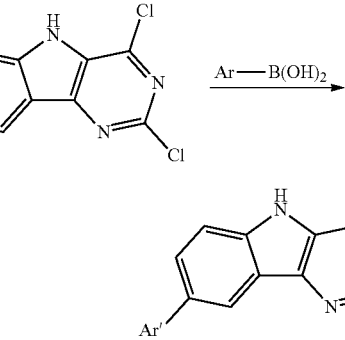

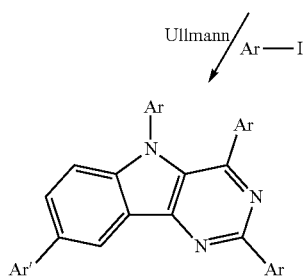

The starting product is a halogenated pyrimidoindole. Aromatic groups may be introduced by C—C coupling reactions, like a Suzuki coupling reaction and by C—N coupling reactions, like Ullmann reactions.

Scheme 4

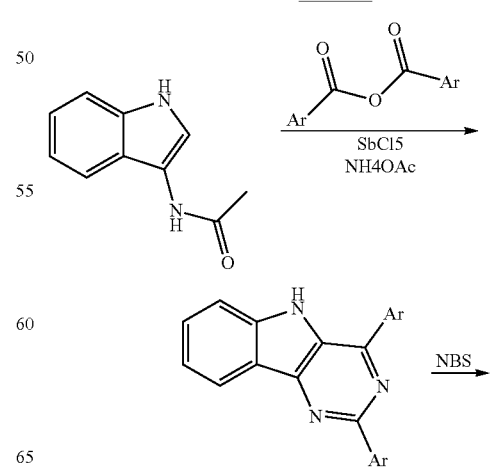

-continued

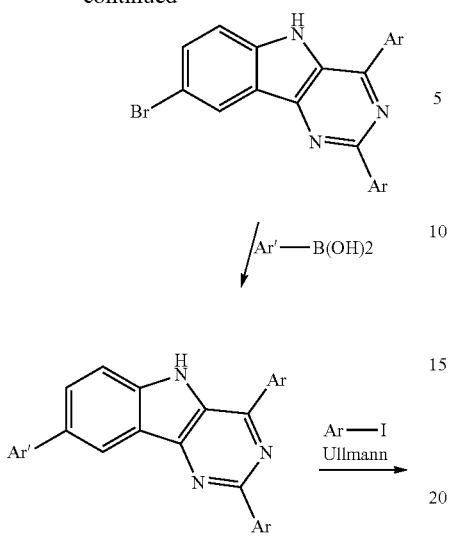

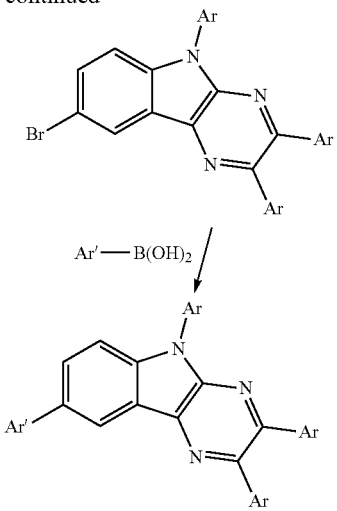

Asian Journal of Organic Chemistry, 2(7), 579-585; 2013
Advanced Synthesis & Catalysis, 352(18), 3241-3245; 2010
Asian Journal of Chemistry, 14(2), 1109-1110; 2002

The compounds of the formula (1) may be synthesised starting from the literature-known compounds corresponding to halogenated isatin derivatives (Asian Journal of Organic Chemistry, 2(7), 579-585, 2013 and Advance Synthesis and Catalysis, 352(18), 3241-3245, 2010 and Asian Journal of Chemistry, 14(2), 1109-1110, 2002). These compound may react with diaryl ethanediamine compounds in order to lead to diarylpyrimidoindole derivatives, where an aromatic/heteroaromatic group (Ar') may be introduced by a C—C coupling reaction, for example by a Suzuki coupling reaction.

The present invention therefore furthermore relates to a process for the synthesis of the compounds according to the invention, starting from a diarylpyrimidoindole derivative, in which an aromatic or heteroaromatic ring system is connected to the nitrogen atom of the 5-membered ring of the indole ring by a C—N coupling reaction and/or at least one aromatic or heteroaromatic ring system is connected to the diarylpyrimidoindole derivative via a C—C coupling reaction.

The C—N coupling reaction is preferably a Ullmann or Buchwald reaction and the C—C coupling reaction is preferably a Suzuki coupling reaction.

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, e-EROS Encyclopedia of Reagents for Organic Synthesis, 2001

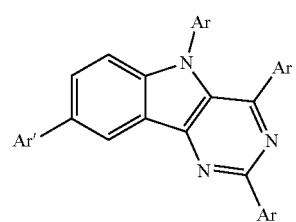

The compounds of the formula (1) may be synthesised starting from the literature-known compounds corresponding to diarylpyrimidoindole derivative (e-EROS Encyclopedia of Reagents for Organic Synthesis, 2001). The compound is halogenated and an aromatic/heteroaromatic group (Ar') is introduced by a C—C coupling reaction, like a Suzuki coupling reaction. An aromatic/heteroaromatic group (Ar') may be then be connected to the nitrogen atom by a C—N coupling reaction, like the Ullmann reaction.

Scheme 5

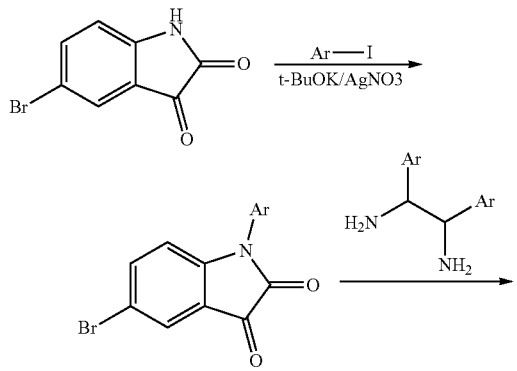

diethylene glycol dibutyl ether, triethylene glycol dimethyl ether, diethylene glycol-monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The present invention therefore furthermore relates to a formulation comprising a compound according to the invention and at least one further compound. The further compound may be, for example, a solvent, in particular one of the above-mentioned solvents or a mixture of these solvents. However, the further compound may also be at least one further organic or inorganic compound which is likewise employed in the electronic device, for example an emitting compound, in particular a phosphorescent dopant, and/or a further matrix material. Suitable emitting compounds and further matrix materials are indicated below in connection with the organic electroluminescent device. This further compound may also be polymeric.

The compounds and mixtures according to the invention are suitable for use in an electronic device. An electronic device here is taken to mean a device which comprises at least one layer which comprises at least one organic compound. However, the component here may also comprise inorganic materials or also layers built up entirely from inorganic materials.

The present invention therefore furthermore relates to the use of the compounds or mixtures according to the invention in an electronic device, in particular in an organic electroluminescent device.

The present invention again furthermore relates to an electronic device comprising at least one of the compounds or mixtures according to the invention mentioned above. The preferences stated above for the compound also apply to the electronic devices.

The electronic device is preferably selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitised solar cells, organic optical detectors, organic photoreceptors, organic field-quench devices (O-FQDs), light-emitting electrochemical cells (LECs), organic laser diodes (O-lasers) and "organic plasmon emitting devices" (D. M. Koller et al., *Nature Photonics* 2008, 1-4), preferably organic electroluminescent devices (OLEDs, PLEDs), in particular phosphorescent OLEDs.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. It is likewise possible for interlayers, which have, for example, an exciton-blocking function, to be introduced between two emitting layers. However, it should be pointed out that each of these layers does not necessarily have to be present. The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). These can be fluorescent or phosphorescent emission layers or hybrid systems, in which fluorescent and phosphorescent emission layers are combined with one another.

The compound according to the invention in accordance with the embodiments indicated above can be employed in various layers, depending on the precise structure. Preference is given to an organic electroluminescent device comprising a compound of the formula (1) or in accordance with the preferred embodiments as matrix material for fluorescent or phosphorescent emitters, in particular for phosphorescent emitters, and/or in an electron-transport layer and/or in an electron-blocking or exciton-blocking layer and/or in a hole-transport layer, depending on the precise substitution. The preferred embodiments indicated above also apply to the use of the materials in organic electronic devices.

In a preferred embodiment of the invention, the compound of the formula (1) or in accordance with the preferred embodiments is employed as matrix material for a fluorescent or phosphorescent compound, in particular for a phosphorescent compound, in an emitting layer. The organic electroluminescent device here may comprise one emitting layer or a plurality of emitting layers, where at least one emitting layer comprises at least one compound according to the invention as matrix material.

If the compound of the formula (1) or in accordance with the preferred embodiments is employed as matrix material for an emitting compound in an emitting layer, it is preferably employed in combination with one or more phosphorescent materials (triplet emitters). Phosphorescence in the sense of this invention is taken to mean the luminescence from an excited state having spin multiplicity>1, in particular from an excited triplet state. For the purposes of this application, all luminescent transition-metal complexes and luminescent lanthanide complexes, in particular all iridium, platinum and copper complexes, are to be regarded as phosphorescent compounds.

The mixture comprising the compound of the formula (1) or in accordance with the preferred embodiments and the emitting compound comprises between 99 and 1% by vol., preferably between 98 and 10% by vol., particularly preferably between 97 and 60% by vol., in particular between 95 and 80% by vol., of the compound of the formula (1) or in accordance with the preferred embodiments, based on the entire mixture comprising emitter and matrix material. Correspondingly, the mixture comprises between 1 and 99% by vol., preferably between 2 and 90% by vol., particularly preferably between 3 and 40% by vol., in particular between 5 and 20% by vol., of the emitter, based on the entire mixture comprising emitter and matrix material.

A further preferred embodiment of the present invention is the use of the compound of the formula (1) or in accordance with the preferred embodiments as matrix material for a phosphorescent emitter in combination with a further matrix material. Particularly suitable matrix materials which can be employed in combination with the compounds of the formula (1) or in accordance with the preferred embodiments are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109 and WO 2011/000455, azacarbazole derivatives, for example in accordance with EP 1617710, EP 1617711, EP 1731584, JP 2005/347160, bipolar matrix materials, for example in accordance with WO 2007/137725, silanes, for example in accordance with WO 005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with US 2009/0136779, WO 2010/050778, WO 2011/042107, WO 2011/088877 or in accordance with the unpublished application EP 11003232.3, triphenylene derivatives, for example in accordance with WO 2012/048781, or lactams, for example in accordance with WO 2011/116865 or WO 2011/137951. A further phosphorescent emitter which emits at shorter wavelength than the actual emitter may likewise be present in the mixture as co-host.

Preferred co-host materials are triarylamine derivatives, in particular monoamines, lactams, carbazole derivatives and indenocarbazole derivatives.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescent emitters used are preferably compounds which contain copper, molybdenum, tungsten, rhenium, ruthenium, osmium, rhodium, iridium, palladium, platinum, silver, gold or europium, in particular compounds which contain iridium or platinum. For the purposes of the present invention, all luminescent compounds which contain the above-mentioned metals are regarded as phosphorescent compounds.

Examples of the emitters described above are revealed by the applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094962, WO 2014/094961 or WO 2014/094960. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is identical or similar to the metal complex in the emitting layer as hole-transport or hole-injection material directly adjacent to the emitting layer, as described, for example, in WO 2009/030981.

It is furthermore possible to employ the compounds according to the invention in a hole-blocking or electron-transport layer. This applies, in particular, to compounds according to the invention which do not have a carbazole structure. These may preferably also be substituted by one or more further electron-transporting groups, for example benzimidazole groups.

In the further layers of the organic electroluminescent device according to the invention, it is possible to use all materials as usually employed in accordance with the prior art. The person skilled in the art will therefore be able, without inventive step, to employ all materials known for organic electroluminescent devices in combination with the compounds of the formula (1) or in accordance with the preferred embodiments.

Preference is furthermore given to an organic electroluminescent device, characterised in that one or more layers are applied by means of a sublimation process, in which the materials are vapour-deposited in vacuum sublimation units at an initial pressure of less than $10^{-5}$ mbar, preferably less than $10^{-6}$ mbar. However, it is also possible for the initial pressure to be even lower or higher, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, ink-jet printing, LITI (light induced thermal imaging, thermal transfer printing), screen printing, flexographic printing, offset printing or nozzle printing. Soluble compounds, which are obtained, for example, by suitable substitution, are necessary for this purpose.

Also possible are hybrid processes, in which, for example, one or more layers are applied from solution and one or more further layers are applied by vapour deposition. Thus, it is possible, for example, to apply the emitting layer from solution and to apply the electron-transport layer by vapour deposition.

These processes are generally known to the person skilled in the art and can be applied by him without inventive step to organic electroluminescent devices comprising the compounds according to the invention.

The compounds according to the invention generally have very good properties on use in organic electroluminescent devices. In particular, the lifetime on use of the compounds according to the invention in organic electroluminescent devices is significantly better compared with similar compounds in accordance with the prior art. The other properties of the organic electroluminescent device, in particular the efficiency and the voltage, are likewise better or at least comparable. Furthermore, the compounds have a high glass transition temperature and high thermal stability.

The invention will now be explained in greater detail by the following examples, without wishing to restrict it thereby.

SYNTHESES EXAMPLES

The following syntheses are carried out, unless indicated otherwise, under a protective-gas atmosphere in dried solvents. The solvents and reagents can be purchased, for example, from Sigma-ALDRICH or ABCR. The corresponding CAS numbers are also indicated in each case from the compounds known from the literature.

a) 5-bromo-1-phenyl-1H-indole-2,3-dione

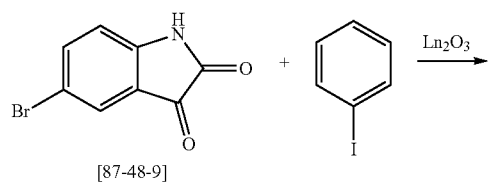

[87-48-9]

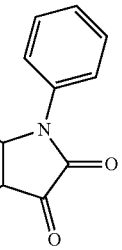

24.5 g (120.0 mmol) of iodobenzene, 4 g (12 mmol) of lanthanum oxide are dissolved in 200 mL of DMSO and suspended with 22.6 g (100 mmol) of 5-bromo-1H-indole-2,3-dione. Subsequently, 2.1 g (24 mmol) DMEDA and 2 equiv. KOH are added to the reaction mixture under a protective gas atmosphere and the reaction mixture is heated for 12 h at 110° C. After cooling, ethyl acetate and water are added to the mixture. Subsequently, the organic phase is separated off, filtered through silica gel, washed three times with 200 ml of water and evaporated to dryness. The residue is recrystallised from toluene and dichloromethane/Heptane. The yield is 20.7 g (68 mmol), corresponding to 69% of theory.

The following compounds are prepared analogously:

| | Reactant 1 | Reactant 2 | Product | Yield |
|---|---|---|---|---|
| 1a | (5-bromo-1H-indole-2,3-dione) | (3-iodo-9-phenyl-9H-carbazole) [502161-03-7] | (5-bromo-1-(9-phenyl-9H-carbazol-3-yl)-1H-indole-2,3-dione) | 68% |
| 2a | (5-bromo-1H-indole-2,3-dione) | (2-chloro-4,6-diphenyl-1,3,5-triazine) [83819-97-0] | (5-bromo-1-(4,6-diphenyl-1,3,5-triazin-2-yl)-1H-indole-2,3-dione) | 56% |

-continued

| | Reactant 1 | Reactant 2 | Product | Yield |
|---|---|---|---|---|
| 3a | 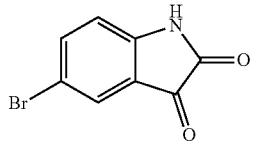 [SMILES: O=C1Nc2ccc(Br)cc2C1=O] | 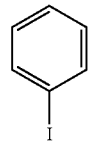 | 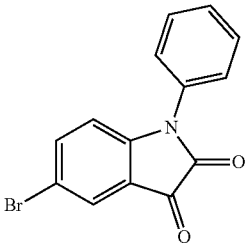 | 69% | b) 8-bromo-2,3,5-triphenyl-5H-pyrazino[2,3-b]indole

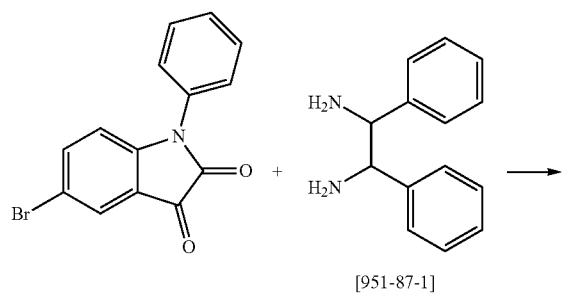

[951-87-1]

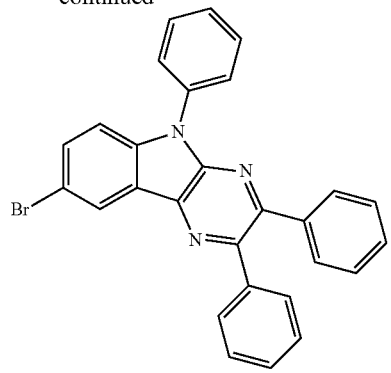

11.8 g (35 mmol) of 5-bromo-1-phenyl-1H-indole-2,3-dione, 7.5 g (35 mmol) of 1,2-diphenyl-1,2-ethanediamine are dissolved in 200 ml of ethanol under a protective gas atmosphere and under reflux for 6 hours. After cooling, the solution is concentrated and the residue is recrystallized from ethanol. The yield is 7.8 g (16 mmol), corresponding to 42% of theory.

The following compounds are prepared analogously:

| | Reactant 1 | Reactant 2 | Product | Yield |
|---|---|---|---|---|
| 1b | 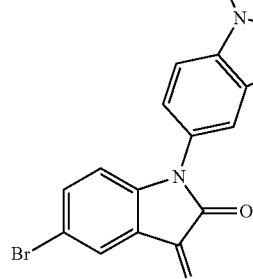 | 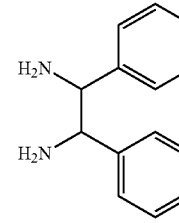<br>[951-87-1] | 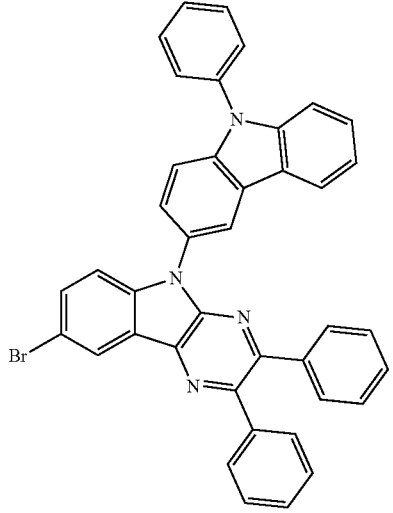 [SMILES: Brc1ccc2c(c1)c1nc(-c3ccccc3)c(-c3ccccc3)nc1n2-c1ccc2c(c1)c1ccccc1n2-c1ccccc1] | 64% |

-continued

| | Reactant 1 | Reactant 2 | Product | Yield |
|---|---|---|---|---|
| 2b | 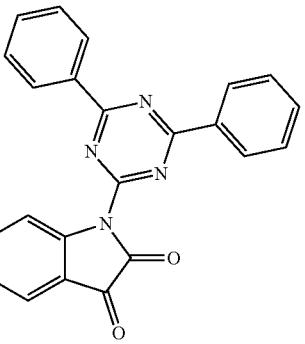 | 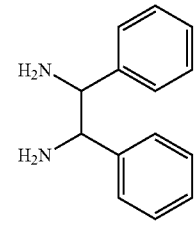 [951-87-1] | 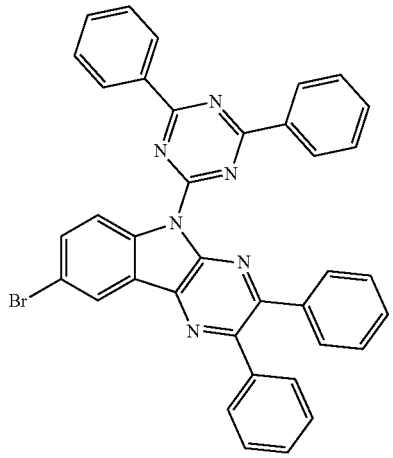 [SMILES: Brc1ccc2c(c1)c1nc(-c3ccccc3)c(-c3ccccc3)nc1n2-c1nc(-c2ccccc2)nc(-c2ccccc2)n1] | 59% |
| 3b | 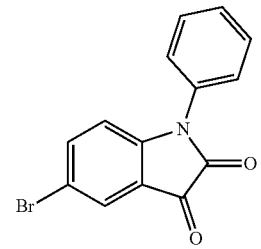 [SMILES: O=C1C(=O)N(c2ccccc2)c2ccc(Br)cc21] | 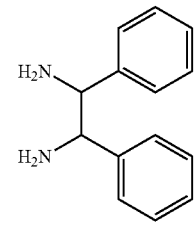 [SMILES: NC(c1ccccc1)C(N)c1ccccc1] [951-87-1] | 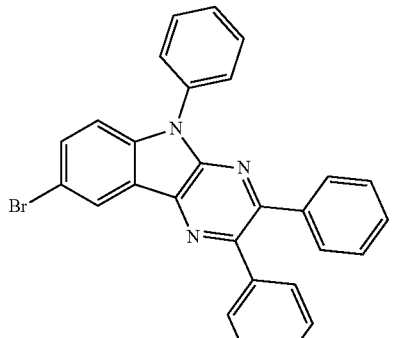 | 62% |
| 4b | 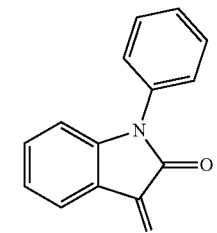 [723-89-7] | 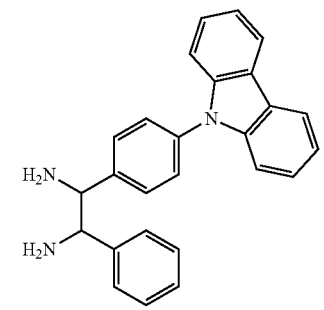 [SMILES: NC(c1ccccc1)C(N)c1ccc(-n2c3ccccc3c3ccccc32)cc1] | 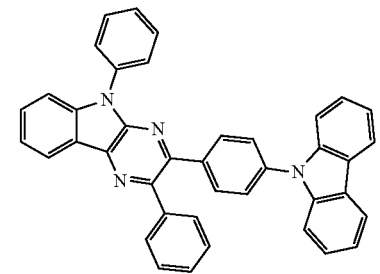 [SMILES: c1ccc(-c2nc3c4ccccc4n(-c4ccccc4)c3nc2-c2ccc(-n3c4ccccc4c4ccccc43)cc2)cc1] | 41% | c) 2,4-diphenyl-9H-pyrimido[4,5-b]indole 13.5 g (120.0 mmol) of phenylboronic acid, 14.2 g (60 mmol) of 2,4-dichloro-benzo [4,5] furo [3,2-d] pyrimidine and 21 g (210.0 mmol) of sodium carbonate are suspended in 500 mL water and 500 mL ethylene glycol diethyl ether. Subsequently, 914 mg (3.0 mmol) of tri-o-tolylphosphine and 113 mg (0.5 mmol) of palladium (II) acetate are added to the mixture, which is heated under reflux for 16 h. After cooling, the organic phase is separated off, filtered through silica gel, washed three times with 200 mL water and then evaporated to dryness. The residue is recrystallized from toluene and dichloromethane/heptane. Yield: 15.8 g (49 mmol), 82% of theory.

The following compounds are prepared analogously:
| | Reactant 1 | Reactant 2 | Product | Yield |
|---|---|---|---|---|
| 1c | 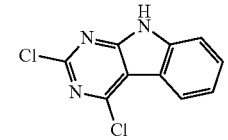 [SMILES: Clc1nc(Cl)c2c(n1)[nH]c1ccccc12]<br>74894-26-1 | 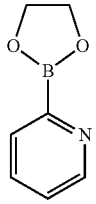<br>[317810-27-8] | 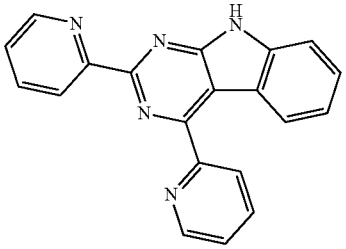 [SMILES: c1ccc(-c2nc(-c3ccccn3)c3c(n2)[nH]c2ccccc23)nc1] | 75% |
| 2c | 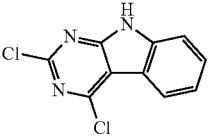 [SMILES: Clc1nc(Cl)c2c(n1)[nH]c1ccccc12]<br>74894-26-1 | 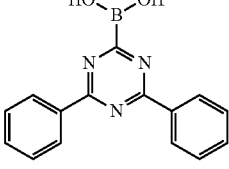<br>[1251825-65-6] | 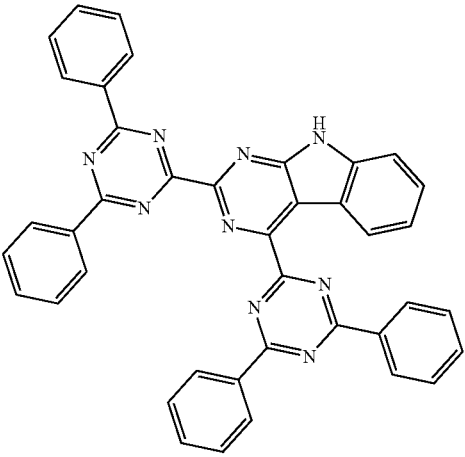 [SMILES: c1ccc(-c2nc(-c3ccccc3)nc(-c3nc(-c4nc(-c5ccccc5)nc(-c5ccccc5)n4)c4c(n3)[nH]c3ccccc34)n2)cc1] | 80% |
| 3c | 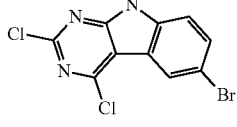 | 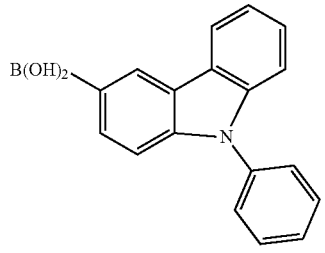 [SMILES: OB(O)c1ccc2c(c1)c1ccccc1n2-c1ccccc1]<br>854952-58-2 | 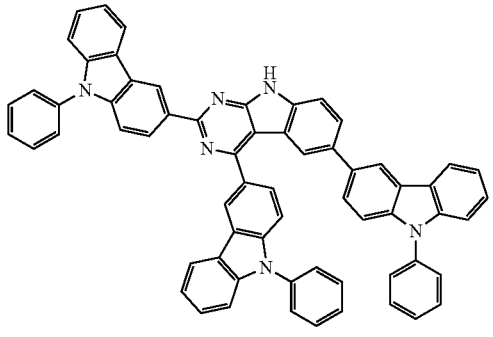 [SMILES: c1ccc(-n2c3ccccc3c3cc(-c4ccc5[nH]c6nc(-c7ccc8c(c7)c7ccccc7n8-c7ccccc7)nc(-c7ccc8c(c7)c7ccccc7n8-c7ccccc7)c6c5c4)ccc32)cc1] | 70% |
| 4c | 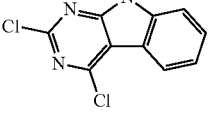<br>74894-26-1 | 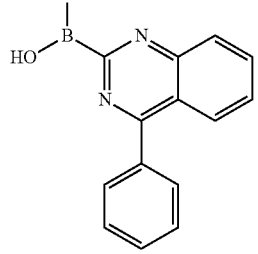<br>[1629973-75-6] | 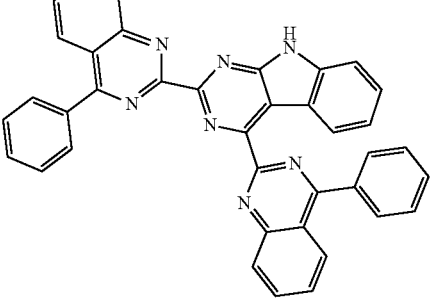 | 81% |

-continued
| | Reactant 1 | Reactant 2 | Product | Yield |
|---|---|---|---|---|
| 5c | 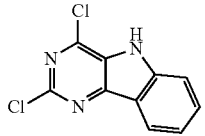 [SMILES: Clc1nc(Cl)c2[nH]c3ccccc3c2n1] [1034194-21-2] | 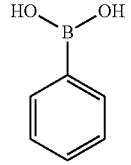 | 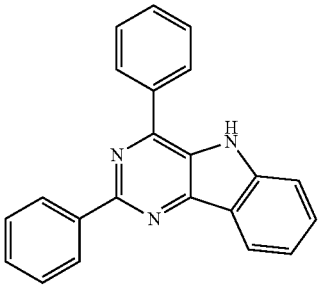 [SMILES: c1ccc(-c2nc(-c3ccccc3)c3[nH]c4ccccc4c3n2)cc1] | 77% |
| 6c | 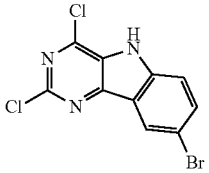 [SMILES: Clc1nc(Cl)c2[nH]c3ccc(Br)cc3c2n1] | 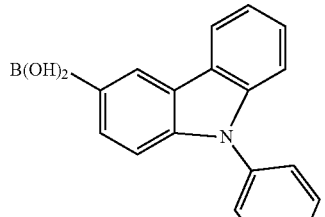 854952-58-2 | 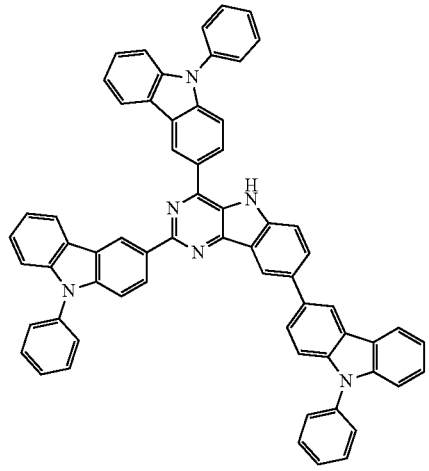 [SMILES: c1ccc(-n2c3ccccc3c3cc(-c4ccc5[nH]c6c(-c7ccc8c(c7)c7ccccc7n8-c7ccccc7)nc(-c7ccc8c(c7)c7ccccc7n8-c7ccccc7)nc6c5c4)ccc32)cc1] | 76% |
| 7c | 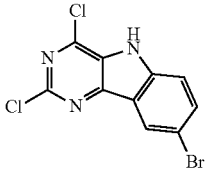 [SMILES: Clc1nc(Cl)c2[nH]c3ccc(Br)cc3c2n1] | 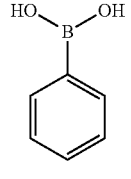 | 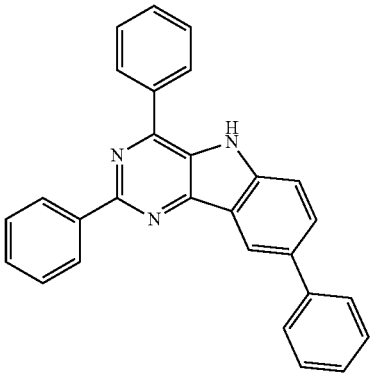 [SMILES: c1ccc(-c2ccc3[nH]c4c(-c5ccccc5)nc(-c5ccccc5)nc4c3c2)cc1] | 83% |
| 8c | 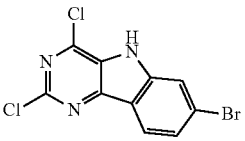 [SMILES: Clc1nc(Cl)c2[nH]c3cc(Br)ccc3c2n1] [1034194-00-7] | 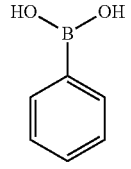 | 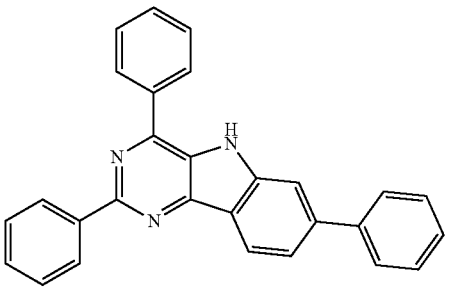 [SMILES: c1ccc(-c2ccc3c(c2)[nH]c2c(-c4ccccc4)nc(-c4ccccc4)nc23)cc1] | 84% |

-continued

| | Reactant 1 | Reactant 2 | Product | Yield |
|---|---|---|---|---|
| 9c | (structure) | (structure) | (structure) | 82% |
| 10c | (structure) | (structure) 854952-58-2 | (structure) | 42% |
| 11c | (structure) | (structure) | (structure) | 44% |
| 12c | (structure) [1034194-21-2] | (structure) [57102-42-8] | (structure) | 54% |
| 13c | (structure) 74894-26-1 | (structure) | (structure) | 52% |

-continued
| Reactant 1 | Reactant 2 | Product | Yield |
|---|---|---|---|
| 14c 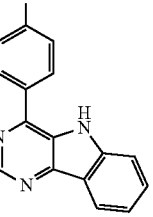 | 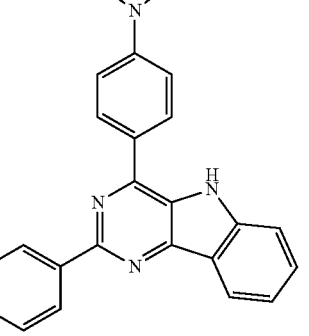 | 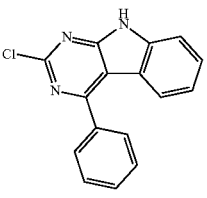 [SMILES: Clc1nc(-c2ccccc2)c2c(n1)[nH]c1ccccc12] | 57% |
| 15c 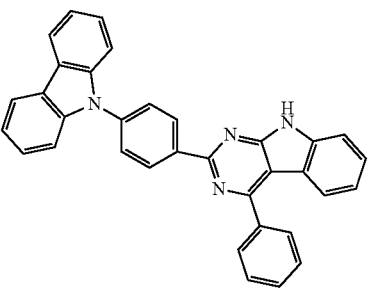 [SMILES: c1ccc(-c2nc(-c3ccc(-n4c5ccccc5c5ccccc54)cc3)nc3[nH]c4ccccc4c23)cc1] | 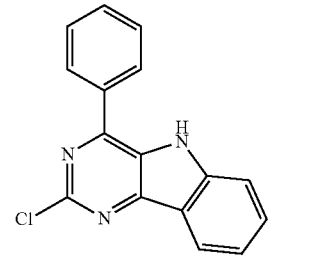 [SMILES: Clc1nc(-c2ccccc2)c2[nH]c3ccccc3c2n1] [57102-42-8] | 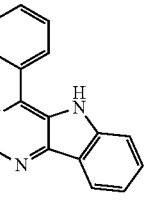 | 66% |
| 16c 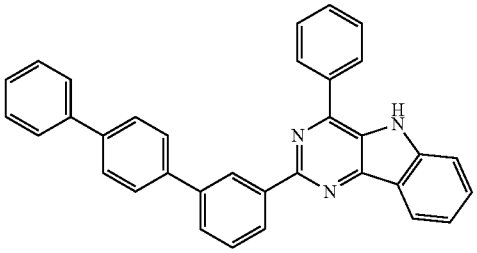 [SMILES: c1ccc(-c2ccc(-c3cccc(-c4nc(-c5ccccc5)c5[nH]c6ccccc6c5n4)c3)cc2)cc1] [1034194-21-2] | HO-B-OH [phenylboronic acid structure] | [product structure] | 54% |
| 17c [chloro pyrimido indole with phenyl] | [biphenyl boronic acid] [881911-81-5] | [terphenyl pyrimido indole product] | 62% | d) 6-bromo-2,4-diphenyl-9H-pyrimido[4,5-b]indole

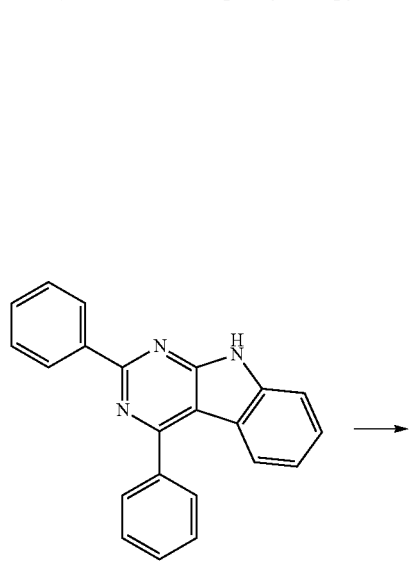

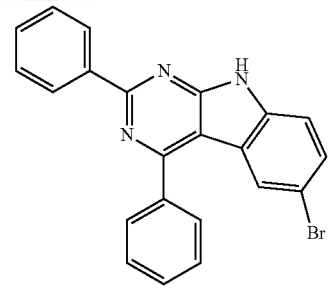

61 g (190.0 mmol) of 2,4-diphenyl-5H-pyrimido[5,4-b] indole are suspended in 2000 ml of acetic acid (100%) and 2000 ml of sulfuric acid (95-98%). Subsequently, 34 g (190 mmol) of NBS is slowly added to the mixture, which is then stirred for 2 hours in darkness. The mixture is then mixed with water/ice and the crude product is separated off and washed with ethanol. Afterwards, the residue is recrystallized from toluene. The yield is 65 g (163 mmol), corresponding to 86% of theory.

The following compounds are prepared analogously:

| | Reactant | Product | Yield |
|---|---|---|---|
| 1d | (structure)<br>74894-26-1 | (structure) | 59% |
| 2d | (structure) | (structure) | 67% |
| 3d | (structure) | (structure) | 64% |

-continued

| | Reactant | Product | Yield |
|---|---|---|---|
| 4d | | | 46% |
| 5d | | | 69% | e) 6-bromo-2,4-diphenyl-9H-pyrimido[4,5-b]indole

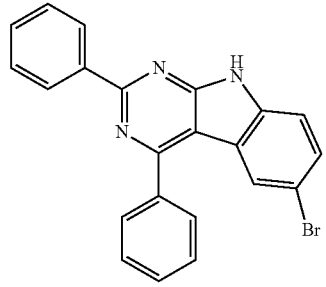

-continued

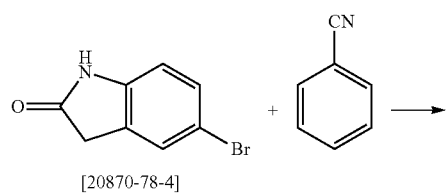

[20870-78-4]

A mixture consisting of 21.2 g (100 mmol) of 5-bromo-1,3-dihydro-2H-indol-2-one, 31 g (300 mmol) of benzonitrile and 2 ml of a saturated NaOH solution is heated in the microwave for 4 min at 180° C. (Synlett, 2008 from 2.177 to 180). After cooling, the organic phase is purified by column chromatography on silica gel with ethyl acetate/heptane (1:4) and recrystallized in ethanol. The yield is 30 g (76 mmol), corresponding to 77% of theory.

The following compounds are prepared analogously:

| | Reactant 1 | Reactant 2 |
|---|---|---|
| 1e | | [1132943-23-7] |

-continued
| | 155 | 156 |
|---|---|---|
| 2e | 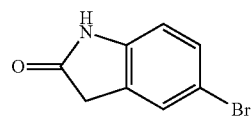 [SMILES: O=C1Cc2cc(Br)ccc2N1] | 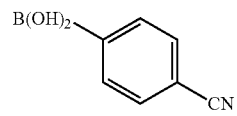 [SMILES: N#Cc1ccc(B(O)O)cc1]<br>[126747-14-6] |
| 3e | 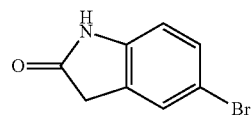 [SMILES: O=C1Cc2cc(Br)ccc2N1] | 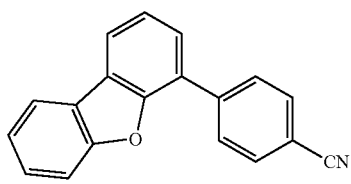 [SMILES: N#Cc1ccc(-c2cccc3c2oc2ccccc23)cc1]<br>[578026-69-4] |
| 4e | 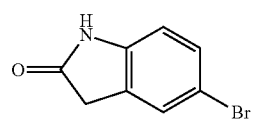 [SMILES: O=C1Cc2cc(Br)ccc2N1] | 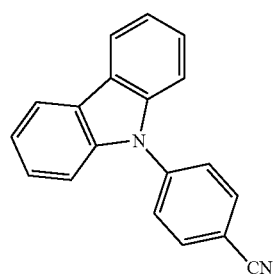 [SMILES: N#Cc1ccc(-n2c3ccccc3c3ccccc32)cc1]<br>[57103-17-0] |
| 5e | 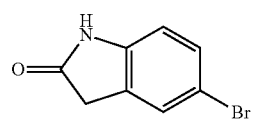 [SMILES: O=C1Cc2cc(Br)ccc2N1] | 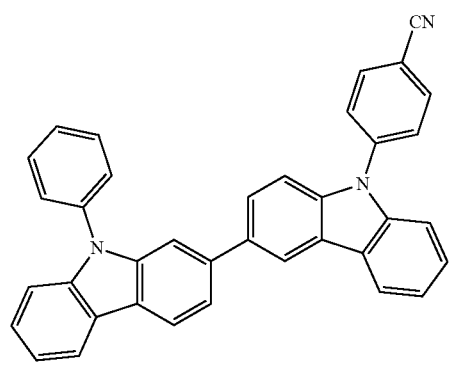 [SMILES: N#Cc1ccc(-n2c3ccccc3c3cc(-c4ccc5c6ccccc6n(-c6ccccc6)c5c4)ccc32)cc1]<br>[1443045-28-0] |
| 6e | 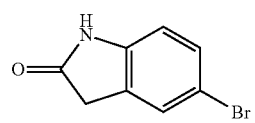 [SMILES: O=C1Cc2cc(Br)ccc2N1] | 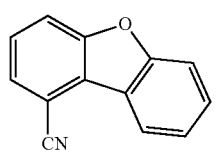 [SMILES: N#Cc1cccc2oc3ccccc3c12]<br>[141104-58-7] |

| | -continued | |
|---|---|---|
| | Product | Yield |
| 1e | (structure) | 67% |
| 2e | (structure) | 74% |
| 3e | (structure) | 72% |

-continued
| | | |
|---|---|---|
| 4e | 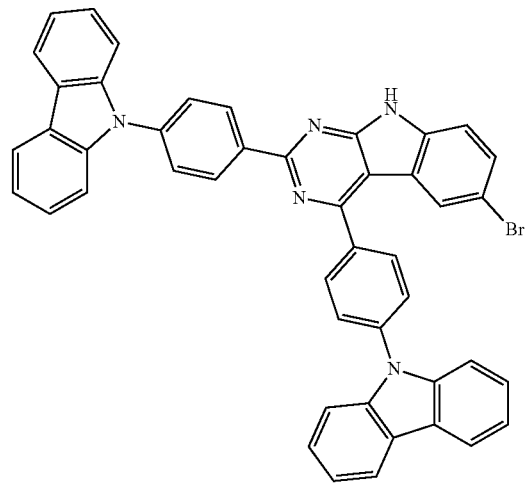 [SMILES: Brc1ccc2[nH]c3nc(-c4ccc(-n5c6ccccc6c6ccccc65)cc4)nc(-c4ccc(-n5c6ccccc6c6ccccc65)cc4)c3c2c1] | 65% |
| 5e | 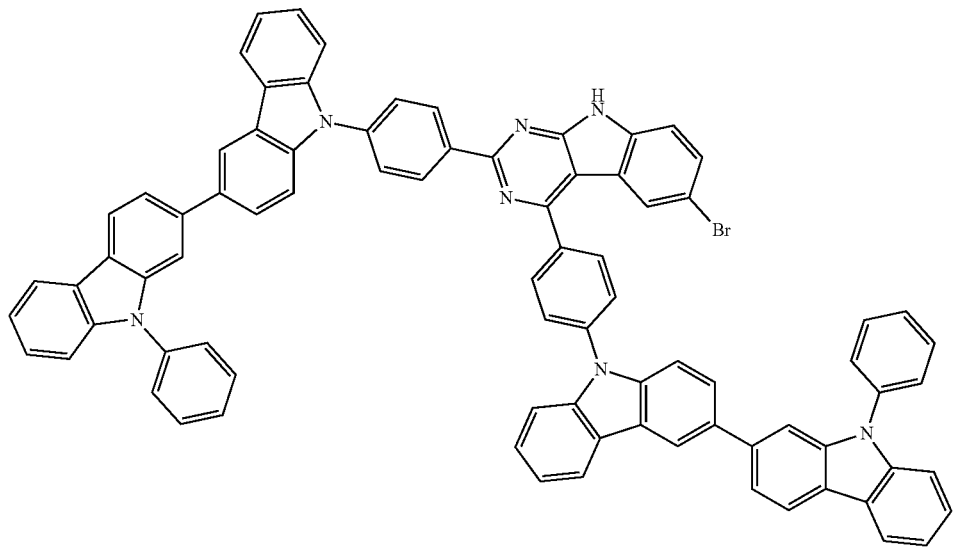 [SMILES: Brc1ccc2[nH]c3nc(-c4ccc(-n5c6ccccc6c6cc(-c7ccc8c9ccccc9n(-c9ccccc9)c8c7)ccc65)cc4)nc(-c4ccc(-n5c6ccccc6c6cc(-c7ccc8c9ccccc9n(-c9ccccc9)c8c7)ccc65)cc4)c3c2c1] | 53% |
| 6e | 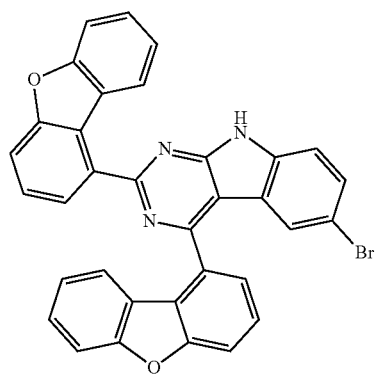 [SMILES: Brc1ccc2[nH]c3nc(-c4cccc5oc6ccccc6c45)nc(-c4cccc5oc6ccccc6c45)c3c2c1] | 68% | f) 2,4-diphenyl-6-(9-phenyl-9H-carbazol-3-yl)-9H-pyrimido[4,5-b]indole

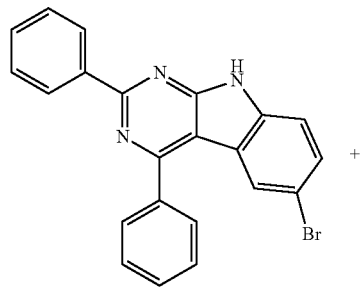

+

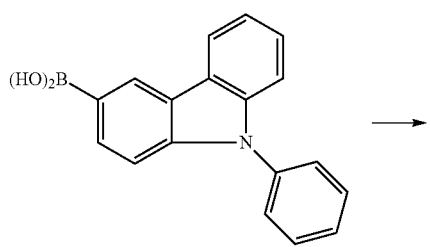

[854952-58-2]

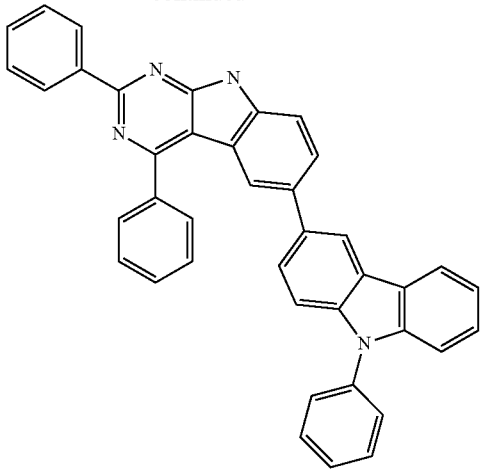

74.3 g (156 mmol) of 6-bromo-2,4-diphenyl-9H-pyrimido[4,5-b] indole, 50 g (172 mmol) of N-phenyl-carbazol-3-boronic acid and 36 g (340 mmol) of sodium carbonate are suspended in 1000 mL ethylene glycol diethyl ether and 280 mL water. Subsequently, 1.8 g (1.5 mmol) of tetrakis(triphenylphosphine)-palladium(0) are added to the reaction mixture, which is heated under reflux for 16 h. After cooling, the organic phase is separated off, filtered through silica gel and then evaporated to dryness. The product is then purified by chromatography on silica gel with toluene/heptane (1:2). The yield is 65 g (102 mmol), corresponding to 66% of theory.

The following compounds are prepared analogously:

| | Reactant 1 | Reactant 2 |
|---|---|---|
| 1f | 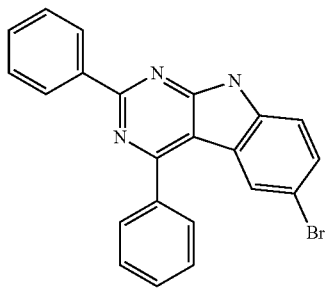 [SMILES: Brc1ccc2[nH]c3nc(-c4ccccc4)nc(-c4ccccc4)c3c2c1] | 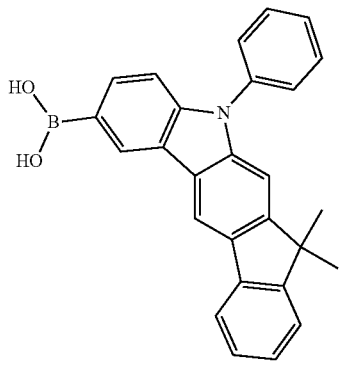 [SMILES: CC1(C)c2ccccc2-c2cc3c4cc(B(O)O)ccc4n(-c4ccccc4)c3cc21] [1379585-25-7] |
| 2f | 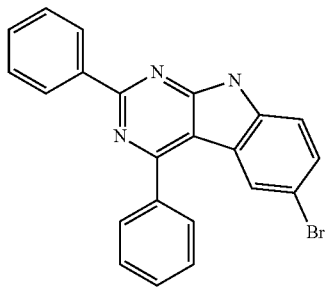 [SMILES: Brc1ccc2[nH]c3nc(-c4ccccc4)nc(-c4ccccc4)c3c2c1] | 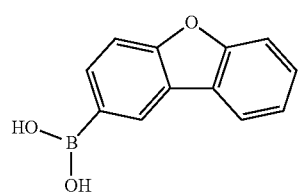 [SMILES: OB(O)c1ccc2oc3ccccc3c2c1] [402936-15-6] |

| | | |
|---|---|---|
| 3f | 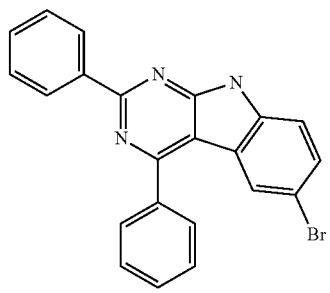 [SMILES: Brc1ccc2[nH]c3nc(-c4ccccc4)nc(-c4ccccc4)c3c2c1] | 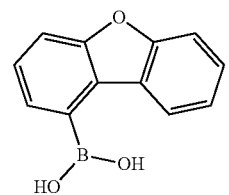 [SMILES: OB(O)c1cccc2oc3ccccc3c12]
[162607-19-4] |
| 4f | 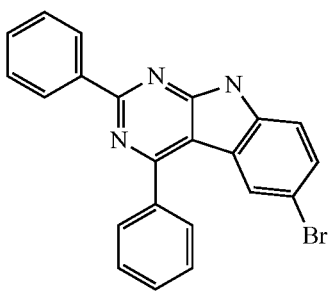 [SMILES: Brc1ccc2[nH]c3nc(-c4ccccc4)nc(-c4ccccc4)c3c2c1] | 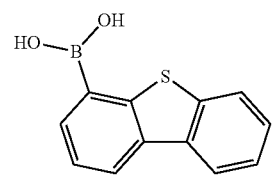 [SMILES: OB(O)c1cccc2c1sc1ccccc12]
[108847-20-7] |
| 5f | 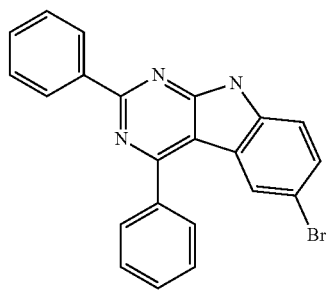 [SMILES: Brc1ccc2[nH]c3nc(-c4ccccc4)nc(-c4ccccc4)c3c2c1] | 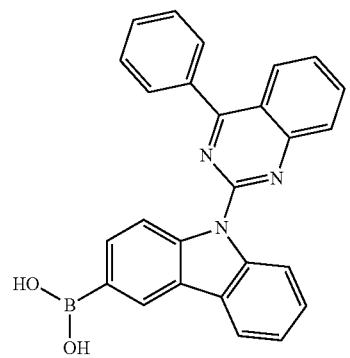 [SMILES: OB(O)c1ccc2c(c1)c1ccccc1n2-c1nc(-c2ccccc2)c2ccccc2n1]
[1642121-58-1] |
| 6f | 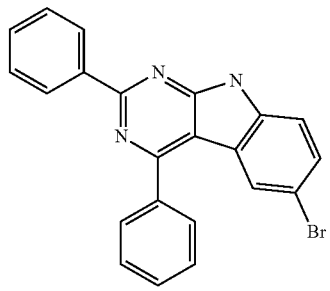 [SMILES: Brc1ccc2[nH]c3nc(-c4ccccc4)nc(-c4ccccc4)c3c2c1] | 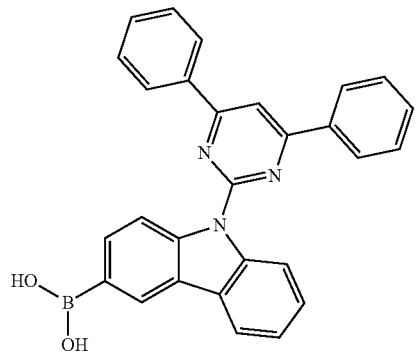 [SMILES: OB(O)c1ccc2c(c1)c1ccccc1n2-c1nc(-c2ccccc2)cc(-c2ccccc2)n1]
[1266389-16-5] |

| | | |
|---|---|---|
| 7f | 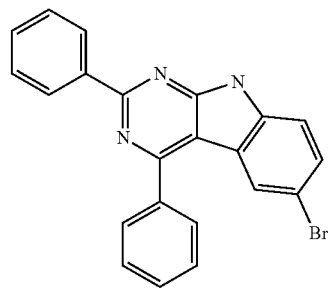 [SMILES: Brc1ccc2[nH]c3nc(-c4ccccc4)nc(-c4ccccc4)c3c2c1] | 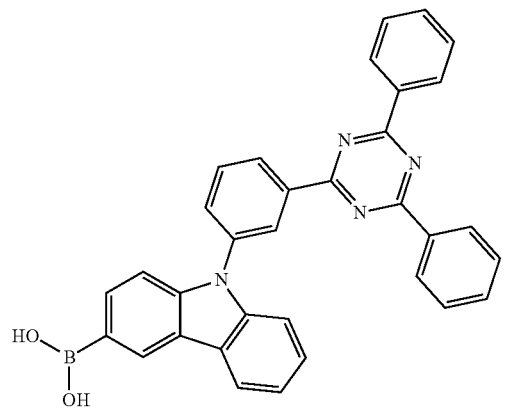 [SMILES: OB(O)c1ccc2c(c1)c1ccccc1n2-c1cccc(-c2nc(-c3ccccc3)nc(-c3ccccc3)n2)c1]
[1642121-53-6] |
| 8f | 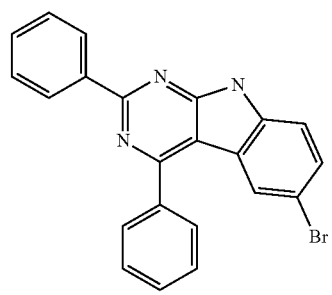 [SMILES: Brc1ccc2[nH]c3nc(-c4ccccc4)nc(-c4ccccc4)c3c2c1] | 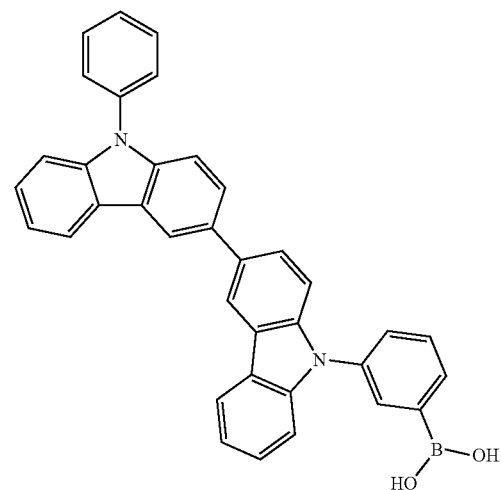 [SMILES: OB(O)c1cccc(-n2c3ccccc3c3cc(-c4ccc5c(c4)c4ccccc4n5-c4ccccc4)ccc32)c1]
[1398394-64-3] |
| 9f | 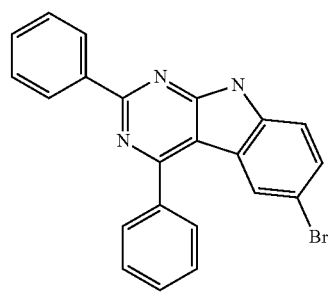 [SMILES: Brc1ccc2[nH]c3nc(-c4ccccc4)nc(-c4ccccc4)c3c2c1] | 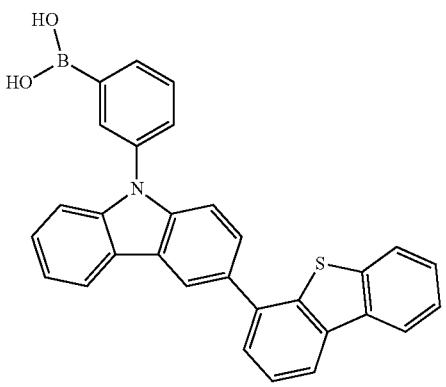 [SMILES: OB(O)c1cccc(-n2c3ccccc3c3cc(-c4cccc5c4sc4ccccc45)ccc32)c1]
[1420067-45-3] |

-continued
10f
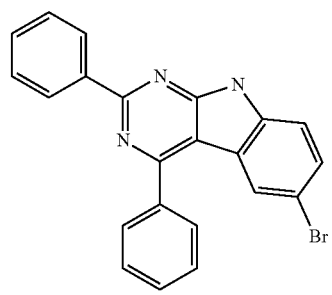 [SMILES: Brc1ccc2[nH]c3nc(-c4ccccc4)nc(-c4ccccc4)c3c2c1]
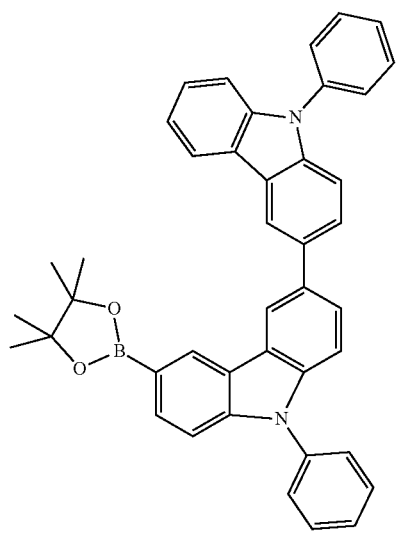 [SMILES: CC1(C)OB(c2ccc3c(c2)c2cc(-c4ccc5c(c4)c4ccccc4n5-c4ccccc4)ccc2n3-c2ccccc2)OC1(C)C]
[1572537-61-1]
11f
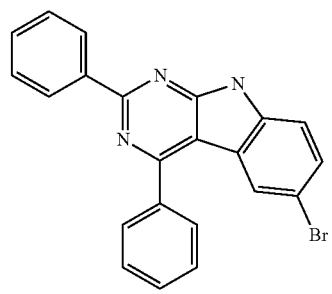 [SMILES: Brc1ccc2[nH]c3nc(-c4ccccc4)nc(-c4ccccc4)c3c2c1]
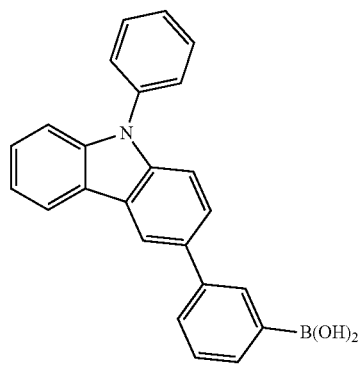 [SMILES: OB(O)c1cccc(-c2ccc3c(c2)c2ccccc2n3-c2ccccc2)c1]
12f
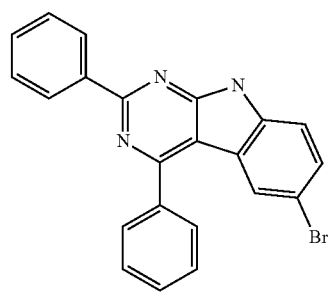 [SMILES: Brc1ccc2[nH]c3nc(-c4ccccc4)nc(-c4ccccc4)c3c2c1]
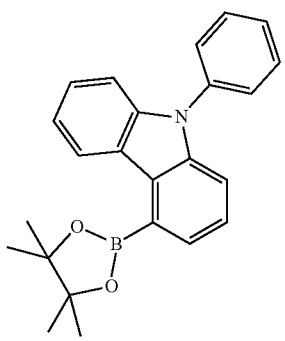 [SMILES: CC1(C)OB(c2cccc3c2c2ccccc2n3-c2ccccc2)OC1(C)C]
[1547492-13-6]

-continued
13f
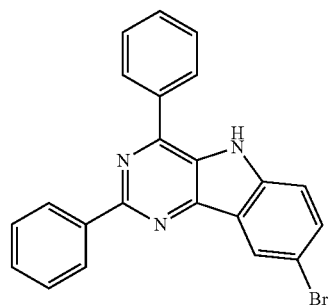 [SMILES: Brc1ccc2[nH]c3c(-c4ccccc4)nc(-c4ccccc4)nc3c2c1]
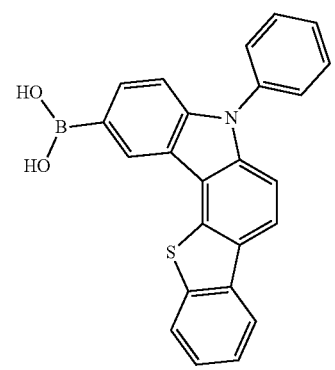
[1391729-63-7]
14f
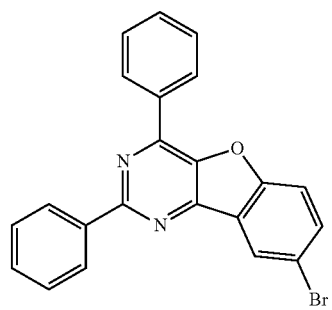 [SMILES: Brc1ccc2oc3c(-c4ccccc4)nc(-c4ccccc4)nc3c2c1]
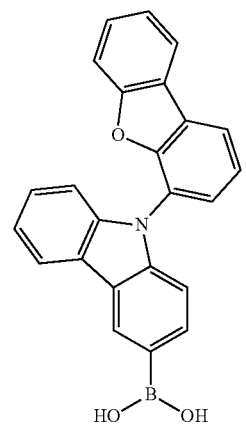 [SMILES: OB(O)c1ccc2c(c1)c1ccccc1n2-c1cccc2c1oc1ccccc12]
[1547397-15-8]
15f
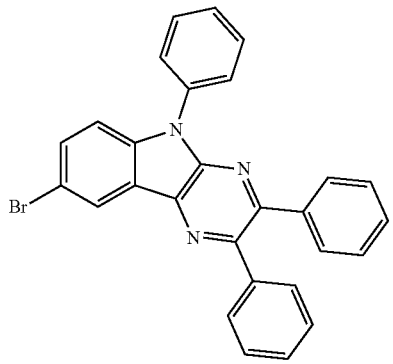 [SMILES: Brc1ccc2c(c1)c1nc(-c3ccccc3)c(-c3ccccc3)nc1n2-c1ccccc1]
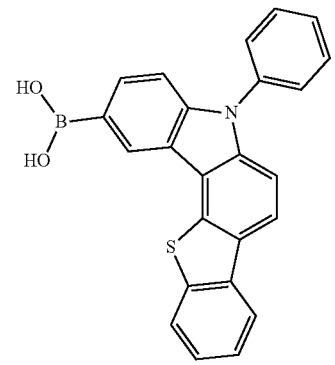 [SMILES: OB(O)c1ccc2c(c1)c1c3sc4ccccc4c3ccc1n2-c1ccccc1]
[1391729-63-7]

-continued
16f
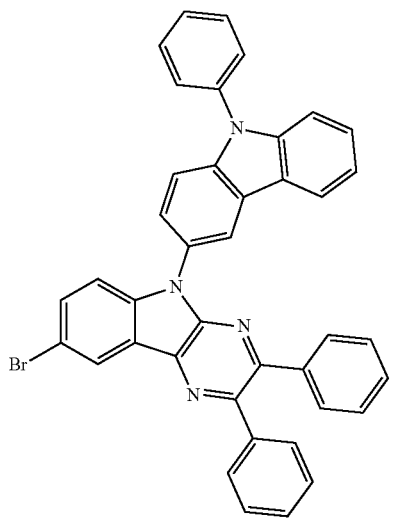 [SMILES: Brc1ccc2c(c1)c1nc(-c3ccccc3)c(-c3ccccc3)nc1n2-c1ccc2c(c1)c1ccccc1n2-c1ccccc1]
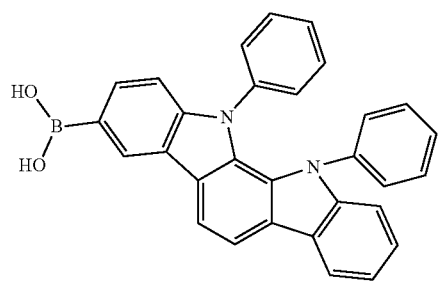 [SMILES: OB(O)c1ccc2c(c1)c1ccc3c4ccccc4n(-c4ccccc4)c3c1n2-c1ccccc1]
[1373359-67-1]
17f
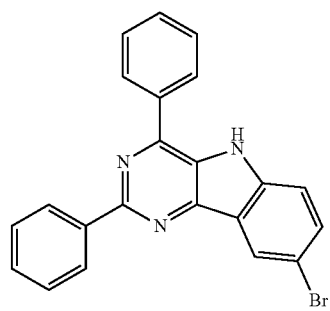 [SMILES: Brc1ccc2[nH]c3c(-c4ccccc4)nc(-c4ccccc4)nc3c2c1]
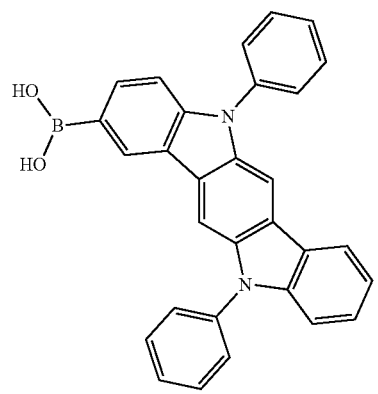 [SMILES: OB(O)c1ccc2c(c1)c1cc3c(cc1n2-c1ccccc1)c1ccccc1n3-c1ccccc1]
[1314019-74-3]
18f
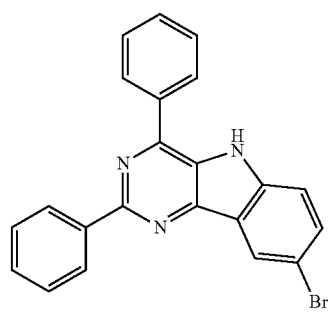 [SMILES: Brc1ccc2[nH]c3c(-c4ccccc4)nc(-c4ccccc4)nc3c2c1]
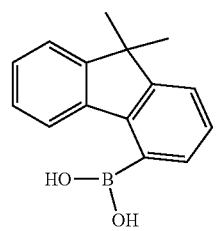 [SMILES: CC1(C)c2ccccc2-c2c(B(O)O)cccc21]
[1246022-50-3]

19f 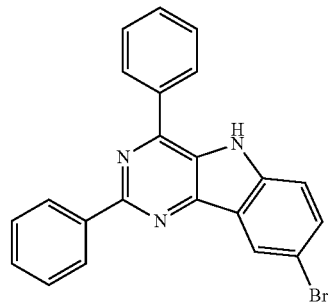 [SMILES: Brc1ccc2[nH]c3c(-c4ccccc4)nc(-c4ccccc4)nc3c2c1] 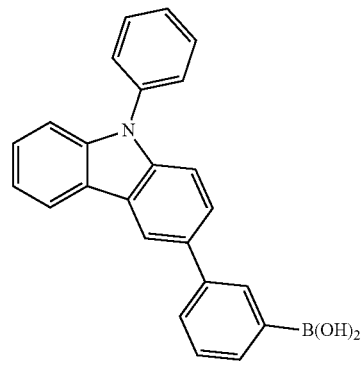 [SMILES: OB(O)c1cccc(-c2ccc3c(c2)c2ccccc2n3-c2ccccc2)c1]
[854952-60-6]
20f 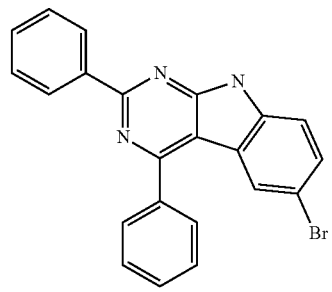 [SMILES: Brc1ccc2[nH]c3nc(-c4ccccc4)nc(-c4ccccc4)c3c2c1] 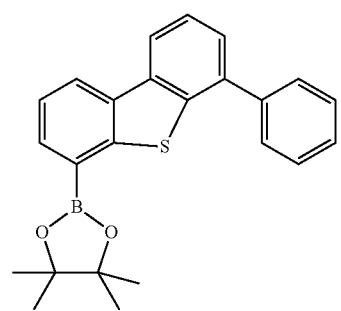 [SMILES: CC1(C)OB(c2cccc3c2sc2c(-c4ccccc4)cccc23)OC1(C)C]
[1556069-50-1]
21f 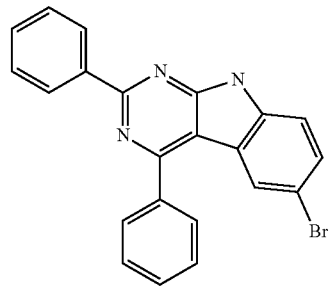 [SMILES: Brc1ccc2[nH]c3nc(-c4ccccc4)nc(-c4ccccc4)c3c2c1] 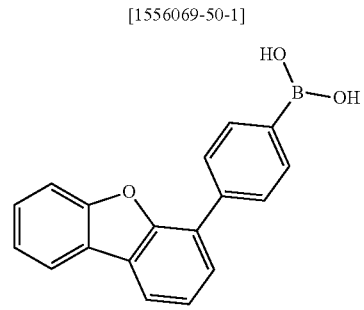
[796071-96-0]
22f 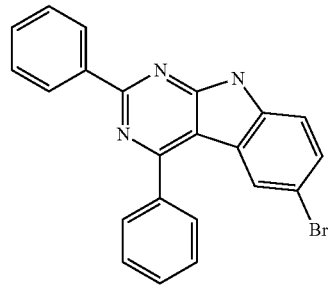 [SMILES: Brc1ccc2[nH]c3nc(-c4ccccc4)nc(-c4ccccc4)c3c2c1] 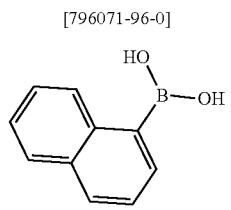
[13922-41-3]

-continued
| | | | |
|---|---|---|---|
| 23f | 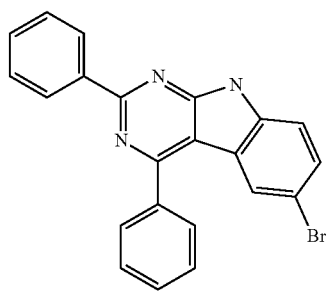 [SMILES: Brc1ccc2[nH]c3nc(-c4ccccc4)nc(-c4ccccc4)c3c2c1] | 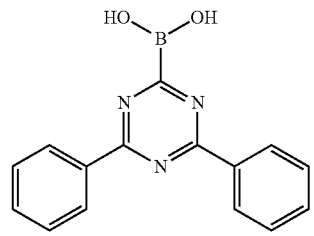 [SMILES: OB(O)c1nc(-c2ccccc2)nc(-c2ccccc2)n1] [1251825-65-6] | |
| 24f | 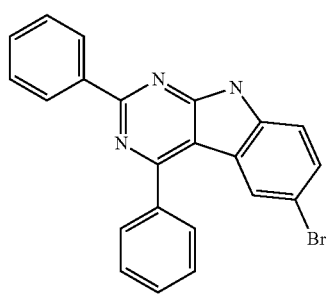 [SMILES: Brc1ccc2[nH]c3nc(-c4ccccc4)nc(-c4ccccc4)c3c2c1] | 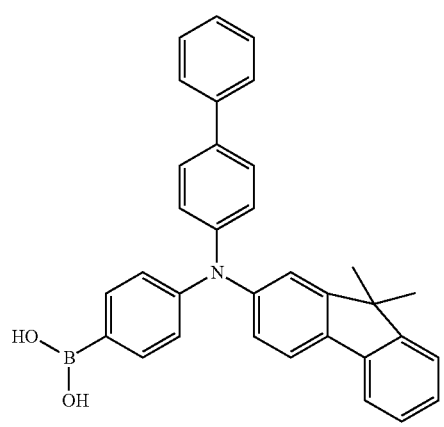 [SMILES: CC1(C)c2ccccc2-c2ccc(N(c3ccc(B(O)O)cc3)c3ccc(-c4ccccc4)cc3)cc21] [1394815-87-2] | |
| 25f | 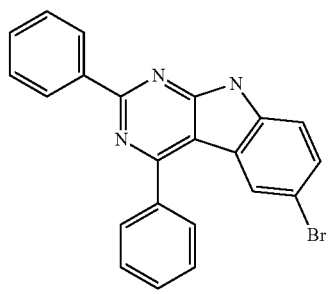 [SMILES: Brc1ccc2[nH]c3nc(-c4ccccc4)nc(-c4ccccc4)c3c2c1] | 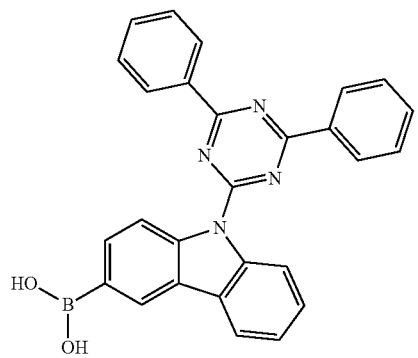 [SMILES: OB(O)c1ccc2c(c1)c1ccccc1n2-c1nc(-c2ccccc2)nc(-c2ccccc2)n1] [1266389-18-7] | |
| 26f | 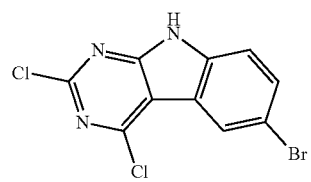 [SMILES: Clc1nc(Cl)c2c(n1)[nH]c1ccc(Br)cc12] | 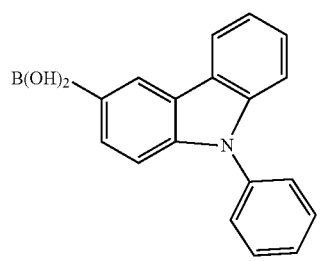 [SMILES: OB(O)c1ccc2c(c1)c1ccccc1n2-c1ccccc1] [854952-58-2] | |

-continued
27f
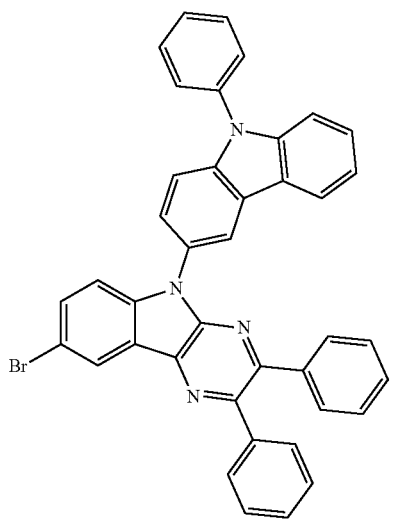 [SMILES: Brc1ccc2c(c1)c1nc(-c3ccccc3)c(-c3ccccc3)nc1n2-c1ccc2c(c1)c1ccccc1n2-c1ccccc1]
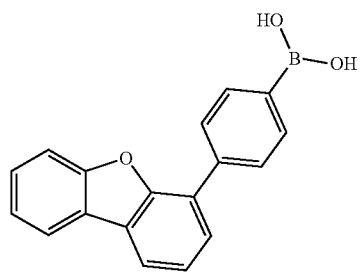 [SMILES: OB(O)c1ccc(-c2cccc3c2oc2ccccc23)cc1]
[796071-96-0]
28f
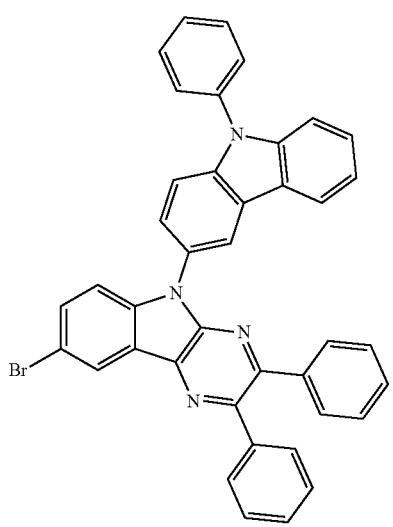 [SMILES: Brc1ccc2c(c1)c1nc(-c3ccccc3)c(-c3ccccc3)nc1n2-c1ccc2c(c1)c1ccccc1n2-c1ccccc1]
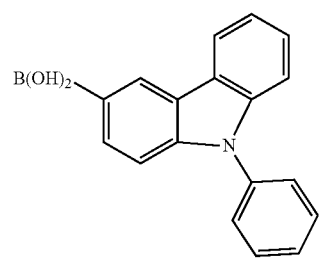 [SMILES: OB(O)c1ccc2c(c1)c1ccccc1n2-c1ccccc1]
[854952-58-2]
29f
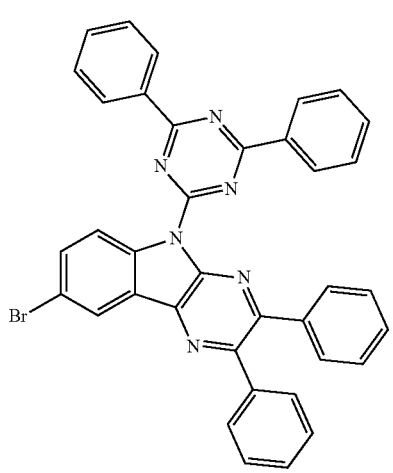 [SMILES: Brc1ccc2c(c1)c1nc(-c3ccccc3)c(-c3ccccc3)nc1n2-c1nc(-c2ccccc2)nc(-c2ccccc2)n1]
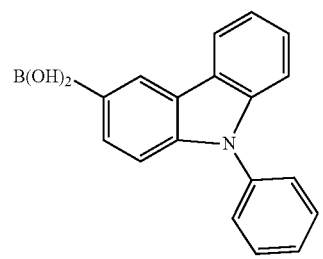 [SMILES: OB(O)c1ccc2c(c1)c1ccccc1n2-c1ccccc1]
[854952-58-2]

-continued
30f
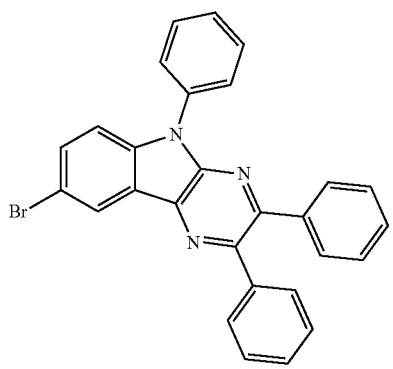 [SMILES: Brc1ccc2c(c1)c1nc(-c3ccccc3)c(-c3ccccc3)nc1n2-c1ccccc1]
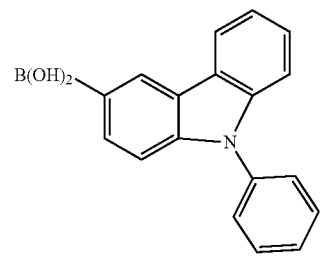 [SMILES: OB(O)c1ccc2c(c1)c1ccccc1n2-c1ccccc1]
[854952-58-2]
31f
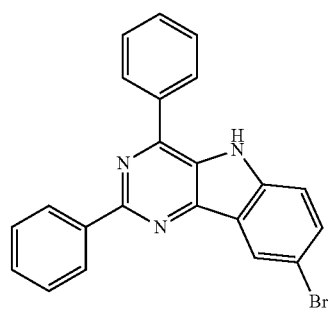 [SMILES: Brc1ccc2[nH]c3c(-c4ccccc4)nc(-c4ccccc4)nc3c2c1]
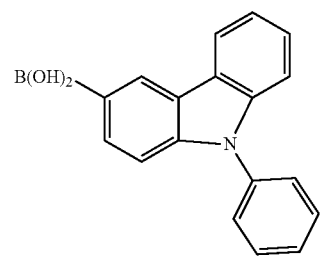 [SMILES: OB(O)c1ccc2c(c1)c1ccccc1n2-c1ccccc1]
[854952-58-2]
32f
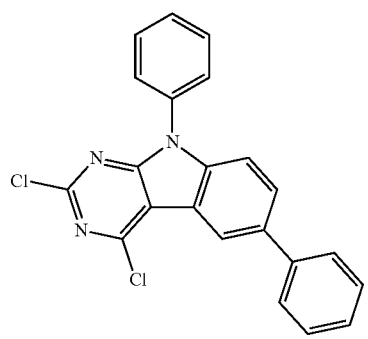 [SMILES: Clc1nc(Cl)c2c3cc(-c4ccccc4)ccc3n(-c3ccccc3)c2n1]
g37
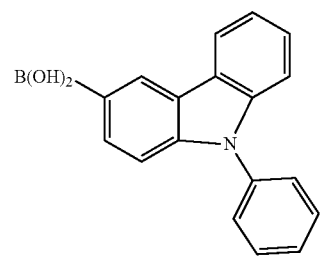 [SMILES: OB(O)c1ccc2c(c1)c1ccccc1n2-c1ccccc1]
[854952-58-2]
33f
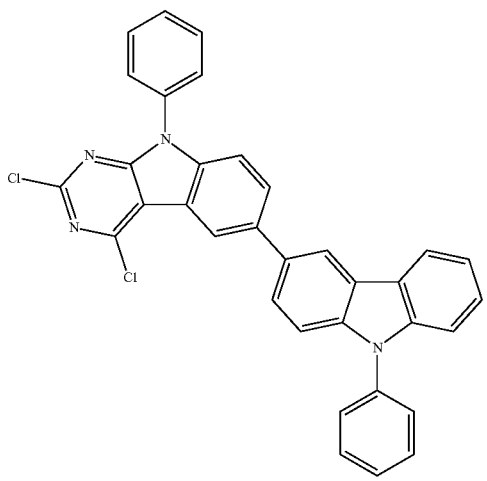 [SMILES: Clc1nc(Cl)c2c3cc(-c4ccc5c(c4)c4ccccc4n5-c4ccccc4)ccc3n(-c3ccccc3)c2n1]
g40
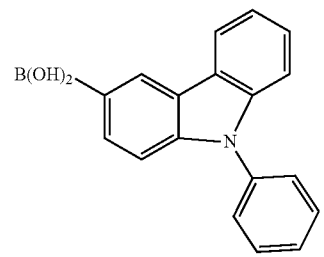 [SMILES: OB(O)c1ccc2c(c1)c1ccccc1n2-c1ccccc1]
[854952-58-2]

-continued
34f 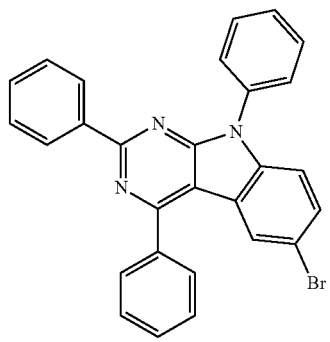 [SMILES: Brc1ccc2c(c1)c1c(-c3ccccc3)nc(-c3ccccc3)nc1n2-c1ccccc1] 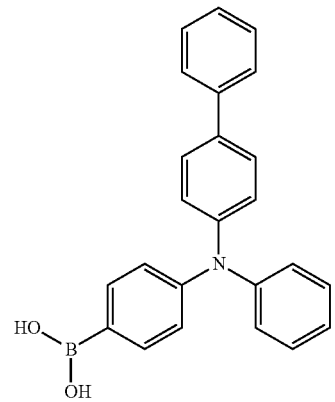 [SMILES: OB(O)c1ccc(N(c2ccccc2)c2ccc(-c3ccccc3)cc2)cc1]
[1084334-86-0]
35f 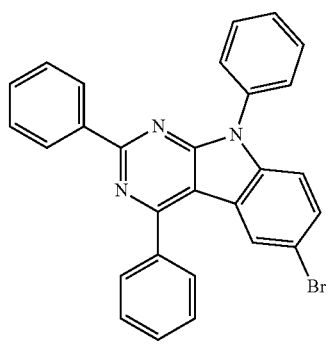 [SMILES: Brc1ccc2c(c1)c1c(-c3ccccc3)nc(-c3ccccc3)nc1n2-c1ccccc1] 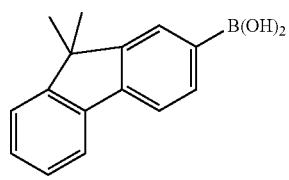 [SMILES: CC1(C)c2ccccc2-c2ccc(B(O)O)cc21]
[333432-28-3]
36f 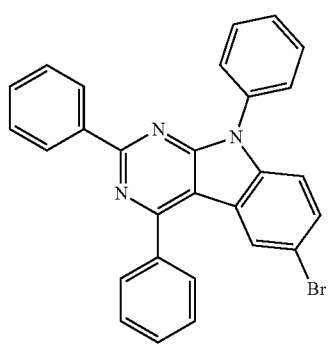 [SMILES: Brc1ccc2c(c1)c1c(-c3ccccc3)nc(-c3ccccc3)nc1n2-c1ccccc1] 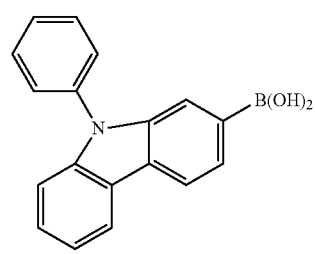 [SMILES: OB(O)c1ccc2c3ccccc3n(-c3ccccc3)c2c1]
[1001911-63-2]
37f 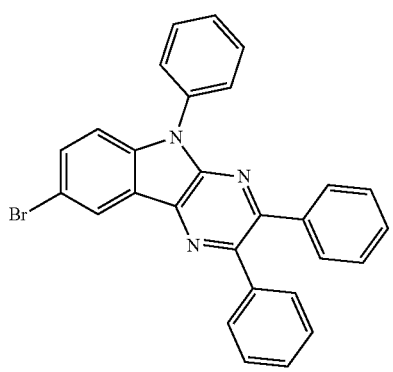 [SMILES: Brc1ccc2c(c1)c1nc(-c3ccccc3)c(-c3ccccc3)nc1n2-c1ccccc1] 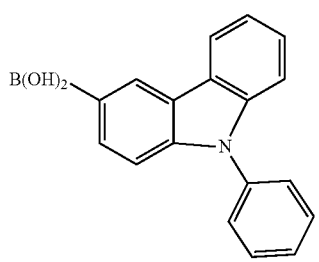 [SMILES: OB(O)c1ccc2c(c1)c1ccccc1n2-c1ccccc1]
[854952-58-2]

-continued
| | | |
|---|---|---|
| 38f | 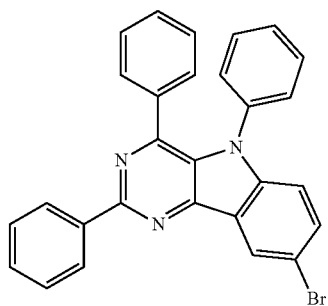 [SMILES: Brc1ccc2c(c1)c1nc(-c3ccccc3)nc(-c3ccccc3)c1n2-c1ccccc1] | 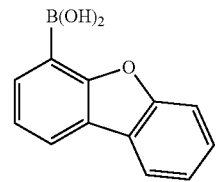 [SMILES: OB(O)c1cccc2c1oc1ccccc12]
[100124-06-9] |
| 39f | 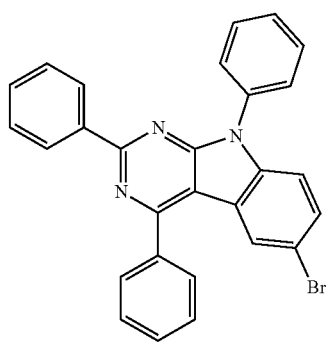 [SMILES: Brc1ccc2c(c1)c1c(-c3ccccc3)nc(-c3ccccc3)nc1n2-c1ccccc1] | 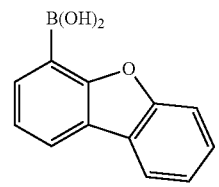
[100124-06-9] |
| 40f | 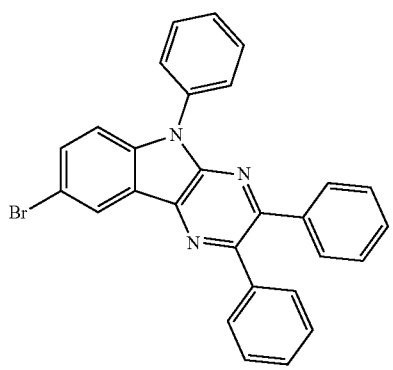 [SMILES: Brc1ccc2c(c1)c1nc(-c3ccccc3)c(-c3ccccc3)nc1n2-c1ccccc1] | 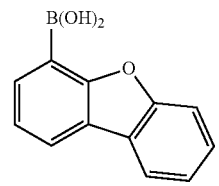 [SMILES: OB(O)c1cccc2c1oc1ccccc12]
[100124-06-9] |
| | Product | Yield |
|---|---|---|
| 1f | 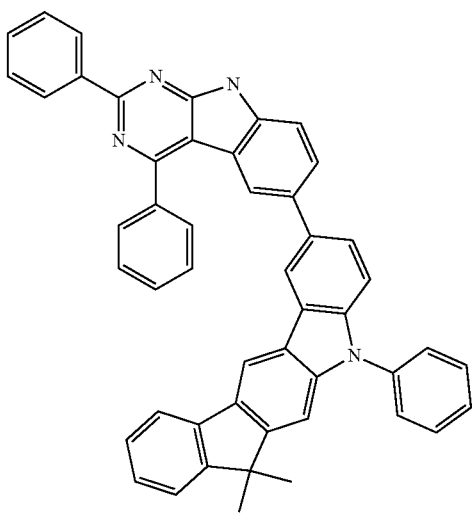 [SMILES: CC1(C)c2ccccc2-c2cc3c4cc(-c5ccc6[nH]c7nc(-c8ccccc8)nc(-c8ccccc8)c7c6c5)ccc4n(-c4ccccc4)c3cc21] | 60% |

| | | |
|---|---|---|
| 2f | 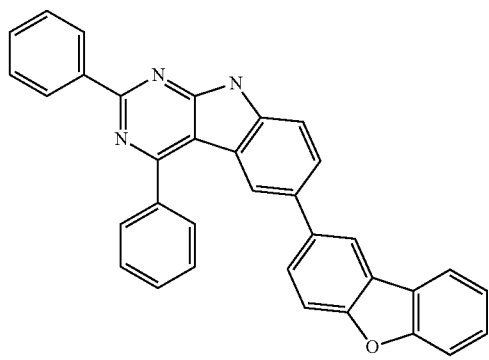 [SMILES: c1ccc(-c2nc(-c3ccccc3)c3c(n2)[nH]c2ccc(-c4ccc5oc6ccccc6c5c4)cc23)cc1] | 73% |
| 3f | 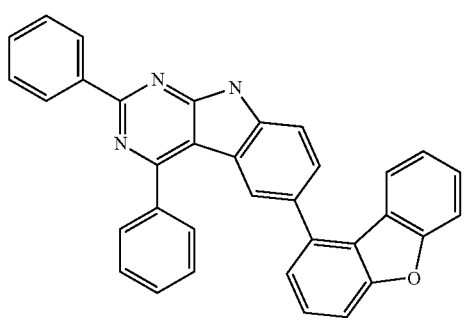 [SMILES: c1ccc(-c2nc(-c3ccccc3)c3c(n2)[nH]c2ccc(-c4cccc5oc6ccccc6c45)cc23)cc1] | 56% |
| 4f | 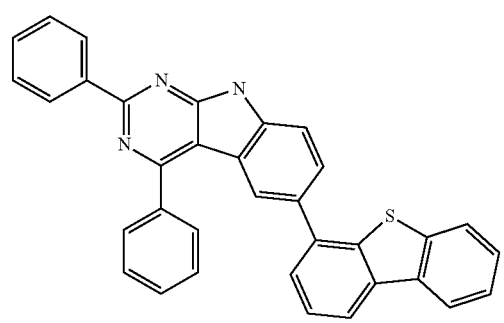 [SMILES: c1ccc(-c2nc(-c3ccccc3)c3c(n2)[nH]c2ccc(-c4cccc5c4sc4ccccc45)cc23)cc1] | 72% |
| 5f | 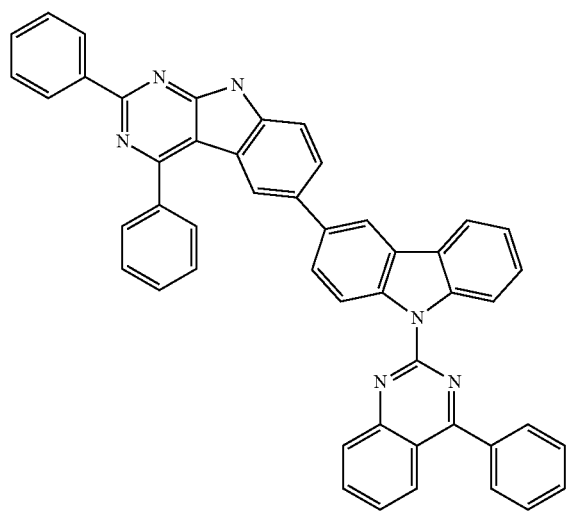 [SMILES: c1ccc(-c2nc(-c3ccccc3)c3c(n2)[nH]c2ccc(-c4ccc5c(c4)c4ccccc4n5-c4nc(-c5ccccc5)c5ccccc5n4)cc23)cc1] | 73% |

| | | |
|---|---|---|
| 6f | 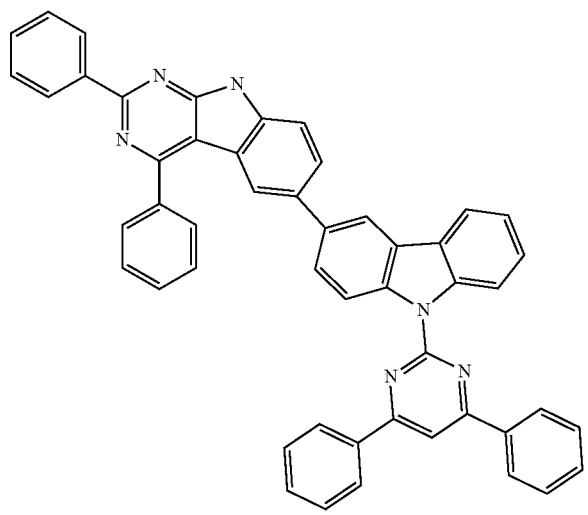 [SMILES: c1ccc(-c2cc(-c3ccccc3)nc(-n3c4ccccc4c4cc(-c5ccc6[nH]c7nc(-c8ccccc8)nc(-c8ccccc8)c7c6c5)ccc43)n2)cc1] | 67% |
| 7f | 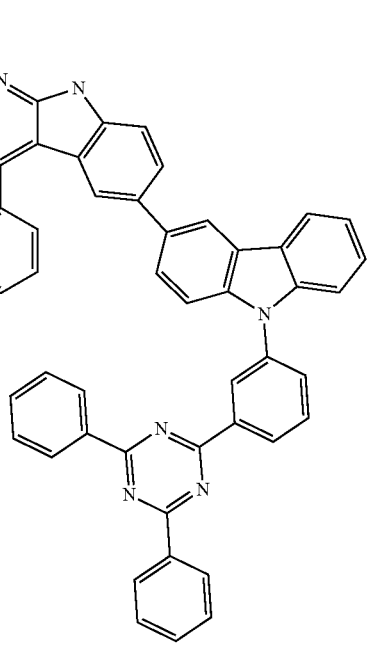 | 65% |

8f 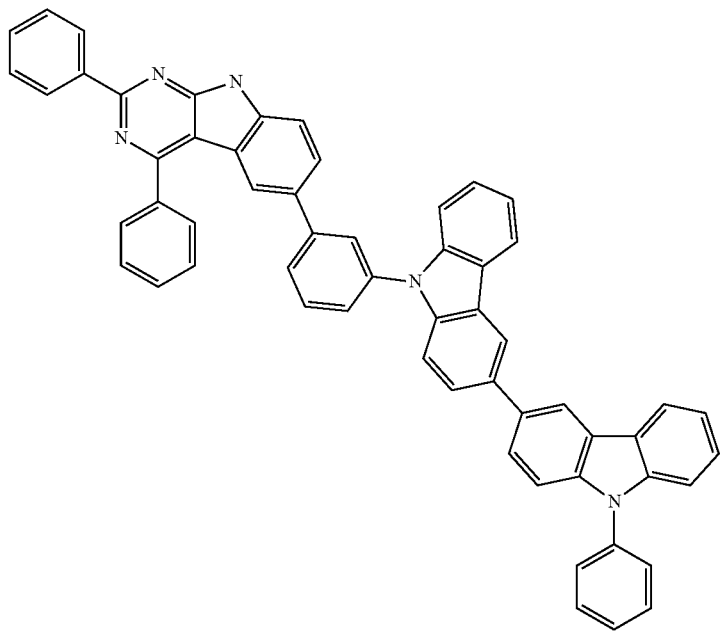 [SMILES: c1ccc(-c2nc(-c3ccccc3)c3c(n2)[nH]c2ccc(-c4cccc(-n5c6ccccc6c6cc(-c7ccc8c(c7)c7ccccc7n8-c7ccccc7)ccc65)c4)cc23)cc1] 77%
9f 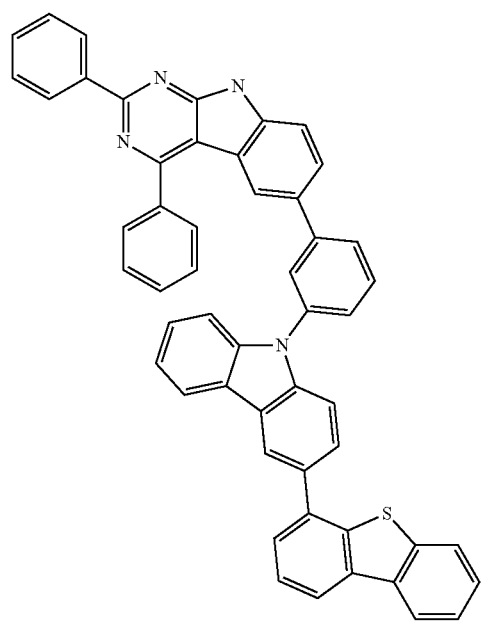 [SMILES: c1ccc(-c2nc(-c3ccccc3)c3c(n2)[nH]c2ccc(-c4cccc(-n5c6ccccc6c6cc(-c7cccc8c7sc7ccccc78)ccc65)c4)cc23)cc1] 67%

| | | |
|---|---|---|
| 10f | 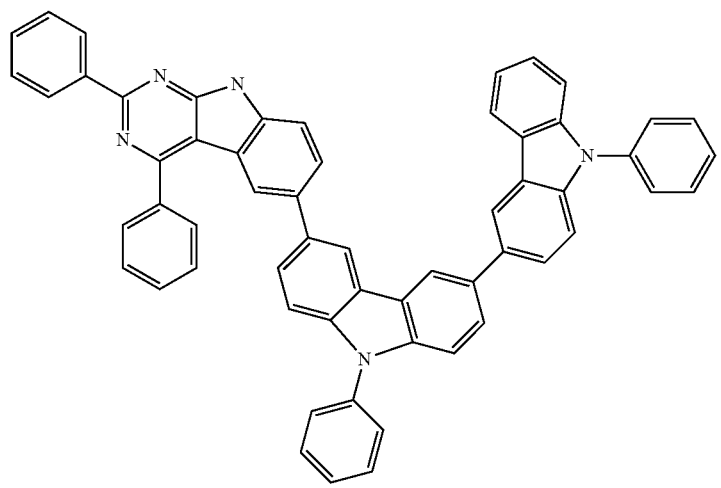 [SMILES: c1ccc(-c2nc(-c3ccccc3)c3c(n2)[nH]c2ccc(-c4ccc5c(c4)c4cc(-c6ccc7c(c6)c6ccccc6n7-c6ccccc6)ccc4n5-c4ccccc4)cc23)cc1] | 61% |
| 11f | 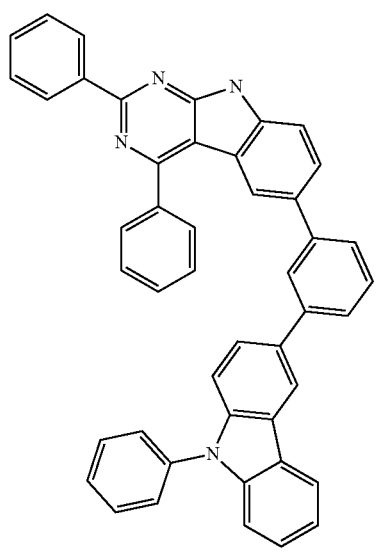 [SMILES: c1ccc(-c2nc(-c3ccccc3)c3c(n2)[nH]c2ccc(-c4cccc(-c5ccc6c(c5)c5ccccc5n6-c5ccccc5)c4)cc23)cc1] | 70% |
| 12f | 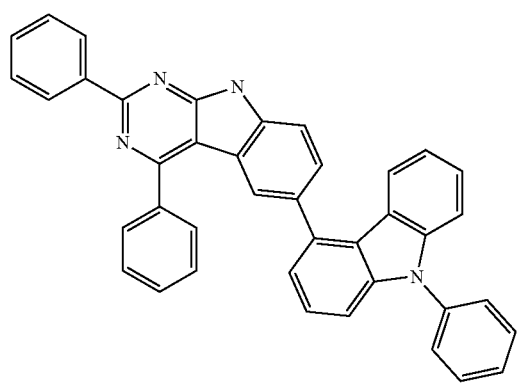 [SMILES: c1ccc(-c2nc(-c3ccccc3)c3c(n2)[nH]c2ccc(-c4cccc5c4c4ccccc4n5-c4ccccc4)cc23)cc1] | 57% |

-continued
13f 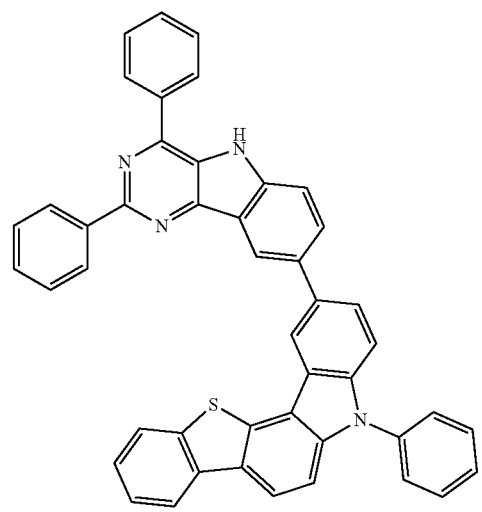 [SMILES: c1ccc(-c2nc(-c3ccccc3)c3[nH]c4ccc(-c5ccc6c(c5)c5c7sc8ccccc8c7ccc5n6-c5ccccc5)cc4c3n2)cc1] 60%
14f 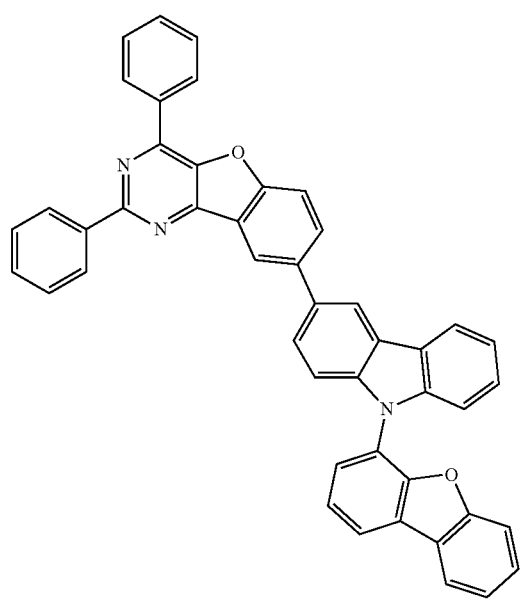 [SMILES: c1ccc(-c2nc(-c3ccccc3)c3oc4ccc(-c5ccc6c(c5)c5ccccc5n6-c5cccc6c5oc5ccccc56)cc4c3n2)cc1] 71%
15f 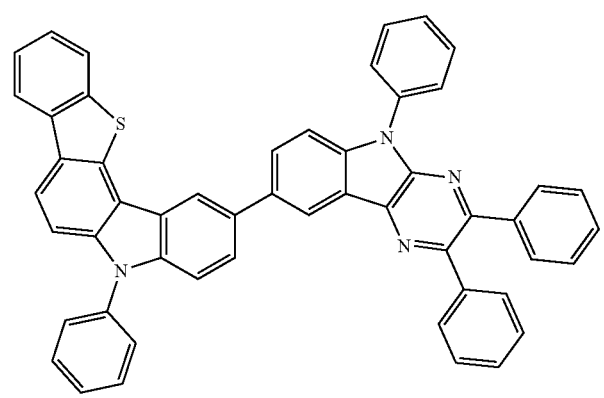 [SMILES: c1ccc(-c2nc3c4cc(-c5ccc6c(c5)c5c7sc8ccccc8c7ccc5n6-c5ccccc5)ccc4n(-c4ccccc4)c3nc2-c2ccccc2)cc1] 69%

16f 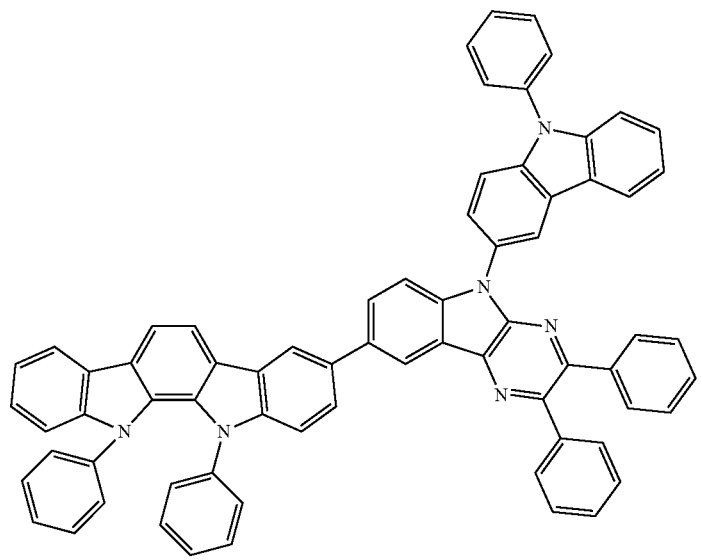 [SMILES: c1ccc(-c2nc3c4cc(-c5ccc6c(c5)c5ccc7c8ccccc8n(-c8ccccc8)c7c5n6-c5ccccc5)ccc4n(-c4ccc5c(c4)c4ccccc4n5-c4ccccc4)c3nc2-c2ccccc2)cc1] 65%
17f 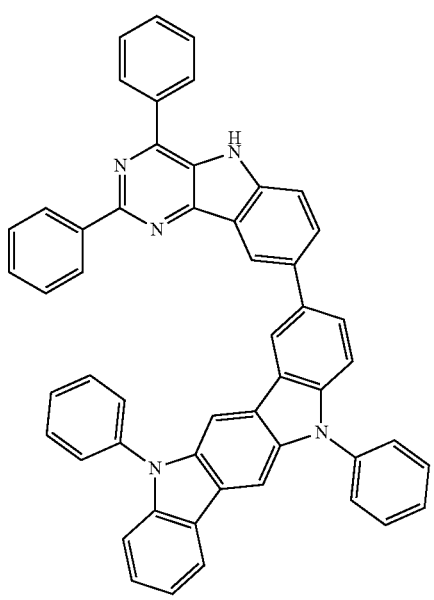 [SMILES: c1ccc(-c2nc(-c3ccccc3)c3[nH]c4ccc(-c5ccc6c(c5)c5cc7c(cc5n6-c5ccccc5)c5ccccc5n7-c5ccccc5)cc4c3n2)cc1] 52%
18f 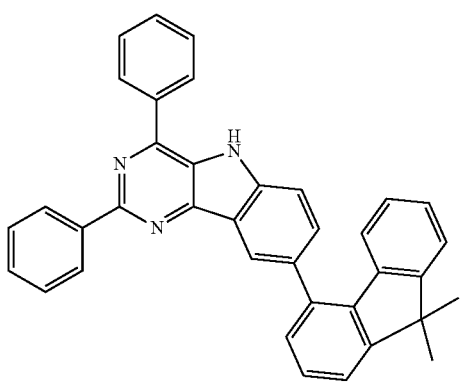 [SMILES: CC1(C)c2ccccc2-c2c(-c3ccc4[nH]c5c(-c6ccccc6)nc(-c6ccccc6)nc5c4c3)cccc21] 62%

-continued
| | | |
|---|---|---|
| 19f | 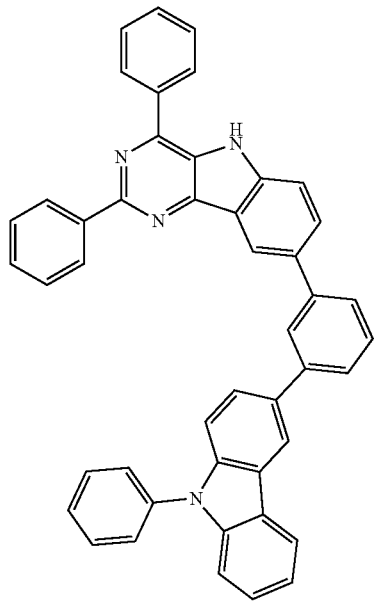 [SMILES: c1ccc(-c2nc(-c3ccccc3)c3[nH]c4ccc(-c5cccc(-c6ccc7c(c6)c6ccccc6n7-c6ccccc6)c5)cc4c3n2)cc1] | 63% |
| 20f | 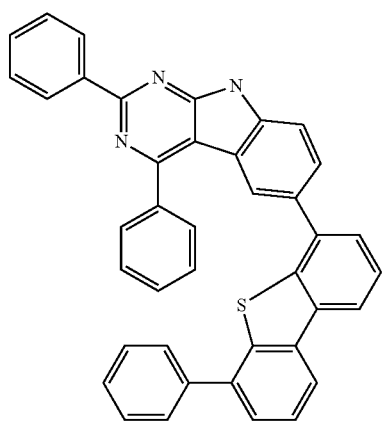 [SMILES: c1ccc(-c2nc(-c3ccccc3)c3c(n2)[nH]c2ccc(-c4cccc5c4sc4c(-c6ccccc6)cccc45)cc23)cc1] | 72% |
| 21f | 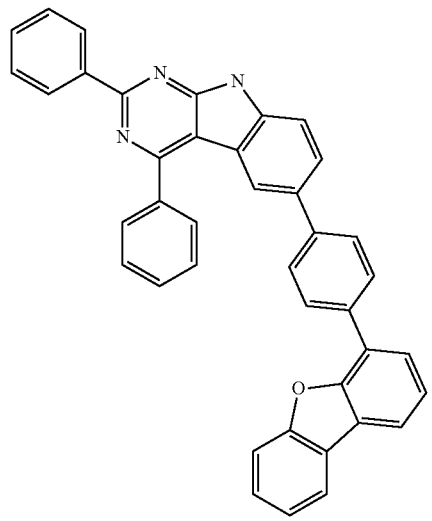 [SMILES: c1ccc(-c2nc(-c3ccccc3)c3c(n2)[nH]c2ccc(-c4ccc(-c5cccc6c5oc5ccccc56)cc4)cc23)cc1] | 70% |

| | | |
|---|---|---|
| 22f | 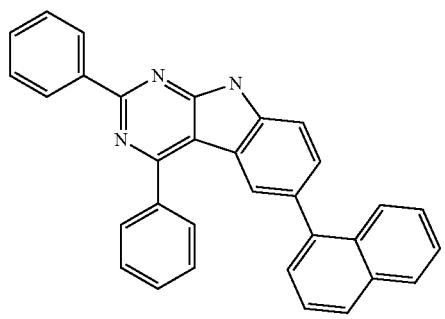 [SMILES: c1ccc(-c2nc(-c3ccccc3)c3c(n2)[nH]c2ccc(-c4cccc5ccccc45)cc23)cc1] | 78% |
| 23f | 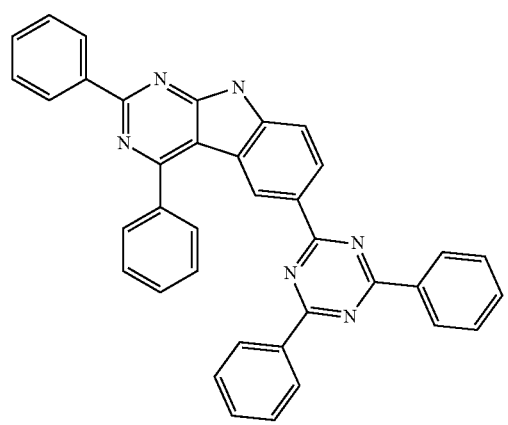 [SMILES: c1ccc(-c2nc(-c3ccccc3)nc(-c3ccc4[nH]c5nc(-c6ccccc6)nc(-c6ccccc6)c5c4c3)n2)cc1] | 69% |
| 24f | 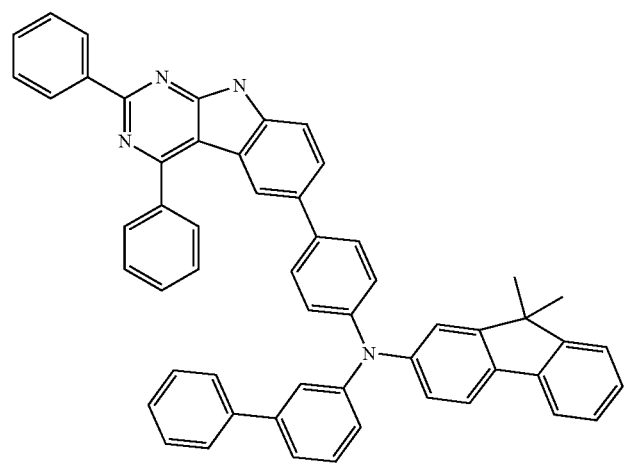 [SMILES: CC1(C)c2ccccc2-c2ccc(N(c3ccc(-c4ccc5[nH]c6nc(-c7ccccc7)nc(-c7ccccc7)c6c5c4)cc3)c3cccc(-c4ccccc4)c3)cc21] | 64% |

| | | |
|---|---|---|
| 25f | 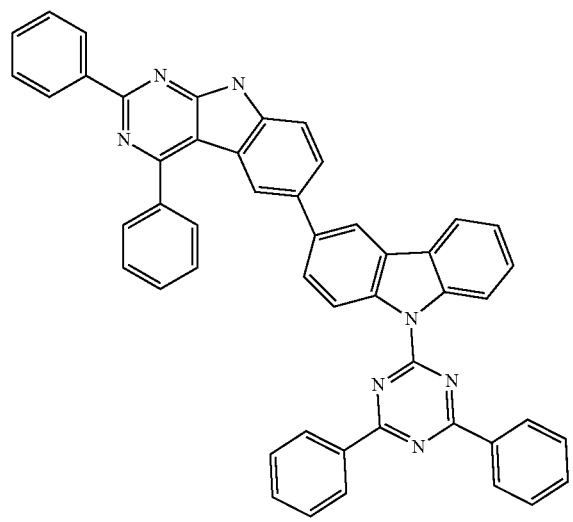 [SMILES: c1ccc(-c2nc(-c3ccccc3)nc(-n3c4ccccc4c4cc(-c5ccc6[nH]c7nc(-c8ccccc8)nc(-c8ccccc8)c7c6c5)ccc43)n2)cc1] | 66% |
| 26f | 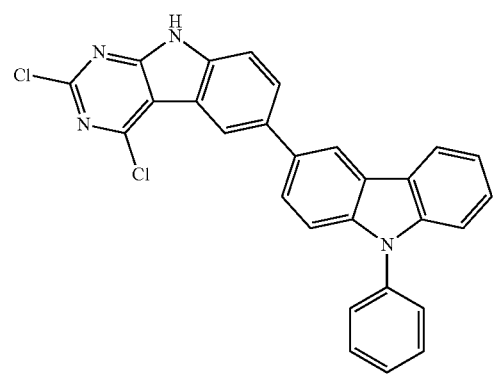 [SMILES: Clc1nc(Cl)c2c(n1)[nH]c1ccc(-c3ccc4c(c3)c3ccccc3n4-c3ccccc3)cc12] | 46% |
| 27f | 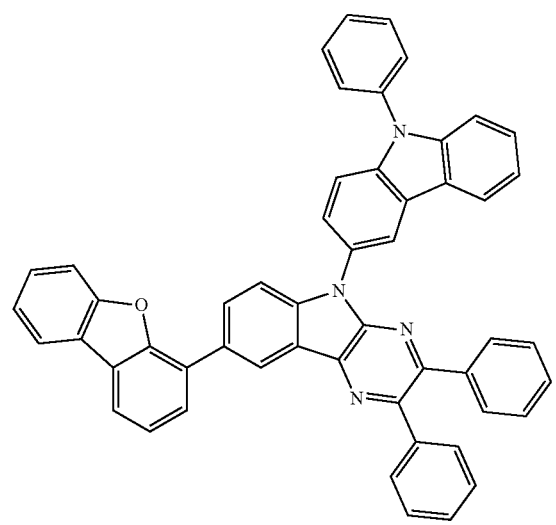 [SMILES: c1ccc(-c2nc3c4cc(-c5cccc6c5oc5ccccc56)ccc4n(-c4ccc5c(c4)c4ccccc4n5-c4ccccc4)c3nc2-c2ccccc2)cc1] | 63% |

-continued
| | | |
|---|---|---|
| 28f | 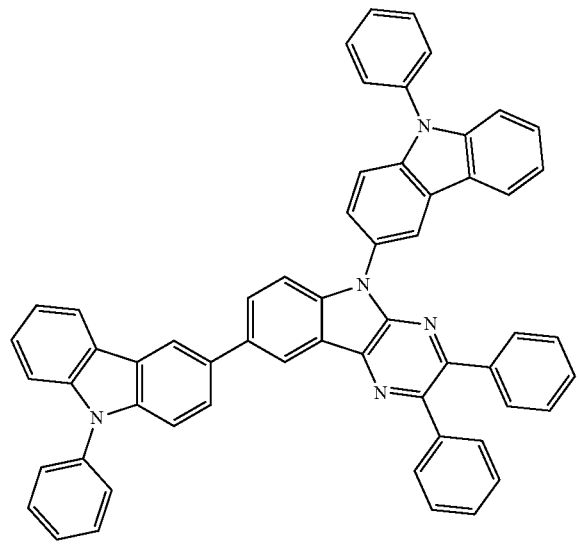 [SMILES: c1ccc(-c2nc3c4cc(-c5ccc6c(c5)c5ccccc5n6-c5ccccc5)ccc4n(-c4ccc5c(c4)c4ccccc4n5-c4ccccc4)c3nc2-c2ccccc2)cc1] | 68% |
| 29f | 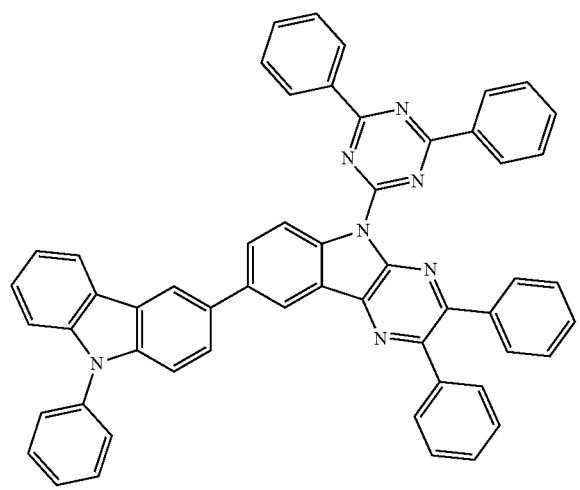 [SMILES: c1ccc(-c2nc(-c3ccccc3)nc(-n3c4ccc(-c5ccc6c(c5)c5ccccc5n6-c5ccccc5)cc4c4nc(-c5ccccc5)c(-c5ccccc5)nc43)n2)cc1] | 69% |
| 30f | 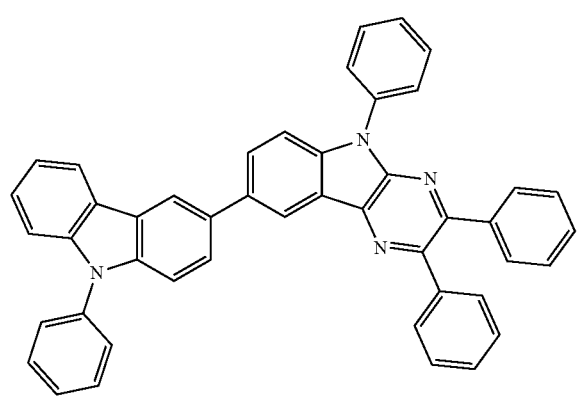 [SMILES: c1ccc(-c2nc3c4cc(-c5ccc6c(c5)c5ccccc5n6-c5ccccc5)ccc4n(-c4ccccc4)c3nc2-c2ccccc2)cc1] | 64% |

| | | |
|---|---|---|
| 31f | 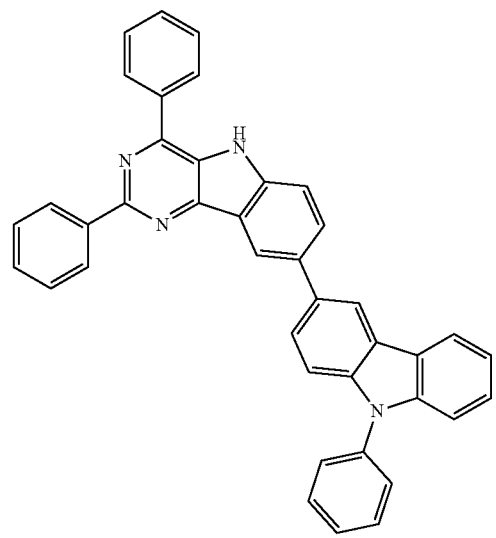 [SMILES: c1ccc(-c2nc(-c3ccccc3)c3[nH]c4ccc(-c5ccc6c(c5)c5ccccc5n6-c5ccccc5)cc4c3n2)cc1] | 69% |
| 32f | 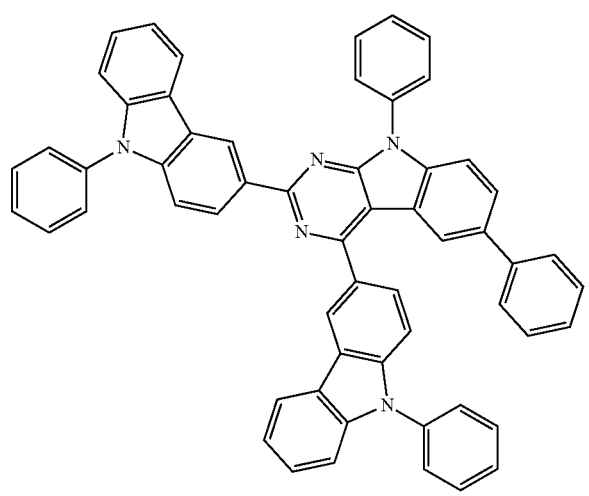 [SMILES: c1ccc(-c2ccc3c(c2)c2c(-c4ccc5c(c4)c4ccccc4n5-c4ccccc4)nc(-c4ccc5c(c4)c4ccccc4n5-c4ccccc4)nc2n3-c2ccccc2)cc1] | 62% |
| 33f | 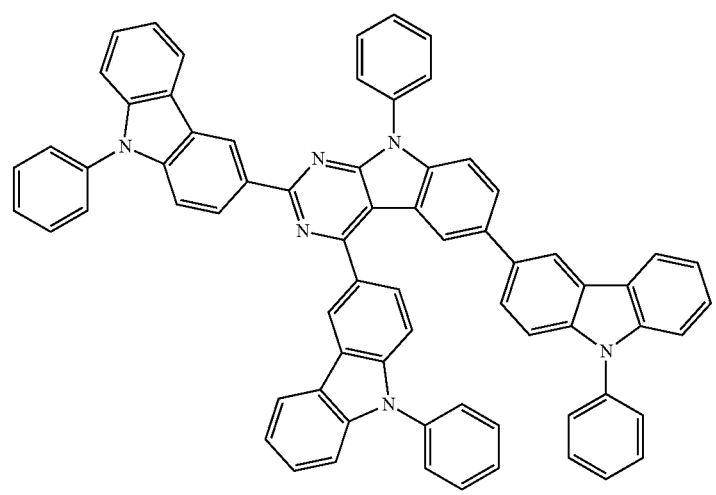 [SMILES: c1ccc(-n2c3ccccc3c3cc(-c4ccc5c(c4)c4c(-c6ccc7c(c6)c6ccccc6n7-c6ccccc6)nc(-c6ccc7c(c6)c6ccccc6n7-c6ccccc6)nc4n5-c4ccccc4)ccc32)cc1] | 69% |

| | | |
|---|---|---|
| 34f | 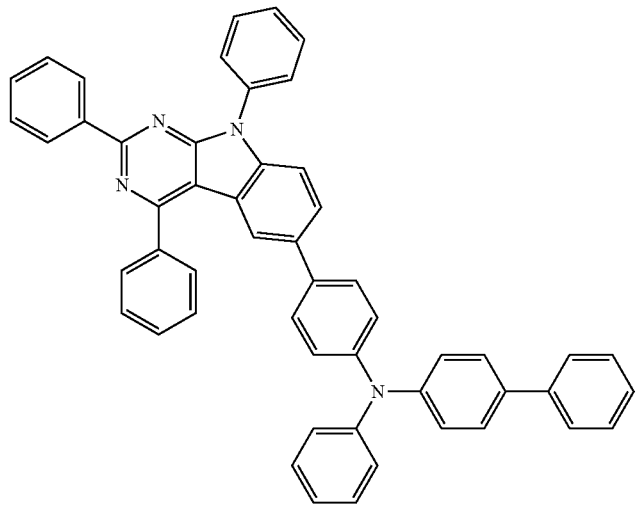 [SMILES: c1ccc(-c2ccc(N(c3ccccc3)c3ccc(-c4ccc5c(c4)c4c(-c6ccccc6)nc(-c6ccccc6)nc4n5-c4ccccc4)cc3)cc2)cc1] | 72% |
| 35f | 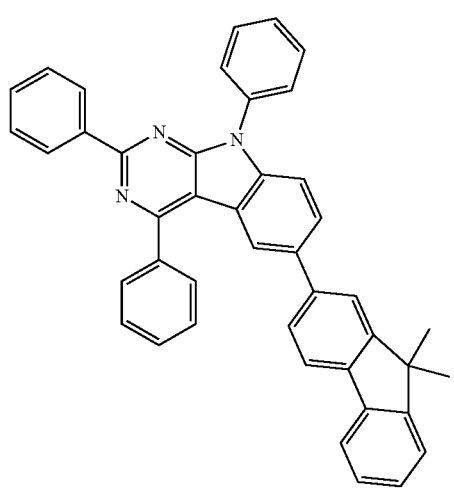 [SMILES: CC1(C)c2ccccc2-c2ccc(-c3ccc4c(c3)c3c(-c5ccccc5)nc(-c5ccccc5)nc3n4-c3ccccc3)cc21] | 75% |
| 36f | 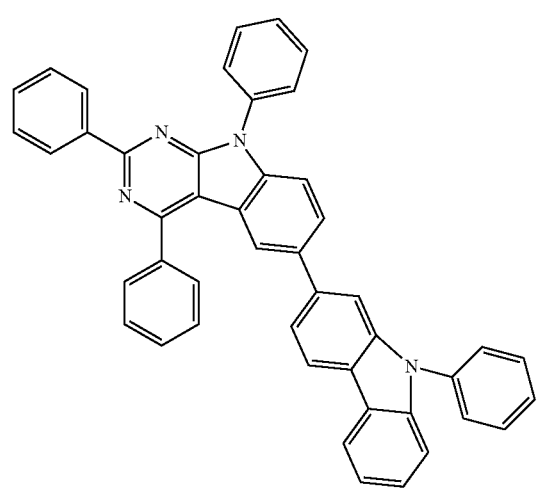 [SMILES: c1ccc(-c2nc(-c3ccccc3)c3c4cc(-c5ccc6c7ccccc7n(-c7ccccc7)c6c5)ccc4n(-c4ccccc4)c3n2)cc1] | 71% |

-continued
| | | |
|---|---|---|
| 37f | 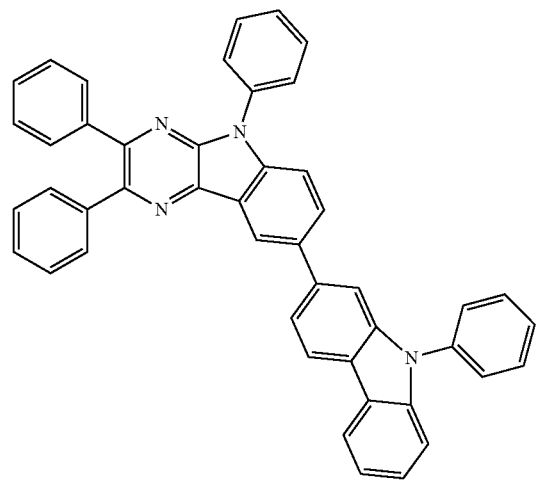 [SMILES: c1ccc(-c2nc3c4cc(-c5ccc6c7ccccc7n(-c7ccccc7)c6c5)ccc4n(-c4ccccc4)c3nc2-c2ccccc2)cc1] | 73% |
| 38f | 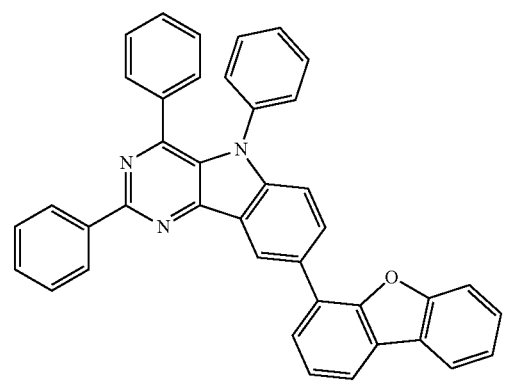 [SMILES: c1ccc(-c2nc(-c3ccccc3)c3c(n2)c2cc(-c4cccc5c4oc4ccccc45)ccc2n3-c2ccccc2)cc1] | 70% |
| 39f | 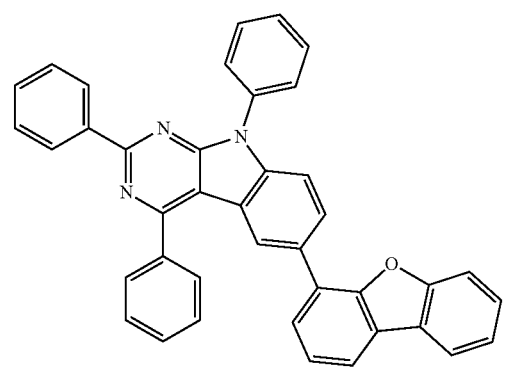 [SMILES: c1ccc(-c2nc(-c3ccccc3)c3c4cc(-c5cccc6c5oc5ccccc56)ccc4n(-c4ccccc4)c3n2)cc1] | 77% |
| 40f | 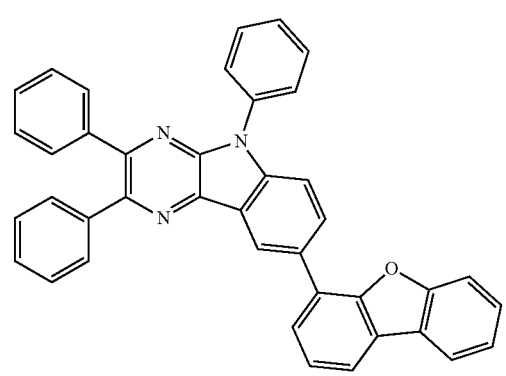 [SMILES: c1ccc(-c2nc3c4cc(-c5cccc6c5oc5ccccc56)ccc4n(-c4ccccc4)c3nc2-c2ccccc2)cc1] | 73% | g) 2,4,9-triphenyl-6-(9-phenyl-9H-carbazol-3-yl)-9H-pyrimido[4,5-b]indole

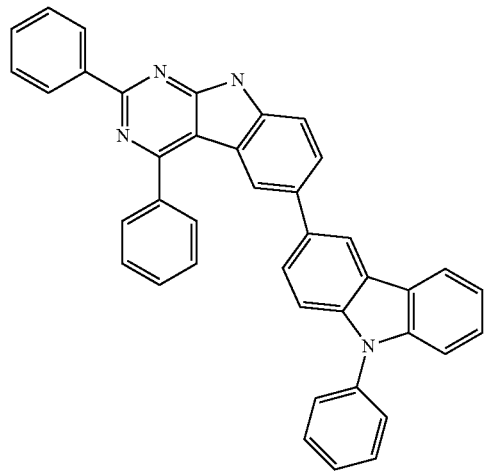 [SMILES: c1ccc(-c2nc(-c3ccccc3)c3c(n2)[nH]c2ccc(-c4ccc5c(c4)c4ccccc4n5-c4ccccc4)cc23)cc1]

+

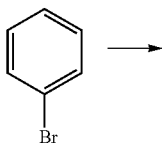

-continued

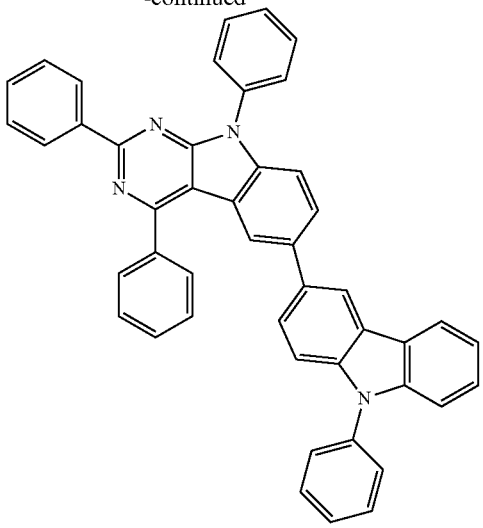

A degassed solution of 25 g (155 mmol) bromobenzene and 84 g (150 mmol) of 2,4-diphenyl-6-(9-phenyl-9H-carbazol-3-yl)-9H-pyrimido [4,5-b]indole in 600 ml of toluene is saturated with $N_2$ for 1 h. Then, firstly 2.09 ml (8.6 mmol) of $P(tBu)_3$, then 1.38 g (6.1 mmol) of palladium(II) acetate are added to the solution, and 17.7 g (185 mmol) of NaOtBu in the solid state are subsequently added. The reaction mixture is heated under reflux for 1 h. After cooling to room temperature, 500 ml of water are carefully added. The aqueous phase is washed with 3×50 ml of toluene, dried over MgSO4 and the solvent removed under vacuum. Thereafter, the crude product is purified by chromatography on silica gel with heptane/acetic ester (20/1). The residue is recrystallized from toluene, and finally sublimed in a high vacuum (p=5× $10^{-6}$ mbar).

The yield is 76 g (120 mmol), corresponding to 80% of theory.

The following compounds are prepared analogously:

The products 13f-16f and 27f-30f are purified by chromatography on silica gel with toluene/heptane (1:2) and finally sublimed in a high vacuum (p=5×$10^{-7}$ mbar) (99.9% purity).

| Reactant 1 | Reactant 2 | Product | Yield |
|---|---|---|---|
| 1g | [2915-16-4] | | 69% |

| Reactant 1 | Reactant 2 | Product | Yield |
|---|---|---|---|
| 2g | [864377-31-1] | | 71% |
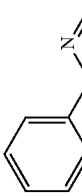

| | Reactant 1 | Reactant 2 | Product | Yield |
|---|---|---|---|---|
| 3g | 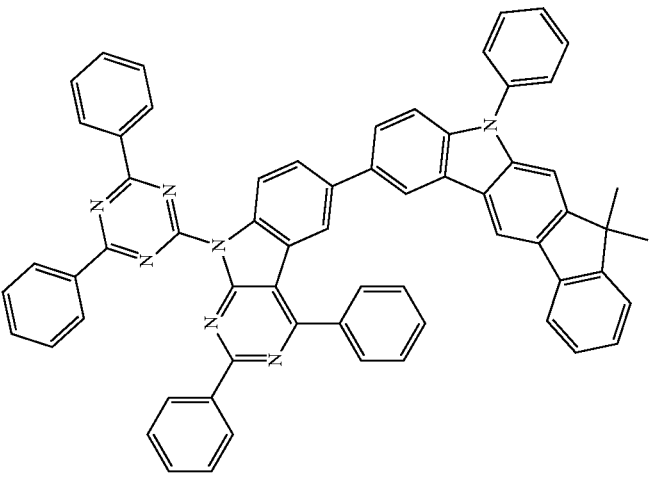 | 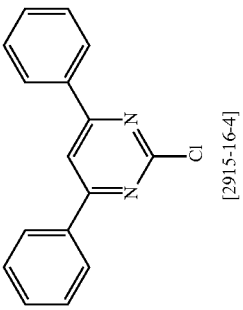
[2915-16-4] | 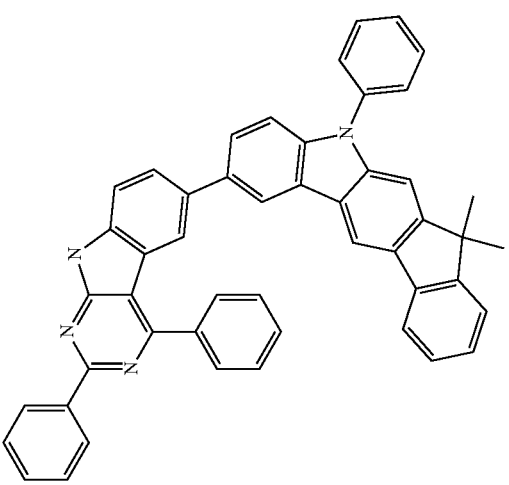 | 85% |

-continued

| Reactant 1 | Reactant 2 | Product | Yield |
|---|---|---|---|
| 4g | [29874-83-7] | | 75% |
| 5g | [5408-56-0] | | 81% |

| | Reactant 1 | Reactant 2 | Product | Yield |
|---|---|---|---|---|
| 6g | (structure) | (structure) [1153-85-1] | (structure) | 67% |

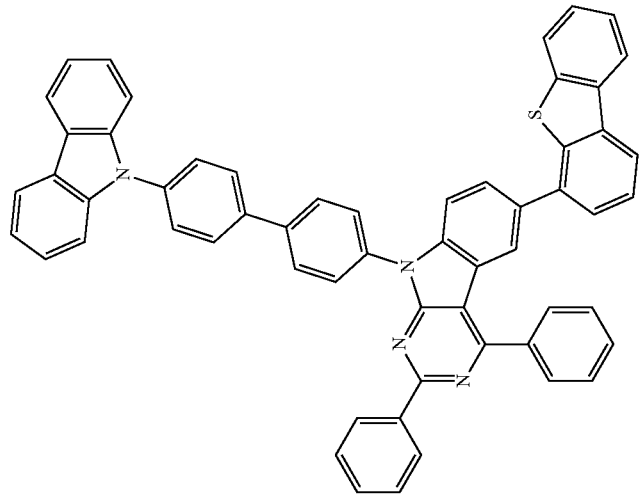

-continued
| | Reactant 1 | Reactant 2 | Product | Yield |
|---|---|---|---|---|
| 8g | 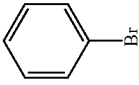 | 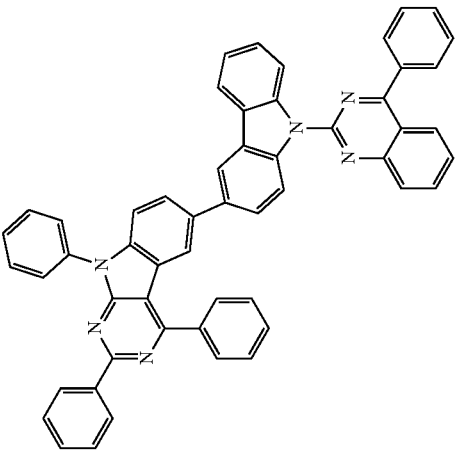 | 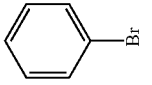 | 67% |
| 9g | 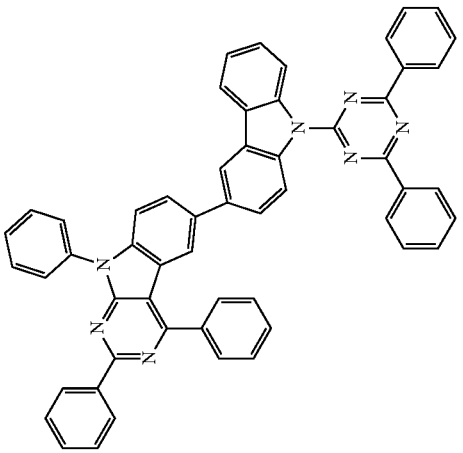 | | | 74% |

| Reactant 1 | Reactant 2 | Product | Yield |
|---|---|---|---|
| 10g | PhBr | | 52% |

| | -continued | | |
|---|---|---|---|
| | Reactant 1 | Reactant 2 | Product | Yield |
| 11g | (structure) | (phenyl bromide) | (structure) | 80% |

| Reactant 1 | Reactant 2 | Product | Yield |
|---|---|---|---|
| 12g | [40734-4-5] | | 83% |

| Reactant 1 | Reactant 2 | Product | Yield |
|---|---|---|---|
| 13g | [3842-55-5] | | 87% |
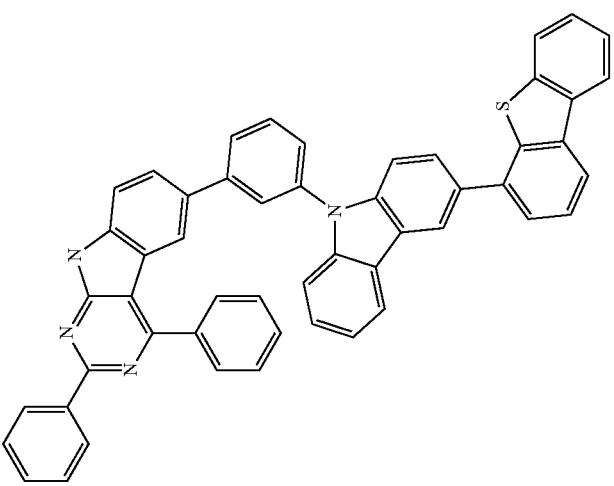

-continued
| | Reactant 1 | Reactant 2 | Product | Yield |
|---|---|---|---|---|
| 14g | 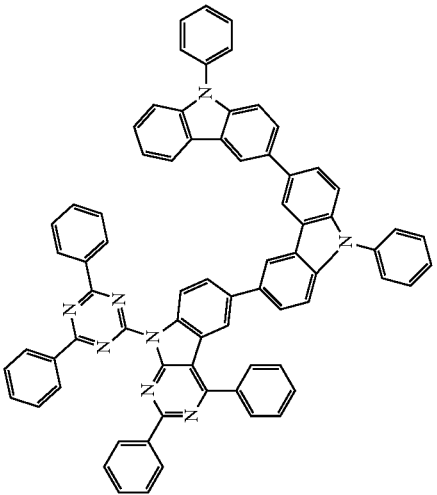 | 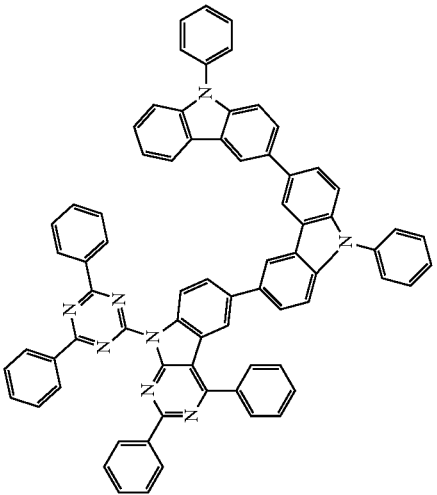  [3842-55-5] | 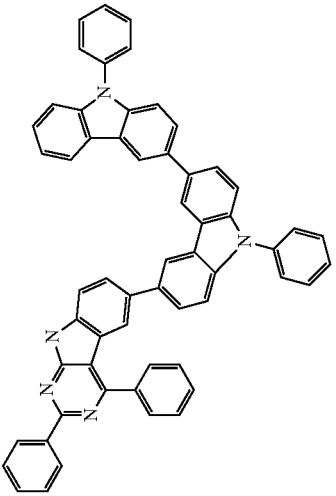 | 80% |

| Reactant 1 | Reactant 2 | Product | Yield |
|---|---|---|---|
| 15g | [3842-55-5] | | 79% |

-continued
| Reactant 1 | Reactant 2 | Product | Yield |
|---|---|---|---|
| 16g 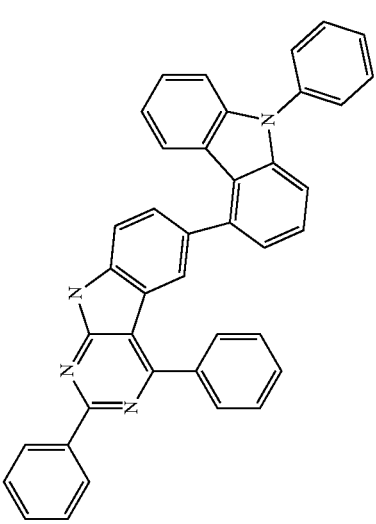 | 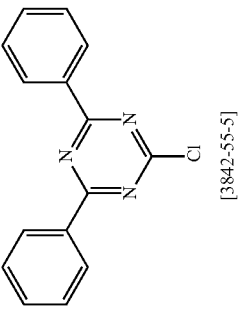 [3842-55-5] | 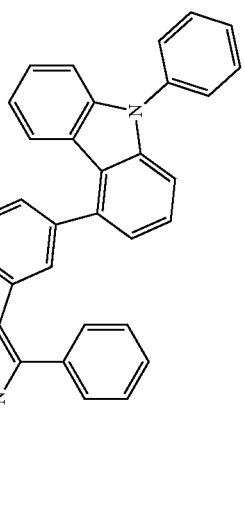 | 77% |

| Reactant 1 | Reactant 2 | Product | Yield |
|---|---|---|---|
| 17g | PhBr | | 81% |

-continued

| Reactant 1 | Reactant 2 | Product | Yield |
|---|---|---|---|
| 18g | [1266389-17-6] | | 63% |

| Reactant 1 | Reactant 2 | Product | Yield |
|---|---|---|---|
| 19g | [1266389-17-6] | | 62% |

| Reactant 1 | Reactant 2 | Product | Yield |
|---|---|---|---|
| 20g | [955959-84-9] | | 78% |

| Reactant 1 | Reactant 2 | Product | Yield |
|---|---|---|---|
| 21g | [29874-83-7] | | 74% |

| | Reactant 1 | Reactant 2 | Product | Yield |
|---|---|---|---|---|
| 22g | | [1171247-63-4] | | 76% |
| 23g | | | | 88% |

-continued
| | Reactant 1 | Reactant 2 | Product | Yield |
|---|---|---|---|---|
| 24g | 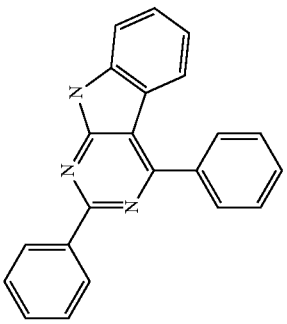 | 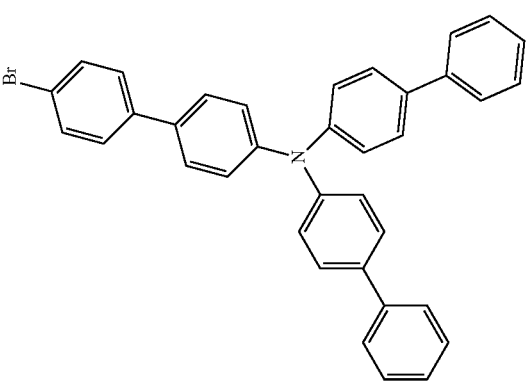 [728039-63-2] | 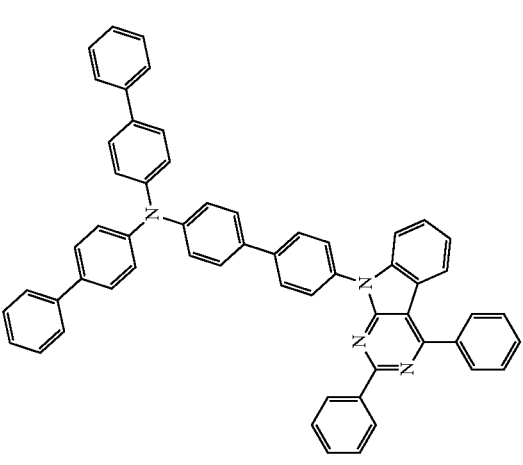 | 79% |
| 25g | 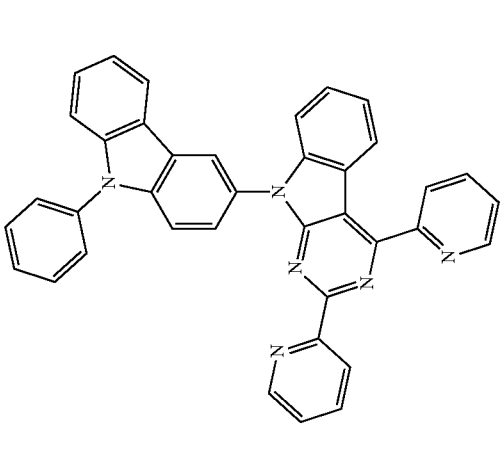 | [1153-85-1] | | 77% |

-continued
| Reactant 1 | Reactant 2 | Product | Yield |
|---|---|---|---|
| 26g  | 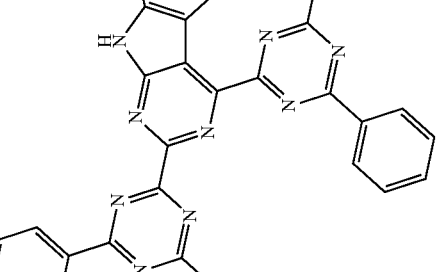 | 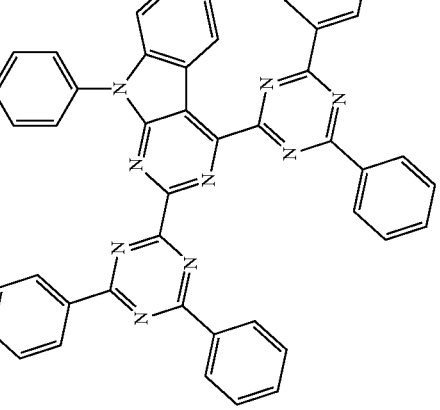 | 76% |
| 27g 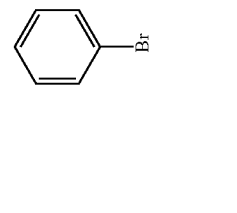 | 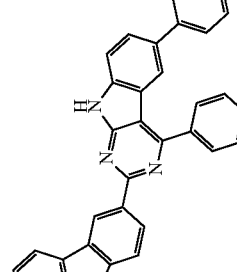 | 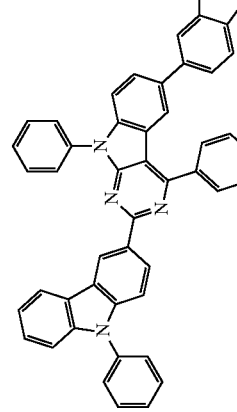 | 79% |

| | Reactant 1 | Reactant 2 | Product | Yield |
|---|---|---|---|---|
| 28g | | [1153-85-1] | | 83% |
| 29g | | [864377-31-1] | | 81% |

| Reactant 1 | Reactant 2 | Product | Yield |
|---|---|---|---|
| 30g | [phenyl bromide] | [product structure] | 85% |

| Reactant 1 | Reactant 2 | Product | Yield |
|---|---|---|---|
| 31g | [1266389-17-6] | | 63% |

| Reactant 1 | Reactant 2 | Product | Yield |
|---|---|---|---|
| 32g | [1266389-17-6] | | 61% |

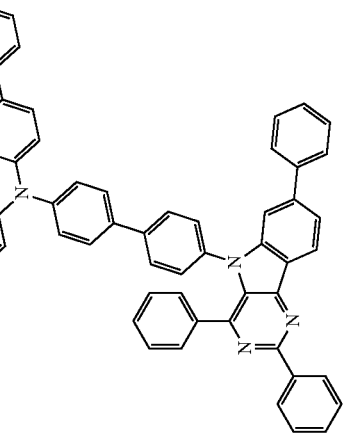

-continued
| | Reactant 1 | Reactant 2 | Product | Yield |
|---|---|---|---|---|
| 34g | 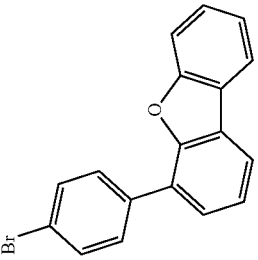 | 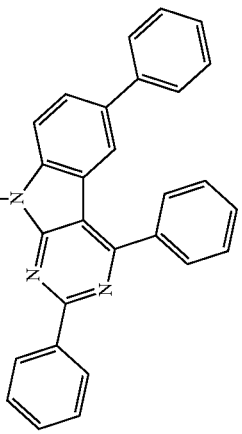 [955959-84-9] | 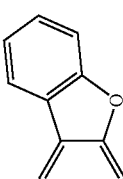 | 87% |
| 35g | 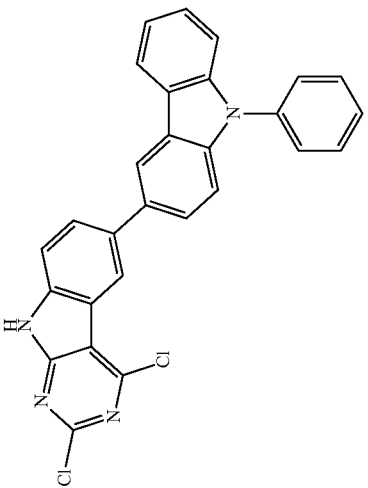 | 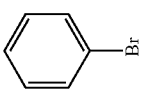 | 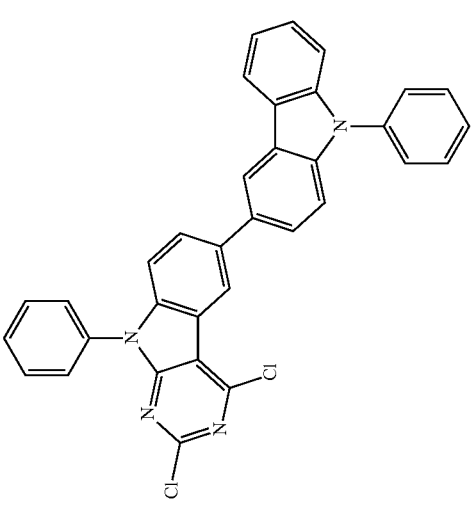 | 57% |

| | Reactant 1 | Reactant 2 | Product | Yield |
|---|---|---|---|---|
| 36g | | | | 52% |
| 37g | | | | 56% |

| | Reactant 1 | Reactant 2 | Product | Yield |
|---|---|---|---|---|
| 38g | | | | 63% |
| 39g | | | | 67% |

| Reactant 1 | Reactant 2 | Product | Yield |
|---|---|---|---|
| 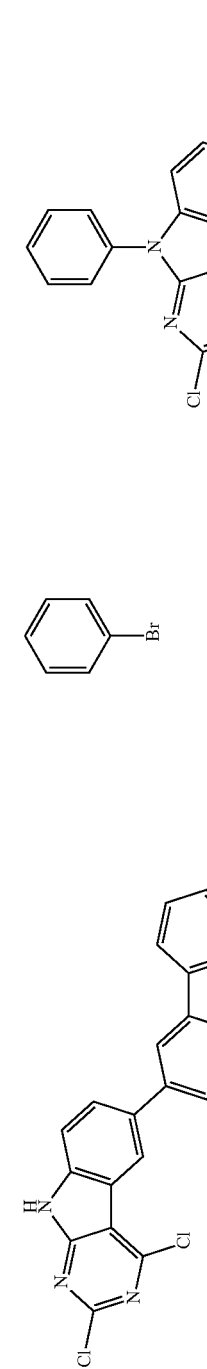<br>40g | 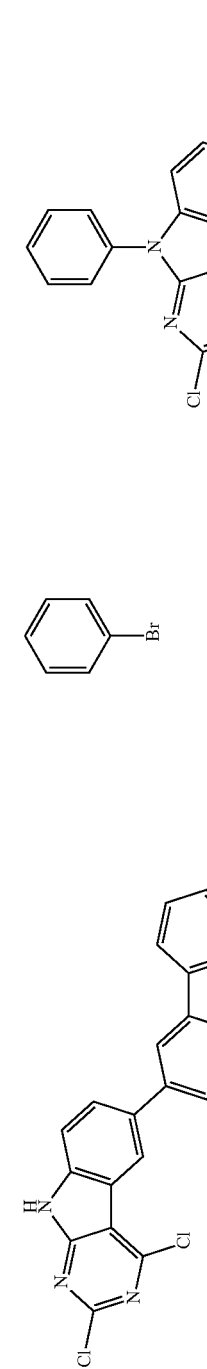 | 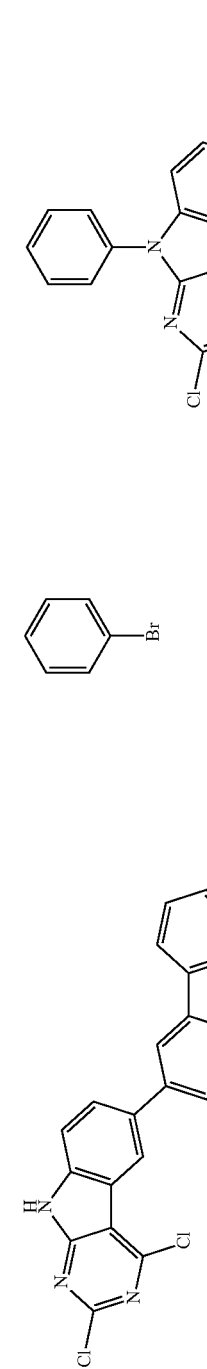 | 52% |

| Reactant 1 | Reactant 2 | Product | Yield |
|---|---|---|---|
| 41g | [1266389-17-6] | | 67% |

-continued

| | Reactant 1 | Reactant 2 | Product | Yield |
|---|---|---|---|---|
| 42g | (structure) | Ph-Br | (structure) | 65% |
| 43g | (structure) g37 | (structure) [1257220-47-5] | (structure) | 77% |

| | Reactant 1 | Reactant 2 | Product | Yield |
|---|---|---|---|---|
| 44g | g37 | [1313395-18-4] | | 76% |
| 45g | | [1313395-18-4] | | 75% |

| Reactant 1 | Reactant 2 | Product | Yield |
|---|---|---|---|
| 46g | [1313395-18-4] | | 77% |
| 47g | 1454679-22-1 | | 76% |

| | Reactant 1 | Reactant 2 | Product | Yield |
|---|---|---|---|---|
| 48g | | [32228-99-2] | | 80% |
| 49g | | [32228-99-2] | | 80% | h) 6-bromo-2,4,9-triphenyl-9H-pyrimido[4,5-b]indole

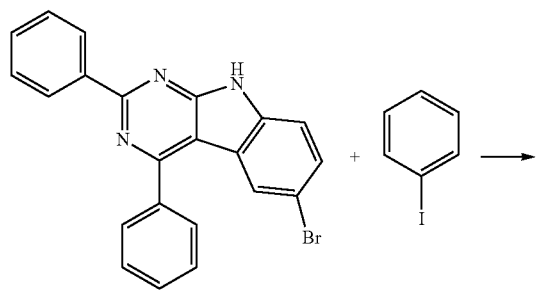

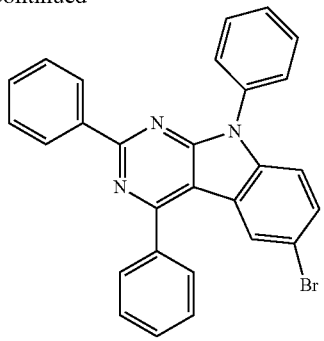

20 g (50 mmol) of 6-bromo-2,4-diphenyl-9H-pyrimido[4,5-b]indole, 560 mg (25 mmol) of Pd(OAc)$_2$, 19.3 g (118 mmol) CuI and 20.8 (100 mmol) of iodobenzene are suspended in 300 ml of degassed DMF under a protective gas atmosphere. The reaction mixture is then heated 24 h under reflux at 140° C. After cooling, the solvent is removed in vacuum, the residue is dissolved in dichloromethane and water is added. Thereafter, the organic phase is separated off and filtered through silica gel. The product is purified by column chromatography on silica gel with toluene/heptane (1:2) and finally sublimed in a high vacuum (p=5×10$^{-7}$ mbar) (99.9% purity). The yield is 15.23 g (32 mmol), corresponding to 64% of theory.

The following compounds are prepared analogously:

| Reactant 1 | Reactant 2 | Product | Yield |
|---|---|---|---|
| 1h 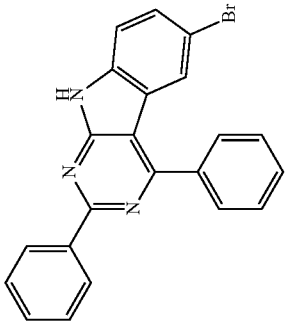 | 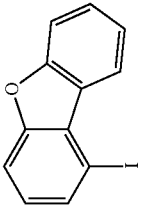 [857784-97-5] | 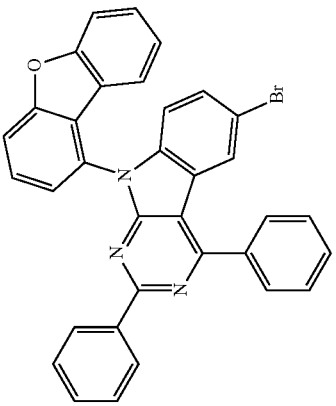 | 61% |
| 2h 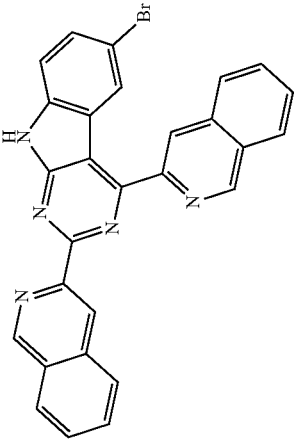 | 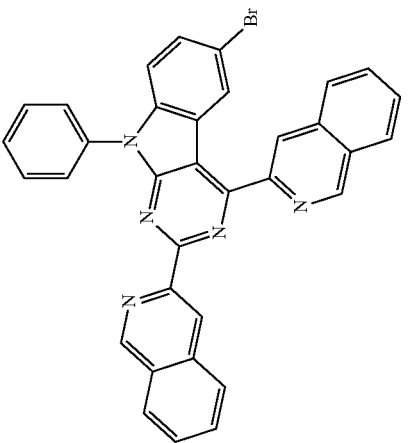 | 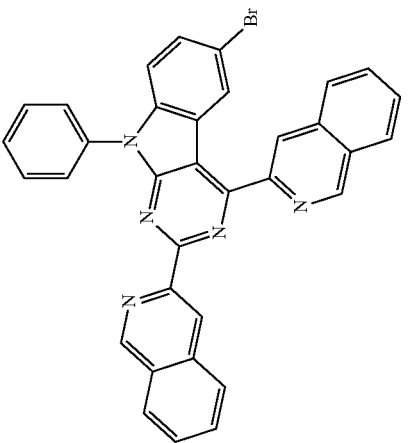 | 57% |

| Reactant 1 | Reactant 2 | Product | Yield |
|---|---|---|---|
| 3h 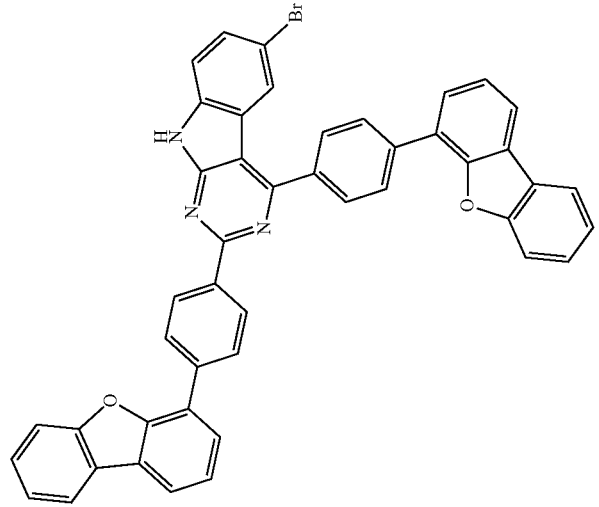 | 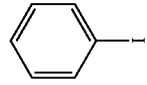 | 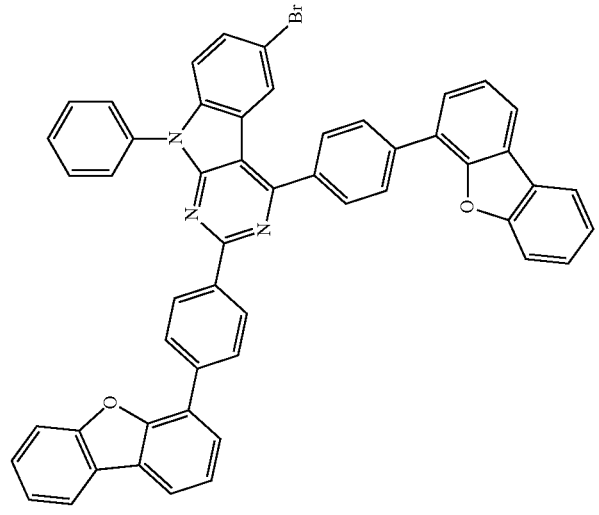 | 74% |

| Reactant 1 | Reactant 2 | Product | Yield |
|---|---|---|---|
| 4h 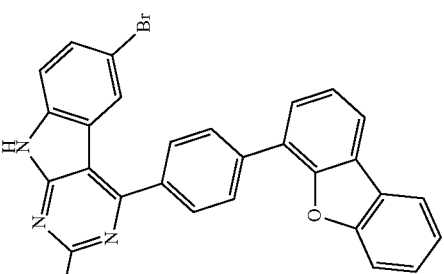 | 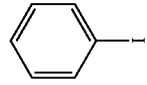 |  | 52% |

-continued

| | Reactant 1 | Reactant 2 | Product | Yield |
|---|---|---|---|---|
| 5h | | | | 55% |
| 6h | | | | 53% |

-continued

| | Reactant 1 | Reactant 2 | Product | Yield |
|---|---|---|---|---|
| 7h | | [65344-26-5] | | 60% |
| 8h | | | | 66% |

-continued

| | Reactant 1 | Reactant 2 | Product | Yield |
|---|---|---|---|---|
| 9h | | | | 81% |
| 10h | | | | 85% |
| 11h | [92750-42-0] | | | 69% |

| Reactant 1 | Reactant 2 | Product | Yield |
|---|---|---|---|
| 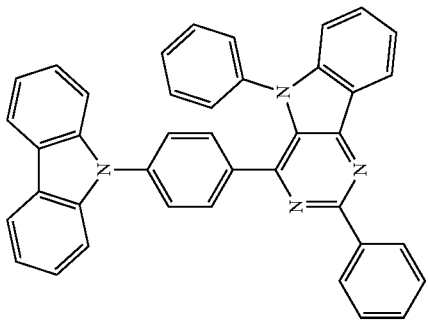 12h | 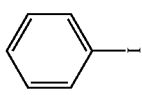 | 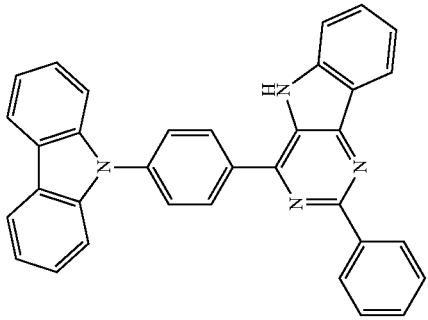 | 71% |
| 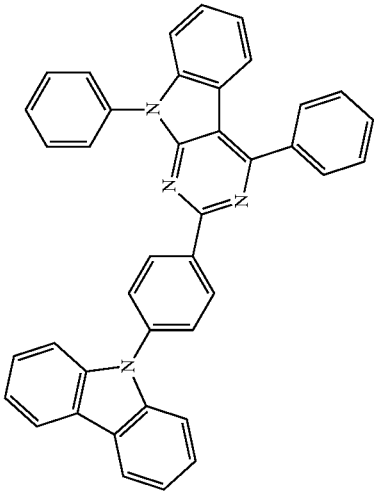 13h | 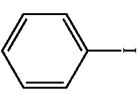 | 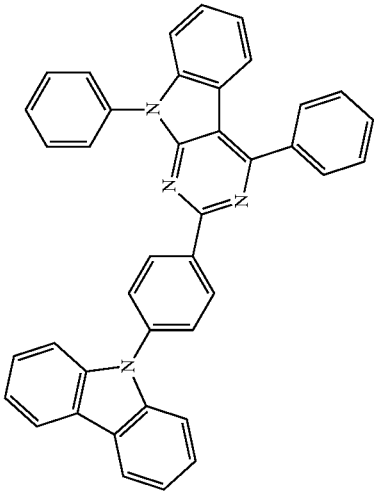 | 75% |

| Reactant 1 | Reactant 2 | Product | Yield |
|---|---|---|---|
| 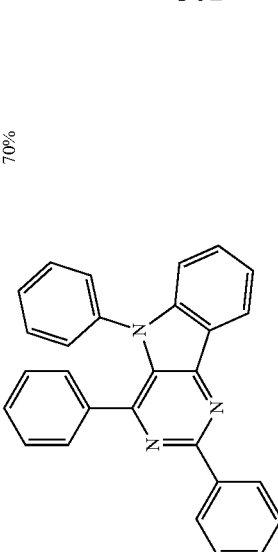 | 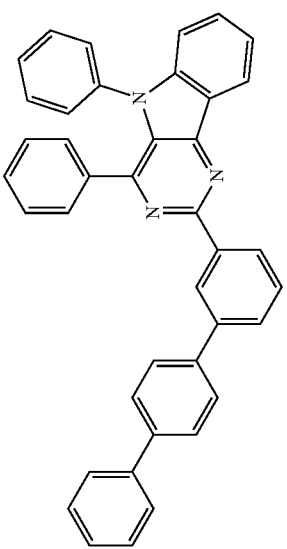 | 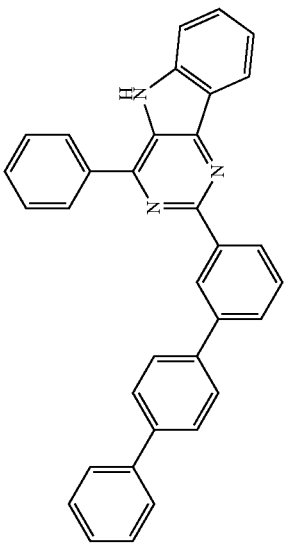 | 70% |
| 14h | | | |

303 i) 6-(3-carbazol-9-yl-phenyl)-2,4,9-triphenyl-9H-pyrimido[4,5-b]indole

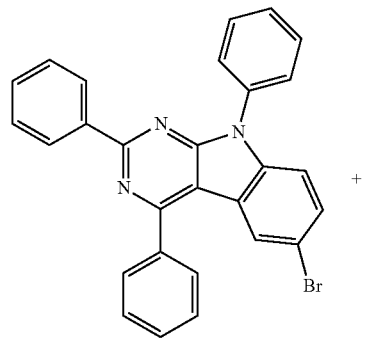

+

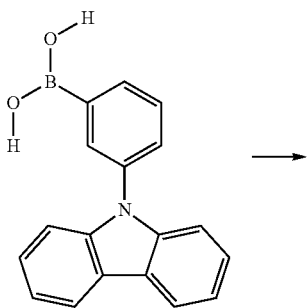

[864377-33-3]

→

304

-continued

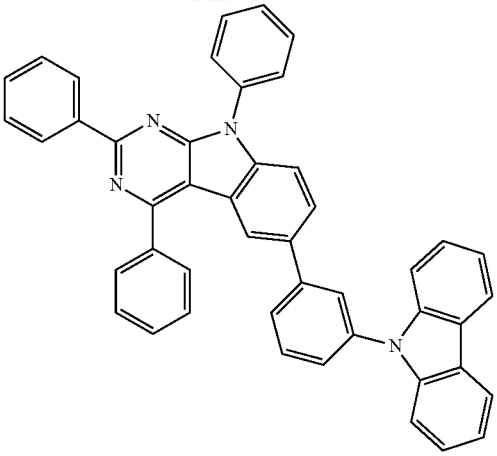

74.2 g (156 mmol) of 6-bromo-2,4-diphenyl-9H-pyrimido[4,5-b]indole, 49.3 g (172 mmol) of 3-(9H-carbazol-9-yl-phenyl]-boronic acid and 36 g (340 mmol) of sodium carbonate are suspended in 1000 mL ethylene glycol diethyl ether and 280 mL of water. Afterwards, 1.8 g (1.5 mmol) of tetrakis(triphenylphosphine)-palladium(0) is added to the reaction mixture, which is heated for 16 hours under reflux After cooling, the organic phase is separated off, filtered through silica gel and then evaporated to dryness. The product is purified by column chromatography on silica gel with toluene/heptane (1:2) and finally sublimed in high vacuum ($p=5 \times 10^{-7}$ mbar) (purity 99.9%). The yield is 84 g (132 mmol), corresponding to 85% of theory.

The following compounds are prepared analogously:

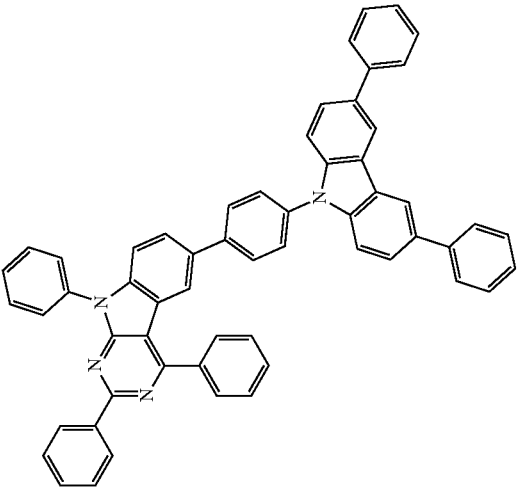

-continued
| | Reactant 1 | Reactant 2 | Product | Yield |
|---|---|---|---|---|
| 2i | 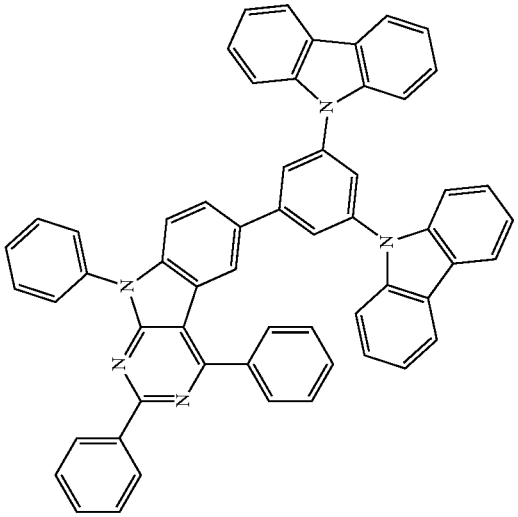 | 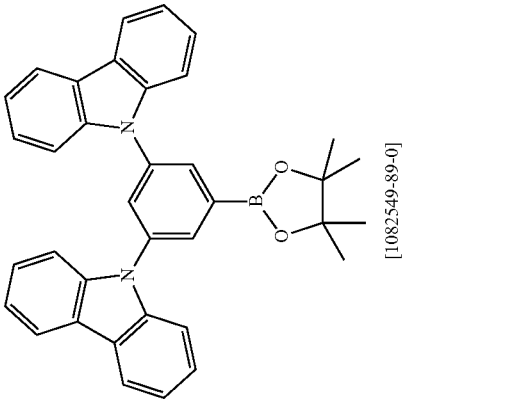 [1082549-89-0] | 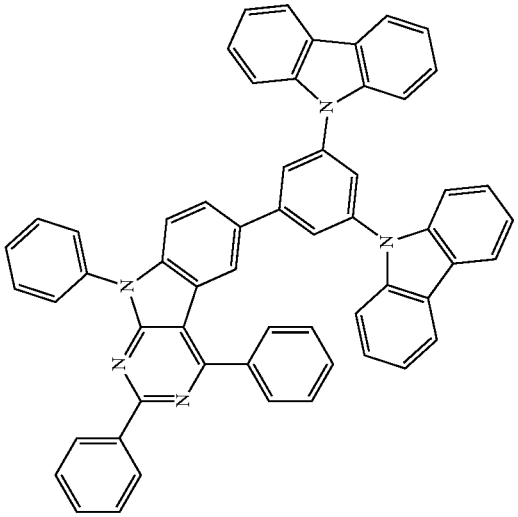 | 75% |

| | Reactant 1 | Reactant 2 | Product | Yield |
|---|---|---|---|---|
| 3i | | [1398394-64-3] | | 70% |

-continued

| | Reactant 1 | Reactant 2 | Product | Yield |
|---|---|---|---|---|
| 4i | | [1369587-25-6] | | 77% |
| 5i | | [1449754-82-8] | | 69% |

-continued

| | Reactant 1 | Reactant 2 | Product | Yield |
|---|---|---|---|---|
| 6i | | [1547492-13-6] | | 64% |
| 7i | | | | 71% |

-continued

| | Reactant 1 | Reactant 2 | Product | Yield |
|---|---|---|---|---|
| 8i | | | | 70% |
| 9i | | | | 79% |

| | Reactant 1 | Reactant 2 | Product | Yield |
|---|---|---|---|---|
| 10i | 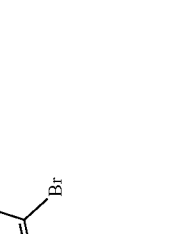 | 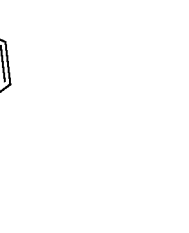 | 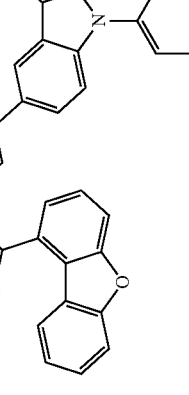 | 78% |
| 11i |  | 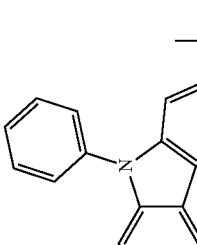 [1379585-25-7] | 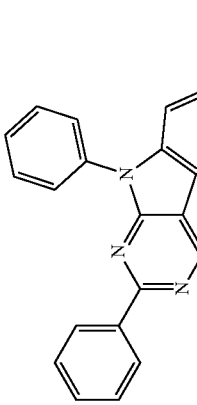 | 75% |

Device Examples

Fabrication of OLEDs

The following examples V1 to E16 (see Table 1 and 2) show data of various OLEDs.

Pre-Treatment for Examples V1-E16:

Glass plates coated with structured ITO (50 nm, indium tin oxide) form the substrates on which the OLEDs are processed. Before evaporation of the OLED materials, the substrates are pre-baked for 15 minutes at 250° C., followed by an $O_2$ and subsequent Argon plasma treatment.

The OLEDs have in principle the following layer structure: substrate/hole-injection layer (HIL)/hole-transport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The exact layer structure is denoted in Table 1. The materials used for the OLED fabrication are presented in Table 3.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by co-evaporation. An expression such as IC1:M1:TEG1 (55%:35%:10%) here means that material IC1 is present in the layer in a proportion by volume of 55%, M1 is present in the layer in a proportion of 35% and TEG1 is present in the layer in a proportion of 10%. Analogously, the electron-transport layer may also consist of a mixture of two materials.

The OLEDs are characterised by standard methods. For this purpose, the electroluminescence spectra, the current efficiency (CE1000, measured in cd/A at 1000 cd/m$^2$), the luminous efficacy (LE1000, measured in lm/W at 1000 cd/m$^2$), the external quantum efficiency (EQE1000, measured in % at 1000 cd/m$^2$) and the voltage (U1000, measured at 1000 cd/m$^2$ in V) are determined from current/voltage/luminance characteristic lines (IUL characteristic lines) assuming a Lambertian emission profile. The electroluminescence (EL) spectra are recorded at a luminous density of 1000 cd/m$^2$ and the CIE 1931 x and y coordinates are then calculated from the EL spectrum.

The device data of various OLEDs is summarized in Table 2. The examples V1-V4 are comparison examples according to the state-of-the-art. The examples E1-E16 show data of inventive OLEDs.

In the following section several examples are described in more detail to show the advantages of the inventive OLEDs.

Use of Inventive Compounds as Host Material in Phosphorescent OLEDs

The use of the inventive compounds as host material results in significantly improved OLED device data compared to state-of-the-art materials, especially with respect to EQE and luminous efficacy.

The use of the inventive materials I2, I3 and I4 as host material in phosphorescent green OLEDs results in 9-15% improved EQE compared to a device with the material C1 (comparison of example V1 with E2, E3 and E4 in Table 2). The data of E1 were not measured as I1 is more suitable as a matrix material for red or yellow emitters rather than for green emitters like TEG2.

The use of the inventive materials I5, I6 and I7 as host material in phosphorescent green OLEDs results in 9-15% improved luminous efficacy compared to a device with the material C2 (comparison of example V2 with E5, E6 and E7).

The use of the inventive materials I8, I9 and I10 as host material in phosphorescent green OLEDs results in 20-25% improved EQE compared to a device with the material C3 (comparison of example V3 with E8, E9 and E10).

The use of the inventive material I11 as host material in phosphorescent green OLEDs results in 5% improved EQE compared to a device with the material C4 (comparison of example V4 with E11).

TABLE 1

| | | | | OLED layer structure | | |
|---|---|---|---|---|---|---|
| Ex. | HIL Thickness | HTL Thickness | EBL Thickness | EML Thickness | HBL Thickness | ETL Thickness |
| V1 | HATCN 5 nm | SpMA1 230 nm | SpMA3 20 nm | IC5:C1:TEG2 (55%:40%:5%) 30 nm | ST2 10 nm | ST2:LiQ (50%:50%) 30 nm |
| V2 | HATCN 5 nm | SpMA1 230 nm | SpMA3 20 nm | IC5:C2:TEG2 (55%:40%:5%) 30 nm | ST2 10 nm | ST2:LiQ (50%:50%) 30 nm |
| V3 | HATCN 5 nm | SpMA1 230 nm | SpMA3 20 nm | IC5:C3:TEG2 (55%:40%:5%) 30 nm | ST2 10 nm | ST2:LiQ (50%:50%) 30 nm |
| V4 | HATCN 5 nm | SpMA1 230 nm | SpMA3 20 nm | IC5:C4:TEG2 (55%:40%:5%) 30 nm | ST2 10 nm | ST2:LiQ (50%:50%) 30 nm |
| E1 | HATCN 5 nm | SpMA1 230 nm | SpMA3 20 nm | IC5:I1:TEG2 (55%:40%:5%) 30 nm | ST2 10 nm | ST2:LiQ (50%:50%) 30 nm |
| E2 | HATCN 5 nm | SpMA1 230 nm | SpMA3 20 nm | IC5:I2:TEG2 (55%:40%:5%) 30 nm | ST2 10 nm | ST2:LiQ (50%:50%) 30 nm |

TABLE 1-continued

| | | | | OLED layer structure | | |
|---|---|---|---|---|---|---|
| Ex. | HIL Thickness | HTL Thickness | EBL Thickness | EML Thickness | HBL Thickness | ETL Thickness |
| E3 | HATCN 5 nm | SpMA1 230 nm | SpMA3 20 nm | IC5:I3:TEG2 (55%:40%:5%) 30 nm | ST2 10 nm | ST2:LiQ (50%:50%) 30 nm |
| E4 | HATCN 5 nm | SpMA1 230 nm | SpMA3 20 nm | IC5:I4:TEG2 (55%:40%:5%) 30 nm | ST2 10 nm | ST2:LiQ (50%:50%) 30 nm |
| E5 | HATCN 5 nm | SpMA1 230 nm | SpMA3 20 nm | IC5:I5:TEG2 (55%:40%:5%) 30 nm | ST2 10 nm | ST2:LiQ (50%:50%) 30 nm |
| E6 | HATCN 5 nm | SpMA1 230 nm | SpMA3 20 nm | IC5:I6:TEG2 (55%:40%:5%) 30 nm | ST2 10 nm | ST2:LiQ (50%:50%) 30 nm |
| E7 | HATCN 5 nm | SpMA1 230 nm | SpMA3 20 nm | IC5:I7:TEG2 (55%:40%:5%) 30 nm | ST2 10 nm | ST2:LiQ (50%:50%) 30 nm |
| E8 | HATCN 5 nm | SpMA1 230 nm | SpMA3 20 nm | IC5:I8:TEG2 (55%:40%:5%) 30 nm | ST2 10 nm | ST2:LiQ (50%:50%) 30 nm |
| E9 | HATCN 5 nm | SpMA1 230 nm | SpMA3 20 nm | IC5:I9:TEG2 (55%:40%:5%) 30 nm | ST2 10 nm | ST2:LiQ (50%:50%) 30 nm |
| E10 | HATCN 5 nm | SpMA1 230 nm | SpMA3 20 nm | IC5:I10:TEG2 (55%:40%:5%) 30 nm | ST2 10 nm | ST2:LiQ (50%:50%) 30 nm |
| E11 | HATCN 5 nm | SpMA1 230 nm | SpMA3 20 nm | IC5:I11:TEG2 (55%:40%:5%) 30 nm | ST2 10 nm | ST2:LiQ (50%:50%) 30 nm |
| E12 | HATCN 5 nm | SpMA1 230 nm | SpMA3 20 nm | 1g:IC3:TEG2 (50%:40%:10%) 30 nm | ST2 10 nm | ST2:LiQ (50%:50%) 30 nm |
| E13 | HATCN 5 nm | SpMA1 125 nm | SpMA3 10 nm | 45g:TER5 (97%:3%) 40 nm | | ST2:LiQ (50%:50%) 35 nm |
| E14 | HATCN 5 nm | SpMA1 125 nm | SpMA3 10 nm | 8g:TER5 (97%:3%) 40 nm | | ST2:LiQ (50%:50%) 35 nm |
| E15 | HATCN 5 nm | SpMA1 230 nm | SpMA3 20 nm | IC5:IC3:TEG2 (60%:30%:10%) 30 nm | ST2 10 nm | 9g:LiQ (50%:50%) 30 nm |
| E16 | HATCN 5 nm | SpMA1 230 nm | SpMA3 20 nm | IC5:IC3:TEG2 (60%:30%:10%) 30 nm | ST2 10 nm | 3g:LiQ (50%:50%) 30 nm |

TABLE 2

| | | OLED device data | | | |
|---|---|---|---|---|---|
| Ex. | U1000 (V) | CE1000 (cd/A) | LE1000 (lm/W) | EQE1000 | CIE x/y at 1000 cd/m$^2$ |
| V1 | 3.4 | 71 | 66 | 19.4% | 0.31/0.64 |
| V2 | 3.5 | 74 | 66 | 20.1% | 0.32/0.63 |
| V3 | 3.3 | 63 | 60 | 17.2% | 0.31/0.64 |
| V4 | 3.3 | 75 | 71 | 20.2% | 0.32/0.64 |
| E2 | 3.3 | 81 | 77 | 22.1% | 0.31/0.64 |
| E3 | 3.5 | 79 | 71 | 21.3% | 0.32/0.64 |
| E4 | 3.4 | 78 | 72 | 21.1% | 0.33/0.63 |
| E5 | 3.4 | 79 | 73 | 21.4% | 0.32/0.64 |
| E6 | 3.3 | 80 | 76 | 21.6% | 0.32/0.63 |
| E7 | 3.4 | 78 | 72 | 21.3% | 0.32/0.64 |
| E8 | 3.4 | 76 | 70 | 20.7% | 0.32/0.64 |
| E9 | 3.4 | 80 | 74 | 21.5% | 0.33/0.63 |
| E10 | 3.3 | 78 | 74 | 21.0% | 0.34/0.63 |
| E11 | 3.4 | 79 | 73 | 21.3% | 0.33/0.63 |
| E12 | 3.2 | 75 | 74 | 20.2% | 0.32/0.64 |
| E13 | 3.4 | 27 | 25 | 22.7% | 0.67/0.33 |
| E14 | 3.6 | 25 | 22 | 22.4% | 0.67/0.33 |
| E15 | 3.4 | 69 | 64 | 18.9% | 0.32/0.64 |
| E16 | 3.3 | 67 | 64 | 18.4% | 0.32/0.63 |

TABLE 3

Chemical structures of the OLED materials

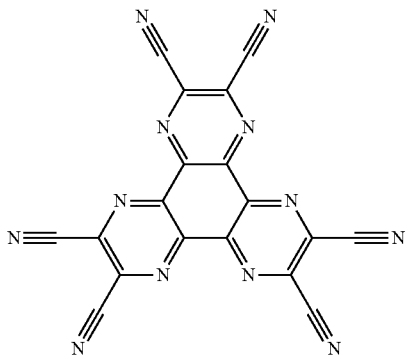 [SMILES: N#Cc1nc2c3nc(C#N)c(C#N)nc3c3nc(C#N)c(C#N)nc3c2nc1C#N]

HATCN

TABLE 3-continued
Chemical structures of the OLED materials
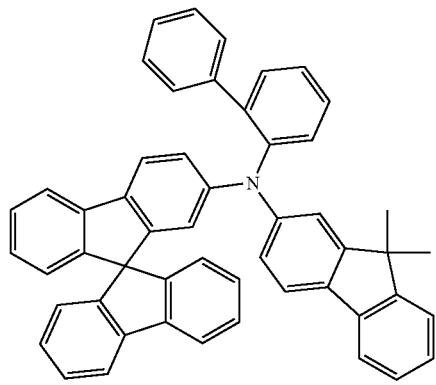 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA1
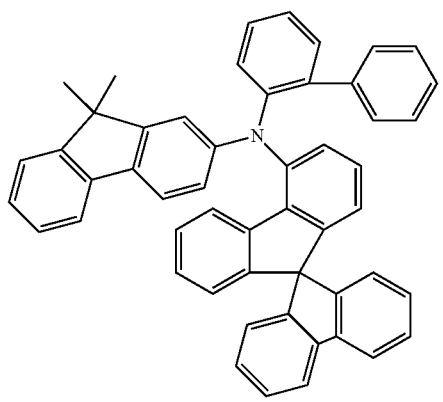 [SMILES: CC1(C)c2ccccc2-c2ccc(N(c3ccccc3-c3ccccc3)c3cccc4c3-c3ccccc3C43c4ccccc4-c4ccccc43)cc21]
SpMA3
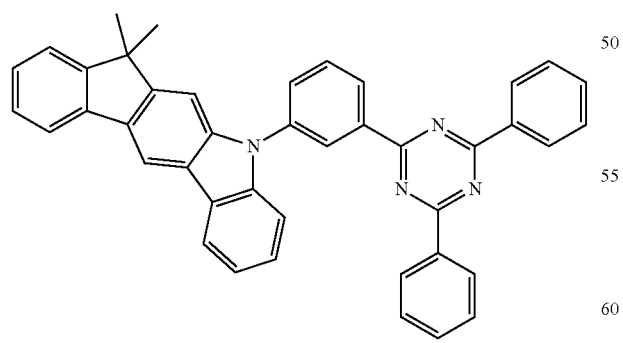
IC5
TABLE 3-continued
Chemical structures of the OLED materials
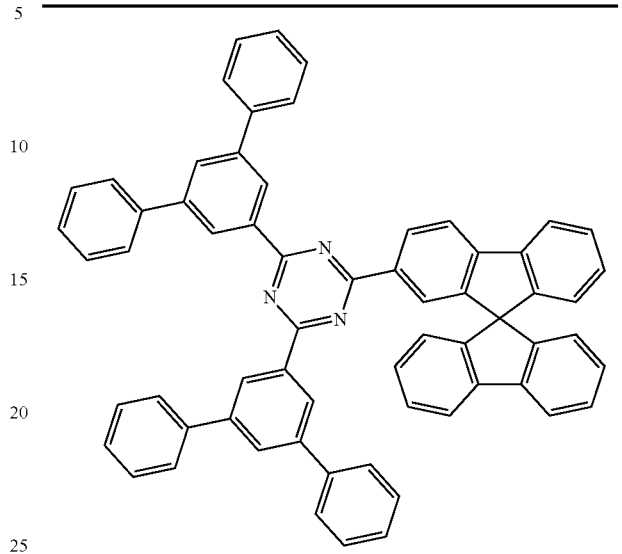
ST2
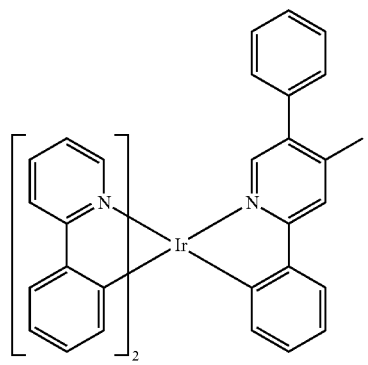
TEG2
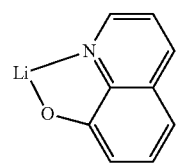
LiQ TABLE 3-continued
Chemical structures of the OLED materials
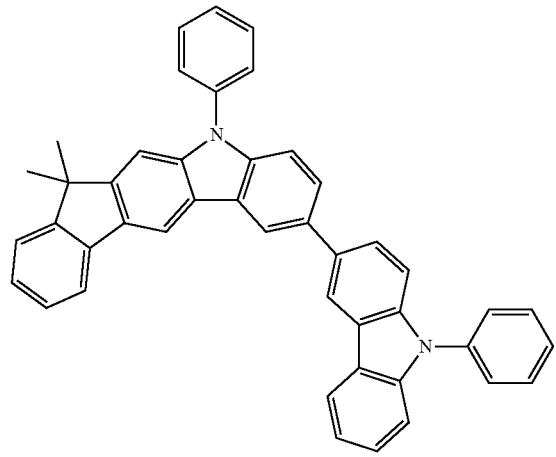 [SMILES: CC1(C)c2ccccc2-c2cc3c4cc(-c5ccc6c(c5)c5ccccc5n6-c5ccccc5)ccc4n(-c4ccccc4)c3cc21]
IC3
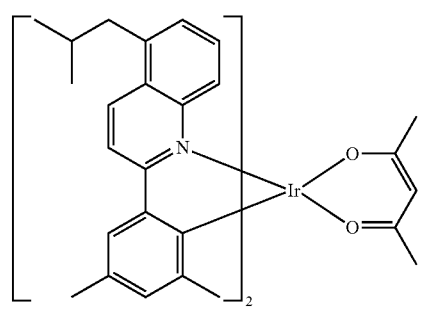
TER5
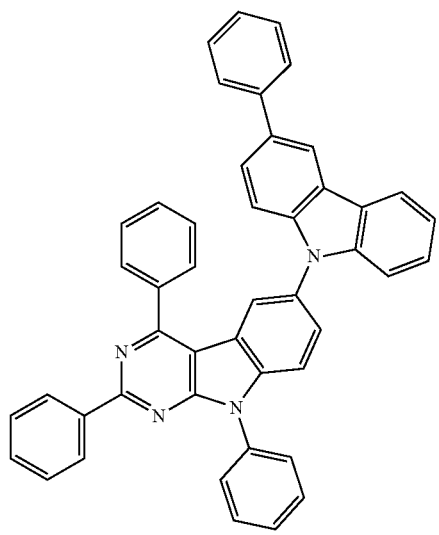
US20147142301
C1
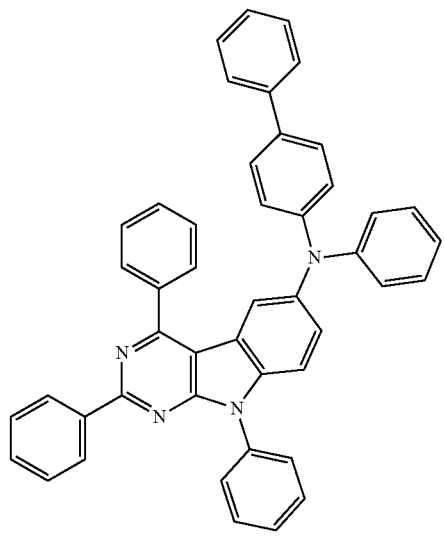 [SMILES: c1ccc(-c2ccc(N(c3ccccc3)c3ccc4c(c3)c3c(-c5ccccc5)nc(-c5ccccc5)nc3n4-c3ccccc3)cc2)cc1]
I1
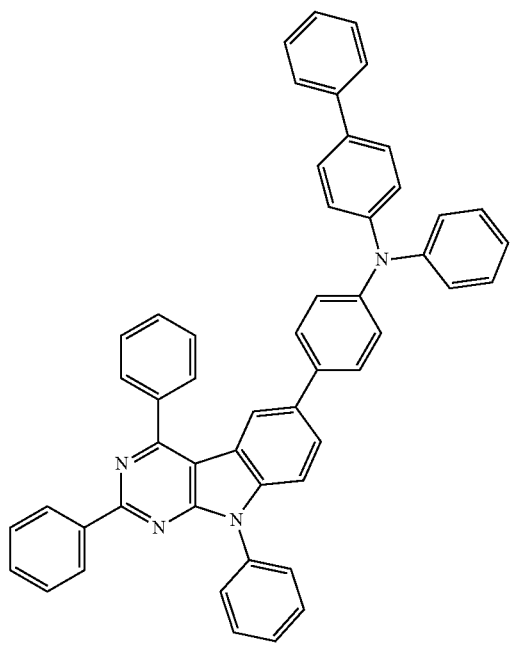 [SMILES: c1ccc(-c2ccc(N(c3ccccc3)c3ccc(-c4ccc5c(c4)c4c(-c6ccccc6)nc(-c6ccccc6)nc4n5-c4ccccc4)cc3)cc2)cc1]
I2

TABLE 3-continued
Chemical structures of the OLED materials
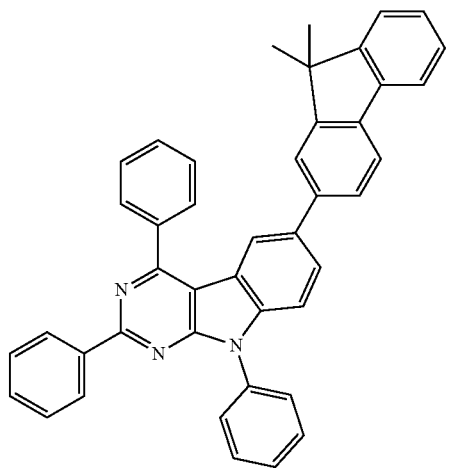 [SMILES: CC1(C)c2ccccc2-c2ccc(-c3ccc4c(c3)c3c(-c5ccccc5)nc(-c5ccccc5)nc3n4-c3ccccc3)cc21]
I3
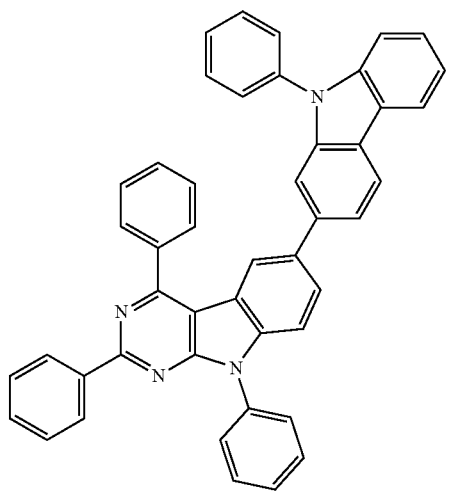 [SMILES: c1ccc(-c2nc(-c3ccccc3)c3c4cc(-c5ccc6c7ccccc7n(-c7ccccc7)c6c5)ccc4n(-c4ccccc4)c3n2)cc1]
I4
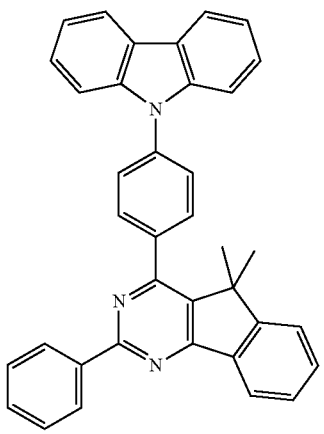
WO2014084612
C2
TABLE 3-continued
Chemical structures of the OLED materials
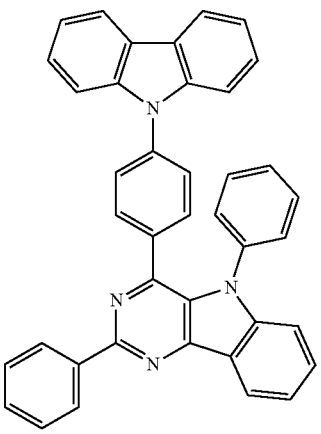 [SMILES: c1ccc(-c2nc(-c3ccc(-n4c5ccccc5c5ccccc54)cc3)c3c(n2)c2ccccc2n3-c2ccccc2)cc1]
I5
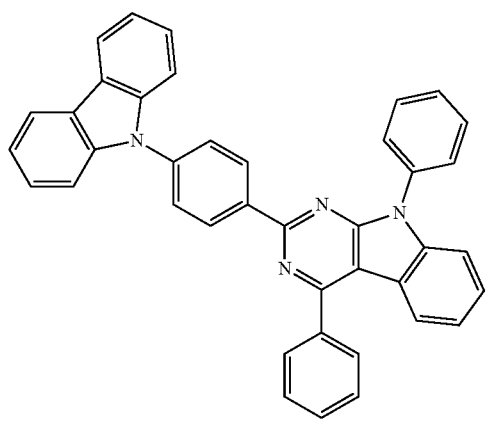 [SMILES: c1ccc(-c2nc(-c3ccc(-n4c5ccccc5c5ccccc54)cc3)nc3c2c2ccccc2n3-c2ccccc2)cc1]
I6
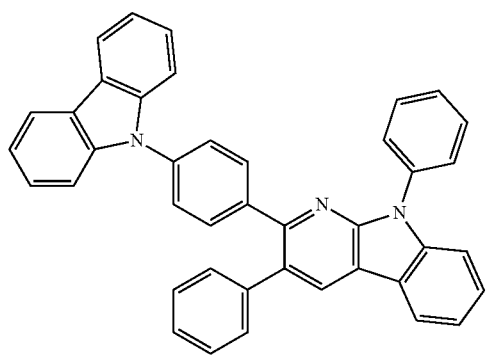 [SMILES: c1ccc(-c2cc3c4ccccc4n(-c4ccccc4)c3nc2-c2ccc(-n3c4ccccc4c4ccccc43)cc2)cc1]
I7

TABLE 3-continued
Chemical structures of the OLED materials
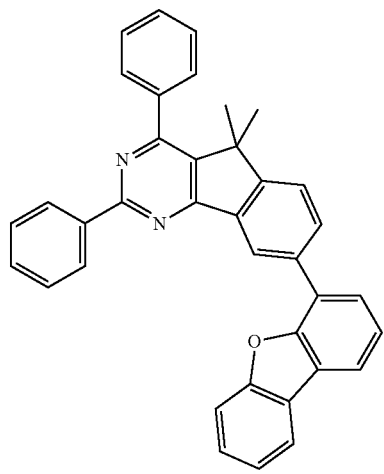
WO2014084612
C3
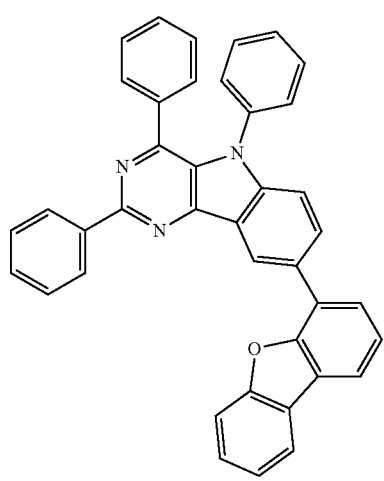 [SMILES: c1ccc(-c2nc(-c3ccccc3)c3c(n2)c2cc(-c4cccc5c4oc4ccccc45)ccc2n3-c2ccccc2)cc1]
I8
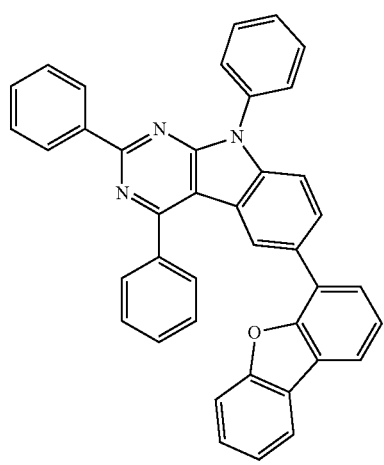 [SMILES: c1ccc(-c2nc(-c3ccccc3)c3c4cc(-c5cccc6c5oc5ccccc56)ccc4n(-c4ccccc4)c3n2)cc1]
I9
TABLE 3-continued
Chemical structures of the OLED materials
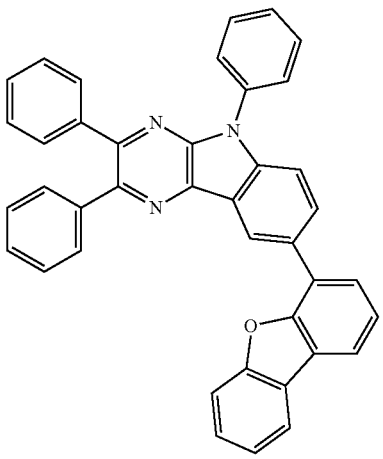 [SMILES: c1ccc(-c2nc3c4cc(-c5cccc6c5oc5ccccc56)ccc4n(-c4ccccc4)c3nc2-c2ccccc2)cc1]
I10
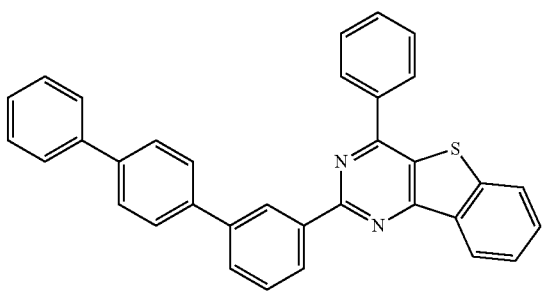 [SMILES: c1ccc(-c2ccc(-c3cccc(-c4nc(-c5ccccc5)c5sc6ccccc6c5n4)c3)cc2)cc1]
C4
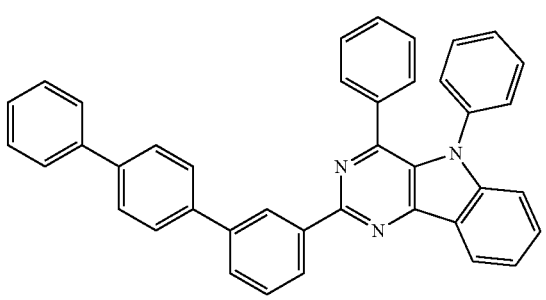 [SMILES: c1ccc(-c2ccc(-c3cccc(-c4nc(-c5ccccc5)c5c(n4)c4ccccc4n5-c4ccccc4)c3)cc2)cc1]
I11

TABLE 3-continued
Chemical structures of the OLED materials
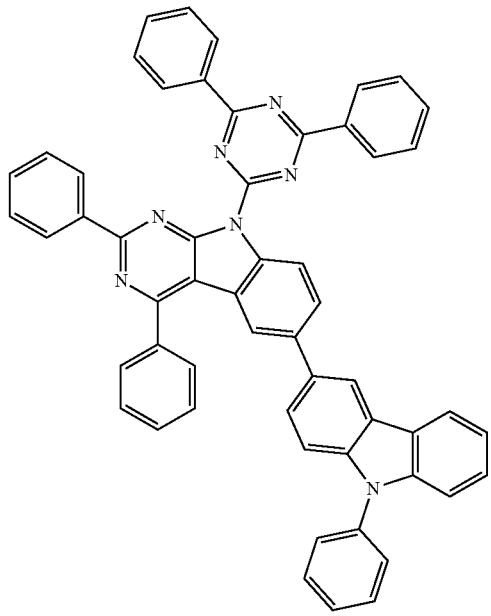 [SMILES: c1ccc(-c2nc(-c3ccccc3)nc(-n3c4ccc(-c5ccc6c(c5)c5ccccc5n6-c5ccccc5)cc4c4c(-c5ccccc5)nc(-c5ccccc5)nc43)n2)cc1]
1g
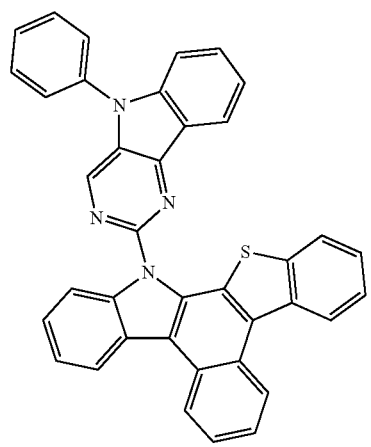 [SMILES: c1ccc(-n2c3ccccc3c3nc(-n4c5ccccc5c5c6ccccc6c6c7ccccc7sc6c54)ncc32)cc1]
45g
TABLE 3-continued
Chemical structures of the OLED materials
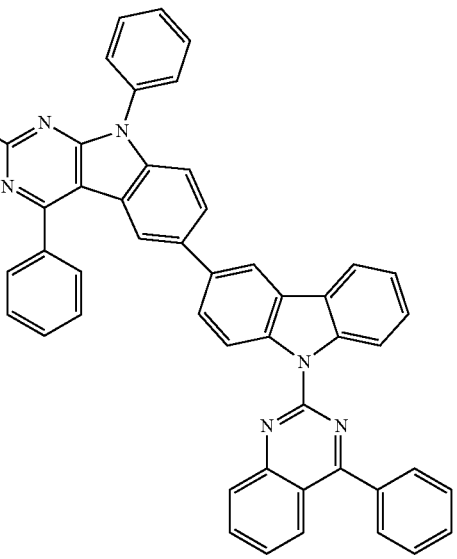
8g
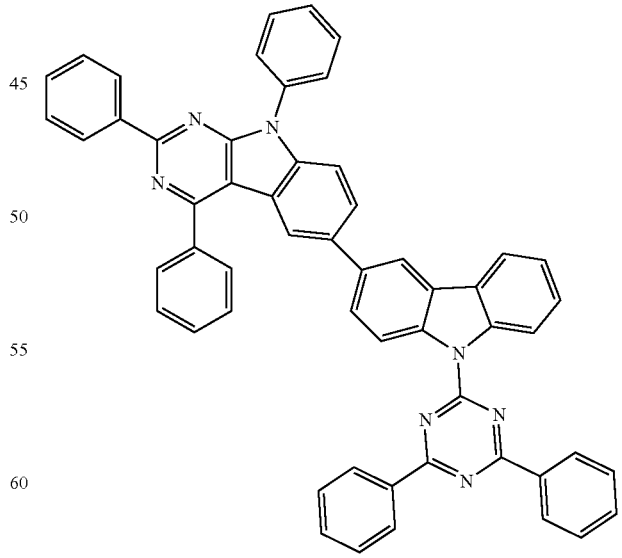
9g TABLE 3-continued Chemical structures of the OLED materials

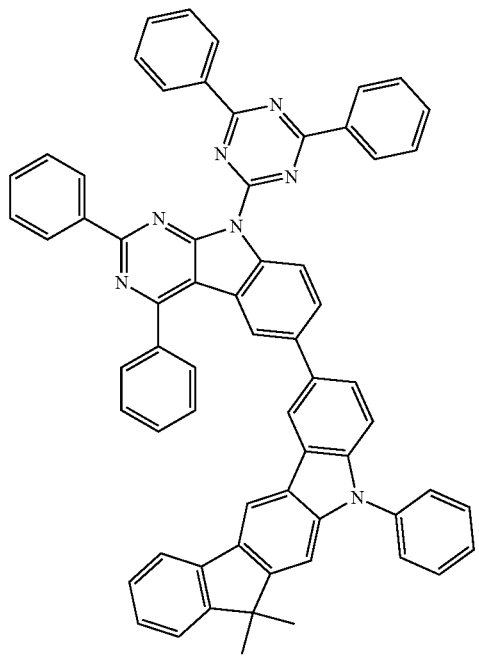 [SMILES: CC1(C)c2ccccc2-c2cc3c4cc(-c5ccc6c(c5)c5c(-c7ccccc7)nc(-c7ccccc7)nc5n6-c5nc(-c6ccccc6)nc(-c6ccccc6)n5)ccc4n(-c4ccccc4)c3cc21]

3g

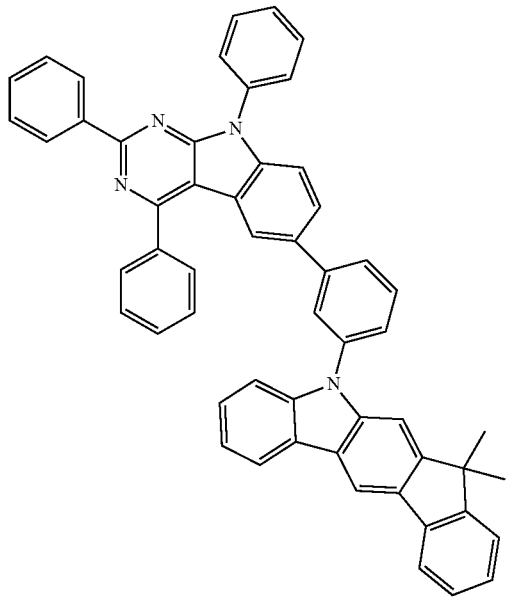 [SMILES: CC1(C)c2ccccc2-c2cc3c4ccccc4n(-c4cccc(-c5ccc6c(c5)c5c(-c7ccccc7)nc(-c7ccccc7)nc5n6-c5ccccc5)c4)c3cc21]

4i

The invention claimed is:
1. A compound of the formula (1),

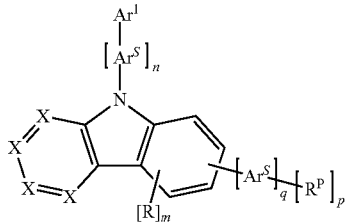

formula (1)

where:
X is N or CR$^X$, with the proviso that exactly two non-adjacent groups X are equal to N;
Ar$^S$ is on each occurrence, identically or differently, an aromatic ring system having 6 to 18 aromatic ring atoms, which may be substituted by one or more radicals R;
Ar$^1$ is an aromatic or heteroaromatic ring system having 5 to 60 aromatic ring atoms, which may be substituted by one or more radicals R;
R$^P$ is N(Ar)$_2$;
R$^X$ is on each occurrence, identically or differently, D, F, Cl, Br, I, CHO, N(Ar)$_2$, C(=O)Ar, P(=O)(Ar)$_2$, S(=O)Ar, S(=O)$_2$Ar, (R)C=C(R)Ar, CN, NO$_2$, Si(R)$_3$, B(OR)$_2$, B(R)$_2$, B(N(R)$_2$)$_2$, OSO$_2$R, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals R, where one or more, non-adjacent CH$_2$ groups may be replaced by (R)C=C(R), C=C, Si(R)$_2$, Ge(R)$_2$, Sn(R)$_2$, C=O, C=S, C=Se, P(=O)(R), SO, SO$_2$, N(R), O, S or CON(R) and where one or more H atoms may be replaced by D, F, Cl, Br, I, CN or NO$_2$, or an aromatic or heteroaromatic ring system having 5 to 60 aromatic ring atoms, which may be substituted by one or more radicals R, or an aryloxy or heteroaryloxy group having 5 to 60 aromatic ring atoms, which may be substituted by one or more radicals R;
R is on each occurrence, identically or differently, H, D, F, Cl, Br, I, CHO, N(Ar)$_2$, C(=O)Ar, P(=O)(Ar)$_2$, S(=O)Ar, S(=O)$_2$Ar, (R)C=C(R)Ar, CN, NO$_2$, Si(R$^1$)$_3$, B(OR$^1$)$_2$, B(R$^1$)$_2$, B(N(R$^1$)$_2$)$_2$, OSO$_2$R$^1$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals R$^1$, where one or more, non-adjacent CH$_2$ groups may be replaced by (R$^1$)C=C(R$^1$), C=C, Si(R$^1$)$_2$, Ge(R$^1$)$_2$, Sn(R$^1$)$_2$, C=O, C=S, C=Se, P(=O)(R$^1$), SO, SO$_2$, N(R$^1$), O, S or CON(R$^1$) and where one or more H atoms may be replaced by D, F, Cl, Br, I, CN or NO$_2$, or an aromatic or heteroaromatic ring system having 5 to 60 aromatic ring atoms, which may be substituted by one or more radicals R$^1$, or an aryloxy or heteroaryloxy group having 5 to 60 aromatic ring atoms, which may be substituted by one or more radicals R$^1$, where optionally two or more adjacent substituents R can form a mono- or polycyclic, aliphatic, aromatic or heteroaromatic ring system with one another;

Ar is an aromatic ring system having 6 to 24 aromatic ring atoms, which may be substituted by one or more radicals $R^1$;

$R^1$ is on each occurrence, identically or differently, H, D, F, Cl, Br, I, CHO, $N(R^2)_2$, $C(=O)R^2$, $P(=O)(R^2)_2$, $S(=O)R^2$, $S(=O)_2R^2$, $(R^2)C=C(R^2)_2$, CN, $NO_2$, $Si(R^2)_3$, $B(OR^2)_2$, $B(R^2)_2$, $B(N(R^2)_2)_2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^2$, where one or more, non-adjacent $CH_2$ groups may be replaced by $(R^2)C=C(R^2)$, C≡C, $Si(R^2)_2$, $Ge(R^2)_2$, $Sn(R^2)_2$, C=O, C=S, C=Se, $P(=O)(R^2)$, SO, $SO_2$, $N(R^2)$, O, S or $CON(R^2)$ and where one or more H atoms may be replaced by D, F, Cl, Br, I, CN or $NO_2$, or an aromatic or heteroaromatic ring system having 5 to 60 aromatic ring atoms, which may be substituted by one or more radicals $R^2$, or an aryloxy or heteroaryloxy group having 5 to 60 aromatic ring atoms, which may be substituted by one or more radicals $R^2$, where optionally two or more adjacent substituents $R^1$ can form a mono- or polycyclic, aliphatic, aromatic or heteroaromatic ring system with one another;

$R^2$ is on each occurrence, identically or differently, H, D, F, Cl, Br, I, CHO, CN, $NO_2$, a straight-chain alkyl, alkoxy or thioalkoxy group having 1 to 20 C atoms or a straight-chain alkenyl or alkynyl group having 2 to 20 C atoms or a branched or cyclic alkyl, alkenyl, alkynyl, alkoxy or thioalkoxy group having 3 to 20 C atoms, or an aromatic or heteroaromatic ring system having 5 to 30 aromatic ring atoms or an aryloxy or heteroaryloxy group having 5 to 30 aromatic ring atoms; where optionally two or more adjacent substituents $R^2$ can form a mono- or polycyclic, aliphatic, aromatic or heteroaromatic ring system with one another;

n, m, q are, identically or differently, 0, 1, 2 or 3;

p is 1.

2. The compound according to claim 1, wherein the compound is a compound of formulae (2), (3) and (4), formula (2)

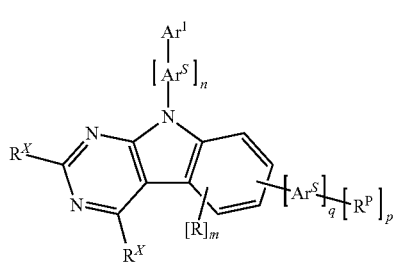

formula (3)

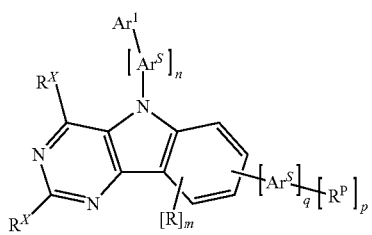

formula (4)

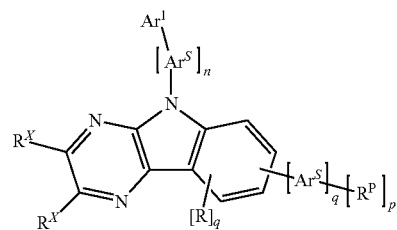

where the symbols and indices used have the same meanings as given in claim 1.

3. The compound according to claim 1, wherein the compound is a compound of formulae (2-2) to (4-6), formula (2-1)

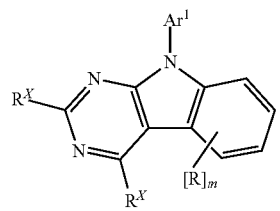

formula (2-2)

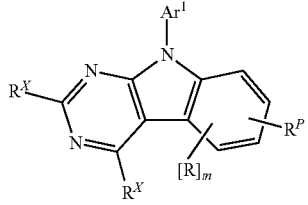

formula (2-3)

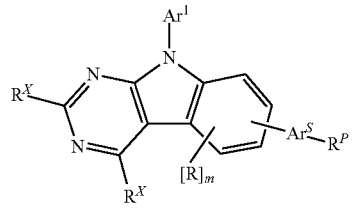

formula (2-4)

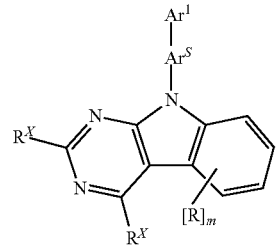

formula (2-5)

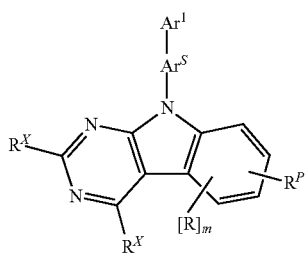

formula (2-6)
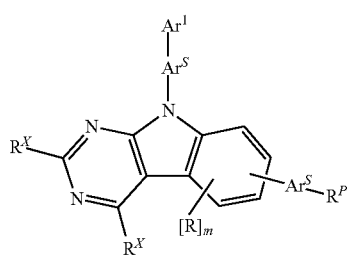
formula (3-1)
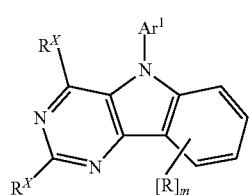
formula (3-2)
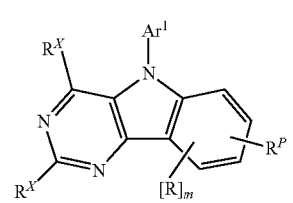
formula (3-3)
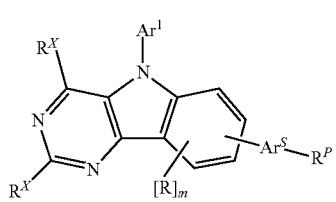
formula (3-4)
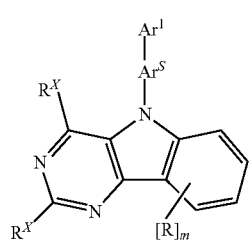
formula (3-5)
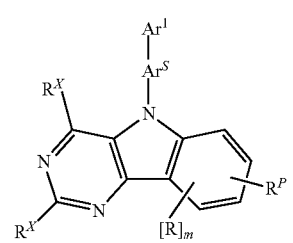
formula (3-6)
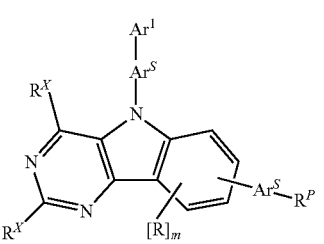
formula (4-1)
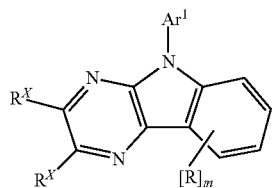
formula (4-2)
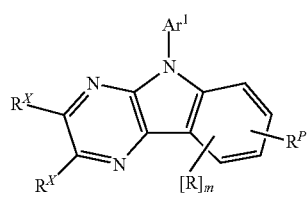
formula (4-3)
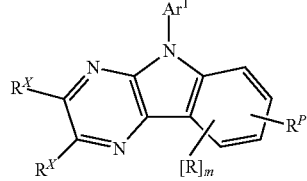
formula (4-4)
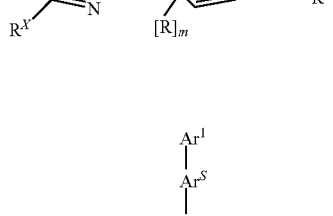
formula (4-5)
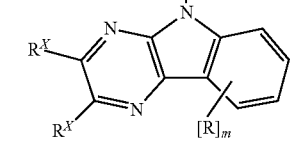
formula (4-6)
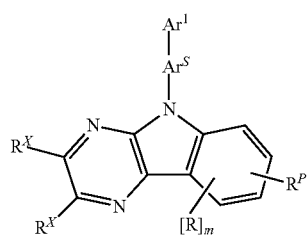
where the symbols and indices used have the same meanings as given in claim 1.

4. The compound according to claim 1, wherein the compound is a compound of formulae (2-2a) to (4-6a),
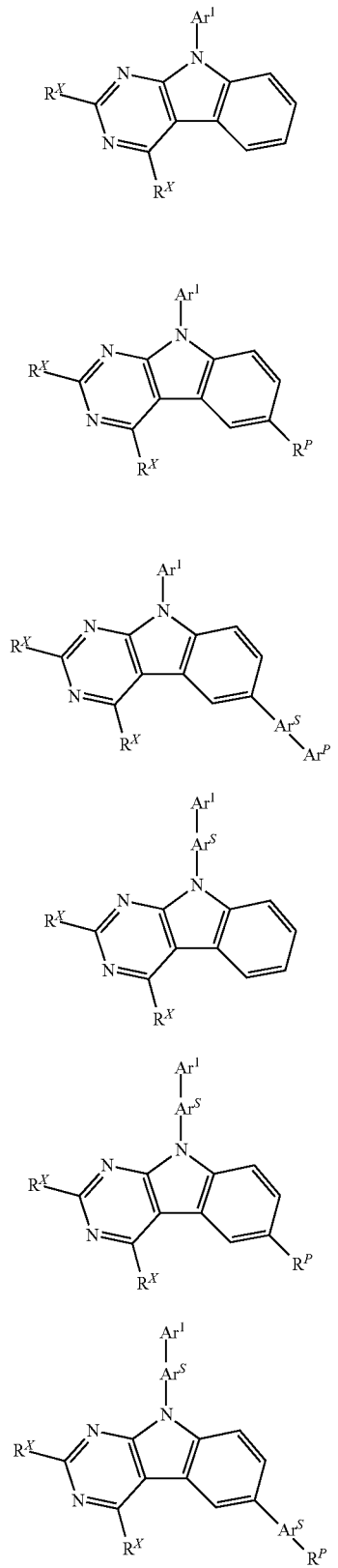
formula (2-1a)
formula (2-2a)
formula (2-3a)
formula (2-4a)
formula (2-5a)
formula (2-6a)
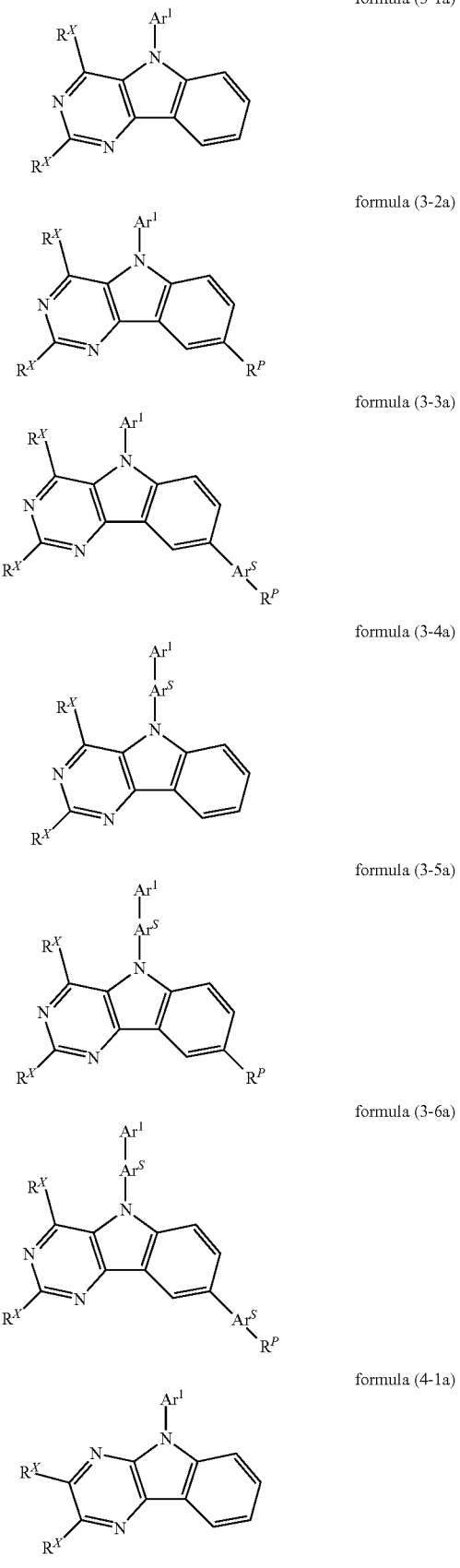
formula (3-1a)
formula (3-2a)
formula (3-3a)
formula (3-4a)
formula (3-5a)
formula (3-6a)
formula (4-1a)

-continued

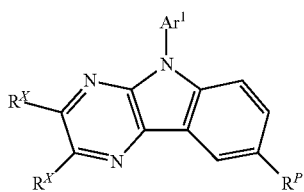

formula (4-2a)

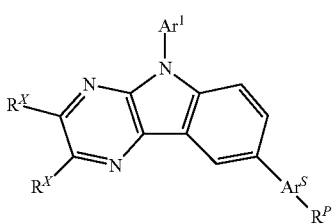

formula (4-3a)

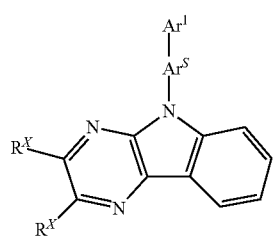

formula (4-4a)

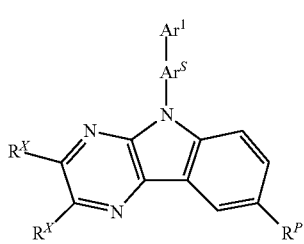

formula (4-5a)

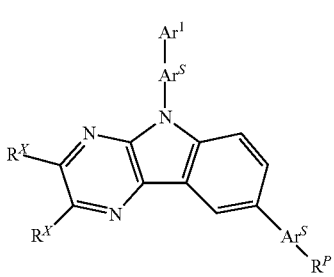

formula (4-6a)

where the symbols and indices used have the same meanings as given in claim 1.

5. The compound according to claim 1, wherein $Ar^1$ stands for benzene, naphthalene, anthracene, biphenyl, terphenyl, fluorene, furan, benzofuran, dibenzofuran, thiophene, benzo-thiophene, dibenzothiophene, carbazole, indolocarbazole, indenocarbazole, pyridine, quinoline, isoquinoline, pyridazine, benzopyridazine, pyrimidine, benzopyrimidine, quinoxaline, pyrazine, azacarbazole, benzocarboline, phenanthroline, 1,3,5-triazine, 1,2,4-triazine or 1,2,3-triazine, each of which may be substituted by one or more radicals R.

6. The compound according to claim 1, wherein $R^X$ is on each occurrence, identically or differently, an aromatic or heteroaromatic ring system having 5 to 24 aromatic ring atoms, which may be substituted by one or more radicals R.

7. The compound according to claim 1, wherein $R^X$ stands on each occurrence, identically or differently, for benzene, naphthalene, anthracene, biphenyl, terphenyl, fluorene, spirobifluorene, cis- or trans-indenofluorene, furan, benzofuran, dibenzofuran, thiophene, benzothiophene, dibenzothiophene, carbazole, indolocarbazole, indenocarbazole, pyridine, quinoline, isoquinoline, pyridazine, benzopyridazine, pyrimidine, benzopyrimidine, quinoxaline, pyrazine, azacarbazole, benzocarboline, phenanthroline, 1,3,5-triazine, 1,2,4-triazine, 1,2,3-triazine, each of which may be substituted by one or more radicals R.

8. The compound according to claim 1, wherein at least one group $Ar^1$ or $R^X$ is selected from triazine, pyrimidine, pyrazine, pyridazine, pyridine, imidazole, pyrazole, oxazole, oxadiazole, triazole, thiazole, thiadiazole, benzimidazole, quinolone, isoquinoline and quinoxaline, which may be substituted by one or more radicals R.

9. The compound according to claim 1, wherein at least one group $Ar^1$ or $R^X$ is selected from pyrrole, furan, thiophene, benzothiophene, benzofuran, indole, carbazole, dibenzothiophene, dibenzofuran and azacarbazole, which may be substituted by one or more radicals R.

10. A process for the preparation of the compound according to claim 1, starting from a diarylpyrimidoindole derivative, in which an aromatic or heteroaromatic ring system is connected to the nitrogen atom of a 5-membered ring of the indole ring by a C—N coupling reaction and/or at least one aromatic or heteroaromatic ring system is connected to the diarylpyrimidoindole derivative via a C—C coupling reaction.

11. A formulation comprising at least one compound according to claim 1 and at least one solvent.

12. An electronic device comprising at least one compound according to claim 1, wherein the device is selected from the group consisting of organic electroluminescent device, organic integrated circuit, organic field-effect transistor, organic thin-film transistor, organic light-emitting transistor, organic solar cell, dye-sensitised organic solar cell, organic optical detector, organic photoreceptor, organic field-quench device, light-emitting electrochemical cell, organic laser diode and organic plasmon emitting device.

13. An organic electroluminescent device which comprises the compound according to claim 1, wherein the compound is employed as one or more of a matrix material for phosphorescent or fluorescent emitters, an electron-blocking or exciton-blocking material, a hole-blocking material, or an electron-transport material.

14. The compound according to claim 1, wherein the compound is a compound of formula (I-1) or (I-2):

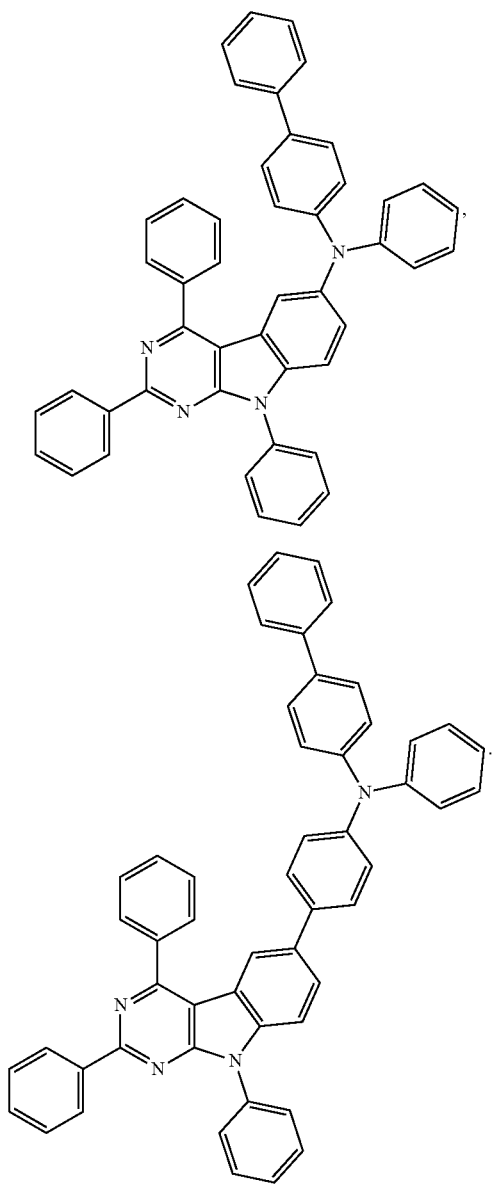

15. The compound according to claim 1, wherein
R is on each occurrence, identically or differently, H, D, F, Cl, Br, I, CHO, N(Ar)$_2$, C(=O)Ar, P(=O)(Ar)$_2$, S(=O)Ar, S(=O)$_2$Ar, (R)C=C(R)Ar, CN, NO$_2$, Si(R$^1$)$_3$, B(OR$^1$)$_2$, B(R$^1$)$_2$, B(N(R$^1$)$_2$)$_2$, OSO$_2$R$^1$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals R$^1$, or an aromatic or heteroaromatic ring system having 5 to 60 aromatic ring atoms, which may be substituted by one or more radicals R$^1$, or an aryloxy or heteroaryloxy group having 5 to 60 aromatic ring atoms, which may be substituted by one or more radicals R$^1$, where optionally two or more adjacent substituents R can form a mono- or polycyclic, aliphatic, aromatic or heteroaromatic ring system with one another;

R$^X$ is on each occurrence, identically or differently, D, F, Cl, Br, I, CHO, N(Ar)$_2$, C(=O)Ar, P(=O)(Ar)$_2$, S(=O)Ar, S(=O)$_2$Ar, (R)C=C(R)Ar, CN, NO$_2$, Si(R)$_3$, B(OR)$_2$, B(R)$_2$, B(N(R)$_2$)$_2$, OSO$_2$R, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, or an aromatic or heteroaromatic ring system having 5 to 60 aromatic ring atoms, which may be substituted by one or more radicals R, or an aryloxy or heteroaryloxy group having 5 to 60 aromatic ring atoms, which may be substituted by one or more radicals R;

R$^1$ is on each occurrence, identically or differently, H, D, F, Cl, Br, I, CHO, N(R$^2$)$_2$, C(=O)R$^2$, P(=O)(R$^2$)$_2$, S(=O)R$^2$, S(=O)$_2$R$^2$, (R$^2$)C=C(R$^2$)$_2$, CN, NO$_2$, Si(R$^2$)$_3$, B(OR$^2$)$_2$, B(R$^2$)$_2$, B(N(R$^2$)$_2$)$_2$, OSO$_2$R$^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, or an aromatic or heteroaromatic ring system having 5 to 60 aromatic ring atoms, which may be substituted by one or more radicals R$^2$, or an aryloxy or heteroaryloxy group having 5 to 60 aromatic ring atoms, which may be substituted by one or more radicals R$^2$, where optionally two or more adjacent substituents R$^1$ can form a mono- or polycyclic, aliphatic, aromatic or heteroaromatic ring system with one another.

16. The compound according to claim 1, wherein R$^X$ is on each occurrence, identically or differently, an aromatic or heteroaromatic ring system having 5 to 40, which may be substituted by one or more radicals R.

17. The compound according to claim 1, wherein R$^X$ stands on each occurrence, identically or differently, for benzene, naphthalene, biphenyl or carbazole, each of which may be substituted by one or more radicals R.

* * * * *